US012760018B2

(12) United States Patent
Vendeville et al.

(10) Patent No.: US 12,760,018 B2
(45) Date of Patent: *Oct. 13, 2026

(54) BICYCLIC COMPOUNDS

(71) Applicant: Aligos Therapeutics, Inc., South San Francisco, CA (US)

(72) Inventors: Sandrine Vendeville, Brussels (BE); David McGowan, Brussels (BE); Yannick Debing, Bilzen (BE); Pierre Jean-Marie Bernard Raboisson, Wavre (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 634 days.

This patent is subject to a terminal disclaimer.

(21) Appl. No.: 18/302,615

(22) Filed: Apr. 18, 2023

(65) Prior Publication Data

US 2023/0382909 A1 Nov. 30, 2023

Related U.S. Application Data

(60) Provisional application No. 63/484,135, filed on Feb. 9, 2023, provisional application No. 63/363,296, filed on Apr. 20, 2022.

(51) Int. Cl.

| | |
|---|---|
| ***C07D 471/04*** | (2006.01) |
| ***A61K 31/513*** | (2006.01) |
| ***A61K 31/519*** | (2006.01) |
| ***A61K 31/5377*** | (2006.01) |
| ***A61K 31/675*** | (2006.01) |
| ***A61K 31/683*** | (2006.01) |
| ***A61K 31/7072*** | (2006.01) |
| ***A61K 31/708*** | (2006.01) |
| ***A61K 38/21*** | (2006.01) |
| ***A61P 31/20*** | (2006.01) |
| ***C07D 519/00*** | (2006.01) |
| ***C07F 9/6561*** | (2006.01) |

(52) U.S. Cl.

CPC .......... *C07D 471/04* (2013.01); *A61K 31/513* (2013.01); *A61K 31/519* (2013.01); *A61K 31/5377* (2013.01); *A61K 31/675* (2013.01); *A61K 31/683* (2013.01); *A61K 31/7072* (2013.01); *A61K 31/708* (2013.01); *A61K 38/212* (2013.01); *A61P 31/20* (2018.01); *C07D 519/00* (2013.01); *C07F 9/6561* (2013.01)

(58) Field of Classification Search

CPC .. C07D 471/04; C07D 519/00; A61K 31/675; A61P 31/20; A61P 31/14; C07F 9/6561

See application file for complete search history.

(56) References Cited

U.S. PATENT DOCUMENTS

| | | | |
|---|---|---|---|
| 11,136,321 | B2 | 10/2021 | Vendeville |
| 11,491,341 | B2 | 11/2022 | Helekar et al. |
| 11,820,773 | B2 | 11/2023 | Vendeville et al. |
| 11,845,752 | B2 | 12/2023 | Vendeville et al. |
| 11,952,374 | B2 | 4/2024 | Vendeville et al. |
| 11,957,683 | B2 | 4/2024 | Vendeville et al. |
| 12,384,779 | B2 | 8/2025 | Vendeville et al. |
| 2020/0147124 | A1 | 5/2020 | Beigelman et al. |
| 2020/0361947 | A1 | 11/2020 | Vendeville et al. |
| 2020/0407361 | A1 | 12/2020 | Vendeville |
| 2022/0000874 | A1 | 1/2022 | Vendeville |
| 2022/0119385 | A1 | 4/2022 | Vendeville et al. |
| 2022/0119395 | A1 | 4/2022 | Vendeville et al. |
| 2022/0169650 | A1 | 6/2022 | Vendeville et al. |
| 2023/0051483 | A1 | 2/2023 | Vendeville et al. |
| 2023/0374008 | A1 | 11/2023 | Vendeville et al. |
| 2024/0150351 | A1 | 5/2024 | Vendeville et al. |

FOREIGN PATENT DOCUMENTS

| | | |
|---|---|---|
| WO | WO 2020/182990 | 9/2020 |
| WO | WO 2020/214728 | 10/2020 |
| WO | WO 2020/243199 | 12/2020 |
| WO | WO 2022/053010 | 3/2022 |
| WO | WO 2022/081758 | 4/2022 |
| WO | WO 2022/087011 | 4/2022 |
| WO | WO 2022/115384 | 6/2022 |
| WO | WO 2022/266193 | 12/2022 |
| WO | WO 2023/205645 | 10/2023 |
| WO | WO 2024/073559 | 4/2024 |
| WO | WO 2024/158904 | 8/2024 |

OTHER PUBLICATIONS

Fan, et al., "Assembly of Primary (Hetero)Arylamines via CuI/Oxalic Diamide-Catalyzed Coupling of Aryl Chlorides and Ammonia" Org. Lett. (2015) 17(23):5934-5937.

(Continued)

*Primary Examiner* — Savitha M Rao

*Assistant Examiner* — Elena V Vishnyakova

(74) *Attorney, Agent, or Firm* — Knobbe, Martens, Olson & Bear, LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

27 Claims, No Drawings

Specification includes a Sequence Listing.

(56) References Cited

OTHER PUBLICATIONS

Leermann et al., "Highly Efficient One-Pot Access to Functionalized Arylboronic Acids via Noncryogenic Bromine/Magnesium Exchanges" Org. Lett. (2011) 13(17):4479-4481.
Mfuh et al., "Scalable, Metal-and Additive-Free, Photoinduced Borylation of Haloarenes and Quaternary Arylammonium Salts" J. Am. Chem. Soc. (2016) 138(9):2985-2988.
Sheng et al. "[(CyPF-tBu)$PdCl_2$]: An Air-Stable, One-Component, Highly Efficient Catalyst for Amination of Heteroaryl and Aryl Halides" Org. Lett. (2008) 10(18):4109-4112.
Zhang et al., "Visible-Light-Induced Organocatalytic Borylation of Aryl Chlorides" J. Am. Chem. Soc. (2019) 141(23):9124-9128.
International Search Report and Written Opinion mailed Jul. 10, 2023 for PCT Application No. PCT/US2023/065907, filed Apr. 18, 2023.
International Preliminary Report on Patentability issued Oct. 8, 2024 for PCT Application No. PCT/US2023/065907, filed Apr. 18, 2023.
Extended European Search Report dated Mar. 9, 2026 for EP Application No. 23792717.3, filed Apr. 18, 2023.

BICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/363,296, filed Apr. 20, 2022, and 63/484,135, filed Feb. 9, 2023.

SEQUENCE STATEMENT

This application contains a Sequence Listing, which has been submitted electronically and is hereby incorporated by reference in its entirety. The sequence listing, was created on Apr. 18, 2023, is named ALIG_084.xml and is 12 kb in size.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroalkyl, hydroxy, alkoxyalkyl, alkoxy, acyl, cyano, halogen, thiocarbonyl, 0-carbamyl, N-carbamyl, 0-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine, a di-substituted amine, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-O-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH(an unsubstituted $C_{1-4}$ alkyl), —O-(an unsubstituted $C_{1-4}$ alkyl)-N(an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g., 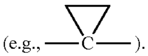 ).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). In some instances, a haloalkoxy can be —OR, wherein R is a $C_{1-4}$ alkyl substituted by 1, 2 or 3 halogens. Such groups include but are not limited to, chloromethoxy, fluoromethoxy, difluoromethoxy, trifluoro-2-ethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(═O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(═O)OR" group in which R can be the same as defined with respect to O-carboxy. An ester and C-carboxy may be substituted or unsubstituted.

A "thiocarbonyl" group refers to a "—C(═S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(═O)— group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(═S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(═S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—$NHR_A$" in which $R_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —$NHR_A$, wherein $R_A$ can be an unsubstituted $C_{1-6}$ alkyl or an unsubstituted or a substituted benzyl.

A "di-substituted amine" refers to a "—$NR_AR_B$" in which $R_A$ and $R_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —$NR_AR_B$, wherein $R_A$ and $R_B$ can be independently an unsubstituted $C_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents are not specified (e.g., haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

(I)

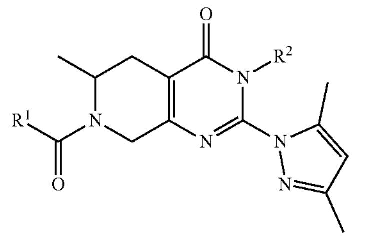

wherein: $R^1$ can be selected from

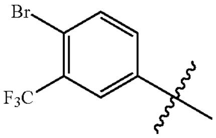,
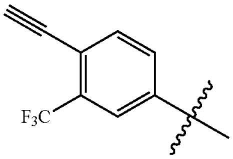,
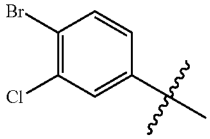,
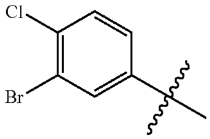,
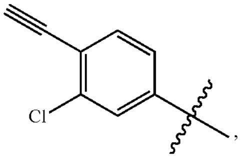,
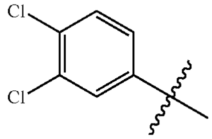 and
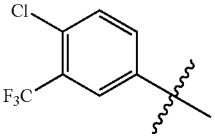;

$R^2$ can be selected from

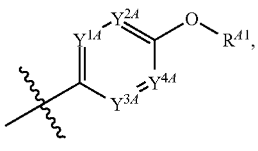,
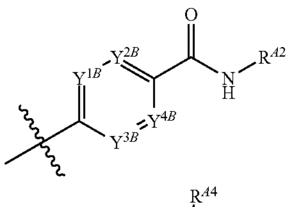,
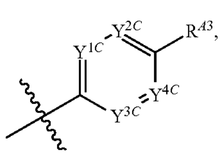,
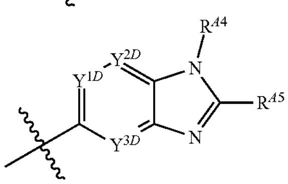,

-continued

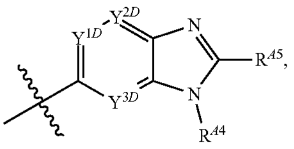,
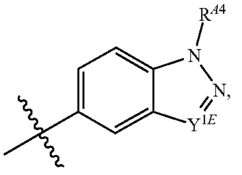,
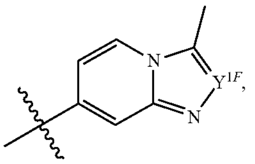,
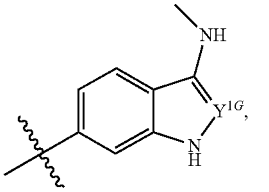,
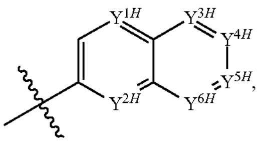,
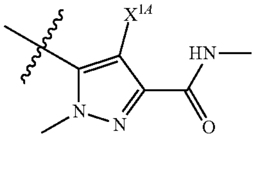,
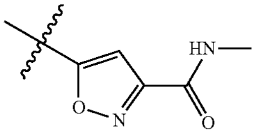,
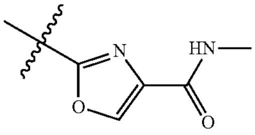,
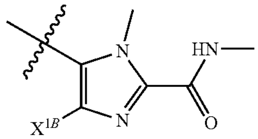,
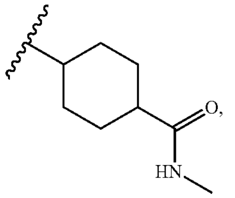,
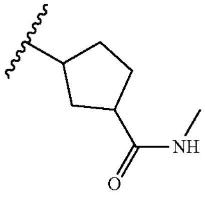,
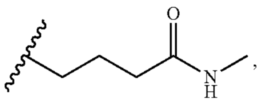,
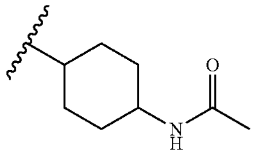

and

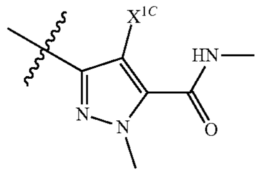;

$X^{1A}$, $X^{1B}$ and $X^{1c}$ can be independently selected from hydrogen, halogen, an unsubstituted $C_{1-5}$ alkyl and an unsubstituted $C_{1-5}$ haloalkyl; $Y^{1A}$ can be CH, C—$CHF_2$, C—F, C—Cl, C($NH_2$), C(NH(unsubstituted $C_{1-5}$ alkyl)), C(N(unsubstituted $C_{1-5}$ alkyl)$_2$) or N; $Y^{2A}$ can be CH, C-halogen, C—$OCH_3$, C($NH_2$), C(NH(unsubstituted $C_{1-5}$ alkyl)), C(N(unsubstituted $C_{1-5}$ alkyl)$_2$) or N; $Y^{3A}$ can be CH or N; $Y^{4A}$ can be CH or N; $Y^{1B}$ can be CH, C—$CHF_2$, C—F, C—Cl, C($NH_2$), C(NH(unsubstituted $C_{1-5}$ alkyl)), C(N(unsubstituted $C_{1-5}$ alkyl)$_2$) or N (nitrogen); $Y^{2B}$ can be CH, C-halogen, C—$OCH_3$, C($NH_2$), C(NH(unsubstituted $C_{1-5}$ alkyl)), C(N(unsubstituted $C_{1-5}$ alkyl)$_2$) or N (nitrogen); $Y^{3B}$ can be CH or N (nitrogen); $Y^{4B}$ can be CH or N (nitrogen); $Y^{1C}$, $Y^{2C}$, $Y^{3C}$ and $Y^{4C}$ can be each independently CH, C-(halogen) or N (nitrogen); $Y^{1D}$ can be CH, C—$CH_3$, C—$OCH_3$, C-(halogen), C—$CHF_2$, C—$CF_3$ or N (nitrogen); $Y^{2D}$ can be CH, C—$CH_3$, C—$OCH_3$, C-(halogen), C—$CHF_2$, C—$CF_3$ or N (nitrogen); $Y^{3D}$ can be CH, C-(halogen) or N (nitrogen); $Y^{1E}$, $Y^{1F}$ and $Y^{1G}$ can be each independently CH, C-(halogen) or N (nitrogen); $Y^{1H}$, $Y^{2H}$, $Y^{3H}$, $Y^{4H}$, $Y^{5H}$ and $Y^{6H}$ can be each independently CH, C-(halogen) or N (nitrogen); $R^{A1}$ can be hydrogen, an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —$NH_2$, an unsubstituted $C_{1-5}$ alkoxy, an unsubstituted —NH(an unsubstituted $C_{1-5}$ alkyl), —N(an unsubstituted $C_{1-5}$ alkyl)$_2$, —C(═O)$NH_2$, —O—P(═O)(OH)$_2$, an unsubstituted 5- or 6-membered monocyclic heterocyclyl and 5- or 6-membered monocyclic heterocyclyl substituted by one or more unsubstituted $C_{1-4}$ alkyl groups; $R^{A2}$ can be —$CH_3$ or -$CD_3$; $R^{A3}$ can be —$NH_2$, —NH(an unsubstituted or a substituted $C_{1-5}$ alkyl), —N(an unsubstituted or a substituted $C_{1-5}$ alkyl)$_2$, —NH(an unsubstituted or a substituted $C_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl; $R^{A4}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(═O)OH and —C(═O)$NH_2$; and $R^{A5}$ can be selected from hydrogen, halogen, —CN, —OH, —$NH_2$, —C(═O)OH, —CH═$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

In various embodiments, $R^1$ in Formula (I) can be selected from

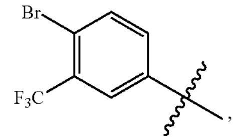,
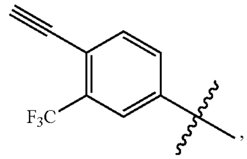,
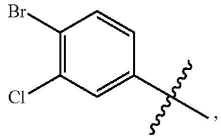,
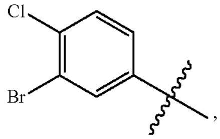,
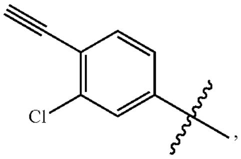,
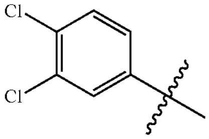

and

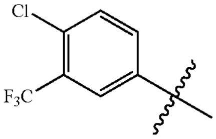.

In an embodiment, $R^1$ can be
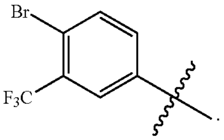 [SMILES: *c1ccc(Br)c(C(F)(F)F)c1]
In another embodiment, $R^1$ can be
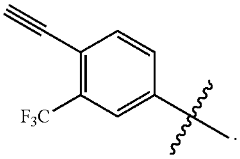 [SMILES: *c1ccc(C#C)c(C(F)(F)F)c1]
In another embodiment, $R^1$ can be
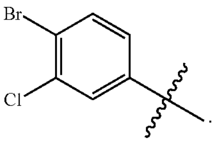 [SMILES: *c1ccc(Br)c(Cl)c1]
In another embodiment, $R^1$ can be
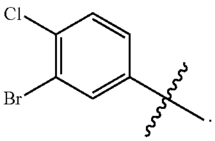
In another embodiment, $R^1$ can be
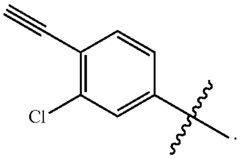
In another embodiment, $R^1$ can be
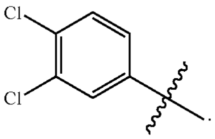 [SMILES: *c1ccc(Cl)c(Br)c1]
In another embodiment, $R^1$ can be
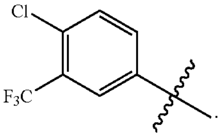
In various embodiments, $R^2$ in Formula (I) can be selected from
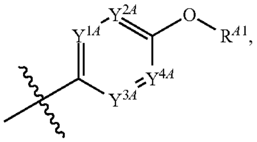
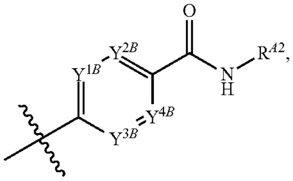
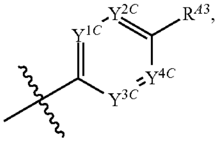
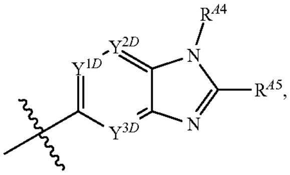
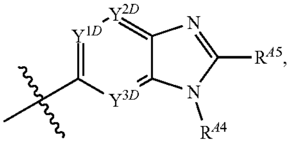
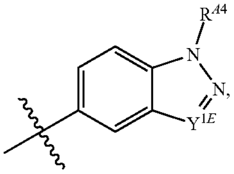
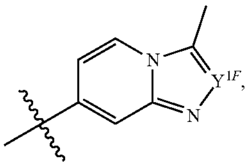
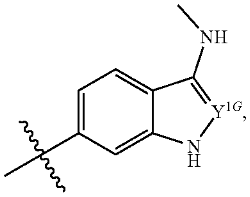
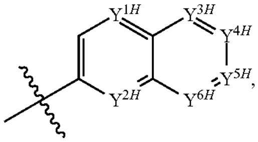
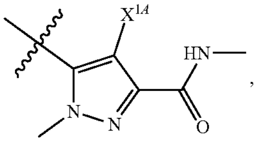
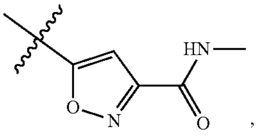
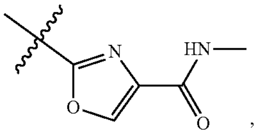
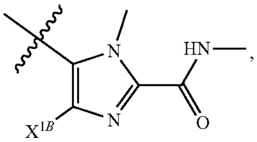
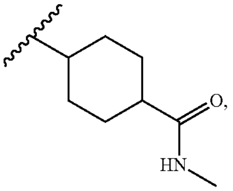
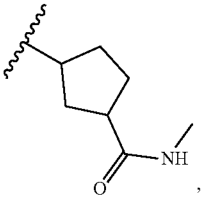
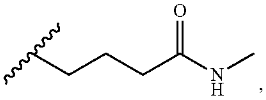

-continued

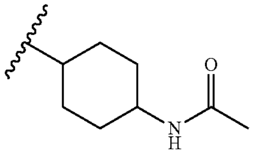

and

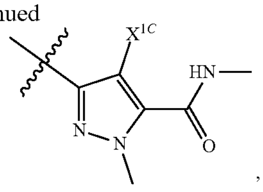

, wherein the variables $X^{1A}$, $X^{1B}$, $X^{1C}$, $Y^{1A}$, $Y^{2A}$, $Y^{3A}$, $Y^{4A}$, $Y^{1B}$, $Y^{2B}$, $Y^{3B}$, $Y^{4B}$, $Y^{1C}$, $Y^{2C}$, $Y^{3C}$, $Y^{4C}$, $Y^{1D}$, $Y^{2D}$, $Y^{3D}$, $Y^{1E}$, $Y^{1F}$, $Y^{1G}$, $Y^{1H}$, $Y^{2H}$, $Y^{3H}$, $Y^{4H}$, $Y^{5H}$, $Y^{6H}$, $R^{A1}$, $R^{A2}$, $R^{A3}$, $R^{A4}$ and $R^{A5}$ can be as defined elsewhere herein.

In some embodiments, $R^2$ in Formula (I) can be

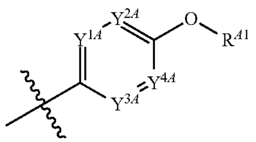

where $R^{A1}$ can be an unsubstituted $C_{1-5}$ alkyl. For example, $R^{A1}$ can be methyl, ethyl, n-propyl, iso-propyl, n-butyl, iso-butyl, sec-butyl, tert-butyl, n-pentyl or a branched pentyl. In still other embodiments, $R^2$ in Formula (I) can be

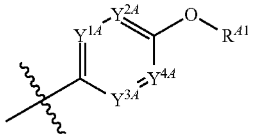

where $R^{A1}$ can be a substituted $C_{1-s}$ alkyl. As provided herein, a $C_{1-s}$ alkyl for $R^A$ can be substituted with one or more hydroxy groups (such as 1, 2 or 3 hydroxy groups), one or more —$NH_2$ groups (for example, 1, 2 or 3 —$NH_2$ groups), one or more an unsubstituted $C_{1-5}$ alkoxy groups (such as 1, 2 or 3 alkoxy groups), one or more an unsubstituted —NH(an unsubstituted $C_{1-5}$ alkyl) groups (such as 1, 2 or 3 —NH(an unsubstituted $C_{1-5}$ alkyl) groups), one or more —N(an unsubstituted $C_{1-5}$ alkyl)$_2$ (for example, 1, 2 or 3 —N(an unsubstituted $C_{1-5}$ alkyl)$_2$ groups), one or more —C(═O)$NH_2$ (for example, 1 or 2-C(═O)$NH_2$ groups), one or more —O—P(═O)$(OH)_2$ (for example, 1 or 2 —O—P(═O)$(OH)_2$ groups), one or more unsubstituted 5- or 6-membered monocyclic heterocyclyls (for example, 1, 2 or 3 unsubstituted 5- or 6-membered monocyclic heterocyclyls) and/or one or more 5- or 6-membered monocyclic heterocyclyls substituted by one or more unsubstituted $C_{1-4}$ alkyl groups (for example, 1, 2 or 3 5- or 6-membered monocyclic heterocyclyls each independently substituted with 1, 2 or 3 unsubstituted $C_{1-4}$ alkyl groups). Exemplary $C_{1-5}$ alkyls substituted with one or more hydroxy groups include —$CH_2CH_2OH$, —$CH_2CH(CH_3)OH$ and —$CH_2CH(OH)CH_2(OH)$. As provided herein, a $C_{1-5}$ alkyl for $R^{A1}$ can be substituted by one or more —$NH_2$ groups, one or more —NH(an unsubstituted $C_{1-5}$ alkyl) groups and/or one or more —N(an unsubstituted $C_{1-5}$ alkyl)$_2$ groups. For example, $R^{A1}$ can be —$(CH_2)_{1-4}NH_2$, —$(CH_2)_{1-4}$NH(an unsubstituted $C_{1-5}$ alkyl) or —$(CH_2)_{1-4}$N(an unsubstituted $C_{1-5}$ alkyl)$_2$. Examples of $C_{1-5}$ alkyls substituted with one or more unsubstituted $C_{1-5}$ alkoxy groups include —$CH_2CH_2OCH_3$ and —$CH_2CH(CH_3)OCH_3$. An example of an $C_{1-5}$ alkyl substituted with —C(═O)$NH_2$ is —$CH_2$—C(═O)$NH_2$. An example of an $C_{1-5}$ alkyl substituted with —O—P(═O)$(OH)_2$ is —$CH_2CH$(O—P(═O)$(OH)_2$)$(CH_3)$. In some embodiments, $R^{A1}$ can be a $C_{1-s}$ alkyl substituted with one moiety selected from hydroxy, —$NH_2$, an unsubstituted $C_{1-5}$ alkoxy, an unsubstituted —NH(an unsubstituted $C_{1-5}$ alkyl), —N(an unsubstituted $C_{1-5}$ alkyl)$_2$, —C(═O)$NH_2$ and —O—P(═O)$(OH)_2$. For example, $R^{A1}$ can be —$(CH_2)_{1-4}OH$, —$(CH_2)_{1-2}CH(CH_3)(OH)$, —$CH_2CH(OH)CH_2(OH)$, —$(CH_2)_{1-4}NH_2$, —$(CH_2)_{1-4}$NH (an unsubstituted $C_{1-5}$ alkyl) or —$(CH_2)_{1-4}$N(an unsubstituted $C_{1-5}$ alkyl)$_2$, —$(CH_2)_{1-4}OCH_3$, —$(CH_2)_{1-4}$C(═O)$NH_2$, —$(CH_2)_{1-4}$(O—P(═O)$(OH)_2$) and —$(CH)_{1-2}$CH(O—P(═O)$(OH)_2$)$(CH_3)$. In some embodiments, $R^{A1}$ can be a $C_{1-5}$ alkyl substituted with an unsubstituted 5- or 6-membered monocyclic heterocyclyls and/or a 5- or 6-membered monocyclic heterocyclyls substituted by one or more unsubstituted $C_{1-4}$ alkyl groups. Exemplary 5- or 6-membered monocyclic heterocyclyls that can be substituted on a $C_{1-5}$ alkyl include pyrrolidinyl, piperidinyl, morpholinyl, 1,2,4-oxadiazol-5(4H)-one, 2,4-dihydro-3H-1,2,4-triazol-3-onyl, pyrazolonyl and piperazinyl. In other embodiments, $R^2$ in Formula (I) can be

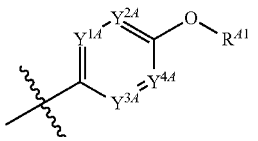

where $R^{A1}$ can be an unsubstituted monocyclic $C_{3-6}$ cycloalkyl. In yet still other embodiments, $R^2$ in Formula (I) can be

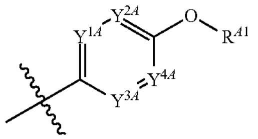

where $R^{A1}$ can be a substituted monocyclic $C_{3-6}$ cycloalkyl substituted with one or more hydroxy groups (such as 1, 2 or 3 hydroxy groups), one or more —$NH_2$ groups (for example, 1, 2 or 3 —$NH_2$ groups), one or more an unsubstituted $C_{1-5}$ alkoxy groups (such as 1, 2 or 3 alkoxy groups), one or more an unsubstituted —NH(an unsubstituted $C_{1-5}$ alkyl) groups (such as 1, 2 or 3 —NH(an unsubstituted $C_{1-5}$ alkyl) groups), one or more —N(an unsubstituted $C_{1-5}$ alkyl)$_2$ (for example, 1, 2 or 3 —N(an unsubstituted $C_{1-5}$ alkyl)$_2$ groups), one or more —C(═O)$NH_2$ (for example, 1 or 2-C(═O)$NH_2$ groups), one or more —O—P(═O)$(OH)_2$ (for example, 1 or 2 —O—P(═O)$(OH)_2$ groups), one or more unsubstituted 5- or 6-membered monocyclic heterocyclyls (for example, 1, 2 or 3 unsubstituted 5- or 6-membered monocyclic heterocyclyls) and/or one or more 5- or 6-membered monocyclic heterocyclyls substituted by one or more unsubstituted $C_{1-4}$ alkyl groups (for example, 1, 2 or 3 5- or 6-membered monocyclic heterocyclyls each independently substituted with 1, 2 or 3 unsubstituted $C_{1-4}$ alkyl groups). Examples of monocyclic $C_{3-6}$ cycloalkyls include cyclopropyl, cyclobutyl, cyclopentyl and cyclohexyl. In some embodiments, $R^{A1}$ can be a substituted monocyclic $C_{3-6}$ cycloalkyl substituted with one moiety selected from hydroxy, —$NH_2$, an unsubstituted $C_{1-5}$ alkoxy, an unsubstituted —NH(an unsubstituted $C_{1-5}$ alkyl) and —N(an unsubstituted $C_{1-5}$ alkyl)$_2$. In some embodiments, $R^{A1}$ can be cyclobutyl substituted with a moiety selected from hydroxy, —$NH_2$, an unsubstituted —NH(an unsubstituted $C_{1-5}$ alkyl) and —N(an unsubstituted $C_{1-5}$ alkyl)$_2$. In some embodiments, $R^{A1}$ can be hydrogen.

In some embodiments, $Y^{1A}$, $Y^{2A}$, $Y^{3A}$ and $Y^{4A}$ can be each CH. In other embodiments, one of $Y^{1A}$, $Y^{2A}$, $Y^{3A}$ and $Y^{4A}$ can be N. In still other embodiments, two or three of $Y^{1A}$, $Y^{2A}$, $Y^{3A}$ and $Y^{4A}$ can be N. In some embodiments, $Y^{1A}$ can be C—$CHF_2$, C—F or C—Cl; and $Y^{2A}$, $Y^{3A}$ and $Y^{4A}$ can be each CH. In some embodiments, $Y^{2A}$ can be C-halogen. In other embodiments, $Y^{2A}$ can be C—$OCH_3$. In some embodiments, $Y^{2A}$ can be C-halogen; and $Y^{1A}$ $Y^{3A}$ and $Y^{4A}$ can be each CH. In some embodiments, $Y^{2A}$ can be C($NH_2$), C(NH(unsubstituted $C_{1-5}$ alkyl)) or C(N(unsubstituted $C_{1-5}$ alkyl)$_2$). In other embodiments, $Y^{2A}$ can be C—$OCH_3$; and $Y^{1A}$, $Y^{3A}$ and $Y^{4A}$ can be each CH. In other embodiments, $Y^{2A}$ can be C($NH_2$), C(NH(unsubstituted $C_{1-5}$ alkyl)) or C(N(unsubstituted $C_{1-5}$ alkyl)$_2$); and $Y^{1A}$, $Y^{3A}$ and $Y^{4A}$ can be each CH. Examples of $R^2$ include the following

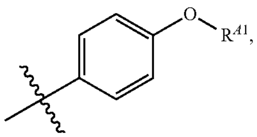,
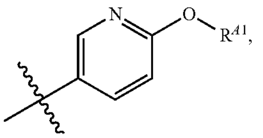,
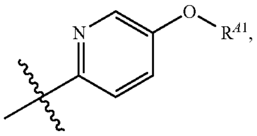,
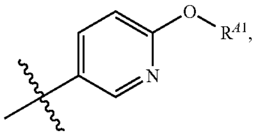,
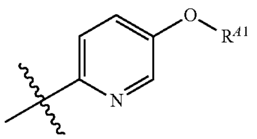
and
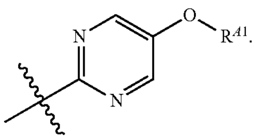.

In another embodiment, $R^2$ in Formula (I) can be

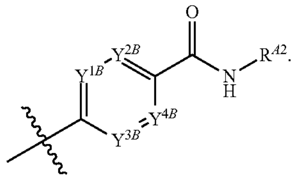.

In various embodiments, $Y^{1B}$ can be CH, C—Cl or N; $Y^{2B}$ can be CH, C—Cl, C—$OCH_3$, C($NH_2$), C(NH(unsubstituted $C_{1-5}$ alkyl)) or C(N(unsubstituted $C_{1-5}$ alkyl)$_2$) or N; $Y^{3B}$ can be CH or N; $Y^{4B}$ can be CH or N; and $R^{A2}$ can be —$CH_3$ or -$CD_3$. In some embodiments, $Y^{1B}$, $Y^{2B}$, $Y^{3B}$ and $Y^{4B}$ can be each CH. In other embodiments, at least one of $Y^{1B}$, $Y^{3B}$ and $Y^{4B}$ can be N (nitrogen). As an example, one of $Y^{1B}$, $Y^{3B}$ and $Y^{4B}$ can be N such that the ring of

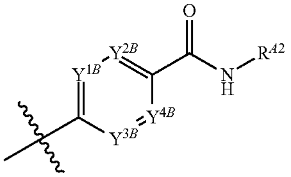

can be pyridinyl. Other examples of rings where at least one of $Y^{1B}$, $Y^{3B}$ and $Y^{4B}$ is nitrogen include pyridazine, pyrimidine and pyrazine. In some embodiments, $Y^{1B}$, $Y^{2B}$, $Y^{3B}$ and $Y^{4B}$ can be each CH. In other embodiments, one of $Y^{1B}$, $Y^{2B}$, $Y^{3B}$ and $Y^{4B}$ can be N. In still other embodiments, two or three of $Y^{1B}$, $Y^{2B}$, $Y^{3B}$ and $Y^{4B}$ can be N. In some embodiments, $Y^{1B}$ can be C—$CHF_2$, C—F or C—Cl; and $Y^{2B}$, $Y^{3B}$ and $Y^{4B}$ can be each CH. In some embodiments, $Y^{2B}$ can be C-halogen. In other embodiments, $Y^{2B}$ can be C—$OCH_3$. In still other embodiments, $Y^{2B}$ can be C($NH_2$), C(NH(unsubstituted $C_{1-5}$ alkyl)) or C(N(unsubstituted $C_{1-5}$ alkyl)$_2$). In some embodiments, $Y^{2B}$ can be C-halogen (such as C—Cl); and $Y^{1B}$, $Y^{3B}$ and $Y^{4B}$ can be each CH. In other embodiments, $Y^{2B}$ can be C—$OCH_3$; and $Y^{1B}$, $Y^{3B}$ and $Y^{4B}$ can be each CH. In still other embodiments, $Y^{2B}$ can be C($NH_2$), C(NH(unsubstituted $C_{1-5}$ alkyl)) or C(N(unsubstituted $C_{1-5}$ alkyl)$_2$); and $Y^{1B}$, $Y^{3B}$ and $Y^{4B}$ can be each CH. Exemplary $R^2$ groups include

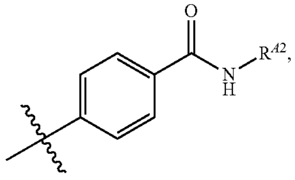,
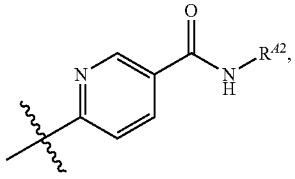,
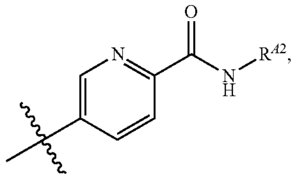,
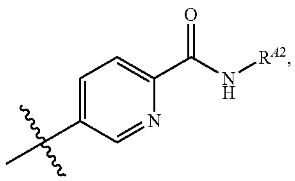,
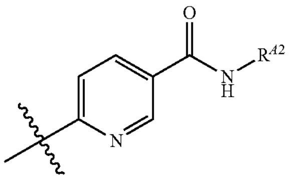
and

-continued

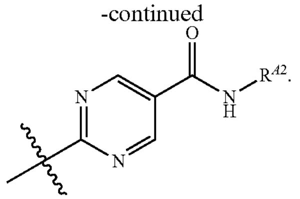

In another embodiment, $R^2$ in Formula (I) can be

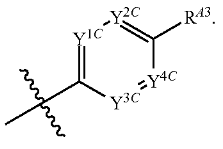

In some embodiments, $Y^{1C}$, $Y^{2C}$, $Y^{3C}$ and $Y^{4C}$ can be each independently CH or N (nitrogen); and $R^{A3}$ can be —$NH_2$, —NH(an unsubstituted or a substituted $C_{1-5}$ alkyl), —N(an unsubstituted or a substituted $C_{1-5}$ alkyl)$_2$, —NH(an unsubstituted or a substituted $C_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl. In some embodiments, $R^{A3}$ can be —$NH_2$. In other embodiments, $R^{A}$ can be —NH(an unsubstituted $C_{1-5}$ alkyl). In still other embodiments, $R^{A}$ can be —NH(a substituted $C_{1-5}$ alkyl). In yet still other embodiments, —N(an unsubstituted $C_{1-5}$ alkyl)$_2$. In some embodiments, $R^{A3}$ can be —N(a substituted $C_{1-5}$ alkyl)$_2$. Examples of $C_{1-5}$ alkyls include methyl, ethyl, n-propyl, iso-propyl, n-butyl, iso-butyl, sec-butyl, tert-butyl, n-pentyl or a branched pentyl. When the $C_{1-5}$ alkyl is substituted, the $C_{1-5}$ alkyl can be substituted with one or more hydroxy groups, for example, 1, 2 or 3 hydroxy groups. For example, —$NH(CH_2)_{1-5}OH$, —$NH(CH_2)_{1-4}CH(OH)(CH_3)$, —$NH(CH_2)_{1-3}CH(OH)CH_2(CH_3)$, —$NH(CH_2)_{1-3}CH(OH)CH_2(OH)$ or —$NH((CH_2)_{1-5}OH)_2$. As provided herein, $R^{A3}$ can be an unsubstituted or a substituted 5- or 6-membered heteroaryl. In some embodiments, $R^{A3}$ can be an unsubstituted or a substituted 5-membered-monocyclic heteroaryl. In other embodiments, $R^{A3}$ can be an unsubstituted or a substituted 6-membered-monocyclic heteroaryl. In some instances, the 5- and/or 6-membered-monocyclic heteroaryl can include 1, 2 or 3 heteroatoms, such as N (nitrogen), O (oxygen) and/or S (sulfur). In some embodiments, $R^{A3}$ can be an unsubstituted or a substituted 5- or 6-membered-monocyclic heteroaryl that includes 1 or 2 nitrogens. Non-limiting examples of suitable 5-membered-monocyclic heteroaryls include pyrazolyl, imidazolyl, 1,2,3-triazolyl, 1,2,4-triazolyl and tetrazolyl. Examples of 6-membered monocyclic heteroaryls includes pyridinyl, pyridazinyl, pyrimidinyl and pyrazinyl. In some embodiments, $R^{A3}$ can be an unsubstituted or a substituted 4-membered-monocyclic heterocyclyl. In other embodiments, $R^{A3}$ can be an unsubstituted or a substituted 5-membered-monocyclic heterocyclyl. In still other embodiments, $R^{A3}$ can be an unsubstituted or a substituted 6-membered-monocyclic heterocyclyl. In some instances, the 4- to 6-membered-monocyclic heterocyclyl can include 1, 2 or 3 heteroatoms N (nitrogen), O (oxygen) and/or S (sulfur). In some embodiments, $R^{A3}$ can be an unsubstituted or a substituted 4- to 6-membered-monocyclic heterocyclyl that includes 1 or 2 nitrogens. Non-limiting examples of suitable 4- to 6-membered-monocyclic heterocyclyls include azetidinyl, pyrrolidinyl, morpholinyl, 1,2,4-oxadiazol-5(4H)-onyl, 2,4-dihydro-3H-1,2,4-triazol-3-onyl, pyrazolonyl and piperazinyl. Possible substitutions that can be present on a —NH(a substituted $C_{3-6}$ monocyclic cycloalkyl), a substituted monocyclic heteroaryl and/or a substituted monocyclic heterocyclyl of $R^{A3}$ include halogen, hydroxy, amino, an unsubstituted $C_{1-5}$ alkyl and an unsubstituted $C_{1-5}$ haloalkyl.

In some embodiments, $Y^{1C}$, $Y^{2C}$, $Y^{3C}$ and $Y^{4C}$ can be each CH such that $R^2$ can be

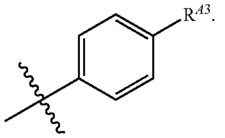

In other embodiments, at least one of $Y^{1C}$, $Y^{2C}$, $Y^{3C}$ and $Y^{4C}$ can be N (nitrogen). Exemplary rings for

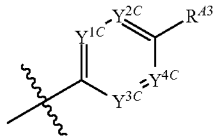

when at least one of $Y^{1C}$, $Y^{2C}$, $Y^{3C}$ and $Y^{4C}$ is N include pyridinyl, pyridazinyl, pyrimidinyl and pyrazinyl. In some embodiments, $Y^{1C}$, $Y^{2C}$, $Y^{3C}$ and $Y^{4C}$ can be each CH. In other embodiments, one of $Y^{1C}$, $Y^{2C}$, $Y^{3C}$ and $Y^{4C}$ can be N. In still other embodiments, $Y^2c$ is CH, C—F or C—Cl. In yet still other embodiments, two or three of $Y^{1C}$, $Y^{2C}$, $Y^{3C}$ and $Y^{4C}$ can be N. In some embodiments, one of $Y^{1C}$, $Y^{2C}$, $Y^{3C}$ and $Y^{4C}$ can be C-(halogen). Examples of $R^2$ include the following

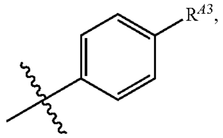

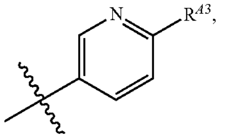

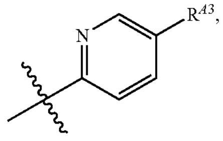

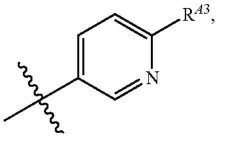

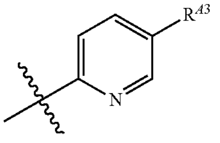

and

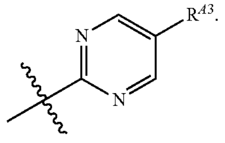

In another embodiment, $R^2$ in Formula (I) can be

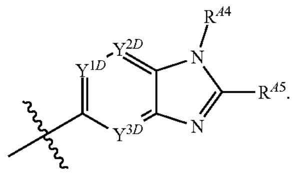

In still another embodiment, $R^2$ in Formula (I) can be

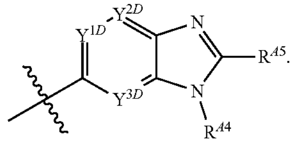

In various embodiments, $Y^{1D}$ can be CH, C—$CH_3$, C—$OCH_3$, C-(halogen), C—$CHF_2$, C—$CF_3$ or N; $Y^{2D}$ can be CH, C—$CH_3$, C—$OCH_3$, C-(halogen), C—$CHF_2$, C—$CF_3$ or N; $Y^{3D}$ can be CH, C-(halogen) or N; $R^{A4}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(=O)OH and —C(=O)$NH_2$; and $R^{A5}$ can be selected from hydrogen, halogen, —CN, —OH, —$NH_2$, —C(=O)OH, —CH=$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

In some embodiments, $Y^{1D}$, $Y^{2D}$ and $Y^{3D}$ can be each CH. In other embodiments, one of $Y^{1D}$ and $Y^{2D}$ can be CH; the other of $Y^{1D}$ and $Y^{2D}$ can be C—$CH_3$, C—$OCH_3$, C-(halogen), C—$CHF_2$, C—$CF_3$; and $Y^{3D}$ can be CH. In still other embodiments, one of $Y^{1D}$ and $Y^{2D}$ can be CH; the other of $Y^{1D}$ and $Y^{2D}$ can be C—$CH_3$, C—$OCH_3$, C-(halogen), C—$CHF_2$, C—$CF_3$; and $Y^{3D}$ can be N (nitrogen). The halogen of C-(halogen) can be F, Cl, Br of I. In some embodiments, $Y^{2D}$ can be N. In some embodiments, $Y^{3D}$ can be N. In some embodiments, $Y^{2D}$ and $Y^{3D}$ can be each N. In some embodiments, C-(halogen) of $Y^{1D}$ and/or $Y^{2D}$ can be C—F or C—Cl. In some embodiments, $R^{A4}$ can be an unsubstituted $C_{1-5}$ alkyl. In other embodiments, $R^{A4}$ can be a substituted $C_{1-5}$ alkyl. In still other embodiments, $R^{A4}$ can be an unsubstituted $C_{1-5}$ haloalkyl. In yet still other embodiments, $R^{A4}$ can be an unsubstituted cyclopropyl, an unsubstituted cyclobutyl, an unsubstituted cyclopentyl or an unsubstituted cyclohexyl. In some embodiments, $R^{A4}$ can be a substituted monocyclic $C_{3-6}$ cycloalkyl, substituted with one or more (such as 1, 2 or 3) hydroxy groups. Examples of $C_{1-5}$ alkyls for $R^{A4}$ include methyl, ethyl, n-propyl, iso-propyl, n-butyl, iso-butyl, sec-butyl, tert-butyl, n-pentyl or a branched pentyl. As provided herein, a $C_{1-5}$ alkyl for $R^{A4}$ can be substituted with one or more hydroxy groups (such as 1, 2 or 3 hydroxy groups), one or more —C(=O)OH groups (for example, 1, 2 or 3-C(=O)OH groups) and/or one or more —C(=O)$NH_2$ groups, such as 1, 2 or 3-C(=O)$NH_2$ groups. Exemplary $C_{1-5}$ alkyls substituted with one or more hydroxy groups, one or more —C(=O)OH groups and/or one or more —C(=O)$NH_2$ groups include, —$CH_2CH_2OH$, —$CH(CH_3)OH$, —$CH_2CH(CH_3)OH$, —$CH_2C$(=O)$NH_2$, —$CH_2CH_2C$(=O)$NH_2$, —$CH(CH_3)C$(=O)$NH_2$, —$CH_2CH(CH_3)C$(=O)$NH_2$, —$CH_2C$(=O)OH, —$CH_2CH_2C$(=O)OH, —$CH(CH_3)C$(=O)OH and —$CH_2CH(CH_3)C$(=O)OH. Examples of $C_{1-5}$ haloalkyls include —$CF_3$, —$CCl_3$, —$CHF_2$, —$C(CH_3)F_2$, —$CHCl_2$, —$CH_2F$, —$CH(CH_3)F$, —$CH_2CH_2F$, —$CH_2CHF_2$, —$CH_2CF_3$, —$CH_2Cl$, —$CH_2CH_2F$, —$CH_2CH_2Cl$, —$CH_2CH_2CH_2F$ and —$CH_2CH_2CH_2Cl$.

In some embodiments, $R^{A5}$ can be hydrogen. In some embodiments, $R^{A5}$ can be halogen, —CN, —OH or —$NH_2$. In still other embodiments, $R^{A}S$ can be —C(=O)OH. In yet still other embodiments, $R^{A}S$ can be —CH=$CH_2$. In some embodiments, $R^{A}S$ can be an unsubstituted $C_{1-5}$ alkyl, such as methyl, ethyl, n-propyl, iso-propyl, n-butyl, iso-butyl, sec-butyl, tert-butyl, n-pentyl or a branched pentyl. In other embodiments, $R^{A5}$ can be an unsubstituted $C_{3-6}$ cycloalkyl. In other embodiments, $R^{A5}$ can be a substituted monocyclic $C_3$-6 cycloalkyl substituted with one or more (for example, 1, 2 or 3) hydroxy groups. The cycloalkyl for $R^{A5}$ can be cyclopropyl, cyclobutyl, cyclopentyl or cyclohexyl.

In another embodiment, $R^2$ in Formula (I) can be

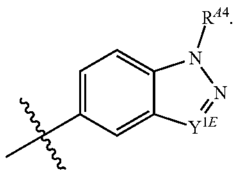

In various embodiments, $Y^{1E}$ can be CH. In other various embodiments, $Y^{1E}$ can be N (nitrogen). In some embodiments, $R^{A4}$ can be an unsubstituted or a substituted $C_{1-5}$ alkyl. In other embodiments, $R^{A4}$ can be an unsubstituted $C_{1-5}$ haloalkyl. In still other embodiments, $R^{A4}$ can be an unsubstituted or a substituted monocyclic $C_{3-6}$ cycloalkyl. For example, $R^{A4}$ can be selected from methyl, ethyl, n-propyl, iso-propyl, n-butyl, iso-butyl, sec-butyl, tert-butyl, n-pentyl, a branched pentyl, —$CF_3$, —$CCl_3$, —$CHF_2$, —$C(CH_3)F_2$, —$CHCl_2$, —$CH_2F$, —$CH(CH_3)F$, —$CH_2CH_2F$, —$CH_2CHF_2$, —$CH_2CF_3$, —$CH_2Cl$, —$CH_2CH_2F$, —$CH_2CH_2Cl$, —$CH_2CH_2CH_2F$, —$CH_2CH_2CH_2Cl$, cyclopropyl, cyclobutyl, cyclopentyl and cyclohexyl. Possible substitutions that can be present on a substituted monocyclic $C_{3-6}$ cycloalkyl include halogen, hydroxy, an unsubstituted $C_{1-6}$ alkyl and an unsubstituted $C_{1-6}$ haloalkyl, and possible substitutions that can be present on a substituted $C_{1-5}$ alkyl include halogen, hydroxy and an unsubstituted $C_{1-6}$ haloalkyl.

In another embodiment, $R^2$ in Formula (I) can be

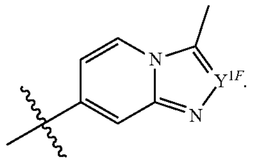

In some embodiments, $Y^{1F}$ can be CH. In other embodiments, $Y^{1F}$ can be N (nitrogen).

In another embodiment, $R^2$ in Formula (I) can be

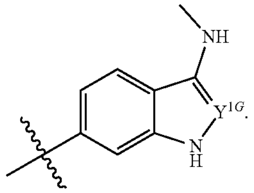

In some embodiments, Formula (I) can be

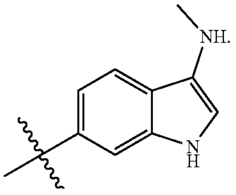 [SMILES: *c1ccc2c(NC)c[nH]c2c1]

In other embodiments, $R^2$ in Formula (I) can be

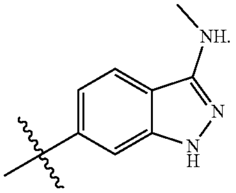 [SMILES: *c1ccc2c(NC)n[nH]c2c1]

In another embodiment, $R^2$ in Formula (I) can be

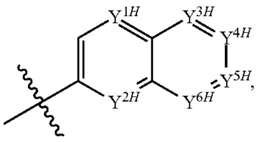

wherein $Y^{1H}$, $Y^{2H}$, $Y^{3H}$, $Y^{4H}$, $Y^{5H}$ and $Y^{6H}$ are each independently CH, C-(halogen) or N (nitrogen). In some embodiments, one of $Y^{1H}$ and $Y^{2H}$ can be N. In other embodiments, each of $Y^{1H}$ and $Y^{2H}$ can be N. In some embodiments, including those of this paragraph, one of $Y^{3H}$, $Y^{4H}$, $Y^{5H}$, and $Y^{6H}$ can be N. In other embodiments, including those of this paragraph, two of $Y^{3H}$, $Y^{4H}$, $Y^{5H}$, and $Y^{6H}$ can be N. In still other embodiments, including those of this paragraph, three or four of $Y^3$H, $Y^{4H}$, $Y^{5H}$ and $Y^{6H}$ can be N. Examples of

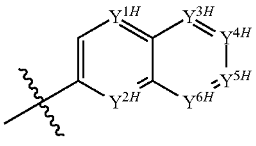

include

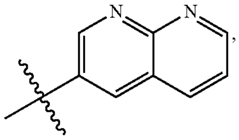, 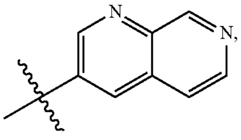,

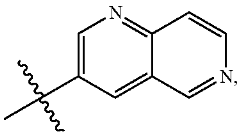, 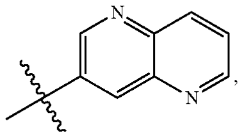,

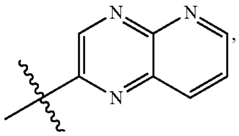, 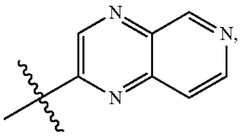,

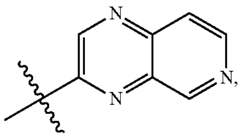, 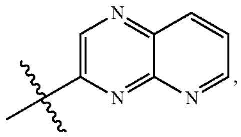,

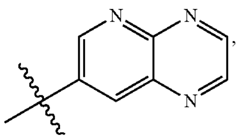, 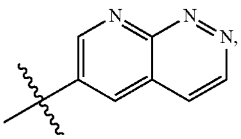,

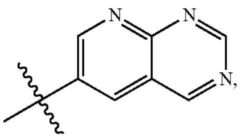, 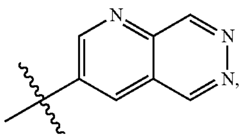,

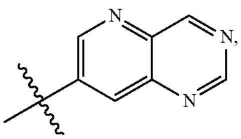, 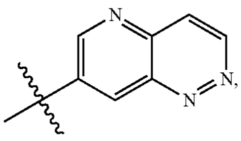,

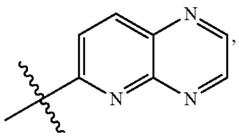, 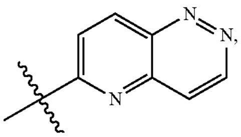,

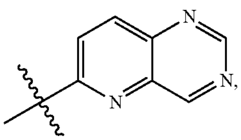, 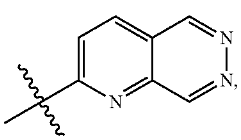,

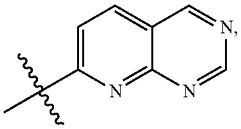, 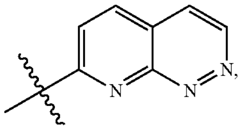,

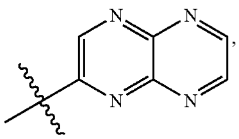, 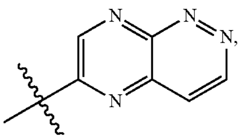,

-continued

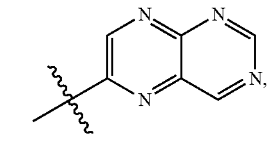

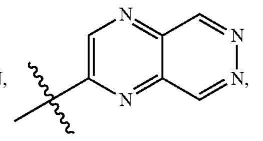

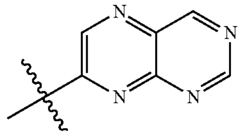

and

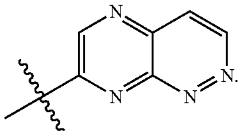

In another embodiment, $R^2$ in Formula (I) can be

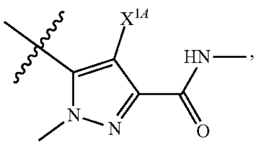

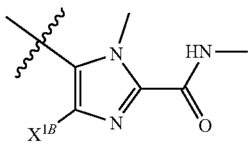

or

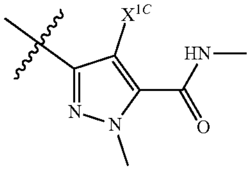

where $X^{1A}$, $X^{1B}$ and $X^{1c}$ can be independently selected from hydrogen, halogen (F, Cl and Br), an unsubstituted $C_{1-5}$ alkyl (such as methyl, ethyl, n-propyl, iso-propyl, n-butyl, iso-butyl, tert-butyl, n-pentyl (straight and branched version) and an unsubstituted $C_{1-5}$ haloalkyl ($-CF_3$, $-CCl_3$, $-CHF_2$, $-C(CH_3)F_2$, $-CHCl_2$, $-CH_2F$, $-CH(CH_3)F$, $-CH_2CH_2F$, $-CH_2CHF_2$, $-CH_2CF_3$, $-CH_2Cl$, $-CH_2CH_2F$, $-CH_2CH_2Cl$, $-CH_2CH_2CH_2F$, $-CH_2CH_2CH_2Cl$). In some embodiments, $R^2$ can be

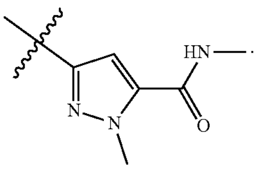 [SMILES: *c1cc(C(=O)NC)n(C)n1]

In another embodiment, $R^2$ in Formula (I) can be

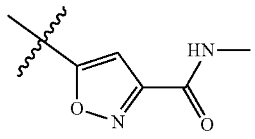

or

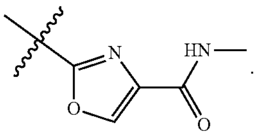

In another embodiment, $R^2$ in Formula (I) can be

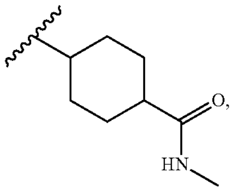

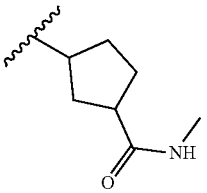

or

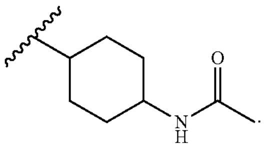

In another embodiment, $R^2$ in Formula (I) can be

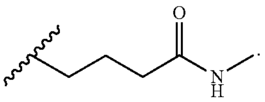 [SMILES: *CCCC(=O)NC]

In some embodiments, $R^2$ can be

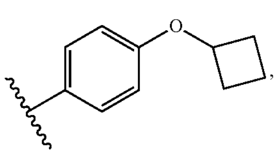

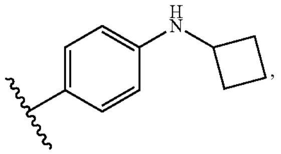

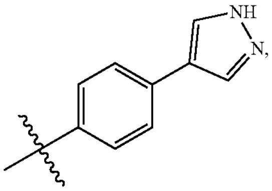

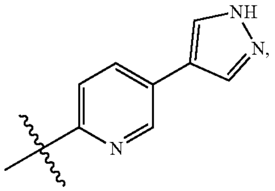

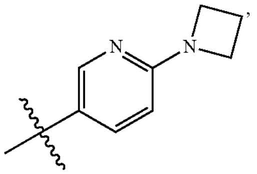

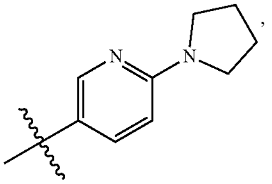

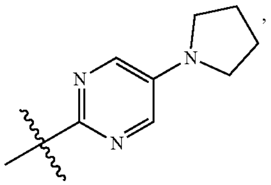

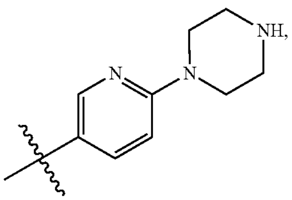

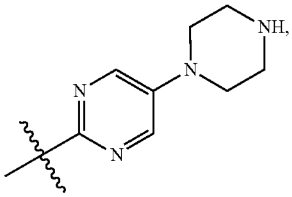

-continued

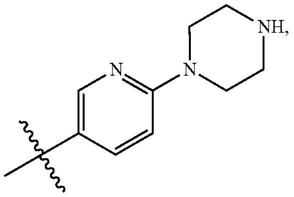

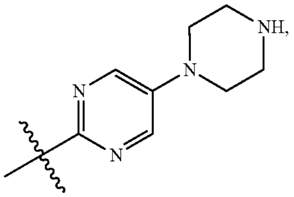

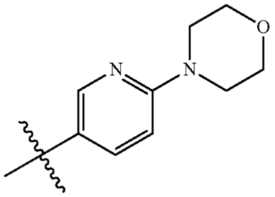

or

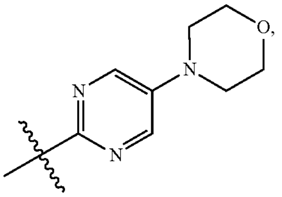 [SMILES: *c1ncc(N2CCOCC2)cn1]

wherein each can be optionally substituted with one or more moieties (1, 2 or 3 moieties) independently selected from halogen, hydroxy, amino, an unsubstituted $C_{1-6}$ alkyl and an unsubstituted $C_{1-6}$ haloalkyl. In some embodiments, a hydrogen on a carbon can be replaced with halogen, hydroxy, amino, an unsubstituted $C_{1-6}$ alkyl or an unsubstituted $C_{1-6}$ haloalkyl, and/or the hydrogen of a NH group can be replaced with an unsubstituted $C_{1-6}$ alkyl or an unsubstituted $C_{1-6}$ haloalkyl. Suitable halogens, unsubstituted $C_{1-6}$ alkyl and $C_{1-6}$ haloalkyls are provided herein and include F, Cl, methyl, ethyl, n-propyl, iso-propyl, n-butyl, iso-butyl, sec-butyl, tert-butyl, pentyl (straight-chained or branched), hexyl (straight-chained or branched), $-CF_3$, $-CCl_3$, $-CHF_2$, $-C(CH_3)F_2$, $-CHCl_2$, $-CH_2F$, $-CH(CH_3)F$, $-CH_2CH_2F$, $-CH_2CHF_2$, $-CH_2CF_3$, $-CH_2Cl$, $-CH_2CH_2F$, $-CH_2CH_2Cl$, $-CH_2CH_2CH_2F$, $-CH_2CH_2CH_2Cl$.

Exemplary R groups include

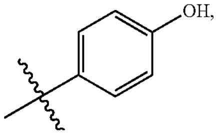

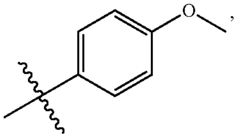

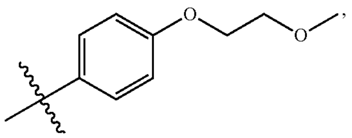

-continued

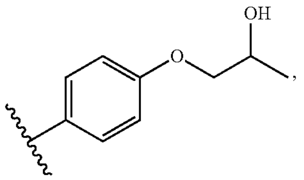

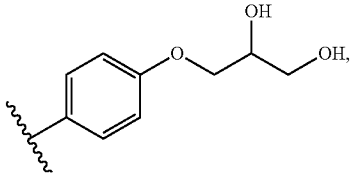

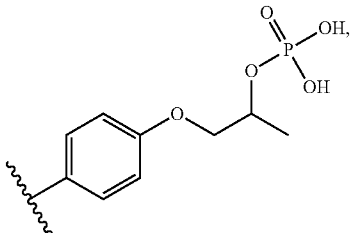

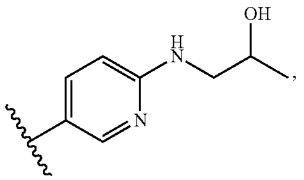

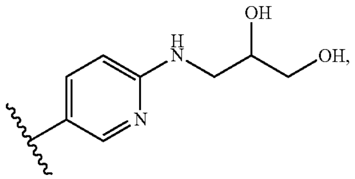

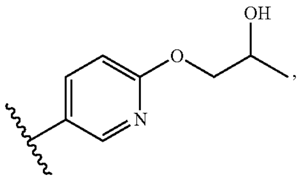

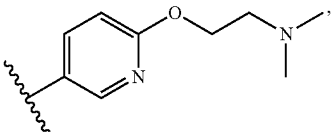

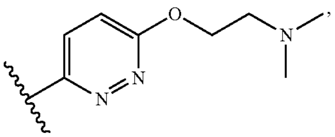

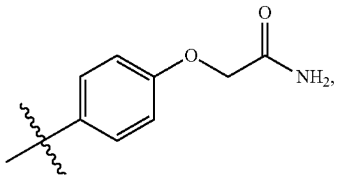

-continued
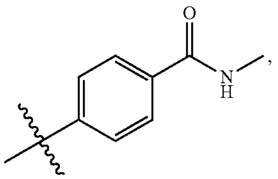
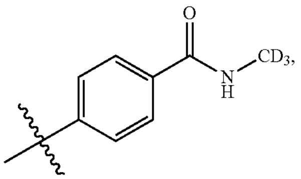
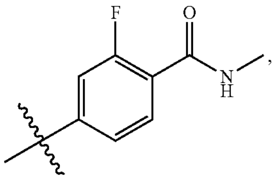
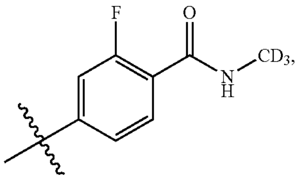
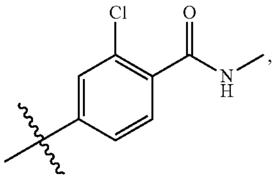
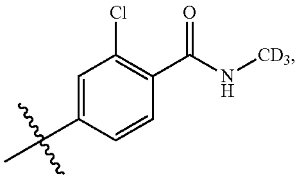
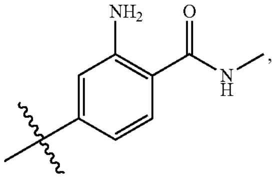
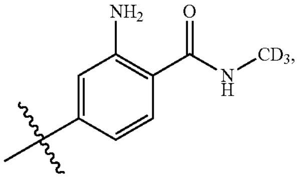
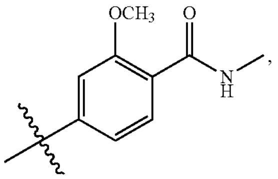
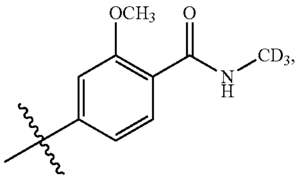
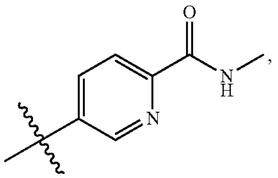
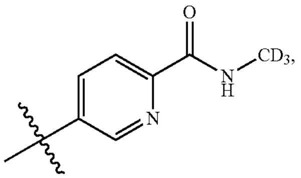
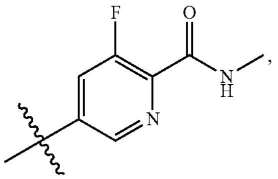
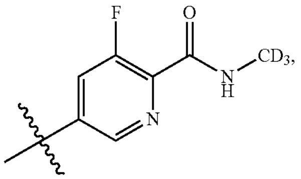
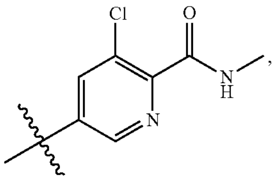
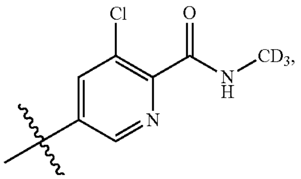
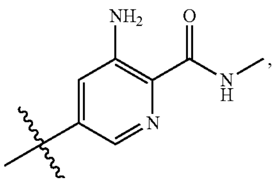
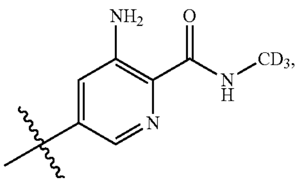
-continued
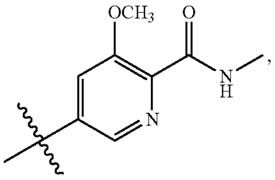
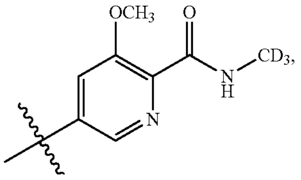
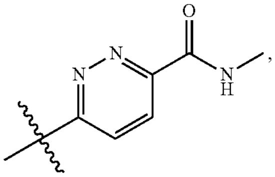
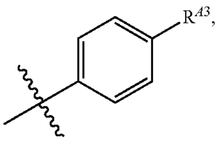
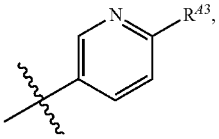
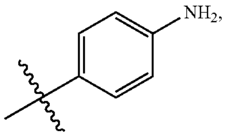
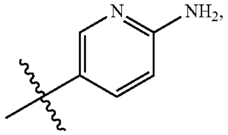
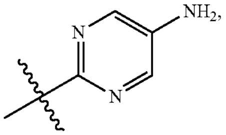
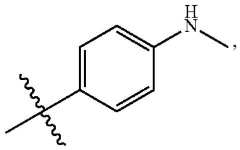
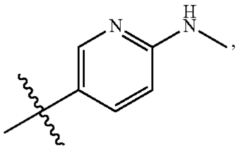
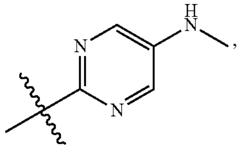
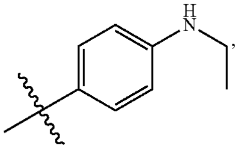
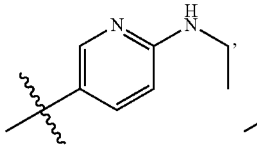
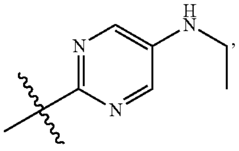
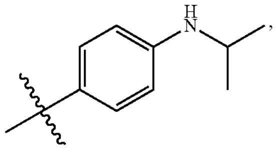
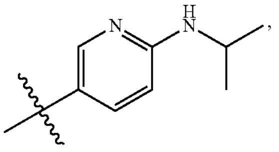
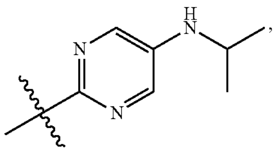
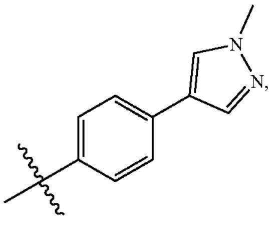
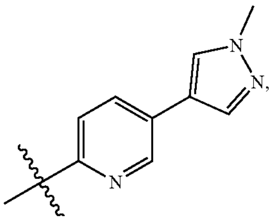
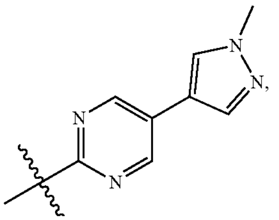

-continued
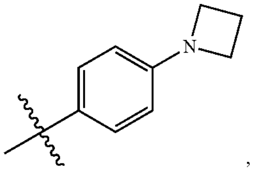,
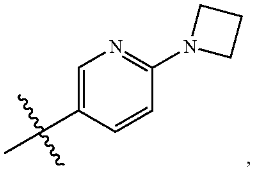,
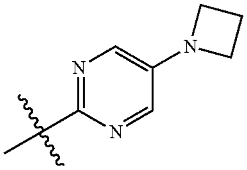,
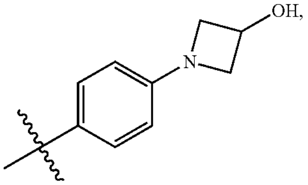,
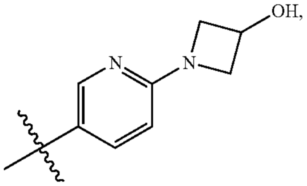,
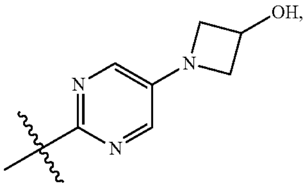,
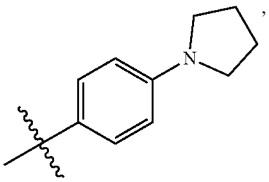,
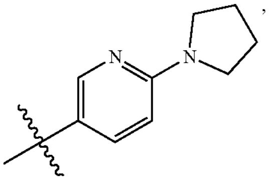,
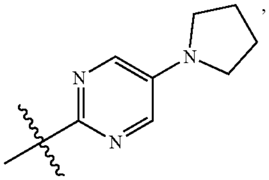,
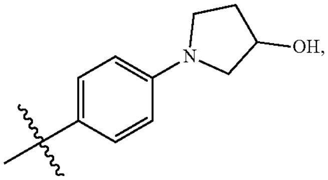,
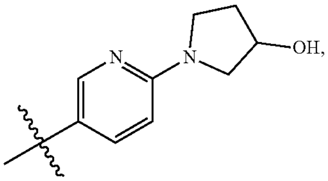,
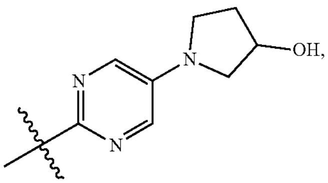,
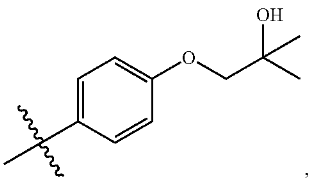,
-continued
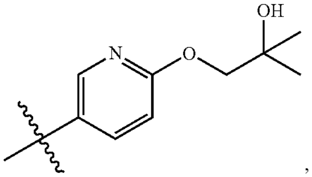,
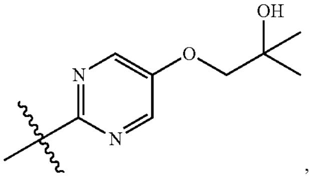,
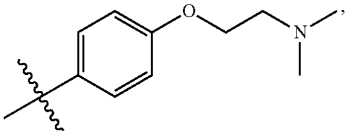,
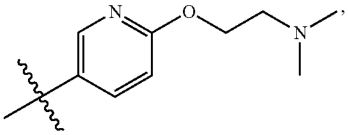,
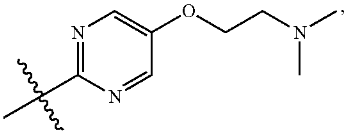,
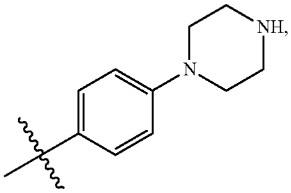,
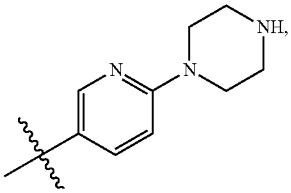,
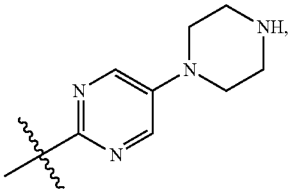,
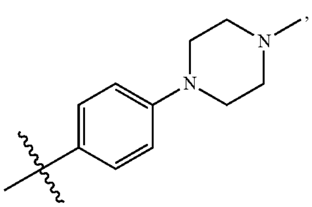, -continued
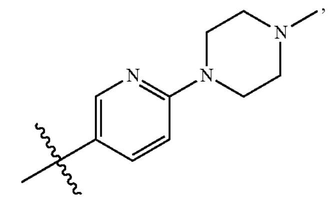
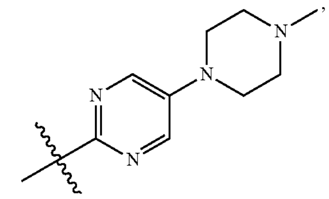
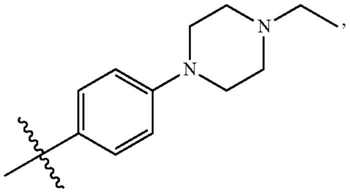
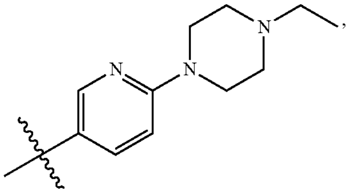
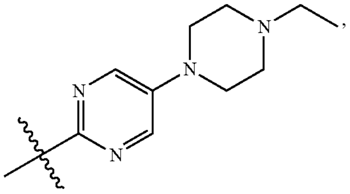
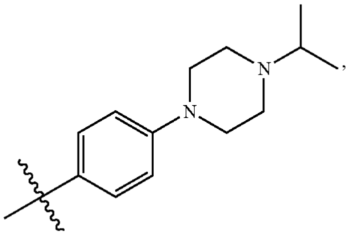
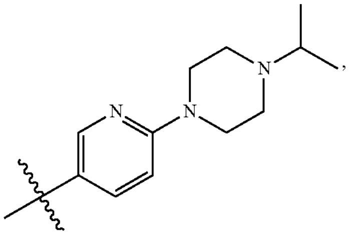
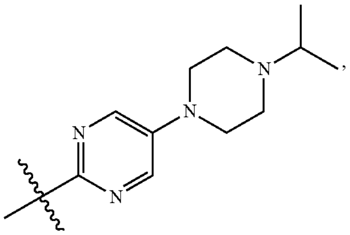
-continued
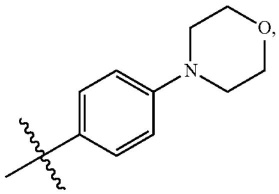
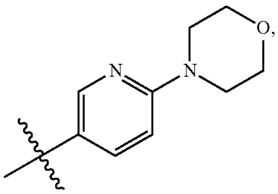
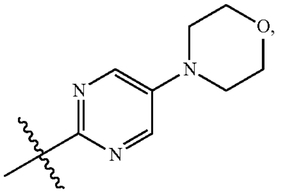
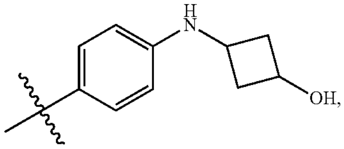
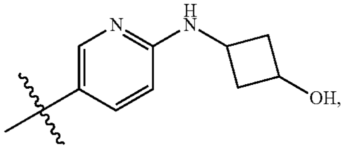
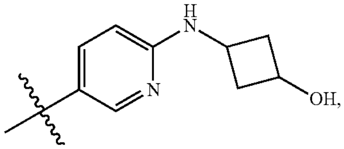
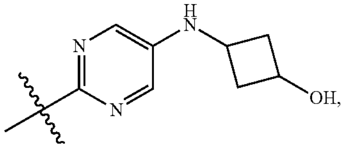
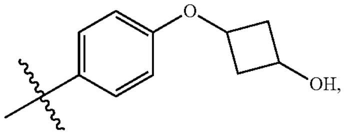
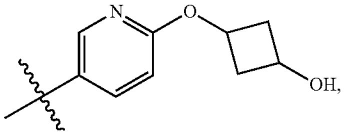
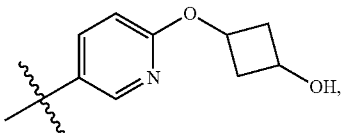
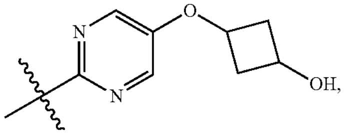
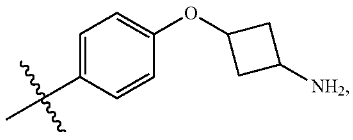

-continued
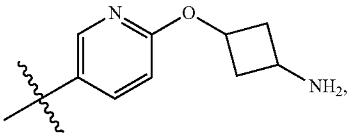
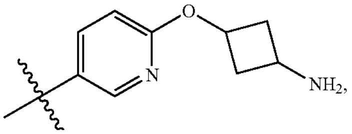
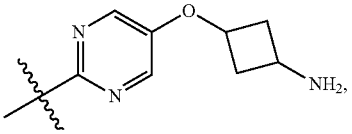
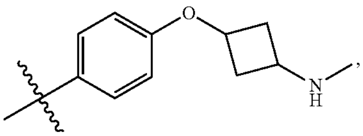
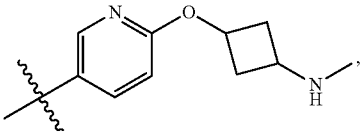
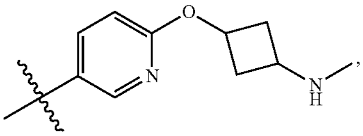
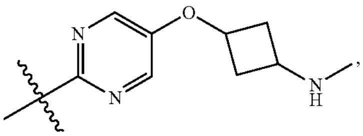
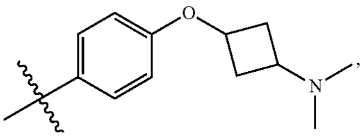
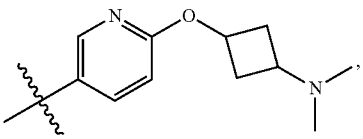
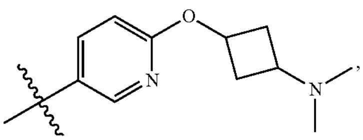
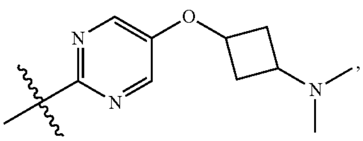
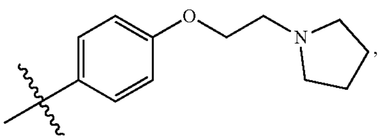
-continued
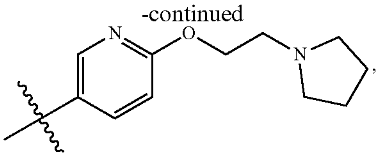
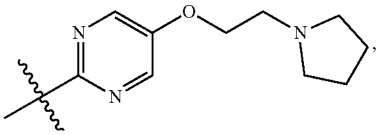
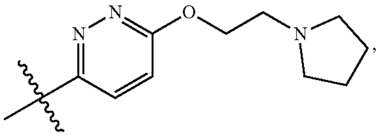
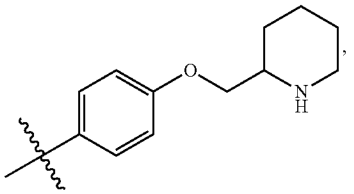
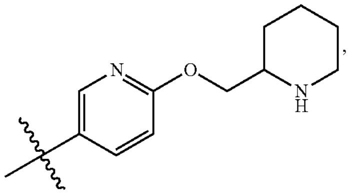
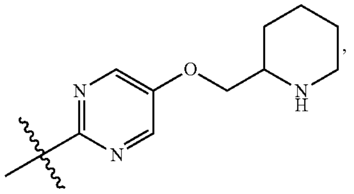
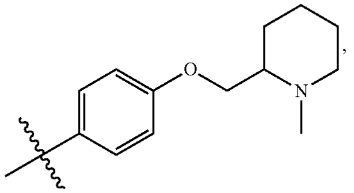
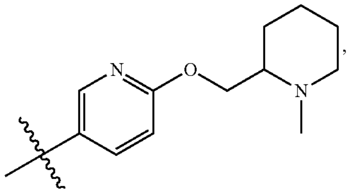
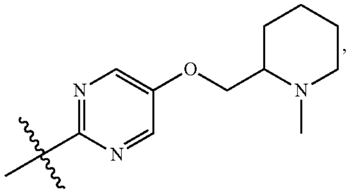
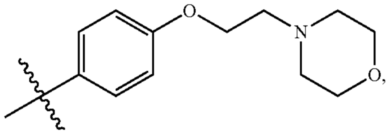

-continued
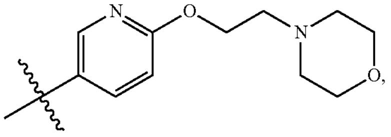
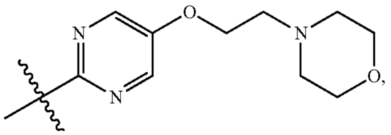
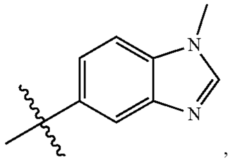, 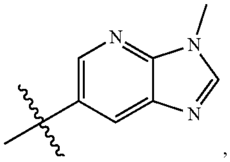,
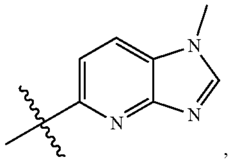, 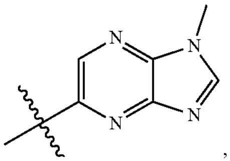,
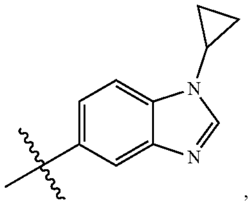, 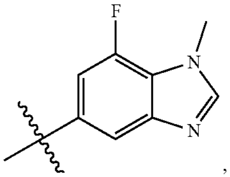,
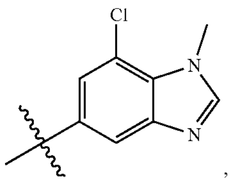, 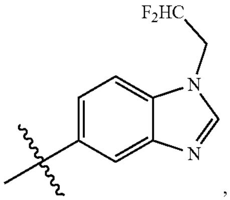,
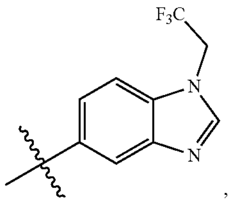, 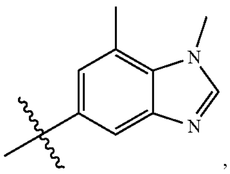,
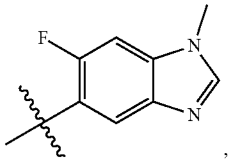, 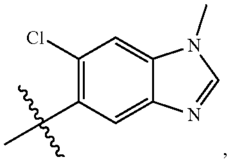,
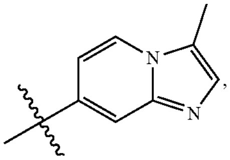 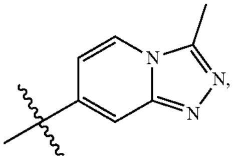
-continued
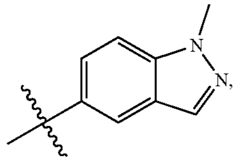 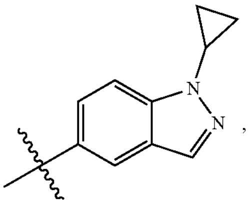,
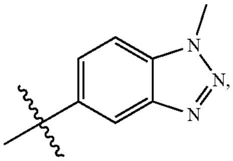 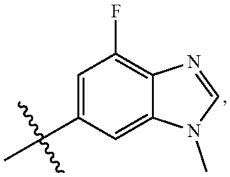
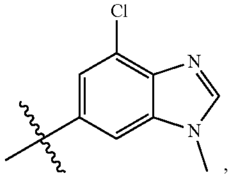, 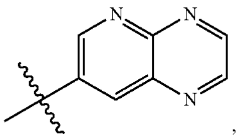,
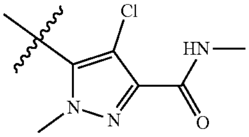, 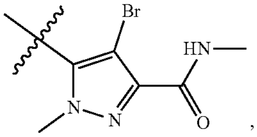,
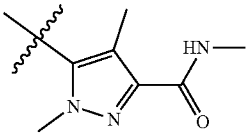, 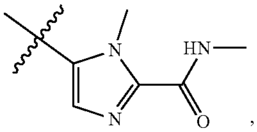,
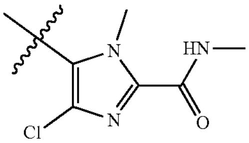, 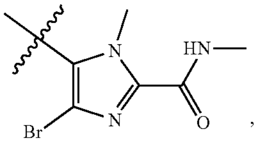,
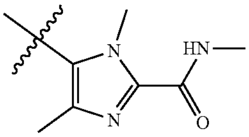, 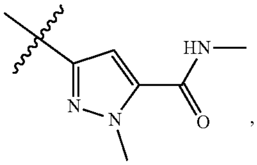,
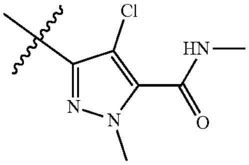, 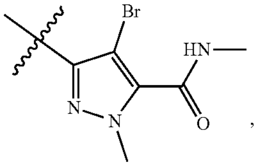,
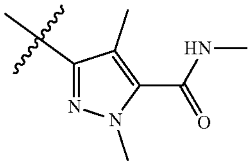 and 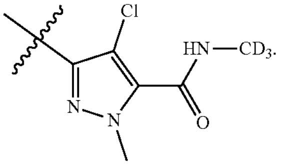
In some embodiments, a compound of Formula (I), or a pharmaceutically acceptable salt thereof, can be where $R^1$ can be selected from

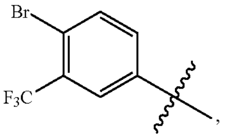 [SMILES: *c1ccc(Br)c(C(F)(F)F)c1]

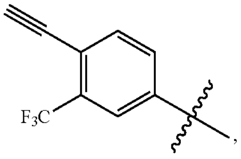

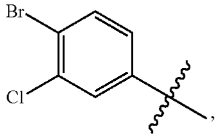

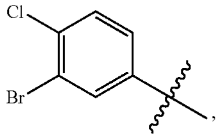

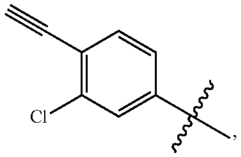

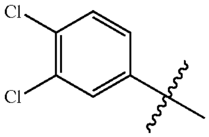

and

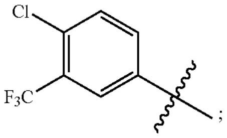

$R^2$ can be selected from

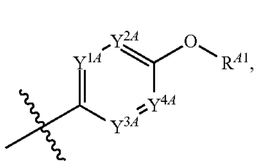

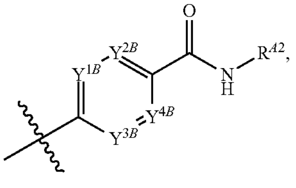

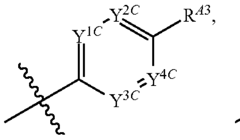

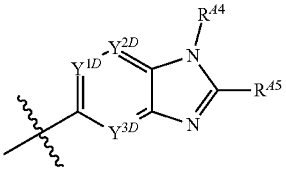

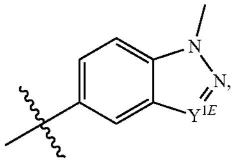

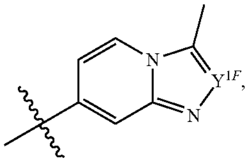

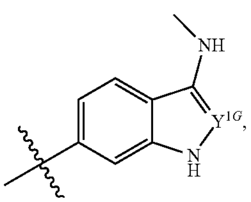

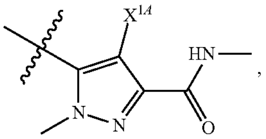

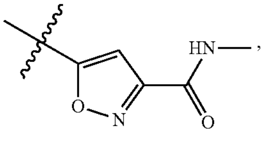

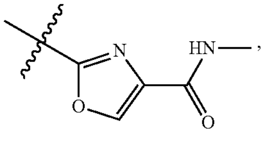

-continued

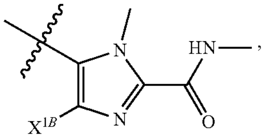

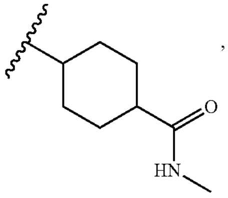

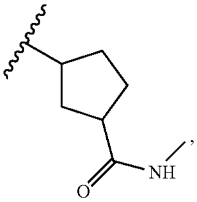

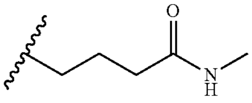

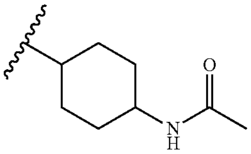

and

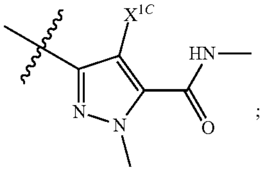

$X^{1A}$, $X^{1B}$ and $X^{1C}$ can be independently selected from hydrogen, halogen, an unsubstituted $C_{1-5}$ alkyl and an unsubstituted $C_{1-5}$ haloalkyl; $Y^{1A}$ can be CH, C—$CHF_2$, C—F, C—Cl or N; $Y^{2A}$ can be CH, C-halogen, C—$OCH_3$ or N; $Y^{3A}$ can be CH or N; $Y^{4A}$ can be CH or N; $Y^{1B}$ can be CH, C—$CHF_2$, C—F, C—Cl or N (nitrogen); $Y^{2B}$ can be CH, C-halogen, C—$OCH_3$ or N (nitrogen); $Y^{3B}$ can be CH or N (nitrogen); $Y^{4B}$ can be CH or N (nitrogen); $Y^{1C}$, $Y^{2C}$, $Y^{3C}$ and $Y^{4C}$ can be each independently CH, C-(halogen) or N (nitrogen); $Y^{1D}$ can be CH, C—$CH_3$, C—$OCH_3$, C-(halogen), C—$CHF_2$, C—$CF_3$ or N (nitrogen); $Y^{2D}$ can be CH, C—$CH_3$, C—$OCH_3$, C-(halogen), C—$CHF_2$, C—$CF_3$ or N (nitrogen); $Y^{3D}$ can be CH or N (nitrogen); $Y^{1E}$, $Y^{1F}$ and $Y^{1G}$ can be each independently CH, C-(halogen) or N (nitrogen); $R^{A1}$ can be an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy and an unsubstituted $C_{1-5}$ alkoxy; $R^{A2}$ can be —$CH_3$ or -$CD_3$; $R^{A3}$ can be an unsubstituted or a substituted 5-membered-monocyclic heteroaryl or an unsubstituted or a substituted 5-membered-monocyclic heterocyclyl; $R^{A4}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(═O)OH and —C(═O)$NH_2$; and $R^{A5}$ can be selected from hydrogen, halogen, —CN, —OH, —$NH_2$, —C(═O)OH, —CH═$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

In some embodiments, a compound of Formula (I), or a pharmaceutically acceptable salt thereof, can be where $R^1$ can be selected from

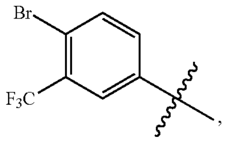
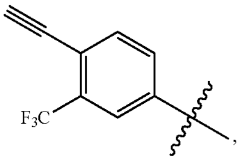
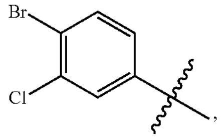
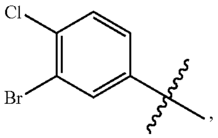
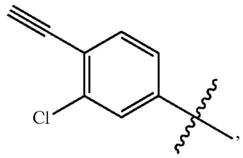
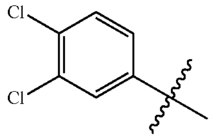
and
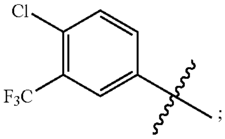

$R^2$ can be selected from

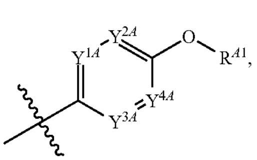
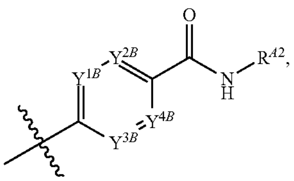
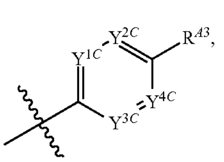
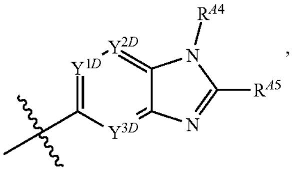
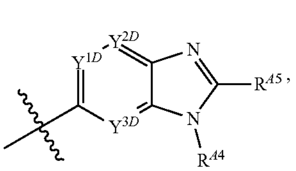
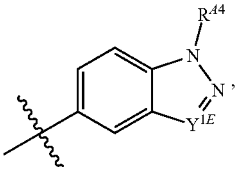
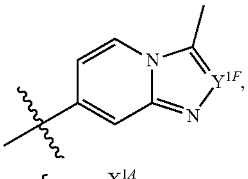
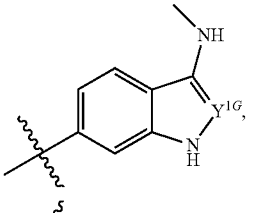
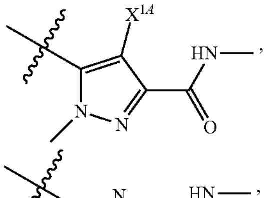
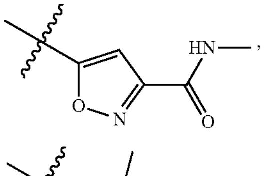
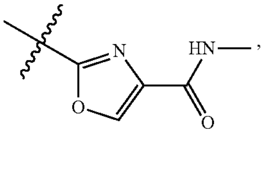
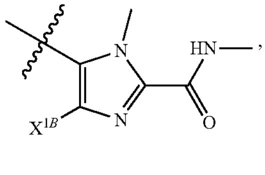

-continued

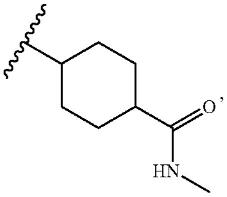
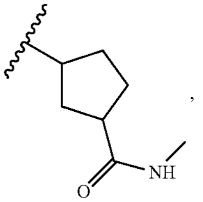
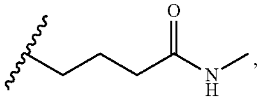
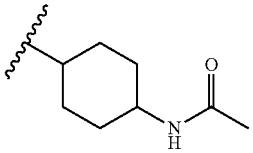
and
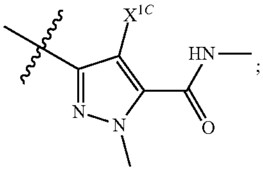

$X^{1A}$, $X^{1B}$ and $X^{1C}$ can be independently selected from hydrogen, halogen, an unsubstituted $C_{1-5}$ alkyl and an unsubstituted $C_{1-5}$ haloalkyl; $Y^{1A}$ can be CH, C—$CHF_2$, C—F, C—Cl, $C(NH_2)$, C(NH(unsubstituted $C_{1-5}$ alkyl)), C(N(unsubstituted $C_{1-5}$ alkyl)$_2$) or N; $Y^{2A}$ can be CH, C-halogen, C—$OCH_3$, $C(NH_2)$, C(NH(unsubstituted $C_{1-5}$ alkyl)), C(N(unsubstituted $C_{1-5}$ alkyl)$_2$) or N; $Y^{3A}$ can be CH or N; $Y^{4A}$ can be CH or N; $Y^{1B}$ can be CH, C—$CHF_2$, C—F, C—Cl, $C(NH_2)$, C(NH(unsubstituted $C_{1-5}$ alkyl)), C(N(unsubstituted $C_{1-5}$ alkyl)$_2$) or N; $Y^{2B}$ can be CH, C-halogen, C—$OCH_3$, $C(NH_2)$, C(NH(unsubstituted $C_{1-5}$ alkyl)), C(N(unsubstituted $C_{1-5}$ alkyl)$_2$) or N; $Y^{3B}$ can be CH or N; $Y^{4B}$ can be CH or N; $Y^{1C}$, $Y^{2C}$, $Y^{3C}$ and $Y^{4C}$ can be each independently CH, C-(halogen) or N; $Y^{1D}$ can be CH, C—$CH_3$, C—$OCH_3$, C-(halogen), C—$CHF_2$, C—$CF_3$ or N; $Y^{2D}$ can be CH, C—$CH_3$, C—$OCH_3$, C-(halogen), C—$CHF_2$, C—$CF_3$ or N; $Y^{3D}$ can be CH, C-(halogen) or N; $Y^{1E}$, $Y^{1F}$ and $Y^{1G}$ can be each independently CH, C-(halogen) or N; $R^{A1}$ can be an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, an unsubstituted $C_{1-5}$ alkoxy, —C(=O)$NH_2$ and —O—P(=O)$(OH)_2$; $R^{A2}$ can be —$CH_3$ or -$CD_3$; $R^{A3}$ can be —NH(an unsubstituted or a substituted $C_{1-5}$ alkyl), —N(an unsubstituted or a substituted $C_{1-5}$ alkyl)$_2$, an unsubstituted or a substituted 5-membered-monocyclic heteroaryl or an unsubstituted or a substituted 4 to 6-membered-monocyclic heterocyclyl; $R^{A4}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(=O)OH and —C(=O)$NH_2$; and $R^{A5}$ can be selected from hydrogen, halogen, —CN, —OH, —$NH_2$, —C(=O)OH, —CH=$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

In some embodiments, a compound of Formula (I), or a pharmaceutically acceptable salt thereof, can be where $R^1$ can be

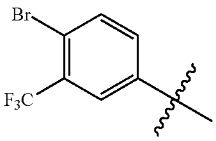
;

$R^2$ can be

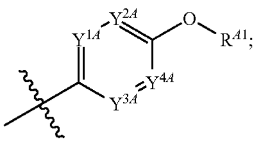
;

$Y^{1A}$ can be CH or N; $Y^{2A}$ can be CH or N; $Y^{3A}$ is CH or N; $Y^{4A}$ is CH or N; and $R^{A1}$ can be a substituted $C_{1-5}$ alkyl or a substituted monocyclic $C_{3-6}$ cycloalkyl. In some embodiments of this paragraph, $Y^{1A}$ can be CH; $Y^{2A}$ can be CH; $Y^{3A}$ is CH; and $Y^{4A}$ is CH. In other embodiments of this paragraph, $Y^{1A}$ can be CH; $Y^{2A}$ can be N; $Y^{3A}$ is CH; and $Y^{4A}$ is CH. In still other embodiments of this paragraph, $Y^{1A}$ can be N; $Y^{2A}$ can be CH; $Y^{3A}$ is N; and $Y^{4A}$ is CH. In some embodiments of this paragraph, $R^{A1}$ can be a substituted $C_{1-5}$ alkyl. In some embodiments of this paragraph, $R^{A1}$ can be a $C_{1-5}$ alkyl substituted with hydroxy —N(an unsubstituted $C_{1-5}$ alkyl)$_2$, —C(═O)$NH_2$, —O—P(═O)$(OH)_2$, an unsubstituted 5- or 6-membered monocyclic heterocyclyl or 5- or 6-membered monocyclic heterocyclyl substituted by one or more unsubstituted $C_{1-4}$ alkyl groups. In some embodiments of this paragraph, $R^{A1}$ can be a $C_{1-5}$ alkyl substituted with hydroxy, such as —$CH_2CH_2OH$, —$CH_2CH(CH_3)OH$ and —$CH_2CH(OH)CH_2(OH)$. In some embodiments of this paragraph, $R^{A1}$ can be a monocyclic $C_{3-6}$ cycloalkyl. In other embodiments of this paragraph, $R^{A1}$ can be a substituted monocyclic $C_{3-6}$ cycloalkyl (such as cyclobutyl) substituted with hydroxy, —$NH_2$ or —N(an unsubstituted $C_{1-5}$ alkyl)$_2$.

In some embodiments, a compound of Formula (I), or a pharmaceutically acceptable salt thereof, can be where $R^1$ can be

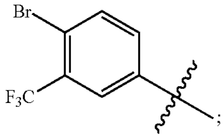
;

$R^2$ can be

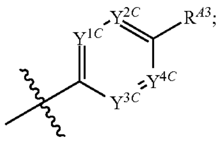
;

and $R^{A3}$ can be $R^{A3}$ is —$NH_2$, —NH(an unsubstituted or a substituted $C_{1-5}$ alkyl), —NH(an unsubstituted or a substituted $C_{3-6}$ monocyclic cycloalkyl), an unsubstituted or a substituted 5-membered-monocyclic heteroaryl or an unsubstituted or a substituted 4 to 6-membered-monocyclic heterocyclyl. In some embodiments of this paragraph, $R^{A3}$ can be —$NH_2$. In other embodiments of this paragraph, $R^{A3}$ can be —NH(an unsubstituted $C_{1-5}$ alkyl). In still other embodiments of this paragraph, $R^{A3}$ can be —NH(a hydroxy-substituted $C_{1-5}$ alkyl), for example, $R^{A3}$ can be —NH(a substituted $C_{1-5}$ alkyl). In yet still other embodiments of this paragraph, $R^{A3}$ can be —NH(an unsubstituted $C_{3-6}$ monocyclic cycloalkyl). In some embodiments of this paragraph, $R^{A3}$ can be —NH(a substituted $C_{3-6}$ monocyclic cycloalkyl), such as —NH(a hydroxy-substituted $C_{3-6}$ monocyclic cycloalkyl). In other embodiments of this paragraph, $R^{A3}$ can be an unsubstituted or a substituted 5-membered-monocyclic heteroaryl. For example, $R^{A3}$ can be 5-membered-monocyclic heteroaryl substituted with an unsubstituted $C_{1-4}$ alkyl. In still other embodiments of this paragraph, $R^{A3}$ can be an unsubstituted 4 to 6-membered-monocyclic heterocyclyl. In yet still other embodiments of this paragraph, $R^{A3}$ can be a substituted 4 to 6-membered-monocyclic heterocyclyl. In some embodiments of this paragraph, $R^{A3}$ can be a 4 to 6-membered-monocyclic heterocyclyl substituted by hydroxy and/or an unsubstituted $C_{1-4}$ alkyl.

In some embodiments, a compound of Formula (I), or a pharmaceutically acceptable salt thereof, can be where $R^1$ can be

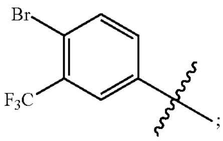
;

and $R^2$ can be

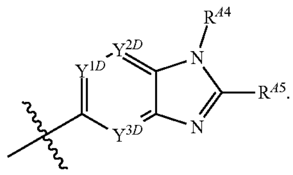
.

In some embodiments of this paragraph, $Y^{1D}$ can be CH or C-(halogen); $Y^{2D}$ can be CH, C-(halogen) or C—$CH_3$; and $Y^{3D}$ can be CH. In other embodiments of this paragraph, $Y^{1D}$ can be CH; $Y^{2D}$ can be CH; and $Y^{3D}$ can be N. In still other embodiments of this paragraph, $Y^{1D}$ can be CH; $Y^{2D}$ can be N; and $Y^{3D}$ can be CH. In yet still other embodiments of this paragraph, $Y^{1D}$ can be CH; $Y^{2D}$ can be N; and $Y^{3D}$ can be N. In some embodiments of this paragraph, $R^{A4}$ can be an unsubstituted $C_{1-5}$ alkyl. In other embodiments of this paragraph, $R^{A4}$ can be an unsubstituted $C_{1-5}$ haloalkyl. In some embodiments of this paragraph, $R^{A5}$ can be hydrogen.

In some embodiments, a compound of Formula (I), or a pharmaceutically acceptable salt thereof, can be where $R^1$ can be

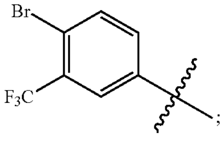 [SMILES: *c1ccc(Br)c(C(F)(F)F)c1]
;

and $R^2$ can be

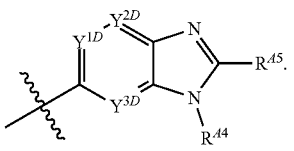

In some embodiments of this paragraph, $Y^{1D}$ can be CH or C-(halogen); $Y^{2D}$ can be CH, C-(halogen) or C—$CH_3$; and $Y^{3D}$ can be CH. In some embodiments of this paragraph, $Y^{1D}$ can be CH; $Y^{2D}$ can be CH, C-(halogen) or C—$CH_3$; and $Y^{3D}$ can be CH. In some embodiments of this paragraph, $Y^{1D}$ can be CH; $Y^{2D}$ can b C-(halogen); and $Y^{3D}$ can be CH.

In some embodiments, a compound of Formula (I), or a pharmaceutically acceptable salt thereof, can be where $R^1$ can be

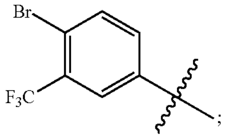

and $R^2$ can be

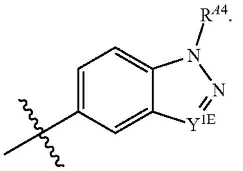

In some embodiments of this paragraph, $Y^{1E}$ can be CH. In some embodiments of this paragraph, $R^{A4}$ can be an unsubstituted $C_{1-5}$ alkyl.

In some embodiments, a compound of Formula (I), or a pharmaceutically acceptable salt thereof, can be where $R^1$ can be

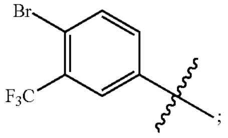

and $R^2$ can be

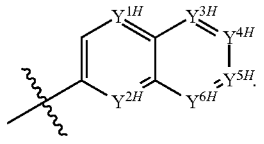

In some embodiments of this paragraph, $Y^{2H}$, $Y^{4H}$ and $Y^{5H}$ are each CH; and $Y^{1H}$, $Y^{3H}$ and $Y^{6H}$ can be each N.

In some embodiments, a compound of Formula (I), or a pharmaceutically acceptable salt thereof, can be where $R^1$ can be

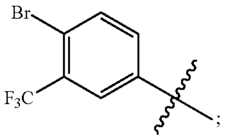

$R^2$ can be

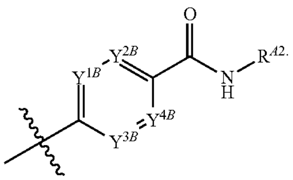

In some embodiments of this paragraph, $Y^{1B}$ can be CH or N; $Y^{2B}$ can be CH, C-halogen, C—($NH_2$) or N; $Y^{3B}$ can be CH; and $Y^{4B}$ can be CH or N. In some embodiments of this paragraph, $Y^{1B}$ can be CH; $Y^{2B}$ can be CH, C-halogen or C—($NH_2$); $Y^{3B}$ can be CH; and $Y^{4B}$ can be CH. In other embodiments of this paragraph, $Y^{1B}$ can be N; $Y^{2B}$ can be N; $Y^{3B}$ can be CH; and $Y^{4B}$ can be CH. In still other embodiments of this paragraph, $Y^{1B}$ can be CH; $Y^{2B}$ can be CH; $Y^{3B}$ can be CH; and $Y^{4B}$ can be N. In some embodiments of this paragraph, $R^{A2}$ can be —$CH_3$. In some embodiments of this paragraph, $R^{A2}$ can be —$CD_3$.

In some embodiments, a compound of Formula (I), or a pharmaceutically acceptable salt thereof, can be where $R^1$ can be

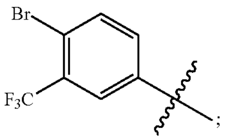 [SMILES: *c1ccc(Br)c(C(F)(F)F)c1]

and $R^2$ can be

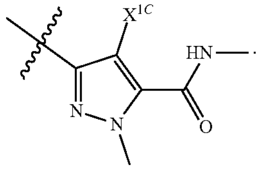

In some embodiments of this paragraph, $X^{1C}$ can be hydrogen. In other embodiments of this paragraph, $X^{1C}$ can be an unsubstituted $C_{1-5}$ alkyl.

Examples of compounds of Formula (I) include:
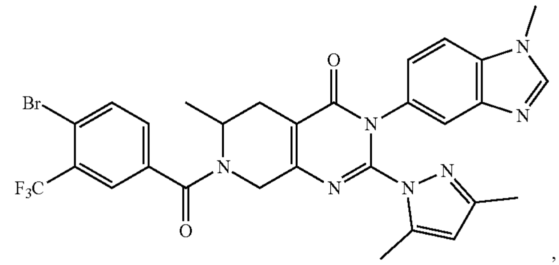
,
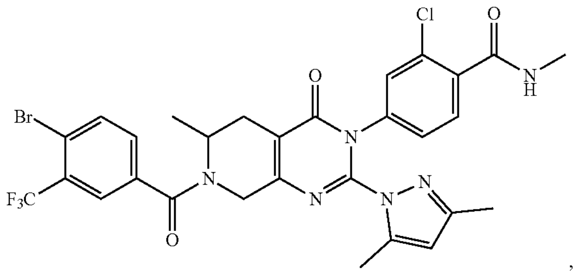
,
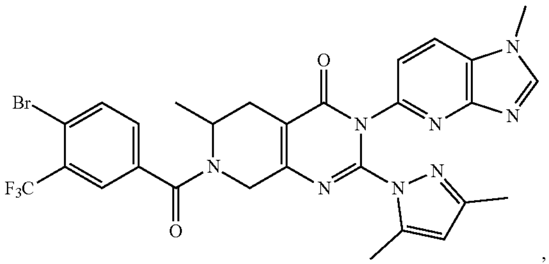
,
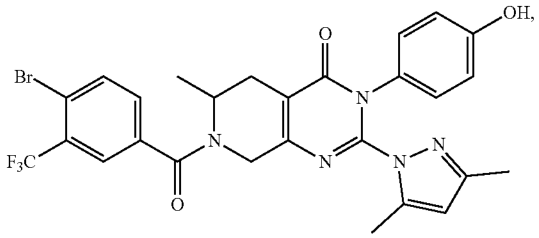
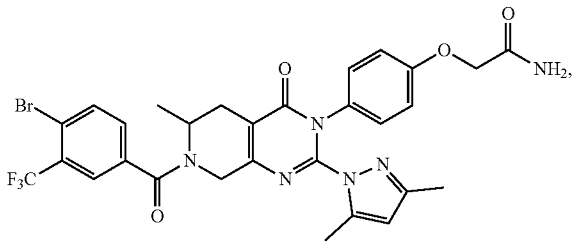
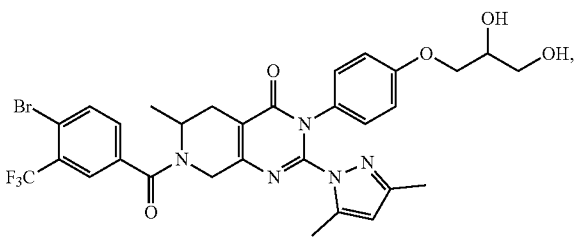
-continued
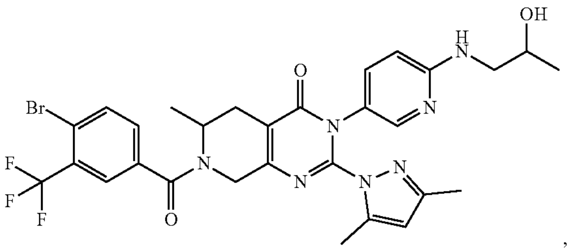
,
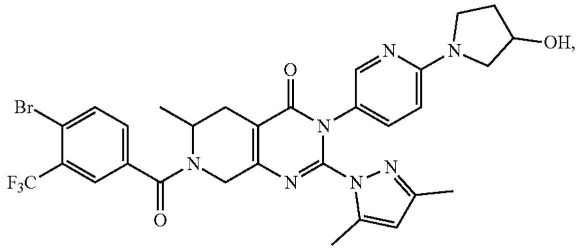
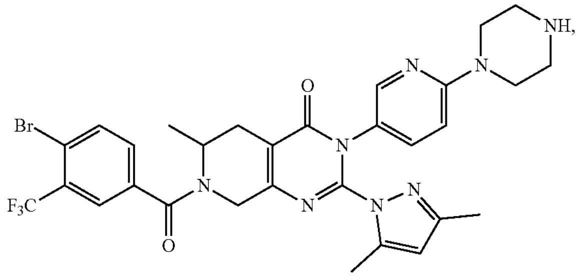
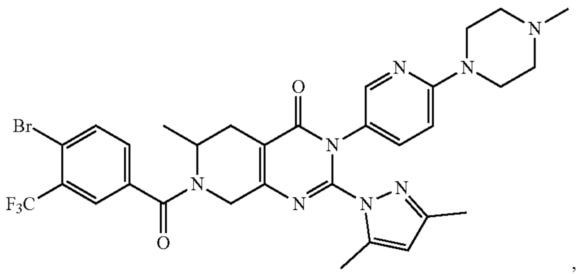
,
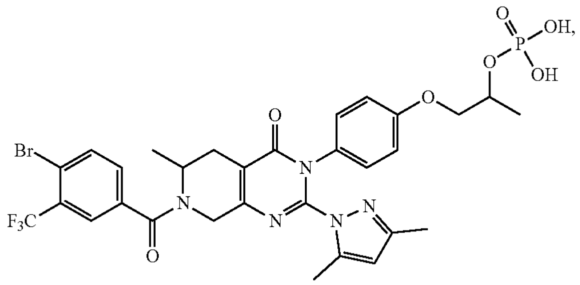
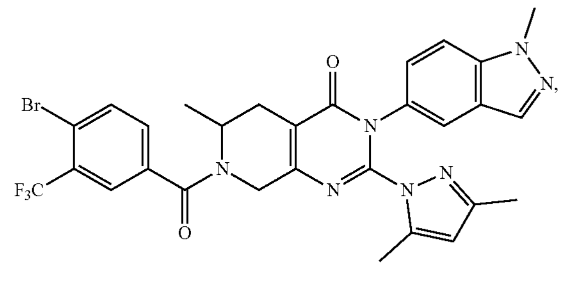

-continued
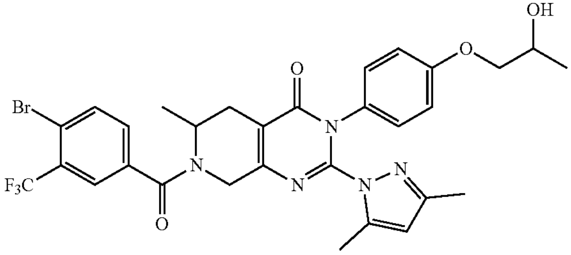
,
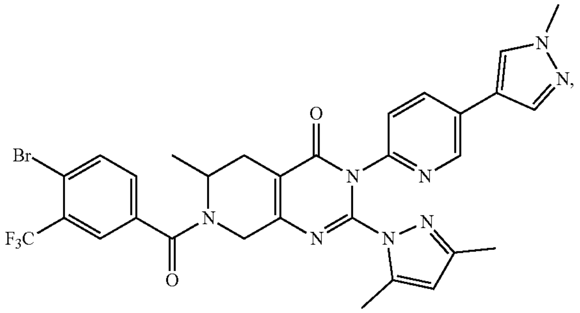
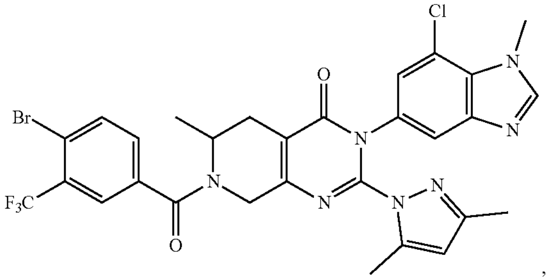
,
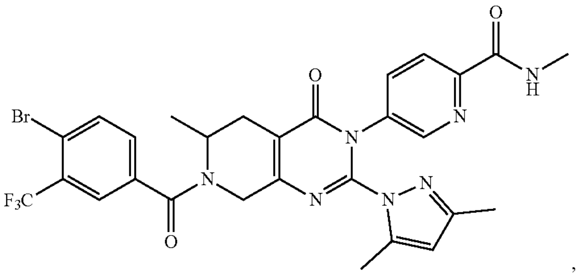
,
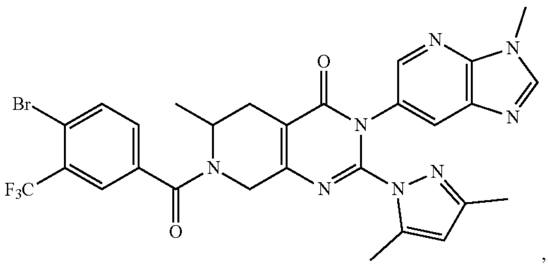
,
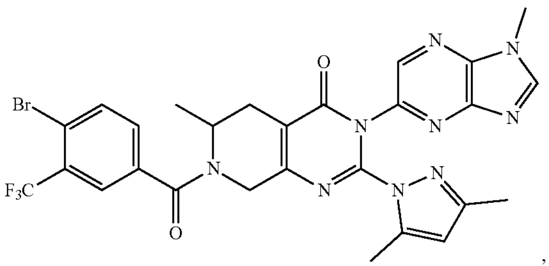
,
-continued
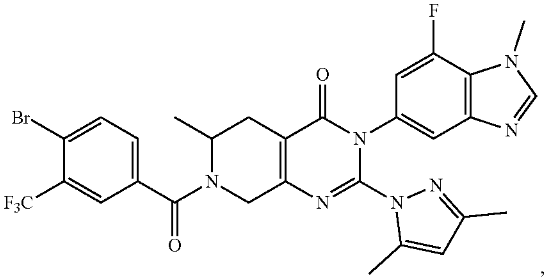
,
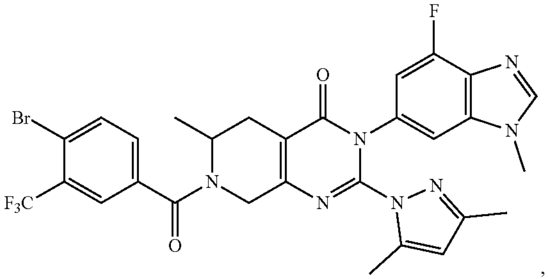
,
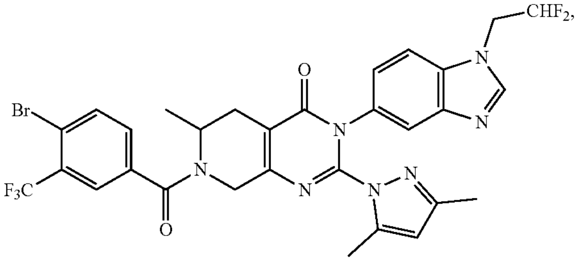
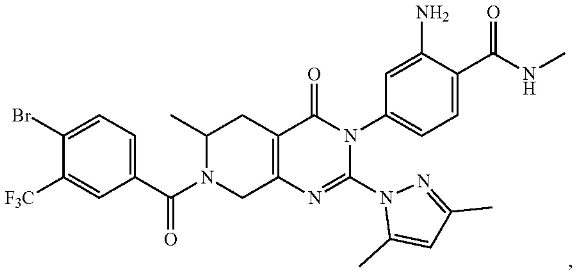
,
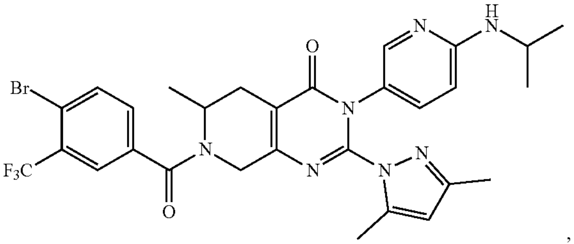
,
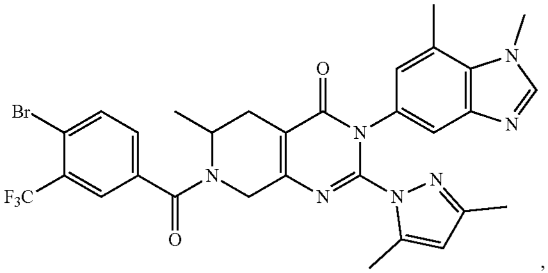
, -continued
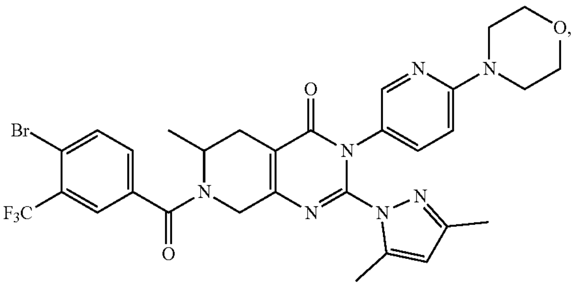
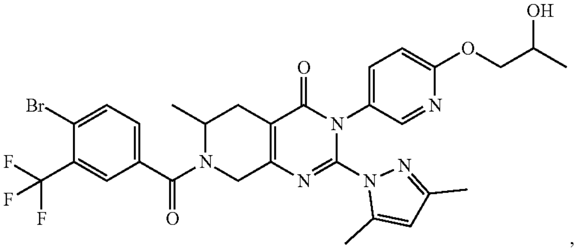
,
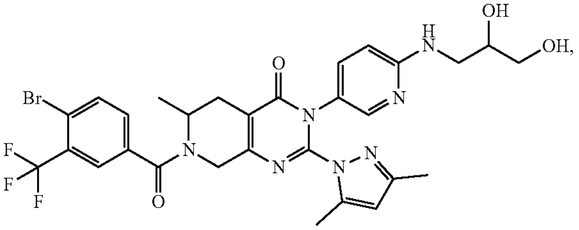
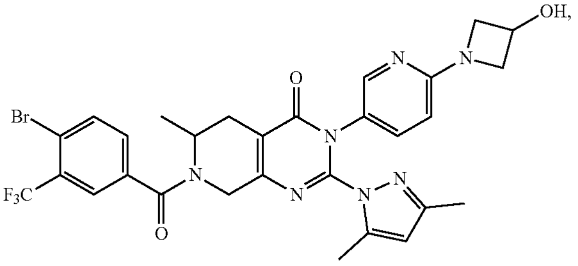
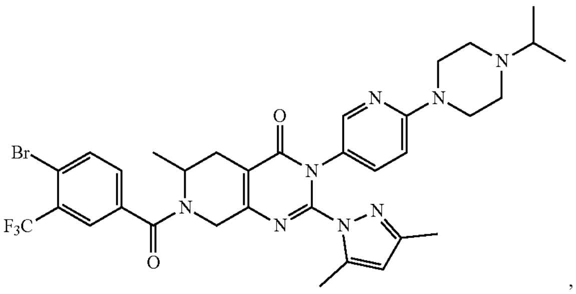
,
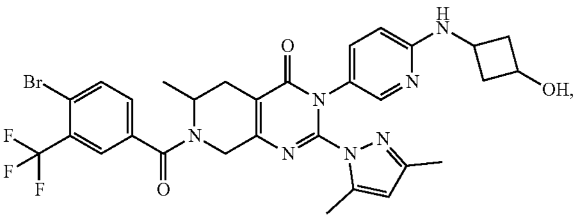
-continued
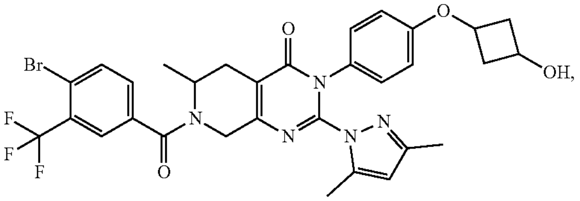
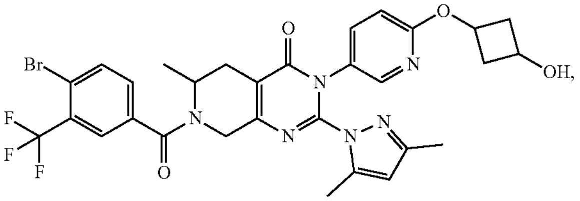
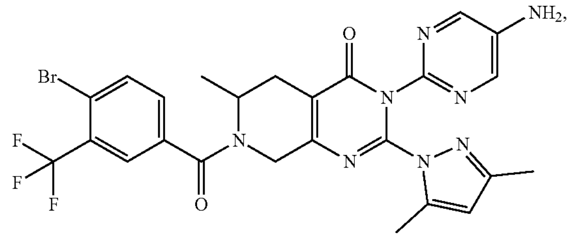
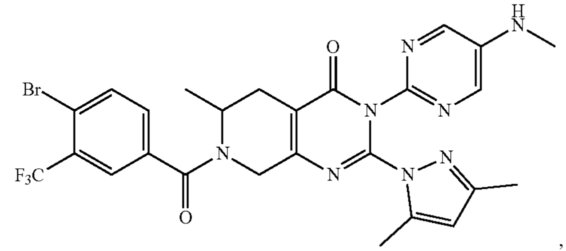
,
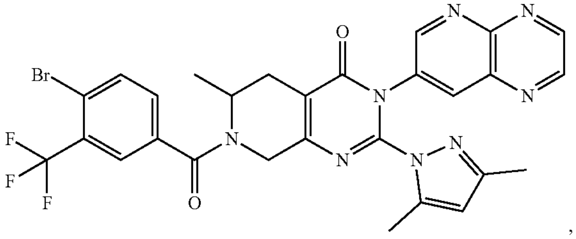
,
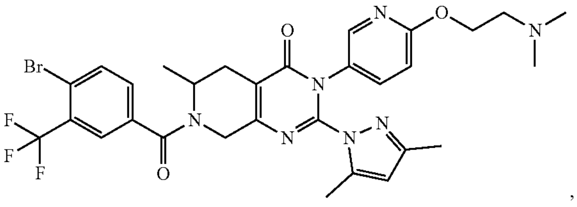
,
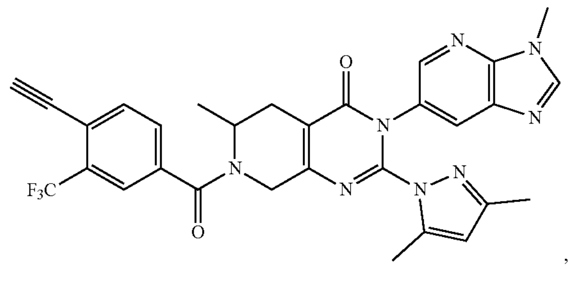
, -continued
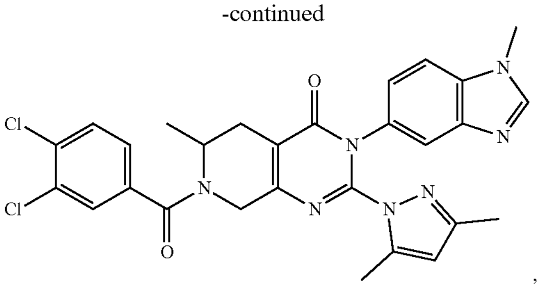
,
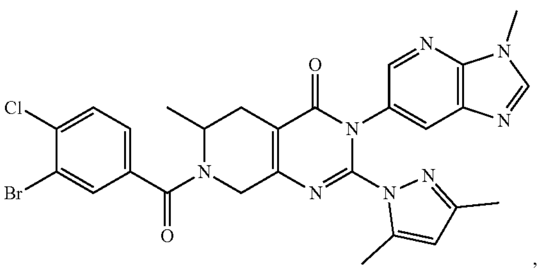
,
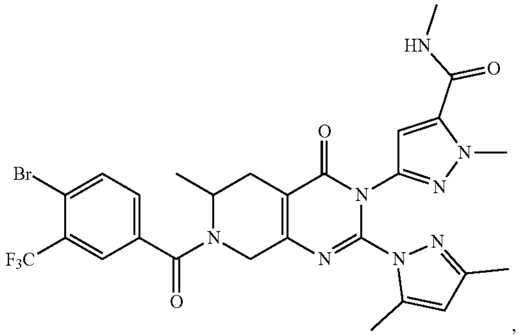
,
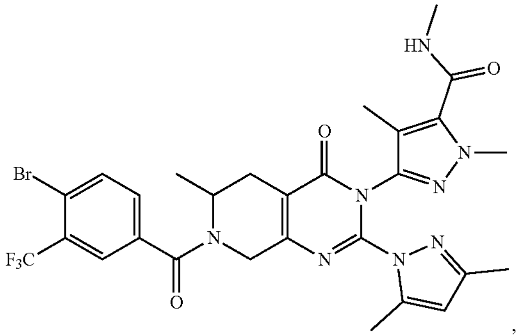
,
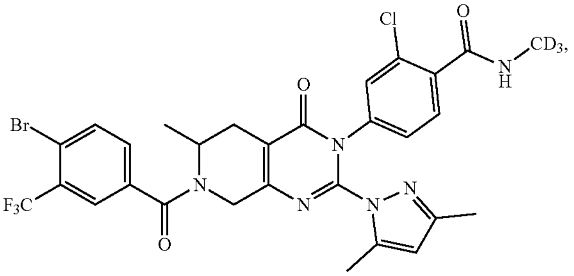
-continued
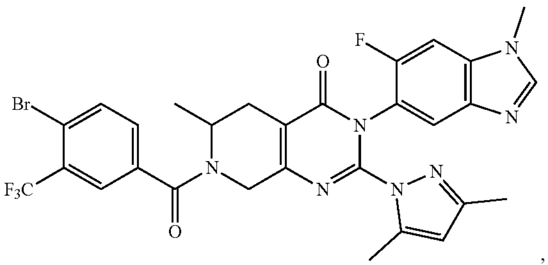
,
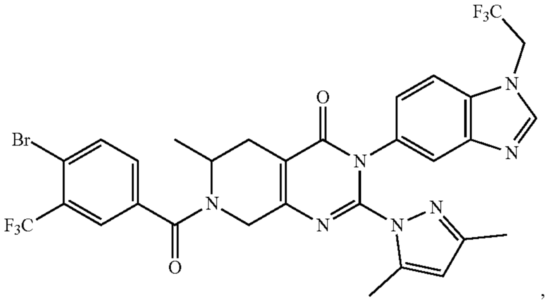
,
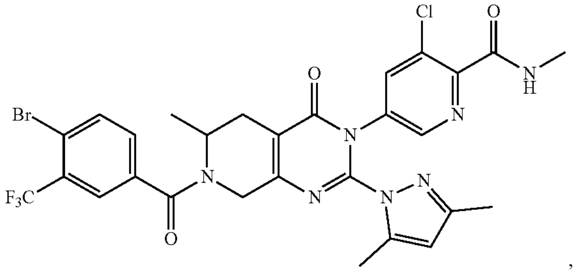
,
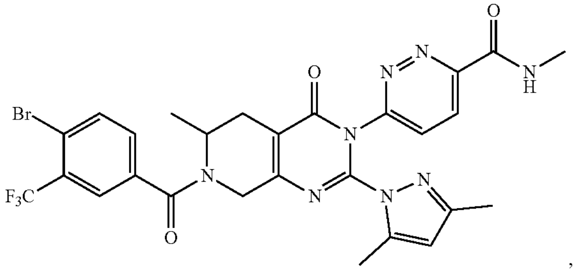
,
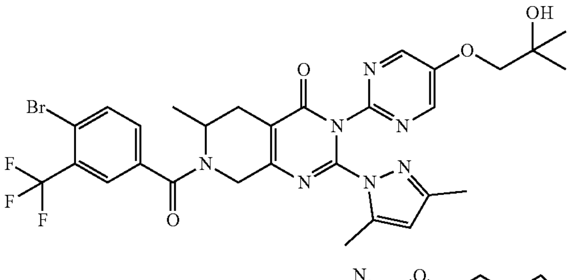
,
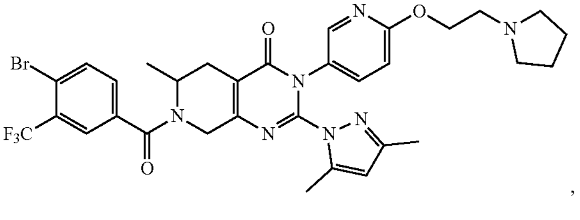
, -continued
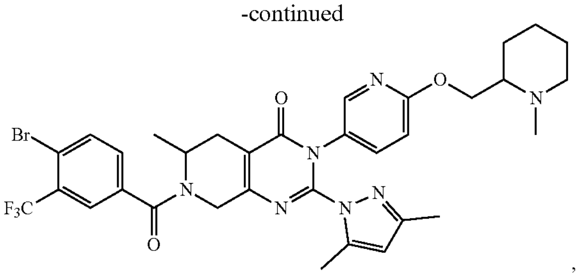
,
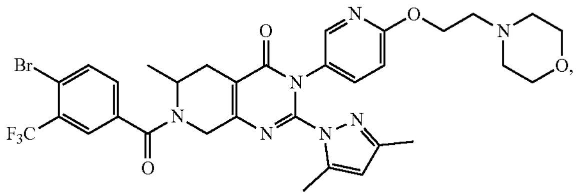
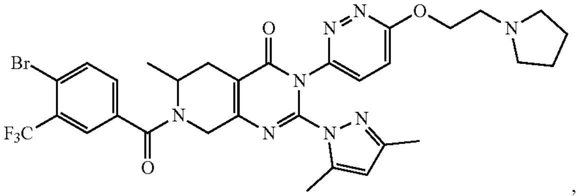
,
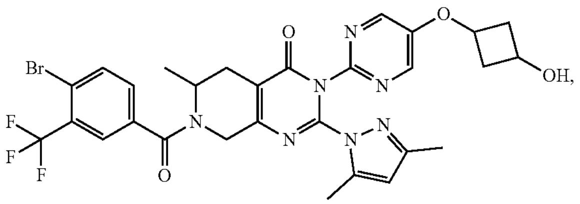
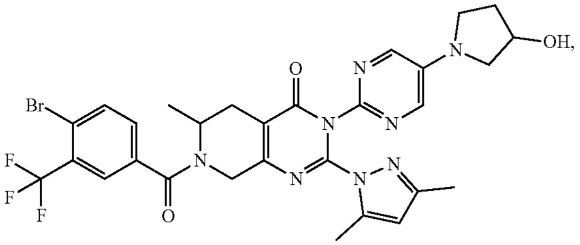
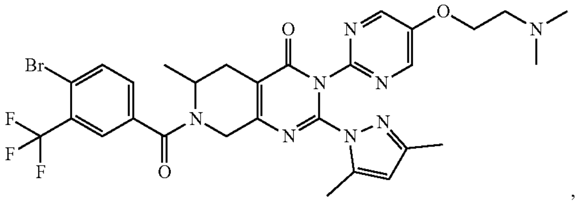
,
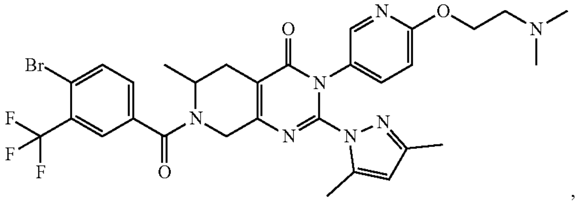
,
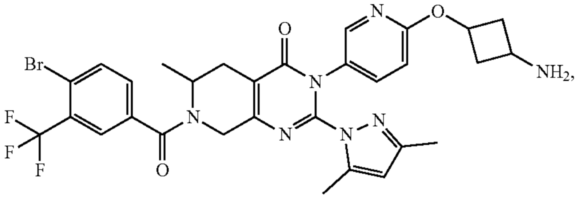
-continued
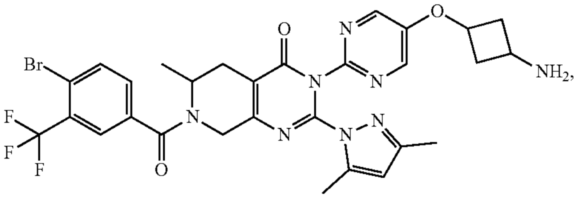
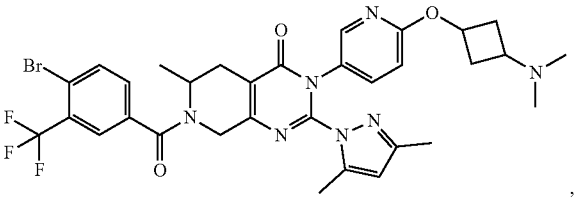
,
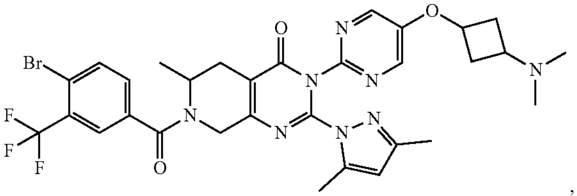
,
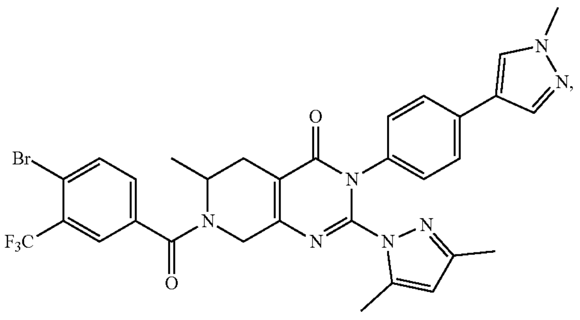
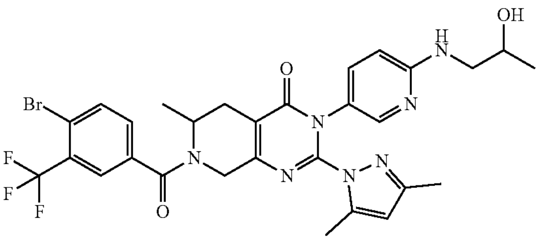
and
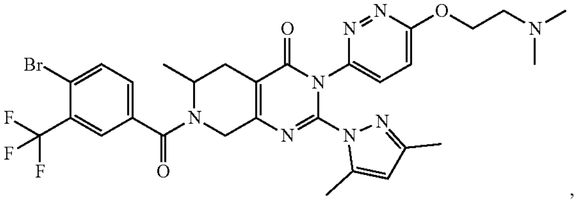
,
or a pharmaceutically acceptable salt of any of the foregoing.
Additional examples of compounds of Formula (I), including pharmaceutically acceptable salts thereof, include:

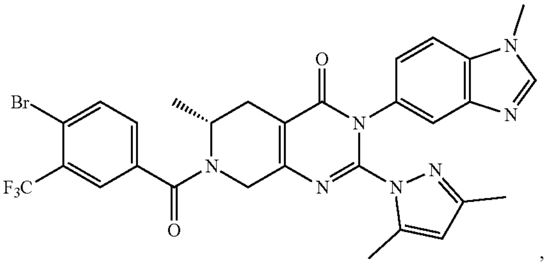
,
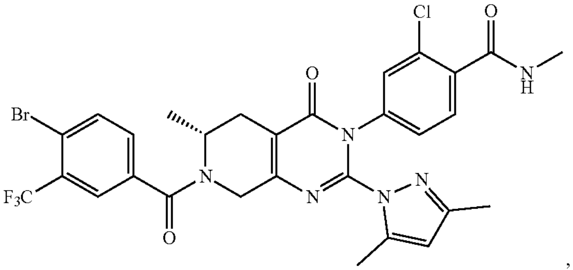
,
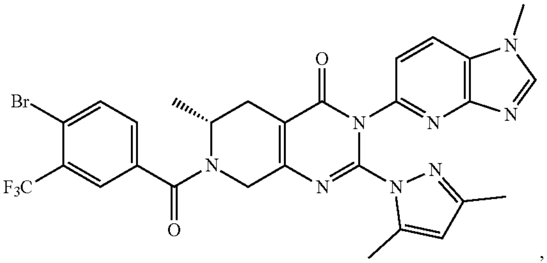
,
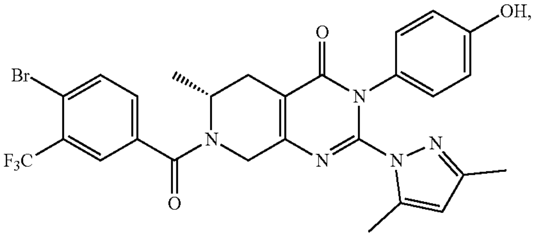
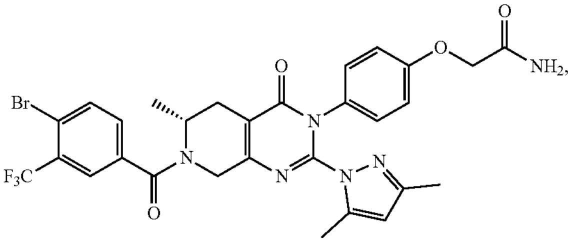
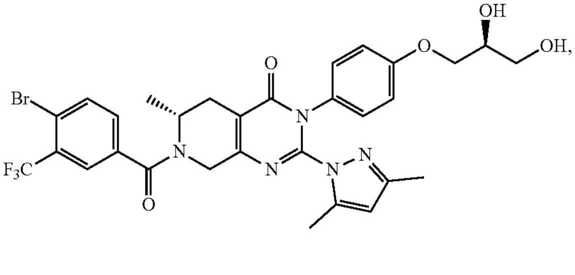
-continued
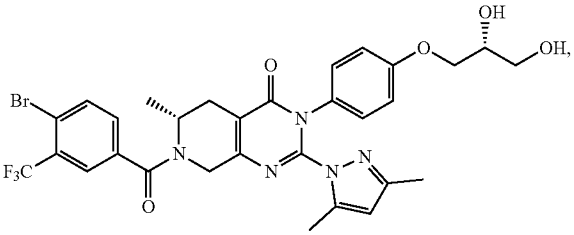
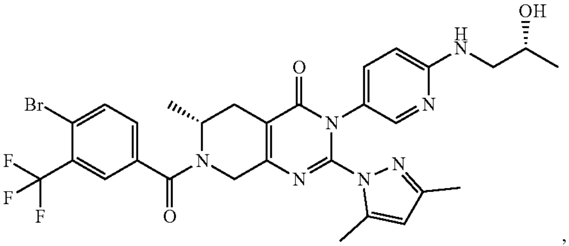
,
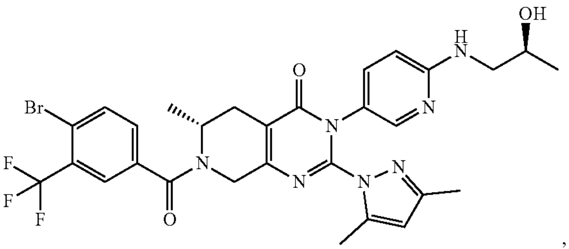
,
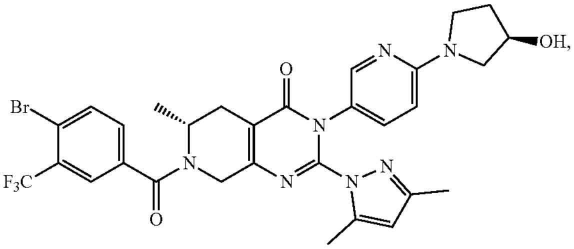
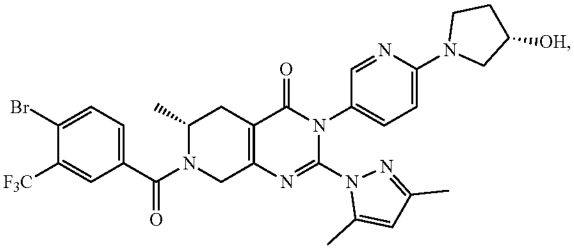
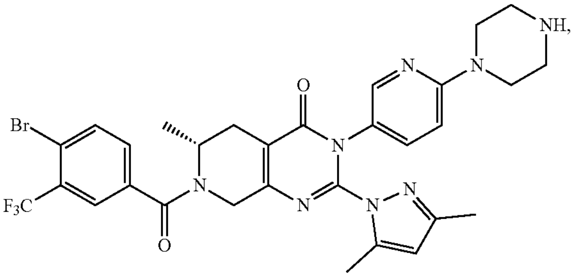

-continued
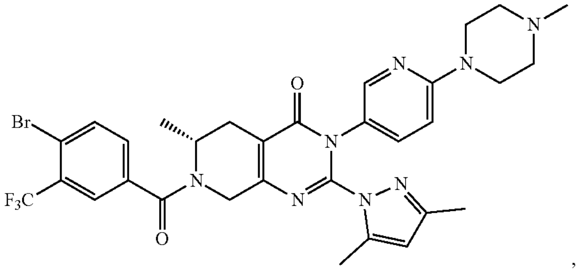
,
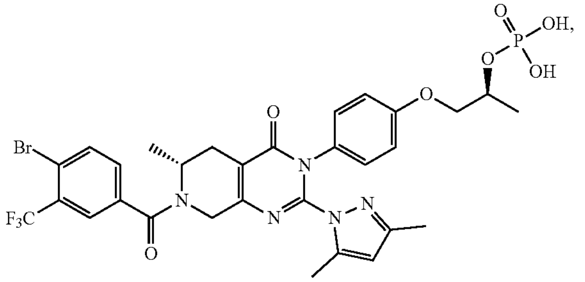
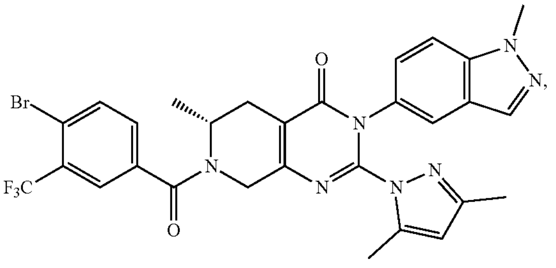
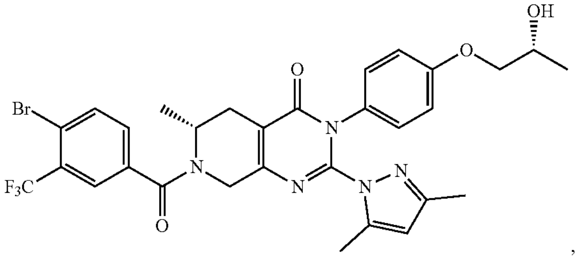
,
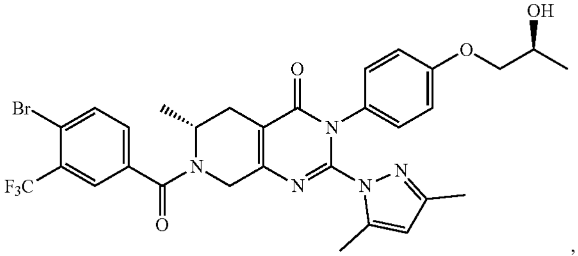
,
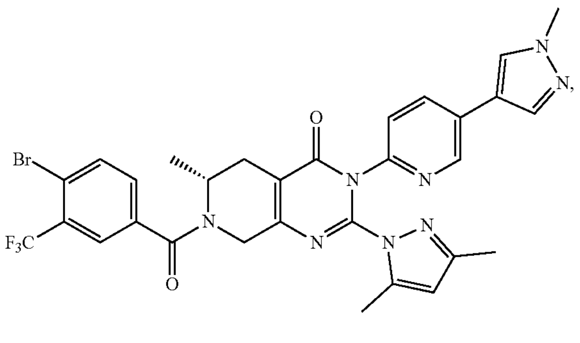
-continued
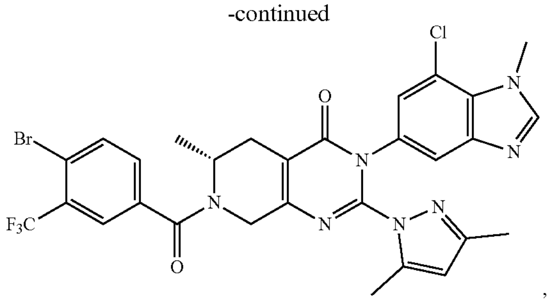
,
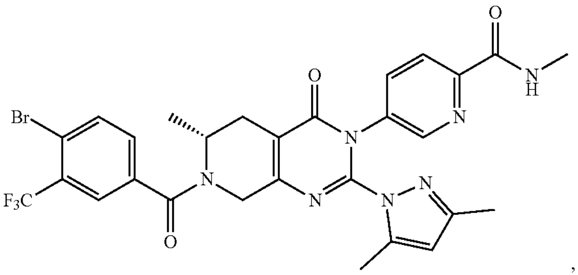
,
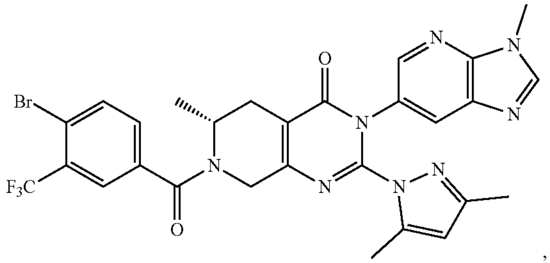
,
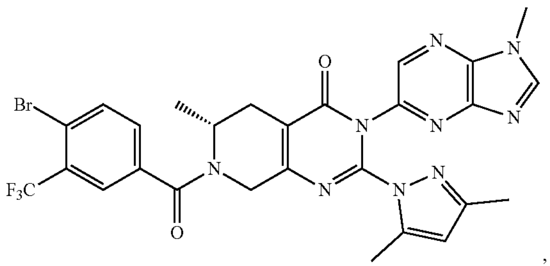
,
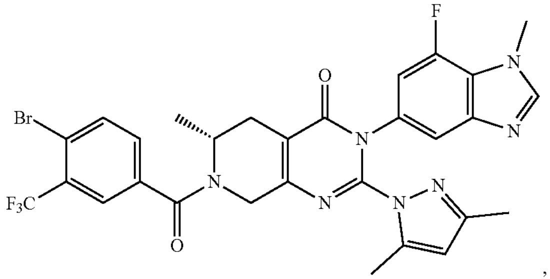
,
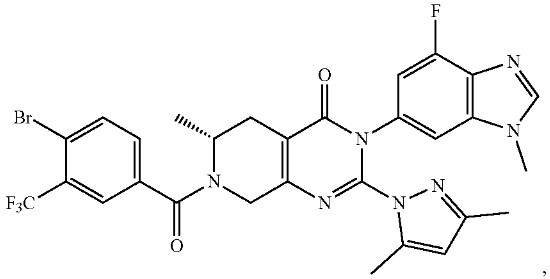
, -continued
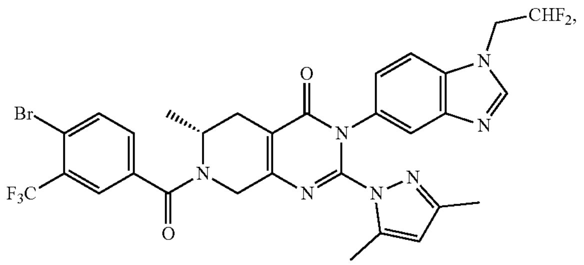
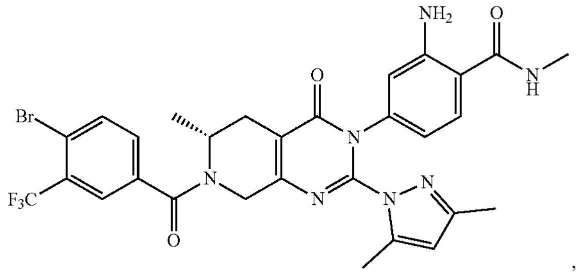
,
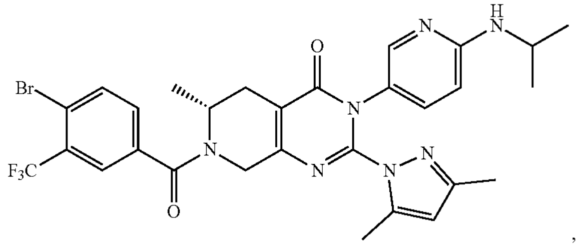
,
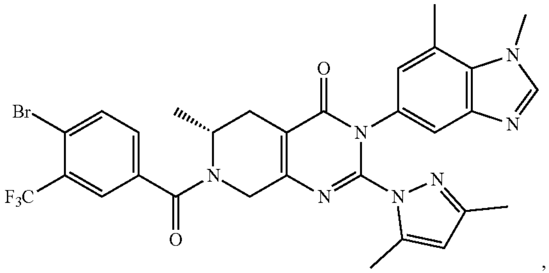
,
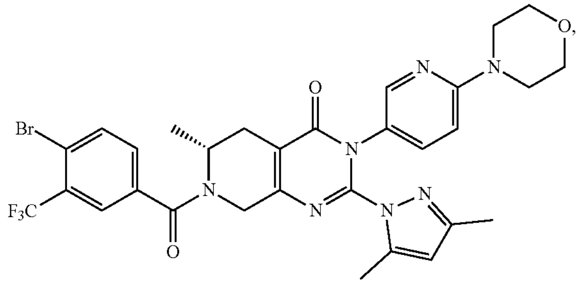
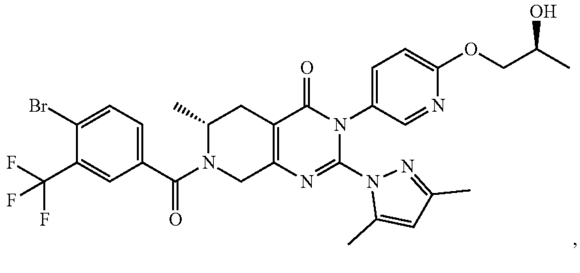
,
-continued
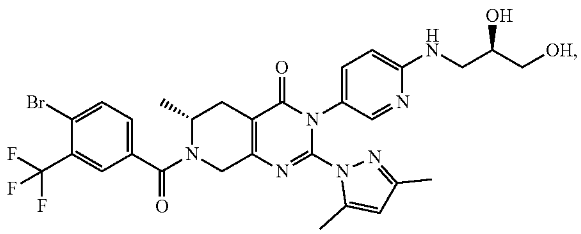
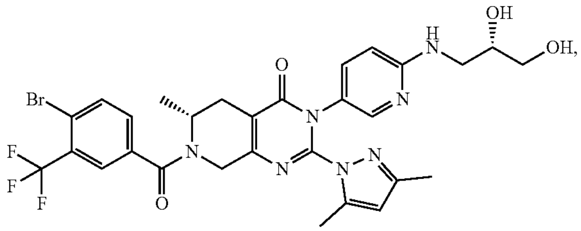
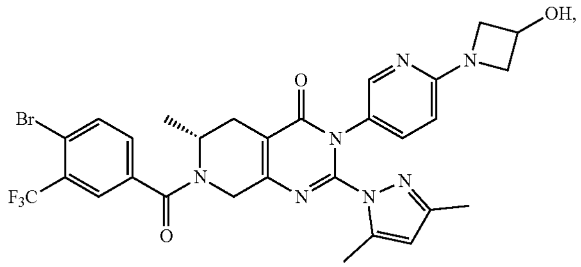
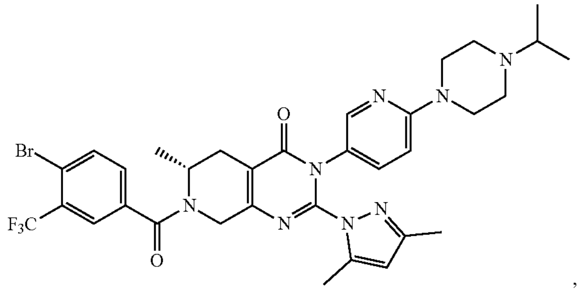
,
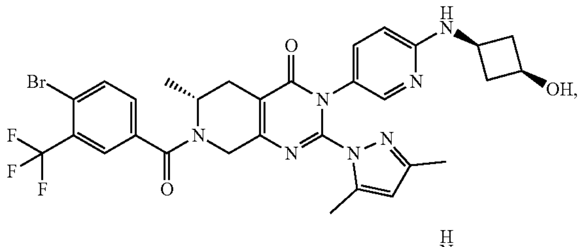
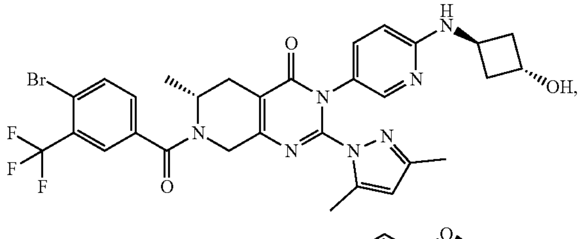
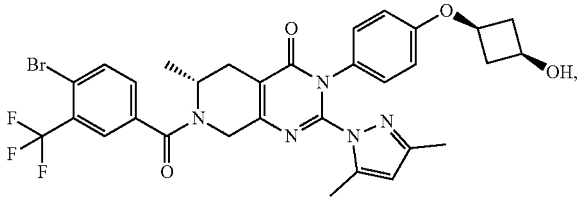

-continued
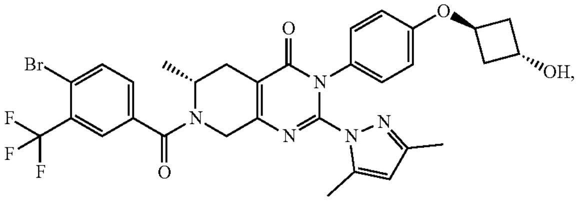
,
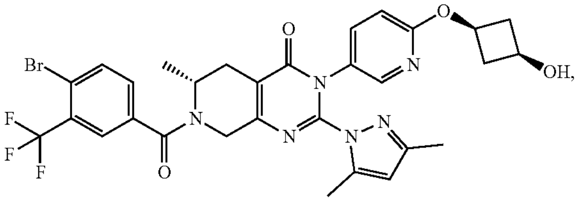
,
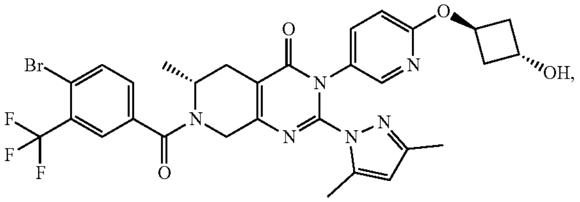
,
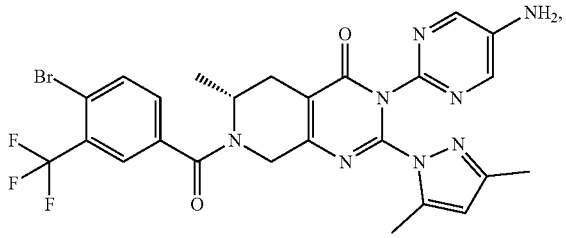
,
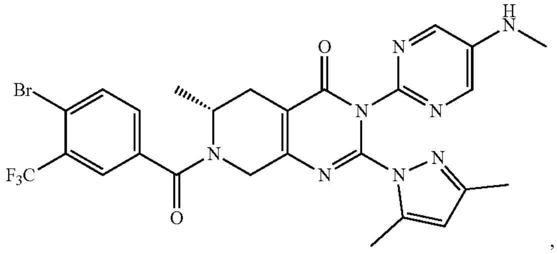
,
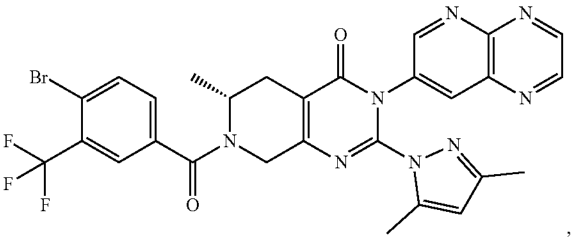
,
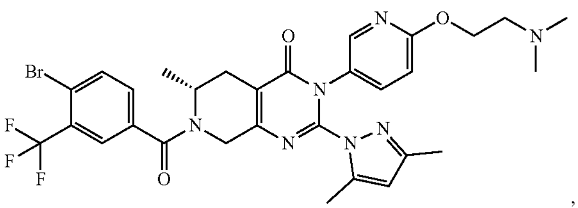
,
-continued
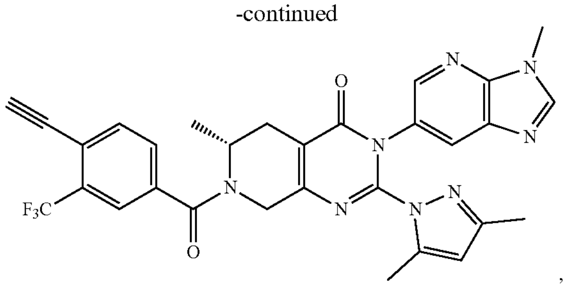
,
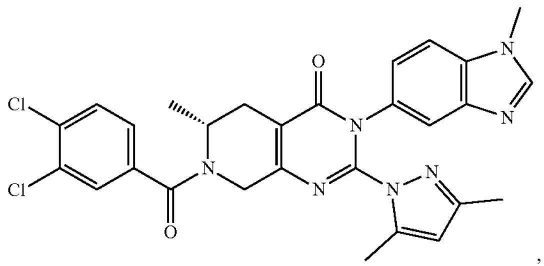
,
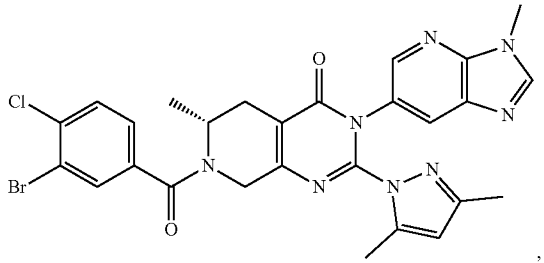
,
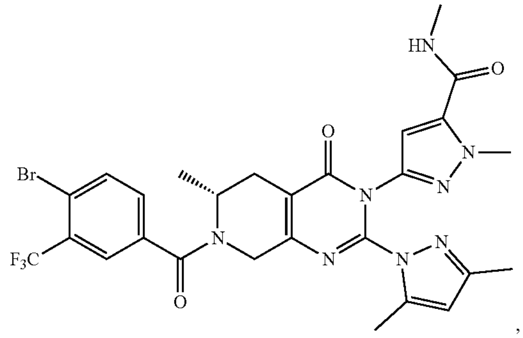
,
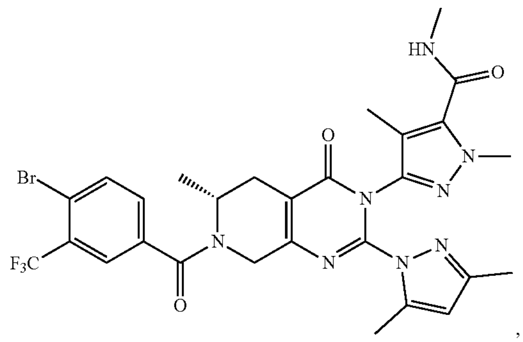
, -continued
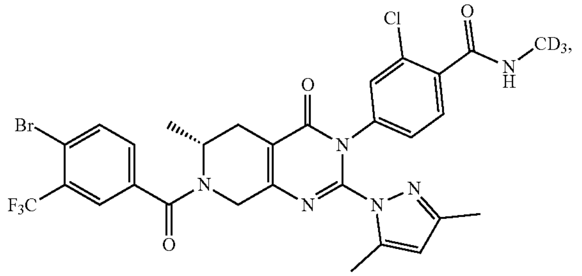
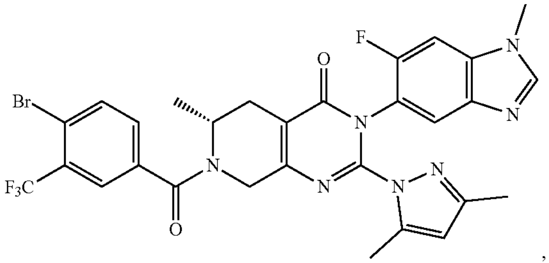
,
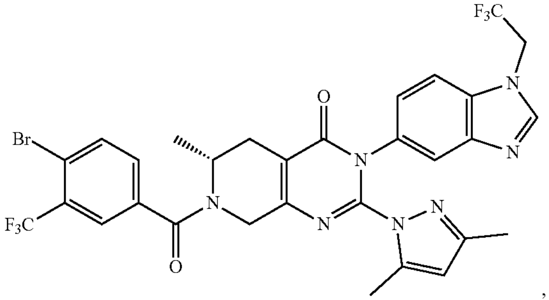
,
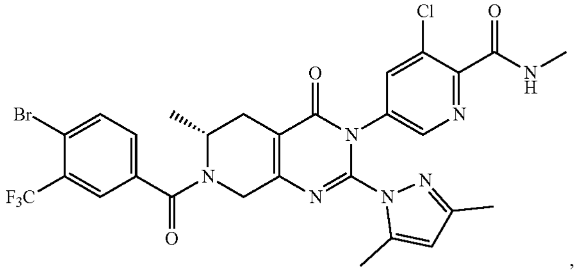
,
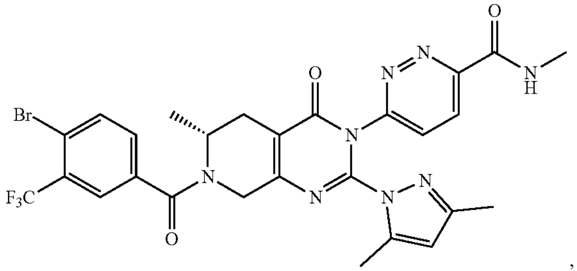
,
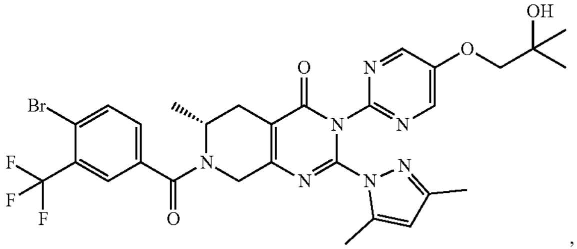
,
-continued
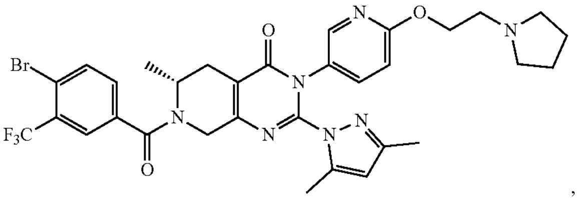
,
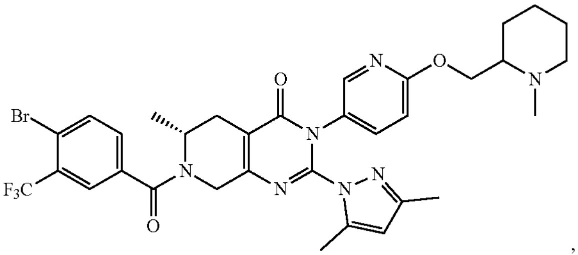
,
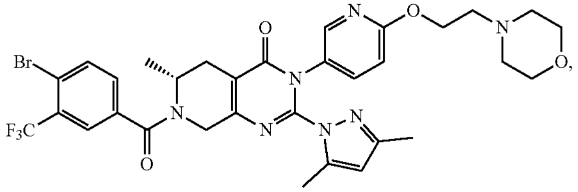
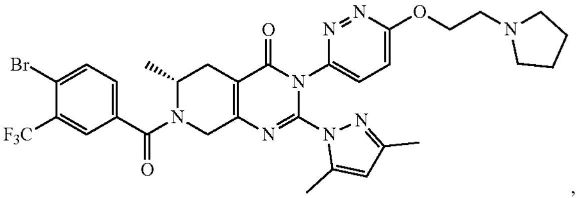
,
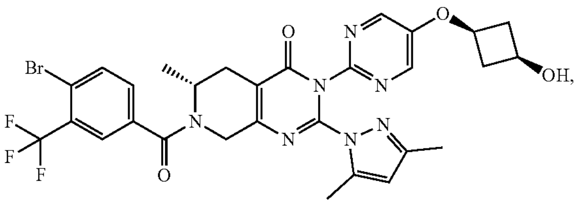
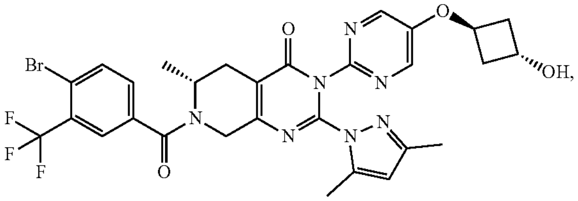
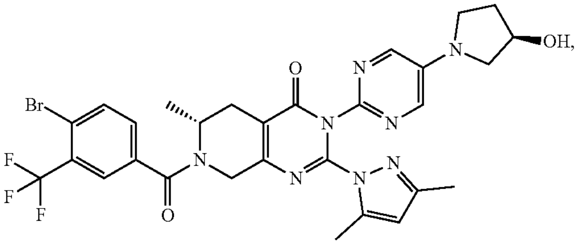

-continued
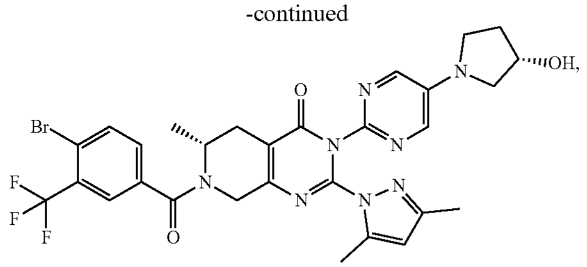
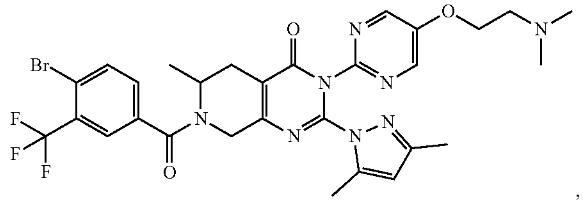
,
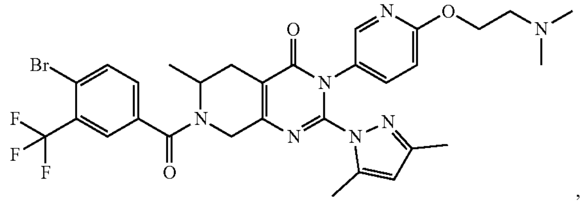
,
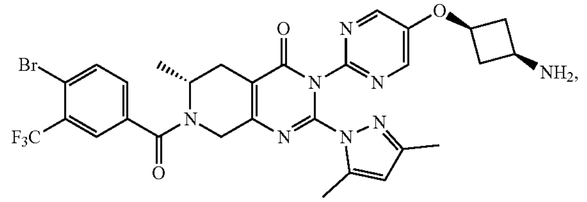
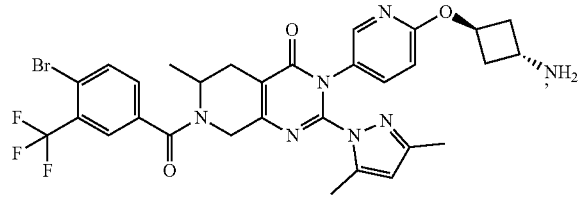
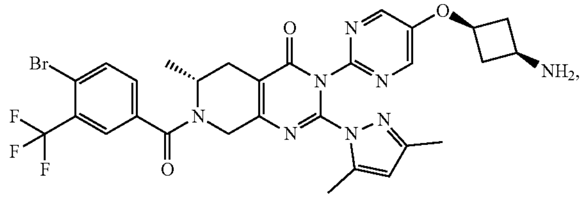
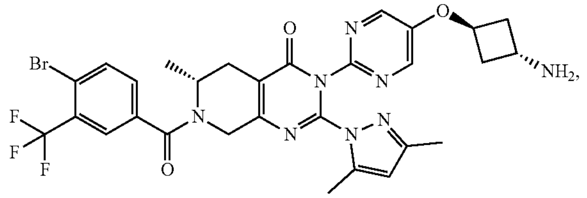
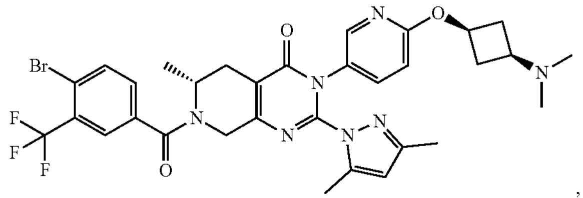
,
-continued
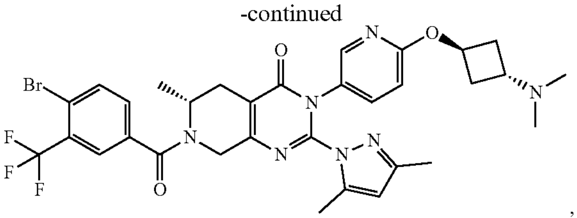
,
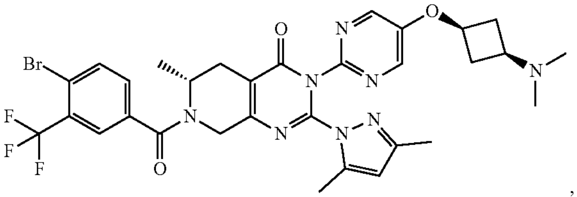
,
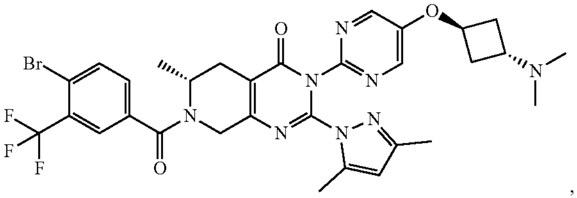
,
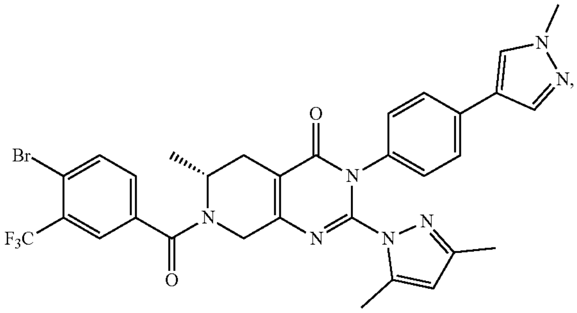
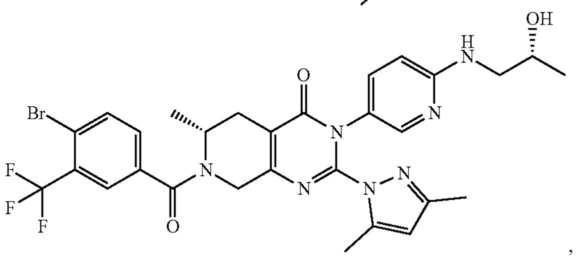
,
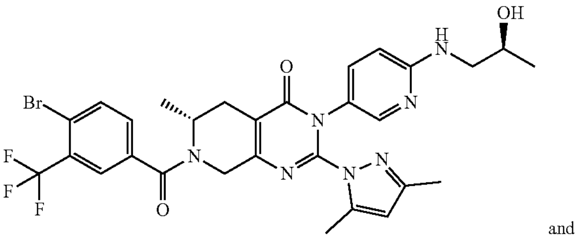
and
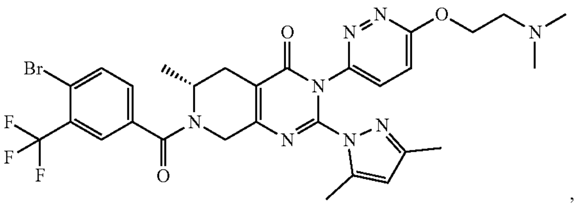
,
or a pharmaceutically acceptable salt of any of the foregoing.
In some embodiments, the compound of Formula (I) is not a compound of the following formula:

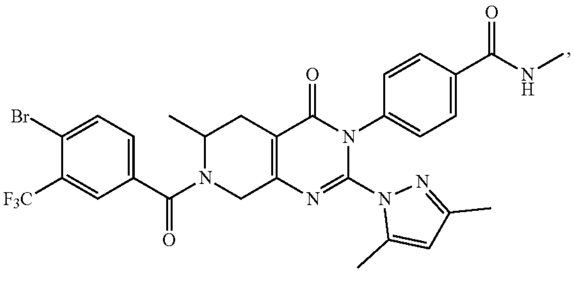 [SMILES: CNC(=O)c1ccc(-n2c(-n3nc(C)cc3C)nc3c(c2=O)CC(C)N(C(=O)c2ccc(Br)c(C(F)(F)F)c2)C3)cc1]

or a pharmaceutically acceptable salt thereof.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

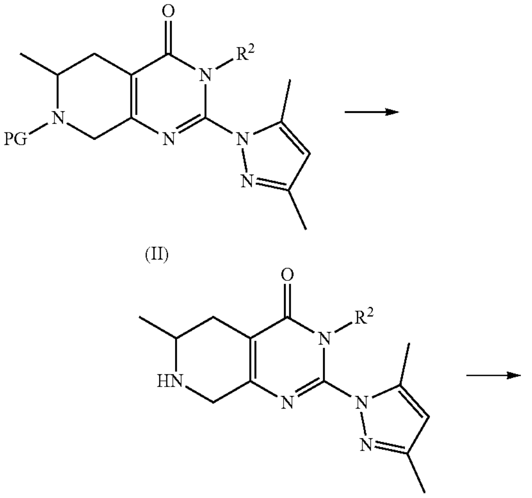

(II)

(I)

(III)

Compounds of Formula (I) (including pharmaceutically acceptable salts thereof) can be prepared from an intermediate of Formula (II), in which PG represents an amino protecting group such as Boc. The PG group can be cleaved from a compound of Formula (II) using methods known in the art. For example, when PG represents a Boc group, PG can be cleaved using acidic conditions, for example, in the presence of HCl in a suitable solvent (such as 1,4-dioxane) or in the presence of copper triflate. The coupling of the intermediate of Formula (III) with a suitable agent can afford a compound of Formula (I), along with pharmaceutically acceptable salts thereof. As an example, compounds of Formula (I), along with pharmaceutically acceptable salts thereof, can be obtained by reacting a compound of Formula (III) with an acyl chloride of general formula $R^1$—C(=O)—Cl, in the presence of a suitable base (e.g., triethylamine) in a suitable solvent (e.g., acetonitrile). As an alternative example, compounds of Formula (I) and its pharmaceutically acceptable salts, can be obtained by reacting a compound of Formula (III) with a carboxylic acid of general formula $R^1$—COOH, in the presence of a suitable base (e.g., triethylamine), in a suitable solvent (e.g., acetonitrile or DMF), using a suitable amino acid coupling agent (e.g., HATU, or EDC). Further compounds of Formula (I), along with pharmaceutically acceptable salts thereof, can be prepared from a compound of Formula (III) using methods known in the art.

Scheme 2

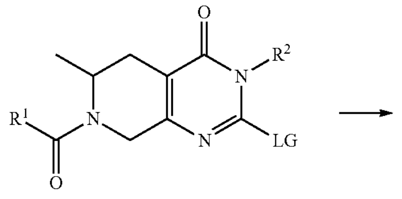

(I)

(IV)

Compounds of Formula (I), including pharmaceutically acceptable salts thereof, can also be prepared from an intermediate of Formula (IV), in which LG represents a leaving group (such as sulfhydryl, methylsulfoxide or halogen (e.g., Cl or Br)). A compound of Formula (I) can be prepared from a compound of Formula (IV) in which LG represents —$SO_2CH_3$ by reacting 3,5-dimethyl-1H-pyrazole, in the presence of a base (such as diisopropylethylamine (DIPEA) or NaH) in a suitable solvent (such as THF, DMF or acetonitrile). A compound of Formula (I) can be prepared from a compound of Formula (IV) in which LG represents chloro by reacting 3,5-dimethyl-1H-pyrazole, in the presence of a base (for example, triethylamine, DBU or DIPEA) in a suitable solvent (such as acetonitrile, DMF or THF), optionally in the presence of a catalyst, such as DMAP.

Scheme 3

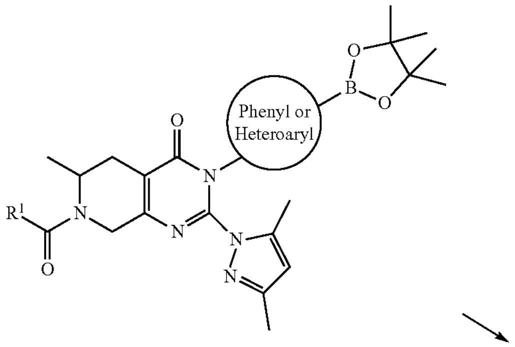

(Va)

(I)

-continued

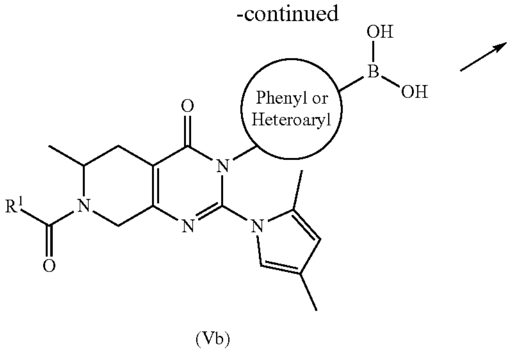

(Vb)

-continued

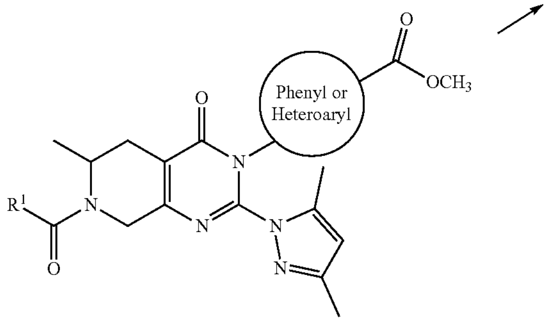

(VIIb)

A compound of Formula (I), along with pharmaceutically acceptable salts thereof, in which $R^2$ represents a phenyl or a heteroaryl, can be prepared from compounds of Formula (Va) and Formula (Vb). Formula (Va) and Formula (Vb) are in turn generated by reacting the corresponding heteroaryl-halide (such as bromo or iodo) with a palladium catalyst (e.g. $Pd(PPh_3)_4$) in the presence of a base (for example, $Cs_2CO_3$) and pinacoldiborane in a suitable solvent or solvent mixture (e.g. 1,4-dioxane/$H_2O$). Alternatively, other methods known to those skilled in the art maybe used to generate boronic acids or boronic esters (for example, Leermann et al., Org. Lett. (2011) 13, 4479-4481; Zhang et al., J. Am. Chem. Soc. (2019) 141, 9124-9128; Mfuh et al., J. Am. Chem. Soc. (2016) 138, 2985-2988).

Scheme 4

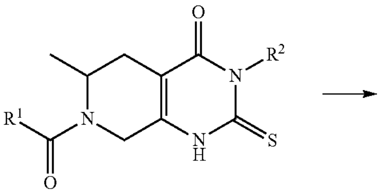

(I)

(VI)

Compounds of Formula (I), along with pharmaceutically acceptable salts thereof, can be prepared from an intermediate of Formula (VI) and 3,5-dimethylpyrazole, in the presence of t-butyl hydroperoxide (TBHP) in a suitable solvent (e.g., acetonitrile).

Scheme 5

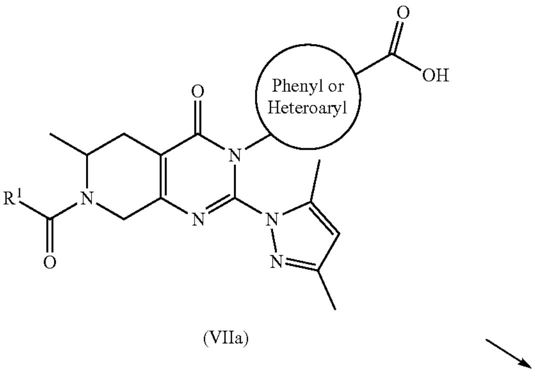

(VIIa)

(I)

Compounds of Formula (I), including pharmaceutically acceptable salts thereof, in which $R^2$ represents a phenyl or heteroaryl substituted with an amide can be prepared from an acid intermediate of Formula (VIIa) and an amine of Formula $NH_2$—$R^{A2}$, using a peptide coupling agent (such as HATU) in the presence of a base (for example, diisopropylethylamine) in a suitable solvent, such as acetonitrile or DMF. Compounds of Formula (I), along with pharmaceutically acceptable salts thereof, in which $R^2$ represents a phenyl substituted with an amide or $R^2$ represents a heteroaryl substituted with an amide can be prepared from an ester intermediate of Formula (VIIb) and an amine of general formula $NH_2$—$R^{A2}$ in a suitable solvent (such as acetonitrile), optionally at elevated temperature.

Scheme 6

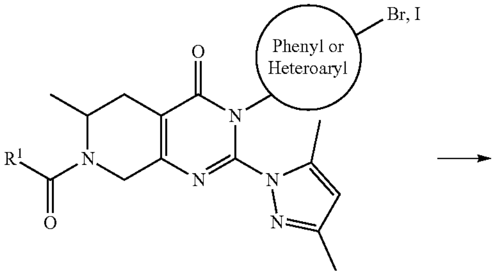

(I)

(VIII)

Compounds of Formula (I), or a pharmaceutically acceptable salt thereof, in which $R^2$ represents a phenyl or a heteroaryl substituted with an amine, can be prepared via Buchwald-Hartwig amination from an intermediate of Formula (VIII) and an amine, using a catalyst (for example, XantPhos Pd G3) in the presence of a base (e.g., $Cs_2CO_3$) in a suitable solvent (such as 1,4-dioxane). Compounds of Formula (I), or a pharmaceutically acceptable salt thereof, in which $R^2$ represents a phenyl or a heteroaryl substituted with a monocyclic heteroaryl, can be prepared from an intermediate of Formula (VIII) and a boronic acid or boronic ester (for example, an optionally substituted 4,4,5,5-tetramethyl-1,3,2-dioxaborolan-2-yl heteroaryl) using a catalyst, such as $Pd(PPh_3)_4$, in the presence of a base (such as $Cs_2CO_3$) in a suitable solvents, such as 1,4-dioxane/$H_2O$. Examples in literature of this reaction are described and the following references are examples: Fan, et al., Org. Lett. (2015) 17, 5934-5937; Sheng et al. Org. Lett. (2008) 10, 4109-4112.

Scheme 7

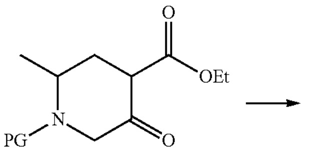

(IX)

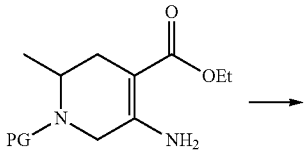

(X)

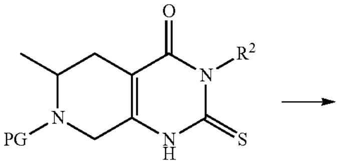

(XI)

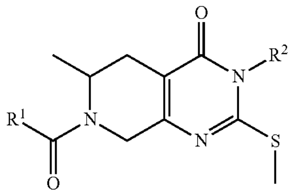

(IIb)

Intermediate of Formula (IIb) can be prepared from a compound of Formula (IX) using ammonium acetate in a suitable solvent (such as ethanol) to afford an intermediate of Formula (X). Treatment of the intermediate of Formula (X) with a base, such as NaH, in a suitable solvent (such as THF) followed by the subsequent addition of an isothiocyanate of general formula $R^2$—NCS can give an intermediate of Formula (XI). The intermediate of Formula (XI) can be subsequently alkylated with an iodomethane, or any alkylhalide, in the presence of a base (such as DBU) in a suitable solvent (such as DMF) to afford a compound of Formula (IIb).

Scheme 8

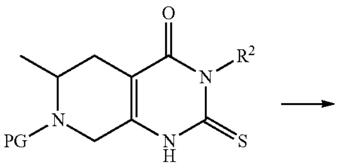

(XI)

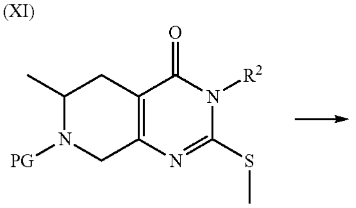

(IIb)

-continued

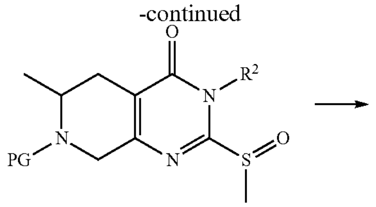

(IIc)

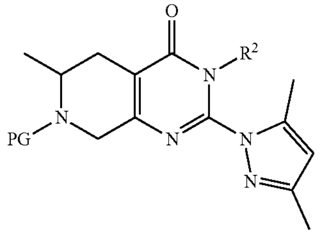

(III)

Intermediate of Formula (III) can be prepared from a compound of Formula (XI) using methyl iodide or methyl bromide, in the presence of a base, such as DBU, in a suitable solvent, such as DMF, to afford an intermediate of Formula (IIb). Oxidation of an intermediate of Formula (IIb) to a sulfoxide intermediate of Formula (IIc) can be achieved by a treatment with an oxidative agent (such as m-CPBA) in the presence of $MgSO_4$ and NaOAc in a suitable solvent (such as dichloromethane). Treatment of intermediate of Formula (IIc) with 3,5-dimethylpyrazole in the presence of a base (such as DIPEA), optionally in the presence of a catalyst (for example, DMAP) in a suitable solvent (such as DMF) can afford an intermediate of Formula (III).

Scheme 9

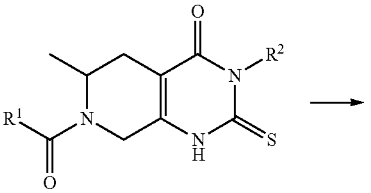

(VI)

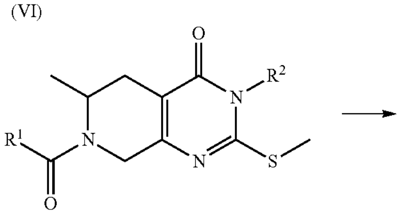

(IV)

(XIV)

Intermediates of Formula (IV) in which the leaving group LG represents a methylsulfoxide can be prepared from an intermediate of Formula (VI) using methyl iodide or methyl bromide, in the presence of a base (for example, DBU) in a suitable solvent, such as DMF, to afford an intermediate of Formula (XIV). Oxidation of an intermediate of Formula (XIV) to a sulfoxide intermediate of Formula (IV, LG is sulfoxide) can be achieved using an oxidative agent, such as m-CPBA, in the presence of $MgSO_4$ and NaOAc in a suitable solvent, such as dichloromethane.

Scheme 10

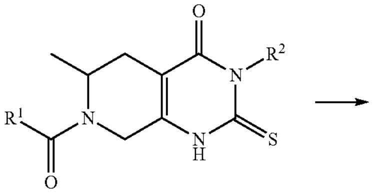

(VI)

(IV)

Intermediates of Formula (IV) in which the leaving group LG is chloro, can be prepared from an intermediate of Formula (VI) using thiophosgene, or sulfuryl chloride in a suitable solvent (such as THF).

Scheme 11

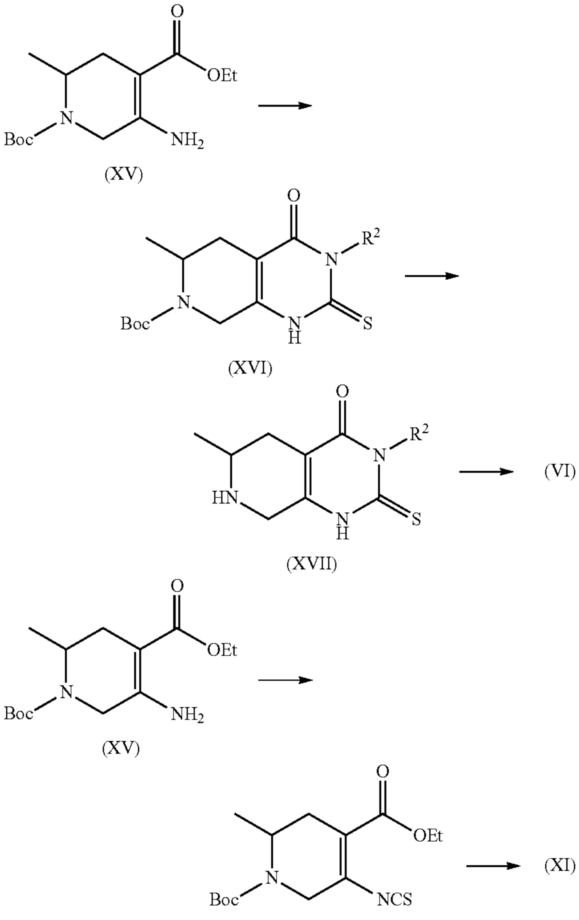

(XV)

(XVI)

(XVII)

(VI)

(XV)

(XXIV)

(XI)

Intermediate of Formula (VI) can be prepared from an intermediate of Formula (XV) in the presence of a base, such as NaH, in a suitable solvent (for example, THF) followed by the subsequent addition of an isothiocyanate of general formula $R^2$—NCS to afford an intermediate of Formula (XVI). The Boc group of an intermediate of Formula (XVI) can be deprotected in the presence of an acid (e.g., HCl or TFA) in a suitable solvent (for example, 1,4-dioxane) to afford an intermediate of Formula (XVII). Intermediates of Formula (VI) can be prepared from an intermediate of Formula (XVII) following several conditions known to those skilled in the art.

Further compounds of Formula (VI) can be obtained by reacting a compound of Formula (XVII) with an acyl chloride of general formula $R^1$—C(═O)—Cl in the presence of a base (e.g., $Et_3N$) in a suitable solvent (e.g., DMF), including bases and solvents known to those skilled in the art. Compounds of Formula (VI) can be obtained by reacting compound of Formula (XVII) with a carboxylic acid of general formula $R^1$—C(═O)—OH in the presence of an amide coupling agent (such as HATU) in a suitable solvent. Additional compounds of Formula (VI) can be prepared from a compound of Formula (XVII) using methods known in the art.

Scheme 12

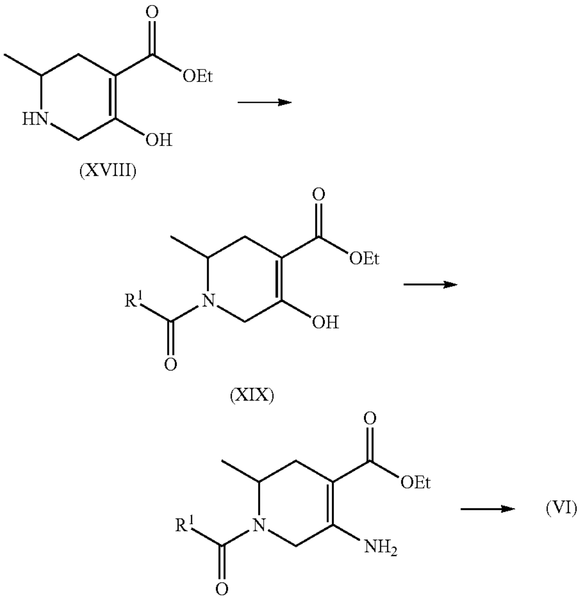

(XVIII)

(XIX)

(XX)

(VI)

An intermediate of Formula (VI) can be prepared from an intermediate of Formula (XVIII) following conditions known in the art, such as conditions used to convert an intermediate of Formula (XVII) to an intermediate for Formula (VI). For example, intermediates of Formula (XIX) can be obtained by reacting a compound of Formula (XVIII) with an acyl chloride of general formula $R^1$—C(═O)—Cl in the presence of a base in a suitable solvent. Additional compounds of Formula (XIX) can be obtained by reacting a compound of Formula (XVIII) with a carboxylic acid of general formula $R^1$—C(═O)—OH in the presence of an amide coupling agent (such as HATU) in a suitable solvent. Suitable solvents are known to those skilled in the art and/or described herein.

Intermediates of Formula (XX) can be prepared from an intermediate of Formula (XI) in the presence of ammonium acetate, in a suitable solvent (such as ethanol). Intermediate of Formula (VI) can be prepared from an intermediate of Formula (XX) in the presence of a base (for example, NaH) in a suitable solvent (e.g., THF) followed by the addition of an isothiocyanate of general formula $R^2$—NCS. An intermediate of Formula (XX) can be treated with thiophosgene/NMM in a suitable solvent, such as dichloromethane, to afford an intermediate isothiocyanate, which can be converted to an intermediate of Formula (VI) by using an amine of general formula $NH_2$—$R^2$, in the presence of a base, such as triethylamine, in a suitable solvent (such as acetonitrile).

Scheme 13

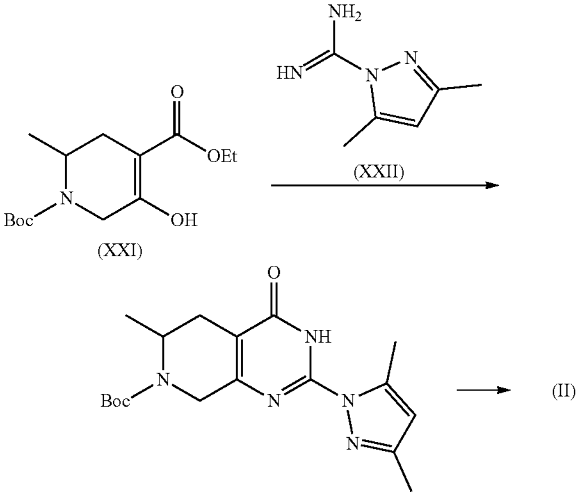

(XXI) (XXII) (XXIII) (II)

Intermediates of Formula (II) in which PG can be a protecting group, such as Boc, can be prepared from an intermediate of Formula (XXI) using a guanidine derivative of Formula (XXII), in the presence of a base, such as DBU, in a suitable solvent (such as $CH_3CN$) to afford an intermediate of Formula (XXIII). An intermediate of Formula (XXIII) can be used to obtain to an intermediate of Formula (II) using methods known in the art. As an example, an intermediate of Formula (XXIII) can be reacted with an aryl or heteroaryl boronic acid of general formula $R^2$—$B(OH)_2$, in the presence of TMEDA and $Cu(OAc)_2$ to afford an intermediate of Formula (II) in which $R^2$ represents a phenyl, a monocyclic heteroaryl or a fused-bicyclic heteroaryl.

Scheme 14

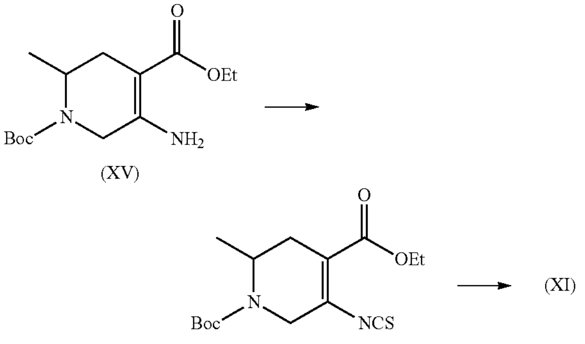

(XV) (XXIV) (XI)

Intermediates of Formula (XI) can be obtained from an intermediate of Formula (XV) using methods known in the art, for example, by treating an intermediate of Formula (XV) with thiophosgene and NMM in a suitable solvent (such as THF). Treatment of an intermediate of Formula (XXIV) with an amine of general formula $R^2$—$NH_2$ affords an intermediate of Formula (XI) in which PG represents a Boc group.

Scheme 15

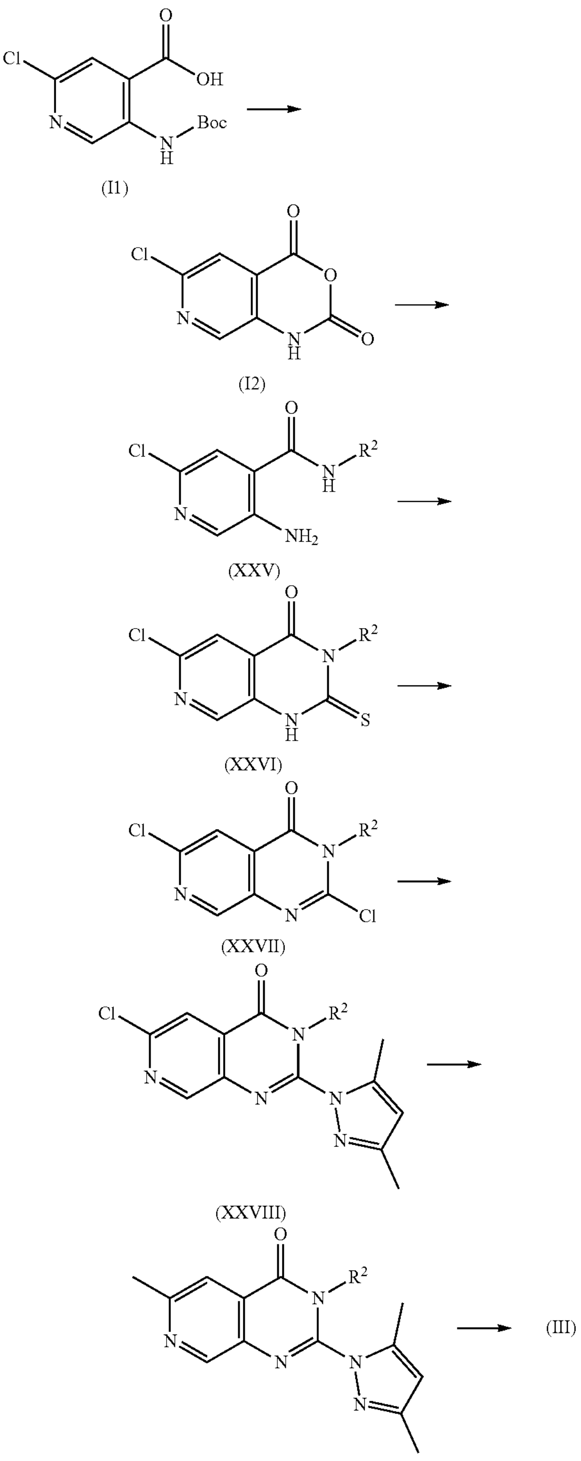

(I1) (I2) (XXV) (XXVI) (XXVII) (XXVIII) (XXIXa) (III)

Intermediates of Formula (III), can be prepared from a chloro-N-Boc-aminopyridinecarboxylic acid intermediate of Formula (II) using a base (such as triethylamine) in the presence of 2-chloro-N-methylpyridinium iodide in a suitable solvent (for example, acetonitrile) to afford an intermediate of Formula (12). An intermediate of Formula (12) can be converted to an intermediate of Formula (XXV) using an amine of general formula $R^2$—$NH_2$, in a suitable solvent (for example, acetic acid). Reaction of an intermediate of Formula (XXV) with 1,1'-Thiocarbonyldiimidazole (TCDI) in DMF can afford a thio intermediate of Formula (XXVI), which can be converted in an intermediate of Formula (XXVII) using thiophosgene or sulfuryl chloride in a suitable solvent (such as 1,4-dioxane). Treatment of an intermediate of Formula (XXVII) with 3,5-dimethylpyrazole can afford an intermediate of Formula (XXVIII). Intermediates of Formula (XXVIII) can be reacted with methylboronic acid using a Pd catalyst (e.g. $Pd(Ph_3)_4$) in a suitable solvent (such as dioxane/water) to afford an intermediate of Formula (XXIXa). An intermediate of Formula (XXIXa) can be converted to an intermediate of Formula (III) by catalytic hydrogenation using $H_2$ in the presence of a catalyst (for example Pt/C) in an appropriate solvent(s) (e.g., acetic acid/THF/ethanol).

Scheme 15

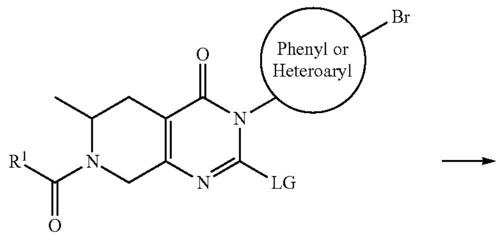

(XXIX)

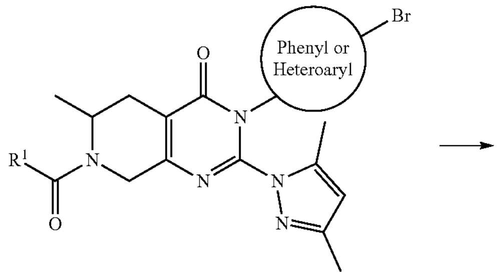

(Va)

(XXX)

Intermediates of Formula (Va) can be prepared from an intermediate of Formula (XXIX), in which LG represents a leaving group (such as, sulfhydryl, methylsulfoxide or halogen (e.g., chloro or bromo)). Intermediates of Formula (XXIX) can be reacted with 3,5-dimethyl-1H-pyrazole, in the presence of a base (such as diisopropylethylamine) in a suitable solvent, such as acetonitrile, to afford an intermediate of Formula (XXX). The conversion of bromo intermediate Formula (XXX) to a boronic ester intermediate of Formula (Va) can be achieved using bis(pinacolato)diboron in the presence of a catalyst (such as $Pd(dppf)Cl_2$) in the presence of a base, such as KOAc, in a suitable solvent (for example, 1,4-dioxane).

Scheme 16

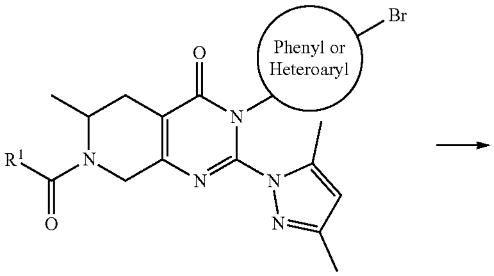

(Vb)

(XXX)

Intermediates of Formula (Vb) can be prepared from an intermediate of Formula (XXX) using bis(pinacolato)diboron, in the presence of a base (e.g., KOAc) and $Pd(dppf)Cl_2$ in a suitable solvent, such as 1,4-dioxane and water, to obtain an intermediate of Formula (Vb).

Scheme 17

(IV)

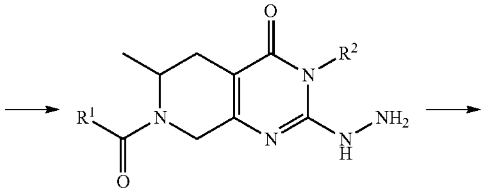

(I)

(XXXI)

Intermediates of Formula (XXXI) can be prepared from an intermediate of Formula (IV) using hydrazine hydrate in an appropriate solvent (such as ethanol). Subsequent formation of compounds of Formula (I), including pharmaceutically acceptable salts thereof, can be accomplished by reacting intermediates of Formula (XXXI) with acetylacetone in a polar solvent (for example, ethanol) at an elevated temperature(s).

Scheme 18

(VI)

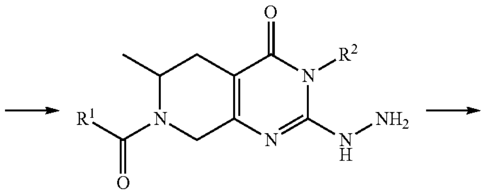

(I)

(XXXI)

Alternatively, intermediates of Formula (XXXI) can be prepared from an intermediate of Formula (VI) using an oxidant such as AcOOH 35% in acetic acid, or urea peroxide, in presence of hydrazine hydrate in an appropriate solvent (such as isopropanol). Subsequent formation of compounds of Formula (I), including pharmaceutically acceptable salts thereof, can be accomplished by reacting intermediates of Formula (XXXI) with acetylacetone in a polar solvent (for example, isopropanol) at an elevated temperature(s).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction $<10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 months after completion of treatment.

Subjects who are clinically diagnosed with HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-αX-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and STOPS™ compounds described in U.S. 2020/0147124 A1, which is hereby incorporated by reference for the purpose of describing the STOPS™ compounds provided therein, such as modified oligonucleotides identified as Nos. 1-392.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Table of Abbreviations

| Abbreviation | Meaning |
|---|---|
| h | hour |
| * | single diastereomer, absolute stereochemistry unknown |
| rt | room temperature |
| EA | ethyl acetate |
| EtOH | ethanol |
| MeOH | methanol |
| MeCN | acetonitrile |
| CyH | cyclohexane |
| DCM | dichloromethane |
| PE | petroleum ether |
| DIPEA | diisopropylethylamine |
| SFC | Supercritical Fluid Chromatography |

4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide

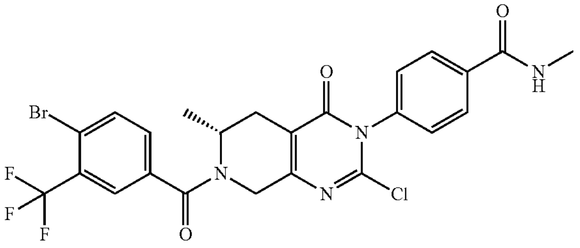 [SMILES: CNC(=O)c1ccc(-n2c(Cl)nc3c(c2=O)C[C@@H](C)N(C(=O)c2ccc(Br)c(C(F)(F)F)c2)C3)cc1]

To a solution of oxalyl dichloride (181 g, 1.43 mol) in $CH_2Cl_2$ (1.5 L) at −65° C. was added DMSO (111 mL) in $CH_2Cl_2$ (500 mL). After stirring for 1 h, t-butyl (R)-(1-hydroxypropan-2-yl)carbamate (250 g, 1.43 mol) in $CH_2Cl_2$ (500 mL) was added dropwise. After stirring for 2 h, $Et_3N$ (144 g, 1.43 mol, 198 mL) was added dropwise. The mixture was gradually warmed to 25° C. and then stirred at 25° C. for 4 h. The reaction was quenched by the addition of $NH_4Cl$ (sat., aq., 2.5 L), and then extracted with $CH_2Cl_2$ (2×2.5 L). The combined organic layers were dried over $Na_2SO_4$. The solids were removed by filtration and the filtrate was concentrated under reduced pressure to give the crude product as a colorless oil, t-butyl (R)-(1-oxopropan-2-yl)carbamate (450 g, 2.60 mol, 91% yield), which was used in the next step without further purification.

To a solution of t-butyl (R)-(1-oxopropan-2-yl)carbamate (225 g, 1.30 mol) in $CH_2Cl_2$ (2.25 L) was added (carbethoxymethylene)triphenylphosphorane (429 g, 1.23 mol). The mixture was stirred at 25° C. for 12 h. The mixture was concentrated under reduced pressure to give the crude product which was purified by silica gel column chromatography (PE:EA=15:1 to 5:1) to afford ethyl (R)-4-((t-butoxycarbonyl)amino)pent-2-enoate (500 g, 2.06 mol, 79.1% yield) as a colorless oil. $^1$HNMR (400 MHz, $CDCl_3$) δ 6.86 (dd, J=15.76, 4.88 Hz, 1H) 5.89 (dd, J=15.70, 1.56 Hz, 1H) 4.58 (br s, 1H) 4.39 (br s, 1H) 4.18 (q, J=7.13 Hz, 2H) 1.44 (s, 9H) 1.24-1.29 (m, 6H) ppm.

To a solution of ethyl (R)-4-((t-butoxycarbonyl)amino)pent-2-enoate (125 g, 513 mmol) in $CH_3OH$ (1.25 L) was added 10% Pd/C (6.00 g) and $Pd(OH)_2$ (6.06 g) under $N_2$. The suspension was degassed under vacuum and purged with $H_2$ (1.04 g, 514 mmol) several times. The mixture was stirred under $H_2$ (50 psi) at 50° C. for 12 h. The solids were removed by filtration under $N_2$, and the filtrate was evaporated to dryness to afford ethyl (R)-4-((t-butoxycarbonyl) amino)pentanoate (480 g, 1.96 mol, 95% yield) as a colorless oil. $^{1}$HNMR (400 MHz, $CDCl_3$) δ 4.29-4.45 (m, 1H) 4.13 (q, J=7.13 Hz, 2H) 3.57-3.75 (m, 1H) 2.35 (t, J=7.69 Hz, 2H) 1.66-1.84 (m, 3H) 1.43 (s, 9H) 1.25 (t, J=7.13 Hz, 3H) 1.14 (d, J=6.50 Hz, 3H) ppm.

To a solution of ethyl (R)-4-((t-butoxycarbonyl)amino) pentanoate (480 g, 1.96 mol) in EA (2 L) was added HCl in EA (4M, 2.5 L). The mixture was stirred at 25° C. for 2 h. The mixture was concentrated under reduced pressure to give ethyl (R)-4-aminopentanoate HCl (450 g, crude) as a yellow oil that was used directly in the next step without purification.

To mixture of ethyl (R)-4-aminopentanoate HCl (225 g, 1.24 mol) in THF (4 L) and $H_2O$ (1 L), was added $K_2CO_3$ (427 g, 3.10 mol) at 25° C. After addition, the yellow solution was stirred at 25° C. for 30 min. A solution of ethyl 2-bromoacetate (206 g, 1.24 mol, 137 mL) was dropwise at 25° C. over 30 min. The yellow solution was stirred at 25° C. for 11 h. The crude product, ethyl (R)-4-((2-ethoxy-2-oxoethyl)amino)pentanoate (400 g, 1.73 mol, 70% yield), was obtained as a colorless oil that used in the next step without work up or purification.

A solution of $(Boc)_2O$ (189 g, 865 mmol, 199 mL) was added dropwise into ethyl (R)-4-((2-ethoxy-2-oxoethyl) amino)pentanoate (200 g, 865 mmol) over 30 min. The yellow solution was stirred for 6 h at 25° C., and then pumped onto a filter. The filter cake was washed with EA (1 L), and the filtrate was collected. To the filtrate was added $H_2O$ (3 L). The mixture was extracted with EA (2×5 L). The combined organic layers were washed with brine (2 L) and dried over $Na_2SO_4$. The solids were removed by filtration. The filtrate was concentrated under reduced pressure to give the crude product, ethyl (R)-4-((t-butoxycarbonyl)(2-ethoxy-2-oxoethyl)amino)pentanoate (400 g, 1.21 mol, 70% yield), as a yellow oil, which used in the next step without purification. $^{1}$HNMR (400 MHz, $CDCl_3$) δ 4.06-4.22 (m, 4H) 3.54-3.93 (m, 2H) 2.26-2.55 (m, 2H) 1.71 (qd, J=7.48, 3.69 Hz, 2H) 1.45-1.55 (m, 6H) 1.42 (s, 4H) 1.22-1.35 (m, 6H) ppm.

To a mixture of ethyl (R)-4-((t-butoxycarbonyl)(2-ethoxy-2-oxoethyl)amino)pentanoate (200 g, 603 mmol) in THF (2 L) was added t-BuOK (135 g, 1.21 mol) at 0° C. under $N_2$. The yellow mixture was stirred at 25° C. for 12 h under $N_2$. The reaction was quenched by the addition of aq. citric acid (250 g in 3 L of $H_2O$) at below 10° C. The mixture was extracted with EA (3×2.5 L). The combined organic layers were washed with brine (2 L×1) and dried over $Na_2SO_4$. The solids were removed by filtration, and the filtrate was concentrated under reduced pressure. The residue was purified by silica column chromatography (PE: EA=15:1 to 10:1) to afford 1-(t-butyl) 4-ethyl 5-oxo-2-(R)-methyl-3,6-dihydropyridine-1,4(2H)-dicarboxylate (210 g, 736 mmol, 61% yield) as a yellow oil. $^{1}$H NMR (400 MHz, $CDCl_3$) δ 12.06 (s, 1H), 4.54 (br s, 1H), 4.33 (br d, J=19.39 Hz, 1H), 4.23 (dtt, J=10.62, 7.07, 7.07, 3.63, 3.63 Hz, 2H), 3.64 (br d, J=19.26 Hz, 1H), 2.45-2.55 (m, 1H), 2.18 (d, J=15.63 Hz, 1H), 1.47 (s, 9H) 1.31 (t, J=7.13 Hz, 3H), 1.11 (d, J=6.88 Hz, 3H) ppm.

To a solution of 1-(t-butyl) 4-ethyl 5-oxo-2-(R)-methyl-3,6-dihydropyridine-1,4(2H)-dicarboxylate (210 g, 736 mmol) in EA (1 L) was added a solution of HCl:EA (4 M, 2 L) dropwise at 25° C. The mixture was stirred at 25° C. for 3 h, and then concentrated under reduced pressure. The crude product was triturated with EA (500 mL) at 25° C. for 30 min to afford ethyl (R)-5-hydroxy-2-methyl-1,2,3,6-tetrahydropyridine-4-carboxylate HCl (140 g, 631 mmol, 86% yield, 100% purity) as a white solid. $^{1}$H NMR (400 MHz, Methanol-$d_4$) δ 4.29 (q, J=6.96 Hz, 2H), 3.92-4.01 (m, 1H), 3.77-3.87 (m, 1H), 3.42-3.54 (m, 1H), 2.66-2.76 (m, 1H), 2.23-2.39 (m, 1H), 1.43 (d, J=6.50 Hz, 3H), 1.32 (t, J=7.07 Hz, 3H) ppm.

A solution of ethyl (R)-5-hydroxy-2-methyl-1,2,3,6-tetrahydropyridine-4-carboxylate HCl (115 g, 519 mmol), in DMF (1 L) was cooled to 0° C. DIPEA (268 g, 2.08 mol, 361 mL), and $T_3P$ (495 g, 778 mmol, 463 mL, 50% purity) were added. The mixture was stirred at 25° C. for 12 h. The reaction was quenched by the addition water 2 L at 25° C. The mixture was diluted with EA (1.5 L) and extracted with EA (3×1 L). The combined organic layers were washed with brine (500 mL) and dried over $Na_2SO_4$. The solids were removed by filtration, and the filtrate was concentrated under reduced pressure. The residue was purified by silica gel chromatography (0 to 10% EA:PE gradient) to afford ethyl (R)-1-(4-bromo-3-(trifluoromethyl)benzoyl)-5-hydroxy-2-methyl-1,2,3,6-tetrahydropyridine-4-carboxylate (130 g, 259 mmol, 50% yield, 87% purity) as a yellow oil. $^{1}$H NMR ($CDCl_3$ 400 MHz), δ 12.10 (br s, 1H), 7.80 (d, J=8.13 Hz, 1H), 7.74 (d, J=1.88 Hz, 1H), 7.42 (dd, J=8.13, 1.88 Hz, 1H), 4.64-5.30 (m, 1H), 4.19-4.34 (m, 2H), 4.08-4.17 (m, 1H), 3.81 (br dd, J=12.13, 2.75 Hz, 1H), 2.58 (br d, J=14.76 Hz, 1H), 2.24 (br d, J=16.01 Hz, 1H), 1.32 (t, J=7.13 Hz, 3H), 1.25 (br t, J=3.13 Hz, 3H) ppm.

To a solution of ethyl (R)-1-(4-bromo-3-(trifluoromethyl) benzoyl)-5-hydroxy-2-methyl-1,2,3,6-tetrahydropyridine-4-carboxylate (90.0 g, 206 mmol) in ethanol (900 mL) was added $NH_4OAc$ (79.5 g, 1.03 mol). The mixture was stirred at 60° C. for 2 h. The mixture was concentrated under reduced pressure, diluted with water (200 mL) and extracted with EA (3×200 mL). The combined organic layers were washed with brine (200 mL) and dried over $Na_2SO_4$. The solids were removed by filtration, and the filtrate was concentrated under reduced pressure. The residue was purified by silica gel chromatography (0 to 50% EA:PE gradient) to afford ethyl (R)-5-amino-1-(4-bromo-3-(trifluoromethyl)benzoyl)-2-methyl-1,2,3,6-tetrahydropyridine-4-carboxylate (55.0 g, 125 mmol, 61% yield, 99% purity) as a yellow solid. $^{1}$H-NMR (DMSO-$d_6$, 400 MHz) δ 7.98 (d, J=8.13 Hz, 1H), 7.84 (d, J=1.75 Hz, 1H), 7.63 (dd, J=8.19, 1.56 Hz, 1H), 6.74-7.47 (m, 2H), 4.63-4.91 (m, 1H), 4.00-4.08 (m, 2H), 3.80-3.95 (m, 1H), 3.59-3.75 (m, 1H), 2.45 (br d, J=5.75 Hz, 1H), 2.14 (br d, J=1.25 Hz, 1H), 1.06-1.20 (m, 6H) ppm.

To a solution of ethyl (R)-5-amino-1-(4-bromo-3-(trifluoromethyl)benzoyl)-2-methyl-1,2,3,6-tetrahydropyridine-4-carboxylate (100 g, 230 mmol) and NMM (102 g, 1.01 mol, 111 mL) in $CH_2Cl_2$ (1 L) was added $SCCl_2$ (55.5 g, 483 mmol, 37.0 mL) at 0° C. The mixture was stirred at 0° C. for 1 h. The reaction was quenched by the addition ice-water (100 mL) at 0° C. The mixture was diluted with $CH_2Cl_2$ (150 mL) and extracted with $CH_2Cl_2$ (3×500 mL). The combined organic layers were washed with brine (500 mL) and dried over $Na_2SO_4$. The solids were removed by filtration, and the solvent of the filtrate was concentrated under reduced pressure. The residue was purified by silica gel chromatography (0 to 20% EA:PE gradient) to afford ethyl (R)-1-(4-bromo-3-(trifluoromethyl)benzoyl)-5-isothiocyanato-2-methyl-1,2,3,6-tetrahydropyridine-4-carboxylate (100 g, 163 mmol, 71% yield, 78% purity) as a yellow oil. $^{1}$H-NMR ($CDCl_3$, 400 MHz) δ 7.74 (d, J=8.13 Hz, 1H), 7.66 (d, J=1.75 Hz, 1H), 7.34 (dd, J=8.13, 2.00 Hz, 1H), 4.55-5.18 (m, 1H), 4.14-4.26 (m, 3H), 3.67-3.85 (m, 2H), 2.51-2.70 (m, 1H), 2.31-2.47 (m, 1H), 1.29 (t, J=7.13 Hz, 3H), 1.18 (dd, J=7.00, 3.38 Hz, 4H) ppm.

To a solution of ethyl (R)-1-(4-bromo-3-(trifluoromethyl)benzoyl)-5-isothiocyanato-2-methyl-1,2,3,6-tetrahydropyridine-4-carboxylate (100 g, 210 mmol) in $CH_3CN$ (1 L) were added 4-amino-N-methylbenzamide (31.5 g, 210 mmol) and $Et_3N$ (53.0 g, 524 mmol, 72.9 mL). The mixture was stirred at 95° C. for 12 h to obtain a yellow suspension. The mixture was concentrated under reduced pressure. The crude product was triturated with EA (500 mL) at 25° C. for 1 h to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 119 mmol, 57% yield, 86% purity) as a white solid. $^1$H-NMR (DMSO-$d_6$, 400 MHz) δ 8.49-8.57 (m, 1H), 8.02 (br d, J=7.63 Hz, 1H), 7.88 (m, 3H), 7.69 (br d, J=7.63 Hz, 1H), 7.29 (br d, J=8.88 Hz, 1H), 7.25 (br s, 1H), 5.08-5.27 (m, 1H), 4.18-4.35 (m, 1H), 4.05-4.14 (m, 1H), 2.80 (d, J=4.50 Hz, 3H), 2.53-2.62 (m, 1H), 2.17-2.36 (m, 1H), 1.18-1.20 (m, 3H) ppm.

To a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 138 mmol) in dioxane (880 mL) was added $SCCl_2$ (31.6 g, 275 mmol, 21.1 mL). The mixture was stirred at 100° C. for 2 h and then concentrated under reduced pressure. The residue was purified by silica gel chromatography (0 to 80% EA:PE gradient) to afford 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (49.0 g, 81.5 mmol, 59% yield, 97% purity) as an off-white solid. $^1$H-NMR ($CD_3OD$, 400 MHz) δ 7.94-8.03 (m, 3H), 7.90 (d, J=1.75 Hz, 1H), 7.61-7.68 (m, 1H), 7.42-7.54 (m, 2H), 5.02-5.49 (m, 1H), 4.13-4.56 (m, 2H), 2.95 (s, 3H), 2.72-2.86 (m, 1H), 2.56 (br d, J=17.89 Hz, 1H), 1.24-1.38 (m, 3H) ppm.

Example 1

Compound 1

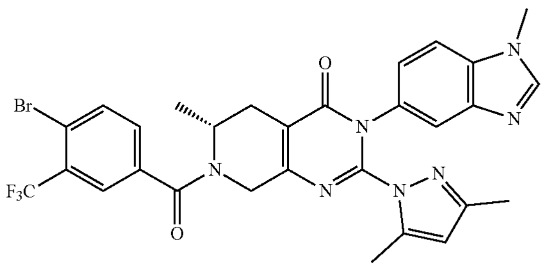 [SMILES: Cc1cc(C)n(-c2nc3c(c(=O)n2-c2ccc4c(c2)ncn4C)C[C@@H](C)N(C(=O)c2ccc(Br)c(C(F)(F)F)c2)C3)n1]

Triethylamine (159 mg, 1.57 mmol) was added to a solution of ethyl-(R)-1-(4-bromo-3-(trifluoromethyl)benzoyl)-5-isothiocyanato-2-methyl-1,2,3,6-tetrahydropyridine-4-carboxylate (500 mg, 1.048 mmol) and 1-methyl-1H-1,3-benzodiazol-5-amine (185 mg, 1.26 mmol) in anhydrous $CH_3CN$ (10 mL) under $N_2$. The mixture was stirred at 95° C. for 1 h. The mixture was evaporated to dryness and purified by chromatography on silica gel (0 to 5% $CH_3OH$ in $CH_2Cl_2$) to afford (R)-7-(4-bromo-3-(trifluoromethyl)benzoyl)-6-methyl-3-(1-methyl-1H-benzo[d]imidazol-5-yl)-2-thioxo-2,3,5,6,7,8-hexahydropyrido[3,4-d]pyrimidin-4(1H)-one (414 mg, 68%) as a yellow solid. $^1$H-NMR (DMSO, 400 MHz, 80° C.) δ 1.25 (d, J=7.8 Hz, 3H), 2.28-2.37 (m, 1H), 2.54-2.63 (m, 1H), 3.87 (s, 3H), 4.04-4.15 (m, 1H), 4.39-4.64 (m, 1H), 4.70-4.97 (m, 1H), 6.98-7.09 (m, 1H), 7.42 (d, J=15.7 Hz, 1H), 7.59 (d, J=8.8 Hz, 1H), 7.65-7.70 (m, 1H), 7.88 (s, 1H), 8.0 (m, 1H), 8.18 (s, 1H), 12.33 (brs, 1H) ppm. LC-MS: $C_{24}H_{19}BrF_3N_5O_2S$ $[M+H]^+$: 578.

$SO_2Cl_2$ (0.14 mL, 1.73 mmol) was added to a solution of (R)-7-(4-bromo-3-(trifluoromethyl)benzoyl)-6-methyl-3-(1-methyl-1H-benzo[d]imidazol-5-yl)-2-thioxo-2,3,5,6,7,8-hexahydropyrido[3,4-d]pyrimidin-4(1H)-one (500 mg, 0.86 mmol) in $CHCl_3$ (10 mL) under $N_2$. The mixture was stirred at rt for 1 h. The mixture was evaporated to dryness to afford (R)-7-(4-bromo-3-(trifluoromethyl)benzoyl)-2-chloro-6-methyl-3-(1-methyl-1H-benzo[d]imidazol-5-yl)-5,6,7,8-tetrahydropyrido[3,4-d]pyrimidin-4(3H)-one as a crude product, which was directly used in the next step.

Hydrazine monohydrate (55.4 mg, 0.86 mmol) was added to a solution of (R)-7-(4-bromo-3-(trifluoromethyl)benzoyl)-2-chloro-6-methyl-3-(1-methyl-1H-benzo[d]imidazol-5-yl)-5,6,7,8-tetrahydropyrido[3,4-d]pyrimidin-4(3H)-one (500 mg, 0.86 mmol) in EtOH (7 mL). The mixture was stirred at 100° C. for 1 h and then concentrated to dryness to obtain (R)-7-(4-bromo-3-(trifluoromethyl)benzoyl)-2-hydrazineyl-6-methyl-3-(1-methyl-1H-benzo[d]imidazol-5-yl)-5,6,7,8-tetrahydropyrido[3,4-d]pyrimidin-4(3H)-one as a crude product, which was directly used in the next step.

Acetylacetone (0.089 mL, 0.87 mmol) was added to a solution of (R)-7-(4-bromo-3-(trifluoromethyl)benzoyl)-2-hydrazineyl-6-methyl-3-(1-methyl-1H-benzo[d]imidazol-5-yl)-5,6,7,8-tetrahydropyrido[3,4-d]pyrimidin-4(3H)-one (500 mg, 0.87 mmol) in EtOH (8.52 mL). The mixture was stirred and heated at 100° C. for 18 h. The mixture was evaporated to dryness to afford the crude product which was purified by flash chromatography on silica gel (0 to 10% $CH_3OH$ in DCM) to afford a yellow solid. The corresponding solid was purified by reverse phase chromatography (5 to 100% $CH_3OH$ in water (+0.1% formic acid) to afford (R)-7-(4-bromo-3-(trifluoromethyl)benzoyl)-2-(3,5-dimethyl-1H-pyrazol-1-yl)-6-methyl-3-(1-methyl-1H-benzo[d]imidazol-5-yl)-5,6,7,8-tetrahydropyrido[3,4-d]pyrimidin-4(3H)-one (1) (110 mg, 20%) as a white solid. $^1$H-NMR (DMSO-$d_6$, 400 MHz, 80° C.) δ 1.26 (d, J=6.9 Hz, 3H), 1.81 (s, 3H), 2.28 (s, 3H), 2.52-2.58 (m, 1H), 2.72-2.82 (m, 1H), 2.83 (s, 3H), 4.27 (d, J=20.3 Hz, 1H), 4.56 (br. s., 1H), 4.78 (br. s., 1H), 5.73 (s, 1H), 7.11 (d, J=9.0 Hz, 1H), 7.45-7.51 (m, 2H), 7.71 (dd, J=8.4 Hz, 2.1 Hz, 1H), 7.89 (d, J=1.9 Hz, 1H), 8.00 (d, J=8.2 Hz, 1H), 8.14 (s, 1H) ppm. LC-MS: $C_{29}H_{25}BrF_3N_7O_2$ $[M+H]^+$: 640/642.

Example 2

Compound 2

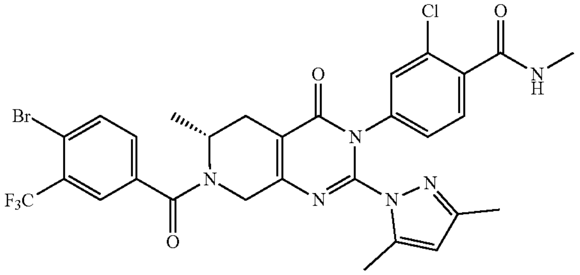 [SMILES: CNC(=O)c1ccc(-n2c(-n3nc(C)cc3C)nc3c(c2=O)C[C@@H](C)N(C(=O)c2ccc(Br)c(C(F)(F)F)c2)C3)cc1Cl]

$NEt_3$ (0.57 mL, 4.08 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1.3 g, 2.72 mmol) and 4-amino-2-chloro-N-methylbenzamide (0.55 g, 3 mmol) in anhydrous $CH_3CN$ (20 mL) under $N_2$. The mixture was stirred at 80° C. for 22 h. The reaction mixture was then evaporated to dryness and purified by chromatography on silica gel (0 to 2.5% $CH_3OH$ in $CH_2Cl_2$) to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-2-chloro-N-methylbenzamide (660 mg, 39%) as a yellow solid. $^1$H-NMR (DMSO-$d_6$, 400 MHz) δ 1.21 (br.s, 3H), 2.27 (br.s, 1H), 2.44 (br.s, 1H), 2.76 (d, J=4.6 Hz, 3H), 3.99-4.08 (br.s, 1H), 4.23 (br.s, 1H), 5.10 (br.s, 1H), 7.25 (m, 1H), 7.45 (m, 1H), 7.5 (m, 1H), 7.68 (m, 1H), 7.90 (br.s, 1H), 8.02 (d, J=8.0 Hz, 1H), 8.52 (m, 1H), 12.89 (br.s, 1H) ppm. LC-MS: $C_{24}H_{19}BrF_3N_4O_3S$ $[M+H]^+$: 615.

Thiophosgene (0.045 mL, 0.49 mmol) was added to a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-2-chloro-N-methylbenzamide (300 mg, 0.49 mmol) in anhydrous dioxane (10 mL) under $N_2$. The mixture was stirred at 100° C. for 0.5 h and then evaporated to dryness to afford (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-2-chloro-N-methylbenzamide as crude product, which was directly used in the next step.

Hydrazine monohydrate (31.1 mg, 0.49 mmol) was added to a solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-2-chloro-N-methylbenzamide (300 mg, 0.49 mmol) in EtOH (4 mL). The mixture was stirred at 100° C. for 1 h. The mixture was evaporated to dryness to afford the crude product which was purified by reverse phase chromatography (C18 column, 5 to 100% $CH_3CN$ in water (+0.1% formic acid) to afford (R)-4-(7-(4-bromo-3-(trifluoromethyl)benzoyl)-2-hydrazineyl-6-methyl-4-oxo-5,6,7,8-tetrahydropyrido[3,4-d]pyrimidin-3(4H)-yl)-2-chloro-N-methylbenzamide (270 mg, 90%) as a white solid. LC-MS: $C_{24}H_{21}BrClF_3N_6O_3$ $[M+H]^+$: 613/615.

Acetylacetone (0.045 mL, 0.44 mmol) was added to a solution of (R)-4-(7-(4-bromo-3-(trifluoromethyl)benzoyl)-2-hydrazineyl-6-methyl-4-oxo-5,6,7,8-tetrahydropyrido[3,4-d]pyrimidin-3(4H)-yl)-2-chloro-N-methylbenzamide (270 mg, 0.44 mmol) in EtOH (4.5 mL). The mixture was stirred and heated at 100° C. for 2 days. The mixture was evaporated to dryness to give the crude product which was purified by reverse phase chromatography C18 (5 to 100% $CH_3CN$ in water (+0.1% formic acid) to afford (R)-4-(7-(4-bromo-3-(trifluoromethyl)benzoyl)-2-(3,5-dimethyl-1H-pyrazol-1-yl)-6-methyl-4-oxo-5,6,7,8-tetrahydropyrido[3,4-d]pyrimidin-3(4H)-yl)-2-chloro-N-methylbenzamide (2) (98 mg, 33%) as a white solid. $^1$H-NMR ($CDCl_3$, 400 MHz) δ 1.26 (d, J=6.7 Hz, 3H), 1.91 (s, 3H), 2.33 (s, 3H), 2.51-2.57 (m, 1H), 2.71-2.79 (m, 4H), 4.26 (d, J=17.7 Hz, 1H), 4.55 (br. s., 1H), 4.77 (br. s., 1H), 5.88 (s, 1H), 7.22 (dd, J=8.1 Hz, 1.5 Hz, 1H), 7.36-7.43 (m, 2H), 7.69 (dd, J=8.1 Hz, 1.5 Hz, 1H), 7.88 (d, J=1.8 Hz, 1H), 8.00 (d, J=8.1 Hz, 1H), 8.10-8.17 (m, 1H) ppm. LC-MS: $C_{29}H_{25}BrClF_3N_6O_3$ $[M+H]^+$: 677/679.

Example 3

Compound 3

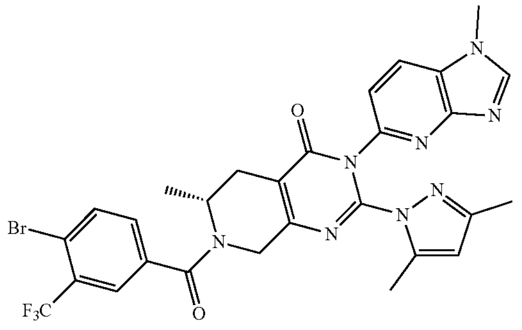 [SMILES: Cc1cc(C)n(-c2nc3c(c(=O)n2-c2ccc4c(ncn4C)n2)C[C@@H](C)N(C(=O)c2ccc(Br)c(C(F)(F)F)c2)C3)n1]

MeI (1.1 eq., 0.14 mL, 2.28 mmol) and DBU (1.2 eq., 0.38 g, 0.37 mL, 2.49 mmol) were added to a solution of (R)-7-(4-bromo-3-(trifluoromethyl)benzoyl)-6-methyl-3-(1-methyl-1H-imidazo[4,5-b]pyridin-5-yl)-2-thioxo-2,3,5,6,7,8-hexahydropyrido[3,4-d]pyrimidin-4(1H)-one (1 eq., 1.2 g, 2.071 mmol) in anhydrous DMF (15 mL) cooled at 0°. The mixture was stirred at rt for 1 h. followed by the addition of water (50 mL) and EA (50 mL) to the mixture. The aqueous phase was extracted with EA (2×50 mL). The combined organic layers were washed with HCl 1N (lx 25 mL), water (2×25 mL) and brine (lx 25 mL), and dried over $Na_2SO_4$. The solids were removed by filtration and the filtrate was evaporated to dryness to give (R)-7-(4-bromo-3-(trifluoromethyl)benzoyl)-6-methyl-3-(1-methyl-1H-imidazo[4,5-b]pyridin-5-yl)-2-(methylthio)-5,6,7,8-tetrahydropyrido[3,4-d]pyrimidin-4(3H)-one (1.2 g, 99%) as a brown solid. LCMS: $C_{24}H_{20}BrF_3N_6O_2S$ $[M+H]^+$: 593/595.

mCPBA (1.2 eq., 0.77 g, 2.47 mmol) was added to a solution of (R)-7-(4-bromo-3-trifluoromethyl)benzoyl)-6-methyl-3-(1-methyl-1H-imidazo[4,5-b]pyridin-5-yl)-2-(methylthio)-5,6,7,8-tetrahydropyrido[3,4-d]pyrimidin-4(3H)-one (1 eq., 1.22 g, 2.056 mmol) in anhydrous DCM (100 mL) at 0° C. The mixture was stirred at rt for 1 h and then sat. aq. $NaHCO_3$ was added. The aqueous phase was extracted with DCM (3×25 mL). The combined organic layers were washed with brine (1×25 mL) and dried over $Na_2SO_4$. The solids were removed by filtration and the filtrate was evaporated to dryness to give (6R)-7-(4-bromo-3-(trifluoromethyl)benzoyl)-6-methyl-3-(1-methyl-1H-imidazo[4,5-b]pyridin-5-yl)-2-(methylsulfinyl)-5,6,7,8-tetrahydropyrido[3,4-d]pyrimidin-4(3H)-one (1.25 g, 99%) as a beige solid. LCMS: $C_{24}H_{20}BrF_3N_6O_3S$ $[M+H]^+$: 609/611.

Hydrazine monohydrate (3 eq., 0.39 g, 6.15 mmol) was added to a solution of (6R)-7-(4-bromo-3-(trifluoromethyl)benzoyl)-6-methyl-3-(1-methyl-1H-imidazo[4,5-b]pyridin-5-yl)-2-(methylsulfinyl)-5,6,7,8-tetrahydropyrido[3,4-d]pyrimidin-4(3H)-one (1 eq., 1.25 g, 2.05 mmol) in EtOH (12 mL). The mixture was stirred at 100° C. fort 1 h, The mixture was evaporated to dryness to give the crude product. The crude product was purified by flash chromatography on silica gel (from 0 to 100% of EA in CyH, then, from 0 to 10% of MeOH in DCM) to afford (R)-7-(4-bromo-3-(trifluoromethyl)benzoyl)-2-hydrazineyl-6-methyl-3-(1-methyl-1H-imidazo[4,5-b]pyridin-5-yl)-5,6,7,8-tetrahydropyrido[3,4-d]pyrimidin-4(3H)-one (905 mg, 76%) as a beige solid. LCMS: $C_{23}H_{20}BrF_3N_8O_2$ [M+H]+: 577/579.

Acetylacetone (1 eq., 0.16 mL, 1.56 mmol) was added to a solution of (R)-7-(4-bromo-3-(trifluoromethyl)benzoyl)-2-hydrazineyl-6-methyl-3-(1-methyl-1H-imidazo[4,5-b]pyridin-5-yl)-5,6,7,8-tetrahydropyrido[3,4-d]pyrimidin-4(3H)-one (1 eq., 900 mg, 1.56 mmol) in EtOH (15 mL). The mixture was stirred and heated at 100° C. for 18 h. The mixture was evaporated to dryness and purified by flash chromatography on silica gel (from 0 to 100% of EA in CyH, then, from 0 to 10% of MeOH in DCM) to afford a yellow solid. The solid was purified by reverse phase chromatography (from 5 to 100% of MeCN in $H_2O$ (+0.1% FA)) to afford (R)-7-(4-bromo-3-(trifluoromethyl)benzoyl)-2-(3,5-dimethyl-1H-pyrazol-1-yl)-6-methyl-3-(1-methyl-1H-imidazo[4,5-b]pyridin-5-yl)-5,6,7,8-tetrahydropyrido[3,4-d]pyrimidin-4(3H)-one (405 mg, 41%) as a white solid. $^1$H-NMR (DMSO-$d_6$, 400 MHz, 80° C.) δ 1.27 (d, J=6.7 Hz, 3H), 1.72 (s, 3H), 2.38 (s, 3H), 2.52-2.58 (m, 1H), 2.73-2.84 (m, 1H), 3.88 (s, 3H), 4.29 (d, J=19.4 Hz, 1H), 4.56 (br. s., 1H), 4.80 (br. s., 1H), 5.76 (s, 1H), 7.37 (d, J=8.3H, 1H), 7.72 (dd, J=8.1 Hz, 1.6 Hz, 1H), 7.91 (d, J=1.5 Hz, 1H), 7.99 (d, J=8.2 Hz, 1H), 8.08 (d, J=8.2 Hz, 1H), 8.37 (s, 1H) ppm. LCMS: $C_{28}H_{24}BrF_3N_8O_2$ [M+H]$^+$: 641/643.

Example 4

Compound 4

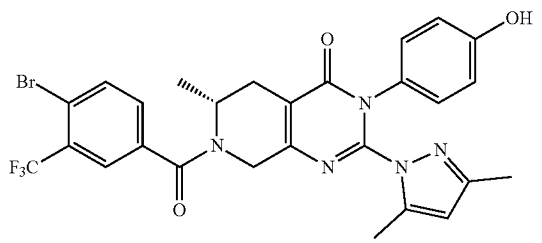 [SMILES: Cc1cc(C)n(-c2nc3c(c(=O)n2-c2ccc(O)cc2)C[C@@H](C)N(C(=O)c2ccc(Br)c(C(F)(F)F)c2)C3)n1]

Hydrazine hydrate (10 eq., 0.42 mL, 6.65 mmol) was added to a solution of crude (R)-7-(4-bromo-3-(trifluoromethyl)benzoyl)-2-chloro-3-(4-hydroxyphenyl)-6-methyl-5,6,7,8-tetrahydropyrido[3,4-d]pyrimidin-4(3H)-one (1 eq., 361 mg, 0.67 mmol) in EtOH (5 mL) under $N_2$. The mixture was stirred at 25° C. for 18 h. The mixture was evaporated to dryness to give a yellow solid which was purified by flash chromatography on silica gel (DCM/MeOH from 100:0 to 90:10) to give (R)-7-(4-bromo-3-(trifluoromethyl)benzoyl)-2-hydrazineyl-3-(4-hydroxyphenyl)-6-methyl-5,6,7,8-tetrahydropyrido[3,4-d]pyrimidin-4(3H)-one (210 mg, 59%) as a yellow solid. LCMS: $C_{22}H_{19}BrF_3N_5O_3$ [M+H]$^+$: 538/540.

A solution of (R)-7-(4-bromo-3-(trifluoromethyl)benzoyl)-2-hydrazineyl-3-(4-hydroxyphenyl)-6-methyl-5,6,7,8-tetrahydropyrido[3,4-d]pyrimidin-4(3H)-one (1 eq., 210 mg, 0.39 mmol) and acetylacetone (2 eq., 0.0801 mL, 0.78 mmol) in EtOH (4 mL) was heated to 100° C. for 1 h. The mixture was evaporated to dryness to give a yellow oil which was purified by flash chromatography on silica gel (DCM:MeOH from 100:0 to 90:10) to give (R)-7-(4-bromo-3-(trifluoromethyl)benzoyl)-2-(3,5-dimethyl-1H-pyrazol-1-yl)-3-(4-hydroxyphenyl)-6-methyl-5,6,7,8-tetrahydropyrido[3,4-d]pyrimidin-4(3H)-one (170 mg, 72%) as a light yellow solid. LCMS: $C_{27}H_{23}BrF_3N_5O_3$ [M+H]$^+$: 602/604. $^1$H-NMR (DMSO-$d_6$, 400 MHz, 80° C.) δ 1.25 (d, J=6.7 Hz, 3H), 1.91 (s, 3H), 2.24 (s, 3H), 2.52-2.59 (m, 1H), 2.69-2.80 (m, 1H), 4.19-4.30 (m, 1H), 4.39-4.90 (m, 2H), 5.80 (s, 1H), 6.63-6.69 (m, 2H), 6.91-6.91 (m, 2H), 7.69 (dd, J=8.2 Hz, 1.8 Hz, 1H), 7.88 (d, J=1.8 Hz, 1H), 7.99 (d, J=8.3 Hz, 1H), 9.36 (s, 1H) ppm.

Example 5

Compound 5

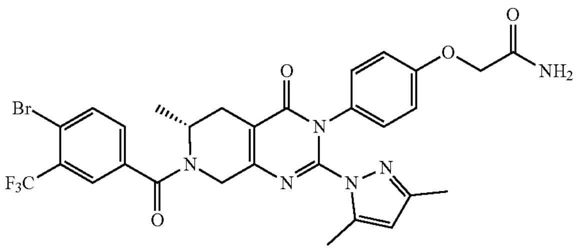 [SMILES: Cc1cc(C)n(-c2nc3c(c(=O)n2-c2ccc(OCC(N)=O)cc2)C[C@@H](C)N(C(=O)c2ccc(Br)c(C(F)(F)F)c2)C3)n1]

$K_2CO_3$ (3 eq., 117.004 mg, 0.85 mmol) was added to a solution of (R)-7-(4-bromo-3-(trifluoromethyl)benzoyl)-2-(3,5-dimethyl-1H-pyrazol-1-yl)-3-(4-hydroxyphenyl)-6-methyl-5,6,7,8-tetrahydropyrido[3,4-d]pyrimidin-4(3H)-one (1 eq., 170 mg, 0.28 mmol) and 2-bromoacetamide (2 eq., 77.87 mg, 0.56 mmol) in anhydrous MeCN (10 mL). The mixture was heated at 75° C. for 19 h, and then diluted with EA/iPrOH (85:15). The mixture was washed with sat. aq. $NaHCO_3$ and brine, and dried over $Na_2SO_4$. The solids were removed by filtration and the filtrate was evaporated to dryness to give a white solid which was purified by flash chromatography on silica gel (DCM:MeOH from 100:0 to 90:10) to give (R)-2-(4-(7-(4-bromo-3-(trifluoromethyl)benzoyl)-2-(3,5-dimethyl-1H-pyrazol-1-yl)-6-methyl-4-oxo-5,6,7,8-tetrahydropyrido[3,4-d]pyrimidin-3(4H)-yl)phenoxy)acetamide (126 mg, 68%) as a white solid. LCMS: $C_{29}H_{26}BrF_3N_6O_4$ [M+H]$^+$: 659/661. $^1$H-NMR (DMSO-$d_6$, 400 MHz, 80° C.) δ 1.26 (d, J=6.9 Hz, 3H), 1.90 (s, 3H), 2.27 (s, 3H), 2.51-2.58 (m, 1H), 2.70-2.80 (m, 1H), 4.18-4.31 (m, 1H), 4.40 (s, 2H), 4.44-4.92 (m, 2H), 5.81 (s, 1H), 6.90 (d, J=8.7 Hz, 2H), 7.10 (d, J=8.7 Hz, 2H), 7.08-7.31 (m, 2H), 7.69 (dd, J=8.2 Hz, 1.8 Hz, 1H), 7.88 (d, J=1.8 Hz, 1H), 7.99 (d, J=8.1 Hz, 1H) ppm.

Example 6

Compound 6

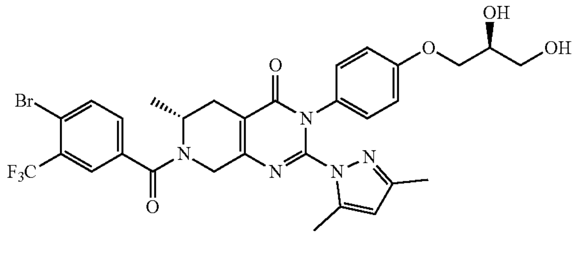 [SMILES: Cc1cc(C)n(-c2nc3c(c(=O)n2-c2ccc(OC[C@@H](O)CO)cc2)C[C@@H](C)N(C(=O)c2ccc(Br)c(C(F)(F)F)c2)C3)n1]

$K_2CO_3$ (3 eq., 206 mg, 1.49 mmol) was added to a solution of (R)-7-(4-bromo-3-(trifluoromethyl)benzoyl)-2-(3,5-dimethyl-1H-pyrazol-1-yl)-3-(4-hydroxyphenyl)-6-methyl-5,6,7,8-tetrahydropyrido[3,4-d]pyrimidin-4(3H)-one (1 eq., 300 mg, 0.5 mmol) and (S)-(2,2-dimethyl-1,3-dioxolan-4-yl)methyl 4-methylbenzenesulfonate 2 (2 eq., 285 mg, 1 mmol) in anhydrous MeCN (15 mL). The mixture was heated at 100° C. for 4 days and then diluted with EA:iPrOH (85:15). The mixture was washed with sat. aq. $NaHCO_3$ and brine, and dried over $Na_2SO_4$. The solids were removed by filtration and the filtrate was evaporated to dryness to give a white solid which was purified by flash chromatography on silica gel (DCM/MeOH from 100:0 to 90:10) to give (R)-7-(4-bromo-3-(trifluoromethyl)benzoyl)-3-(4-(((R)-2,2-dimethyl-1,3-dioxolan-4-yl)methoxy)phenyl)-2-(3,5-dimethyl-1H-pyrazol-1-yl)-6-methyl-5,6,7,8-tetrahydropyrido[3,4-d]pyrimidin-4(3H)-one (334 mg, 94%) as a white solid. $^1$H-NMR (DMSO-$d_6$, 400 MHz) δ 1.18-1.36 (m, 3H), 1.29 (s, 3H), 1.34 (s, 3H), 1.88 (s 3H), 2.12-2.37 (m, 4H), 2.68-2.80 (m, 1H), 3.67-3.74 (m, 1H), 3.90-4.26 (m, 5H), 4.33-4.42 (m, 1H), 4.93-5.30 (m, 1H), 5.83 (s, 1H), 6.82-6.94 (m, 2H), 6.98-7.22 (m, 2H), 7.71 (dd, J=8.3 Hz, 1.4 Hz, 1H), 7.91 (d, J=1.6 Hz, 1H), 8.01 (d, J=8.4 Hz, 1H) ppm. LCMS: $C_{33}H_{33}BrF_3N_5O_5$ $[M+H]^+$: 716/718.

HCl (10 eq., 4.66 mL, 4.66 mmol) was added to a solution of (R)-7-(4-bromo-3-(trifluoromethyl)benzoyl)-3-(4-(((R)-2,2-dimethyl-1,3-dioxolan-4-yl)methoxy)phenyl)-2-(3,5-dimethyl-1H-pyrazol-1-yl)-6-methyl-5,6,7,8-tetrahydropyrido[3,4-d]pyrimidin-4(3H)-one (1 eq., 334 mg, 0.47 mmol) in THF (16 mL). The mixture was stirred at rt for 18 h, diluted with EA/iPrOH (85:15) and neutralized by the addition of sat. aq. $NaHCO_3$. The layers were separated and the aqueous layer was extracted with EA:iPrOH (85:15). The combined organic layers were washed with brine and dried over $Na_2SO_4$. The solids were removed by filtration and the filtrate was evaporated to dryness to give a yellow sticky solid which was purified by flash chromatography on silica gel (DCM/MeOH from 100:0 to 90:10) to give (R)-7-(4-bromo-3-(trifluoromethyl)benzoyl)-3-(4-((S)-2,3-dihydroxypropoxy)phenyl)-2-(3,5-dimethyl-1H-pyrazol-1-yl)-6-methyl-5,6,7,8-tetrahydropyrido[3,4-d]pyrimidin-4(3H)-one (151 mg, 48%) as a white solid. $^1$H-NMR (DMSO-$d_6$, 400 MHz, 80° C.) δ 1.26 (d, J=6.8 Hz, 3H), 1.91 (s, 3H), 2.25 (s, 3H), 2.51-2.58 (m, 1H), 2.70-2.80 (m, 1H), 3.46 (t, J=5.5 Hz, 2H), 3.73-3.82 (m, 1H), 3.83-3.90 (m, 1H), 3.99 (dd, J=10.0 Hz, 4.3 Hz, 1H), 4.25 (d, J=19.1 Hz, 1H), 4.35 (t, J=5.7 Hz, 1H), 4.43-4.90 (m, 2H), 4.63 (d, J=4.7 Hz, 1H), 5.80 (s, 1H), 6.86 (d, J=9.1 Hz, 2H), 7.07 (d, J=8.9 Hz, 2H), 7.69 (dd, J=8.3 Hz, 2.0 Hz, 1H), 7.88 (d, J=1.8 Hz, 1H), 7.99 (d, J=8.2 Hz, 1H) ppm. LCMS: $C_{30}H_{29}BrF_3N_5O_5$ $[M+H]^+$: 676/678.

Example 7

Compound 7

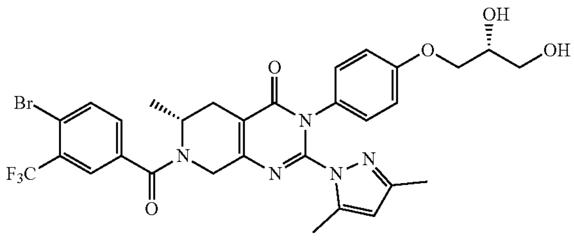 [SMILES: Cc1cc(C)n(-c2nc3c(c(=O)n2-c2ccc(OC[C@H](O)CO)cc2)C[C@@H](C)N(C(=O)c2ccc(Br)c(C(F)(F)F)c2)C3)n1]

(R)-7-(4-bromo-3-(trifluoromethyl)benzoyl)-3-(4-((R)-2,3-dihydroxypropoxy)phenyl)-2-(3,5-dimethyl-1H-pyrazol-1-yl)-6-methyl-5,6,7,8-tetrahydropyrido[3,4-d]pyrimidin-4(3H)-one was synthesized following the route described for the synthesis of Compound 24, using (R)-(2,2-dimethyl-1,3-dioxolan-4-yl)methyl 4-methylbenzenesulfonate in place of (S)-(2,2-dimethyl-1,3-dioxolan-4-yl)methyl 4-methylbenzenesulfonate in the penultimate step. $^1$H-NMR (DMSO-$d_6$, 400 MHz, 80° C.) δ 1.26 (d, J=6.8 Hz, 3H), 1.91 (s, 3H), 2.25 (s, 3H), 2.51-2.57 (m, 1H), 2.71-2.80 (m, 1H), 3.46 (t, J=5.7 Hz, 2H), 3.74-3.83 (m, 1H), 3.84-3.90 (m, 1H), 3.99 (dd, J=10.0 Hz, 4.3 Hz, 1H), 4.25 (d, J=19.4 Hz, 1H), 4.36 (t, J=5.7 Hz, 1H), 4.44-4.92 (m, 2H), 4.63 (d, J=5.0 Hz, 1H), 5.80 (s, 1H), 6.86 (d, J=9.3 Hz, 2H), 7.07 (d, J=8.6 Hz, 2H), 7.69 (dd, J=7.9 Hz, 1.4 Hz, 1H), 7.88 (d, J=1.4 Hz, 1H), 7.99 (d, J=8.3 Hz, 1H) ppm. LCMS: $C_{30}H_{29}BrF_3N_5O_5$ [M+H]+: 676/678.

Example 8

Compound 8

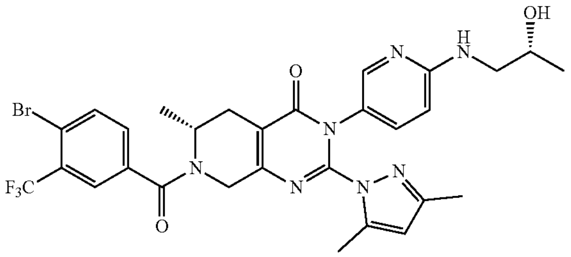 [SMILES: Cc1cc(C)n(-c2nc3c(c(=O)n2-c2ccc(NC[C@@H](C)O)nc2)C[C@@H](C)N(C(=O)c2ccc(Br)c(C(F)(F)F)c2)C3)n1]

AcOOH 35% in AcOH (4 eq., 24 mL, 1.27 mmol) was added to a solution of (R)-7-(4-bromo-3-(trifluoromethyl)benzoyl)-3-(6-(((R)-2-hydroxypropyl)amino)pyridin-3-yl)-6-methyl-2-thioxo-2,3,5,6,7,8-hexahydropyrido[3,4-d]pyrimidin-4(1H)-one (1 eq., 190 mg, 0.32 mmol) and hydrazine monohydrate (10 eq., 0.15 mL, 3.17 mmol) in isopropanol (10 mL). The mixture was stirred at rt for 16 h and then pentan-2,4-dione (20 eq., 0.65 mL, 6.35 mmol) was added. The mixture was stirred at 100° C. for 2 h. The mixture was evaporated to dryness and purified by flash chromatography on silica gel (from 0 to 100% of EA, then, from 0 to 10% of MeOH in DCM) to give a yellow solid which was purified by reverse flash chromatography (from 5 to 100% of MeCN in water (+0.1% of FA)) to afford (R)-7-(4-bromo-3-(trifluoromethyl)benzoyl)-2-(3,5-dimethyl-1H-pyrazol-1-yl)-3-(6-(((R)-2-hydroxypropyl)amino)pyridin-3-yl)-6-methyl-5,6,7,8-tetrahydropyrido[3,4-d]pyrimidin-4(3H)-one (105 mg, 50%) as a white solid. $^1$H-NMR (DMSO-$d_6$, 400 MHz, 80° C.) δ 1.07 (d, J=6.3 Hz, 3H), 1.25 (d, J=6.8 Hz, 3H), 1.94 (s, 3H), 2.27 (s, 3H), 2.50-2.55 (m, 1H), 2.71-2.79 (m, 1H), 3.10-3.26 (m, 2H), 3.77 (hept, J=5.8 Hz, 1H), 4.25 (d, J=19.5 Hz, 1H), 4.35-4.97 (m, 3H), 5.85 (s, 1H), 6.35-6.42 (m, 1H), 6.44 (d, J=8.9 Hz, 1H), 7.18 (dd, J=8.9 Hz, 2.4 Hz, 1H), 7.66 (d, J=2.3 Hz, 1H), 7.69 (dd, J=8.1 Hz, 1.5 Hz, 1H), 7.88 (d, J=1.5 Hz, 1H), 7.99 (d, J=8.1 Hz, 1H) ppm. LCMS: $C_{29}H_{29}BrF_3N_7O_3$ $[M+H]^+$: 660/662.

Example 9

Compound 9

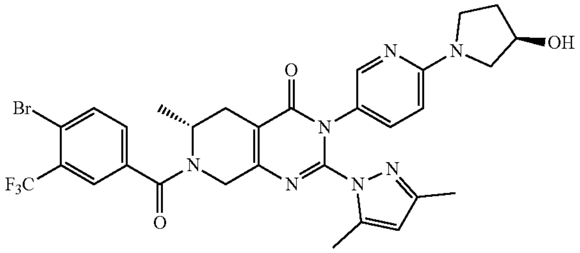 [SMILES: Cc1cc(C)n(-c2nc3c(c(=O)n2-c2ccc(N4CC[C@@H](O)C4)nc2)C[C@@H](C)N(C(=O)c2ccc(Br)c(C(F)(F)F)c2)C3)n1]

Urea hydrogen peroxide (10 eq., 770.5 mg, 8.19 mmol) was added to a solution of (R)-7-(4-bromo-3-(trifluoromethyl)benzoyl)-3-(6-((R)-3-hydroxypyrrolidin-1-yl)pyridin-3-yl)-6-methyl-2-thioxo-2,3,5,6,7,8-hexahydropyrido[3,4-d]pyrimidin-4(1H)-one (1 eq., 500 mg, 0.82 mmol) and hydrazine monohydrate (10 eq., 409.53 mg, 8.19 mmol) in isopropanol (7 mL). The mixture was stirred at rt for 18 h and then pentan-2,4-dione (20 eq., 1.68 mL, 16.38 mmol) was added. The mixture was stirred at 100° C. for 2 h. Sat. $Na_2S_2O_3$ was added to the mixture. The isopropanol was removed under vacuum and the resulting aqueous phase was extracted with EtOAc (3×). The combined organic layers were washed with brine and dried over $Na_2SO_4$. The solids were removed by filtration and the filtrate was evaporated to dryness to give the crude product. The crude product was purified by flash chromatography on silica gel (from 0 to 100% of EA, and then, from 0 to 10% of MeOH in DCM) to give a yellow solid which was purified by reverse flash chromatography (from 5 to 100% of MeCN in water (+0.1% of FA)) to afford (R)-7-(4-bromo-3-(trifluoromethyl)benzoyl)-2-(3,5-dimethyl-1H-pyrazol-1-yl)-3-(6-((R)-3-hydroxypyrrolidin-1-yl)pyridin-3-yl)-6-methyl-5,6,7,8-tetrahydropyrido[3,4-d]pyrimidin-4(3H)-one (204 mg, 37%) as a white solid. $^1$H-NMR (DMSO-$d_6$, 400 MHz, 80° C.) δ 1.24 (d, J=6.4 Hz, 3H), 1.83-1.92 (m, 1H), 1.95 (s, 3H), 1.98-2.09 (m, 1H), 2.27 (s, 3H), 2.52-2.59 (m, 1H), 2.70-2.81 (m, 1H), 3.27 (d, J=10.5 Hz, 1H), 3.37-3.52 (m, 3H), 4.25 (d, J=20.3 Hz, 1H), 4.39 (br. s., 1H), 4.45-4.92 (m, 3H), 5.85 (s, 1H), 6.34 (d, J=8.9 Hz, 1H), 7.31 (dd, J=8.6 Hz, 1.9 Hz, 1H), 7.69 (d, J=8.3 Hz, 1H), 7.79 (s, 1H), 7.88 (s, 1H), 7.99 (d, J=7.6 Hz, 1H) ppm. LCMS: $C_{30}H_{29}BrF_3N_7O_3$ [M+H]$^+$: 672/674.

Example 10

Compound 10

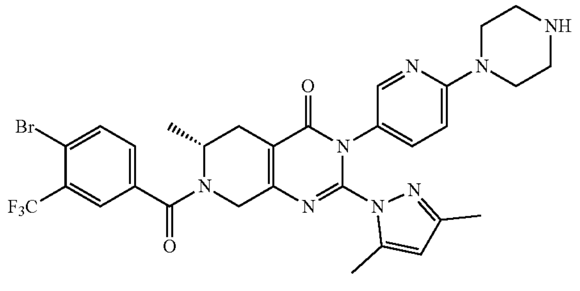 [SMILES: Cc1cc(C)n(-c2nc3c(c(=O)n2-c2ccc(N4CCNCC4)nc2)C[C@@H](C)N(C(=O)c2ccc(Br)c(C(F)(F)F)c2)C3)n1]

Urea hydrogen peroxide (10 eq., 1.3 g, 14.09 mmol) was added to a solution of tert-butyl (R)-4-(5-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)pyridin-2-yl)piperazine-1-carboxylate (1 eq., 1 g, 1.40 mmol) and hydrazine monohydrate (10 eq., 705 mg, 14.09 mmol) in isopropanol (20 mL). The mixture was stirred at rt for 18 h and the pentan-2,4-dione (20 eq., 2.89 mL, 28.19 mmol) was added. The mixture was stirred at 100° C. for 2 h. Sat. aq. $NaHCO_3$ (100 mL) and EtOAc (50 mL) were added to the mixture. The layers were separated and the aqueous layer was extracted using EtOAc (3×80 mL). The combined organic layers were washed with 1 N HCl (100 mL), brine (100 mL) and dried over $Na_2SO_4$. The solids were removed by filtration and the filtrate was evaporated to dryness to give the crude product. The crude product was purified by flash chromatography on silica gel (from 0 to 100% of EA, then, from 0 to 10% of MeOH in DCM) to give tert-butyl (R)-4-(5-(7-(4-bromo-3-(trifluoromethyl)benzoyl)-2-(3,5-dimethyl-1H-pyrazol-1-yl)-6-methyl-4-oxo-5,6,7,8-tetrahydropyrido[3,4-d]pyrimidin-3(4H)-yl)pyridin-2-yl)piperazine-1-carboxylate (820 mg, 75%) as a white solid. $^1$H-NMR (DMSO-$d_6$, 400 MHz) δ 1.21-1.26 (m, 3H), 1.41 (s, 9H), 1.90 (s, 3H), 2.26-2.35 (m, 3H), 2.44-2.50 (m, 1H), 2.66-2.78 (m, 1H), 3.35-3.42 (m, 4H), 3.43-3.51 (m, 4H), 4.08-4.61 (m, 2H), 4.95-5.33 (m, 1H), 5.88 (s, 1H), 6.78 (d, J=8.7 Hz, 1H), 7.32-7.56 (m, 1H), 7.66-7.73 (m, 1H), 7.78-7.94 (m, 2H), 7.98-8.04 (m, 1H) ppm. LCMS: $C_{35}H_{38}BrF_3N_8O_4$ [M+H]$^+$: 771/773.

HCl 4 N in Dioxane (40 eq., 10.6 mL, 42.4 mmol) was added onto tert-butyl (R)-4-(5-(7-(4-bromo-3-(trifluoromethyl)benzoyl)-2-(3,5-dimethyl-1H-pyrazol-1-yl)-6-methyl-4-oxo-5,6,7,8-tetrahydropyrido[3,4-d]pyrimidin-3(4H)-yl) pyridin-2-yl)piperazine-1-carboxylate (1 eq., 0.82 g, 1.06 mmol). The mixture was stirred at rt for 1 h. The mixture was evaporated to dryness, then, sat. aq. $NaHCO_3$ (100 mL) and EtOAc (50 mL) were added to the mixture. The layers were separated and the aqueous layer was extracted using EtOAc (3×100 mL). The combined organic layers were washed brine (100 mL) and dried over $Na_2SO_4$. The solids were removed by filtration and the filtrate was evaporated to dryness to give (R)-7-(4-bromo-3-(trifluoromethyl)benzoyl)-2-(3,5-dimethyl-1H-pyrazol-1-yl)-6-methyl-3-(6-(piperazin-1-yl)pyridin-3-yl)-5,6,7,8-tetrahydropyrido[3,4-d]pyrimidin-4(3H)-one (609 mg, 86%) as a yellow solid. LCMS: $C_{30}H_{30}BrF_3N_8O_2$ [M+H]$^+$: 671/673.

In a sealed microwave tube under $N_2$ with molecular sieve, HCl 4N in dioxane (5 eq., 0.16 mL, 0.65 mmol) was added to a solution of (R)-7-(4-bromo-3-(trifluoromethyl) benzoyl)-2-(3,5-dimethyl-1H-pyrazol-1-yl)-6-methyl-3-(6-(piperazin-1-yl)pyridin-3-yl)-5,6,7,8-tetrahydropyrido[3,4-d]pyrimidin-4(3H)-one (1 eq., 87 mg, 0.13 mmol) in 1,4-dioxane (2 mL). The mixture was stirred at rt for 1 h. The mixture was evaporated to dryness, triturated with DCM and co-evaporated with MeCN (3×) to give (R)-7-(4-bromo-3-(trifluoromethyl)benzoyl)-2-(3,5-dimethyl-1H-pyrazol-1-yl)-6-methyl-3-(6-(piperazin-1-yl)pyridin-3-yl)-5,6,7,8-tetrahydropyrido[3,4-d]pyrimidin-4(3H)-one hydrochloride (60 mg, 65%) as a beige solid $^1$H-NMR (DMSO-$d_6$, 400 MHz, 80° C.) δ 1.26 (br. s., 3H); 2.92 (br. s., 3H); 2.30 (br. s., 3H); 2.53-2.60 (m, 1H); 2.67-2.82 (m, 1H); 3.14 (br. s., 4H); 4.25 (d, J=18.3 Hz, 1H); 4.57 (br. s., 1H); 4.75 (br. s., 1H); 5.87 (s, 1H); 6.85 (d, J=6.0 Hz, 1H); 7.45 (d, J=5.8 Hz, 1H); 7.69 (d, J=5.8 Hz, 1H); 7.89 (m, 2H); 7.99 (d, J=5.4 Hz, 1H); 9.44 (br. s., 2H) ppm. LCMS: $C_{30}H_{31}BrClF_3N_8O_2$ [M+H]$^+$: 671/673.

Example 11

Compound 11

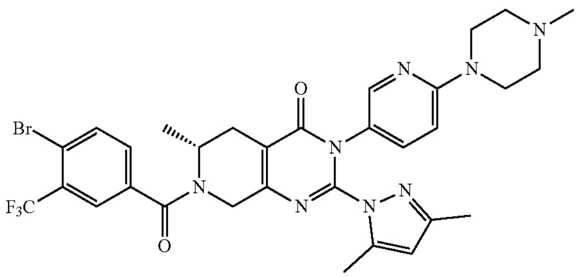 [SMILES: Cc1cc(C)n(-c2nc3c(c(=O)n2-c2ccc(N4CCN(C)CC4)nc2)C[C@@H](C)N(C(=O)c2ccc(Br)c(C(F)(F)F)c2)C3)n1]

$Et_3N$ (4 eq., 0.25 mL, 1.79 mmol) was added to a solution of (R)-7-(4-bromo-3-(trifluoromethyl)benzoyl)-2-(3,5-dimethyl-1H-pyrazol-1-yl)-6-methyl-3-(6-(piperazin-1-yl)pyridin-3-yl)-5,6,7,8-tetrahydropyrido[3,4-d]pyrimidin-4(3H)-one (1 eq., 300 mg, 0.45 mmol) in EtOH (10 mL). The mixture was stirred at rt for 30 min and then formaldehyde 37% in water (5 eq., 0.17 mL, 2.23 mmol) and acetic acid (6 eq., 0.15 mL, 2.68 mmol) were added. The mixture was stirred at rt for 1 h. $NaBH_3CN$ (2 eq., 56.15 mg, 0.89 mmol) was added to the mixture and then further stirred at rt for 1 h. Sat. aq. $NaHCO_3$ (20 mL) and DCM (20 mL) were added. The layers were separated and the aqueous layer was extracted with DCM (3×30 mL). The combined organic layers were washed with sat aq. $NaHCO_3$ (20 mL) and brine (30 mL), and dried over $Na_2SO_4$. The solids were removed by filtration and the filtrate was evaporated to dryness and purified by flash chromatography on silica gel (from 0 to 100% of EA, then, from 0 to 10% of MeOH in DCM) to give a yellow solid. The solid was purified by reverse phase chromatography (from 5 to 100% of MeCN in water (+0.1)% of FA)). Tubes containing the product were combined and the MeCN was evaporated. Sat. aq. $NaHCO_3$ (20 mL) and EtOAc (30 mL) were added to the solution, and the layers were separated. The aqueous layer was extracted using EtOAc (3×30 mL). The combined organic phases were washed with sat. aq. $NaHCO_3$ (30 mL) and water (30 mL), and dried over $Na_2SO_4$. The solids were filtered and the filtrate was evaporated to dryness to give (R)-7-(4-bromo-3-(trifluoromethyl)benzoyl)-2-(3,5-dimethyl-1H-pyrazol-1-yl)-6-methyl-3-(6-(4-methylpiperazin-1-yl)pyridin-3-yl)-5,6,7,8-tetrahydropyrido[3,4-d]pyrimidin-4(3H)-one (128 mg, 41%) as a white solid. $^1H$-NMR (DMSO-$d_6$, 400 MHz, 80° C.) δ 1.25 (d, J=6.9 Hz, 3H); 1.93 (s, 3H); 2.22 (s, 3H); 2.29 (s, 3H); 2.34-2.39 (m, 4H); 2.52-2.57 (m, 1H); 2.70-2.81 (m, 1H); 3.44-3.52 (m, 4H); 4.25 (d, J=19.1 Hz, 1H); 4.36-5.10 (m, 2H); 5.86 (s, 1H); 6.72 (d, J=9.1 Hz, 1H); 7.34 (dd, J=9.0 Hz, 2.6 Hz, 1H); 7.69 (dd, J=8.3 Hz, 1.6 Hz, 1H); 7.83 (d, J=2.5 Hz, 1H); 7.88 (d, J=1.9 Hz, 1H); 7.99 (d, J=8.3 Hz, 1H) ppm. LCMS: $C_{31}H_{32}BrF_3N_8O_2$ $[M+H]^+$: 685/687.

Example 12

Compound 12

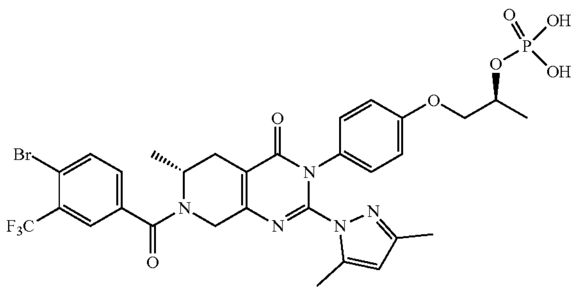 [SMILES: Cc1cc(C)n(-c2nc3c(c(=O)n2-c2ccc(OC[C@H](C)OP(=O)(O)O)cc2)C[C@@H](C)N(C(=O)c2ccc(Br)c(C(F)(F)F)c2)C3)n1]

$POCl_3$ (3 eq., 0.42 mL, 4.54 mmol) and pyridine (10 eq., 1.22 mL, 15.14 mmol) were added to a solution of (R)-7-(4-bromo-3-(trifluoromethyl)benzoyl)-2-(3,5-dimethyl-1H-pyrazol-1-yl)-3-(4-((S)-2-hydroxypropoxy)phenyl)-6-methyl-5,6,7,8-tetrahydropyrido[3,4-d]pyrimidin-4(3H)-one (1 eq., 1 g, 1.51 mmol) in anhydrous THF (14 mL) cooled at 0° C. The mixture was slowly left to warm to rt and stirred for 1 h. The mixture was filtered and the filtrate was cooled to 0° C. Water was added and the pH was adjusted to pH ~2 with 1 N HCl. DCM was added and the layers were separated. The aqueous layer was extracted with DCM. The combined organic layer were combined and dried over $Na_2SO_4$. The solids were removed and the filtrate was evaporated to dryness under reduced pressure with a water bath at 30° C. to give a yellow oil which was purified by reverse phase chromatography (Water (0.5% FA):MeCN from 95:5 to 0:100). The fractions were combined and pH was adjusted to pH ~2 by addition of 1 N HCl and extracted with DCM:iPrOH (95:5). The organic layer was dried over $Na_2SO_4$ and evaporated under reduced pressure with a water bath at 30° C. to give (S)-1-(4-((R)-7-(4-bromo-3-(trifluoromethyl)benzoyl)-2-(3,5-dimethyl-1H-pyrazol-1-yl)-6-methyl-4-oxo-5,6,7,8-tetrahydropyrido[3,4-d]pyrimidin-3(4H)-yl)phenoxy)propan-2-yl dihydrogen phosphate (409 mg, 36%) as a white solid. $^1H$-NMR (DMSO-$d_6$, 600 MHz, 80° C.) δ 1.26 (d, J=6.9 Hz, 3H), 1.33 (d, J=5.9 Hz, 3H), 1.90 (s, 3H), 2.25 (s, 3H), 2.48-2.57 (m, 1H), 2.69-2.80 (m, 1H), 3.93-4.07 (m, 2H), 4.20-4.31 (m, 1H), 4.45-4.97 (m, 3H), 5.81 (s, 1H), 6.89 (d, J=8.7 Hz, 2H), 7.09 (d, J=8.7 Hz, 2H), 7.66-7.73 (m, 1H), 7.85-7.89 (m, 1H), 7.99 (d, J=8.7 Hz, 1H) ppm. LCMS: $C_{30}H_{30}BrF_3N_5O_7P$ [M+H]+: 740/742.

Example 13

Synthesis of Compounds 13-44

Compounds 14-35 were synthesized using the protocols and intermediates described herein as well as methods known in the art. The different methods described in Schemes 2, 4, 10, 17 and 18 were used to introduce the 3,5-dimethylpyrazole moiety and are described in Table 1.

TABLE 1

Description of methods 1-6 used to synthesize compounds 13-44 of Formula (I) from compounds of Formula (VI)

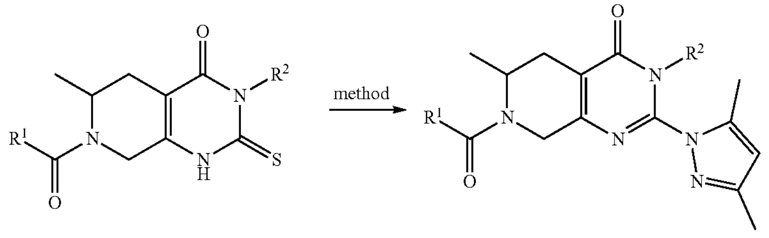

(VI) (I)

| Method name | reagents | Protocol example |
|---|---|---|
| Method 1 | 1) $SO_2Cl_2$; 2) hydrazine monohydrate; 3) acetylacetone | Compound 1 |
| Method 2 | 1) $SCCl_2$; 2) hydrazine monohydrate; 3) acetylacetone | Compound 2 |
| Method 3 | 1) MeI, DBU; 2) mCPBA; 3) hydrazine monohydrate; 4) acetylacetone | Compound 3 |
| Method 4 | 1) AcOOH; hydrazine monohydrate; 2) acetylacetone | Compound 8 |
| Method 5 | 1) Urea hydrogen peroxide, hydrazine monohydrate; 2) acetylacetone | Compound 9 |

In Table 2 are described compounds 13-44, as well as the methods used to synthesize them.

TABLE 2

| Structure | Cmpd. # | Name | Meth-od | LCMS [M + H]+ | $^1$H NMR |
|---|---|---|---|---|---|
| 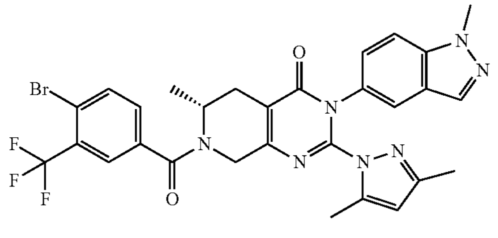 [SMILES: Cc1cc(C)n(-c2nc3c(c(=O)n2-c2ccc4c(cnn4C)c2)C[C@@H](C)N(C(=O)c2ccc(Br)c(C(F)(F)F)c2)C3)n1] | 13 | (6R)-7-[4-bromo-3-(trifluoromethyl) benzoyl]-2-(3,5-dimethyl-pyrazol-1-yl)-6-methyl-3-(1-methylindazol-5-yl)-6,8-dihydro-5H-pyrido[3,4-d] pyrimidin-4-one | 2 | 640/ 642 | (DMSO-$d_6$, 400 MHz, 80° C.): 1.26 (d, J = 6.4 Hz, 3H), 1.78 (s, J = 3H), 2.27 (s, 3H), 2.51-2.55 (m, 1H), 2.71-2.80 (d, 1H), 4.01 (s, 3H), 4.26 (d, J = 19.5 Hz, 1H), 4.56 (br. s., 1H), 4.79 (br. s., 1H), 5.72 (s, 1H), 7.20 (d, J = 9.3 Hz, 1H), 7.51-7.59 (m, 2H), 7.69 (dd, J = 8.2 Hz, 1.8 Hz, 1H), 7.88 (d, J = 1.9 Hz, 1H), 7.96-8.01 (m, 2H) ppm |
| 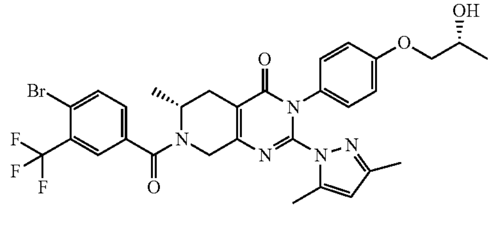 [SMILES: Cc1cc(C)n(-c2nc3c(c(=O)n2-c2ccc(OC[C@@H](C)O)cc2)C[C@@H](C)N(C(=O)c2ccc(Br)c(C(F)(F)F)c2)C3)n1] | 14 | (6R)-7-[4-bromo-3-(trifluoromethyl) benzoyl]-2-(3,5-dimethylpyrazol-1-yl)-3-[4-[(2R)-2-hydroxy-propoxy]phenyl]-6-methyl-6,8-dihydro-5H-pyrido[3,4-d] pyrimidin-4-one | 2 | 660/ 662 | (DMSO-$d_6$, 400 MHz, 80° C.): 1.15 (d, J = 6.3 Hz, 3H), 1.26 (d, J = 6.6 Hz, 3H), 1.90 (s, 3H), 2.26 (s, 3H), 2.51-2.57 (m, 1H), 2.70-2.80 (m, 1H), 3.74-3.86 (m, 2H), 3.89-3.99 (m, 1H), 4.25 (d, J = 18.8 Hz, 1H), 4.44-4.65 (m, 2H), 4.76 (br. s., 1H), 5.81 (s, 1H), 6.86 (d, J = 8.9 Hz, 2H), 7.07 (d, J = 8.6 Hz, 2H), 7.69 (dd, J = 8.2 Hz, 1.7 Hz, 1H), 7.88 (d, J = 1.5 Hz, 1H), 7.99 (d, J = 8.0 Hz, 1H) ppm |
| 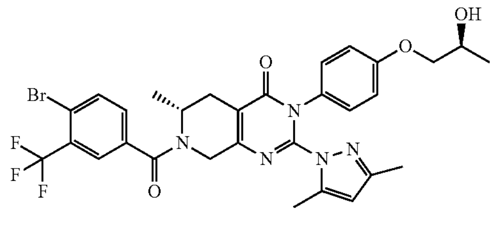 [SMILES: Cc1cc(C)n(-c2nc3c(c(=O)n2-c2ccc(OC[C@H](C)O)cc2)C[C@@H](C)N(C(=O)c2ccc(Br)c(C(F)(F)F)c2)C3)n1] | 15 | (6R)-7-[4-bromo-3-(trifluoromethyl) benzoyl]-2-(3,5-dimethyl-pyrazol-1-yl)-3-[4-[(2S)-2-hydroxypro-poxy]phenyl]-6-methyl-6,8-dihydro-5H-pyrido[3,4-d] pyrimidin-4-one | 2 | 660/ 662 | (DMSO-$d_6$, 400 MHz, 80° C.): 1.15 (d, J = 1.15 Hz, 3H), 1.26 (d, J = 6.9 Hz, 3H), 1.9 (s, 3H), 2.26 (s, 3H), 2.49-2.55 (m, 1H), 2.72-2.78 (m, 1H), 3.76-3.85 (m, 2H), 3.91-3.96 (m, 1H), 4.22-4.28 (m, 1H), 4.56-4.75 (m, 3H), 5.81 (s, 1H), 6.86 (d, J = 8.4 Hz, 2H), 7.07 (d, J = 8.3 Hz, 2H), 7.69 (dd, J = 8.2 Hz, J = 2.0 Hz, 1H), 7.88 (d, J = 2.3 Hz, 1H), 7.99 (d, J = 8.2 Hz, 1H) ppm |

TABLE 2-continued

| Structure | Cmpd. # | Name | Meth-od | LCMS [M + H]+ | $^1$H NMR |
|---|---|---|---|---|---|
| 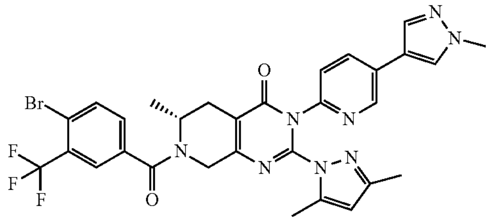 [SMILES: Cc1cc(C)n(-c2nc3c(c(=O)n2-c2ccc(-c4cnn(C)c4)cn2)C[C@@H](C)N(C(=O)c2ccc(Br)c(C(F)(F)F)c2)C3)n1] | 16 | (6R)-7-[4-bromo-3-(trifluoromethyl)benzoyl]-2-(3,5-dimethyl-pyrazol-1-yl)-6-methyl-3-[5-(1-methylpyrazol-4-yl)-2-pyridyl]-6,8-dihydro-5H-pyrido[3,4-d]pyrimidin-4-one | 2 | 667/669 | (DMSO-$d_6$, 400 MHz, 80° C.): 1.26 (d, J = 6.7 Hz, 3H), 1.79 (s, 3H), 2.38 (s, 3H), 2.51-2.5 (m, 1H), 2.73-2.83 (m, 1H), 3.88 (s, 3H), 4.28 (d, J = 18.2 Hz, 1H), 4.56 (br. s., 1H), 4.79 (br. s., 1H), 5.86 (s, 1H), 7.45 (d, J = 8.3 Hz, 1H), 7.71 (dd, J = 8.4 Hz, 1.6 Hz, 1H), 7.89-7.92 (m, 2H), 7.97-8.04 (m, 2H), 8.19 (s, 1H), 8.52 (d, J = 2.3 Hz, 1H) ppm |
| 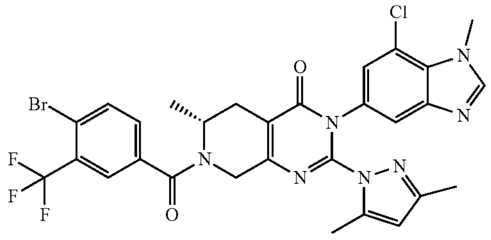 [SMILES: Cc1cc(C)n(-c2nc3c(c(=O)n2-c2cc(Cl)c4c(c2)ncn4C)C[C@@H](C)N(C(=O)c2ccc(Br)c(C(F)(F)F)c2)C3)n1] | 17 | (6R)-7-[4-bromo-3-(trifluoromethyl)benzoyl]-3-(7-chloro-1-methyl-benzimidazol-5-yl)-2-(3,5-dimethyl-pyrazol-1-yl)-6-methyl-6,8-dihydro-5H-pyrido[3,4-d]pyrimidin-4-one | 2 | 674/676 | (DMSO-$d_6$, 400 MHz, 80° C.): 1.26 (d, J = 6.7 Hz, 3H), 1.82 (s, 3H), 2.29 (s, 3H), 2.50-2.57 (m, 1H), 2.71-2.79 (m, 1H), 4.06 (s, 3H), 4.26 (d, J = 18.7 Hz, 1H), 4.56 (br. s., 1H), 4.77 (br. s., 1H), 5.76 (s, 1H), 7.21 (s, 1H), 7.46 (s, 1H), 7.69 (dd, J = 8.3 Hz, 1.6 Hz, 1H), 7.87 (d, J = 1.7 Hz, 1H), 7.98 (d, J = 8.1 Hz, 1H), 8.17 (s, 1H) ppm |
| 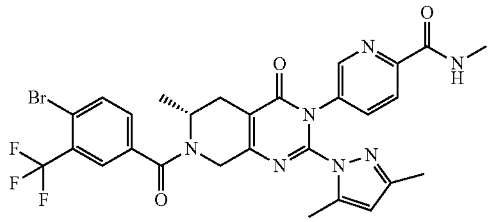 [SMILES: CNC(=O)c1ccc(-n2c(-n3nc(C)cc3C)nc3c(c2=O)C[C@@H](C)N(C(=O)c2ccc(Br)c(C(F)(F)F)c2)C3)cn1] | 18 | 5-[(6R)-7-[4-bromo-3-(trifluoromethyl)benzoyl]-2-(3,5-dimethyl-pyrazol-1-yl)-6-methyl-4-oxo-6,8-dihydro-5H-pyrido[3,4-d]pyrimidin-3-yl]-N-methyl-pyridine-2-carboxamide | 2 | 644/646 | (DMSO-$d_6$, 400 MHz, 80° C.): 1.26 (d, J = 6.7 Hz, 3H), 1.80 (s, 3H), 2.38 (s, 3H), 2.54 (d, J = 17.5 Hz, 1H), 2.70-2.79 (m, 1H), 2.83 (d, J = 4.9 Hz, 3H), 4.27 (d, J = 18.7 Hz, 1H), 4.55 (br. s., 1H), 4.78 (br. s., 1H), 5.87 (s, 1H), 7.68 (dd, J = 8.3 Hz, 1.8 Hz, 1H), 7.82 (dd, J = 8.4 Hz, 2.4 Hz, 1H), 7.86 (d, J = 1.9 Hz, 1H), 7.96-8.00 (m, 2H), 8.44 (d, J = 2.3 Hz, 1H), 8.49-8.56 (m, 1H) ppm |
| 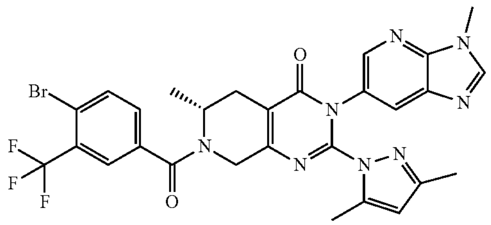 [SMILES: Cc1cc(C)n(-c2nc3c(c(=O)n2-c2cnc4c(c2)ncn4C)C[C@@H](C)N(C(=O)c2ccc(Br)c(C(F)(F)F)c2)C3)n1] | 19 | (6R)-7-[4-bromo-3-(trifluoromethyl)benzoyl]-2-(3,5-dimethyl-pyrazol-1-yl)-6-methyl-3-(3-methylimidazo[4,5-b]pyridin-6-yl)-6,8-dihydro-5H-pyrido[3,4-d]pyrimidin-4-one | 2 | 641/643 | (DMSO-$d_6$, 400 MHz, 80° C.): 1.28 (d, J = 6.8 Hz, 3H), 1.78 (s, 3H), 2.35 (s, 3H), 2.53-2.61 (m, 1H), 2.71-2.82 (m, 1H), 3.84 (s, 3H), 4.23-4.35 (m, 1H), 4.45-4.91 (m, 2H), 5.79 (s, 1H), 7.70 (dd, J = 8.2 Hz, 2.0 Hz, 1H), 7.89 (d, J = 1.6 Hz, 1H), 7.96 (br. s., 1H), 8.00 (d, J = 8.2 Hz, 1H), 8.22 (s, 1H), 8.39 (s, 1H) ppm |
| 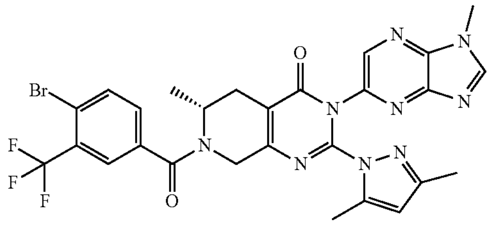 [SMILES: Cc1cc(C)n(-c2nc3c(c(=O)n2-c2cnc4c(ncn4C)n2)C[C@@H](C)N(C(=O)c2ccc(Br)c(C(F)(F)F)c2)C3)n1] | 20 | (6R)-7-[4-bromo-3-(trifluoromethyl)benzoyl]-2-(3,5-dimethylpyrazol-1-yl)-6-methyl-3-(1-methyl-imidazo[4,5-b]pyrazin-5-yl)-6,8-dihydro-5H-pyrido[3,4-d]pyrimidin-4-one | 3 | 642/644 | (DMSO-$d_6$, 400 MHz, 80° C.): 1.26 (d, J = 6.7 Hz, 3H), 1.65 (s, 3H), 2.41 (s, 3H), 2.50-2.57 (m, 1H), 2.73-2.82 (m, 1H), 3.89 (s, 3H), 4.29 (d, J = 19.0 Hz, 1H), 4.54 (br. s., 1H), 4.82 (br. s., 1H), 5.82 (s, 1H), 7.70 (dd, J = 8.0 Hz, 1.8 Hz, 1H), 7.89 (d, J = 1.6 Hz, 1H), 7.89 (d, J = 8.1 Hz, 1H), 8.54 (s, 1H), 8.69 (s, 1H) ppm |

TABLE 2-continued

| Structure | Cmpd. # | Name | Meth-od | LCMS [M + H]+ | $^1$H NMR |
|---|---|---|---|---|---|
| 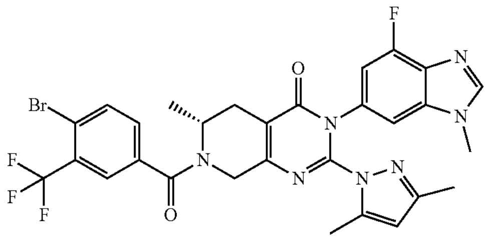 [SMILES: Cc1cc(C)n(-c2nc3c(c(=O)n2-c2cc(F)c4ncn(C)c4c2)C[C@@H](C)N(C(=O)c2ccc(Br)c(C(F)(F)F)c2)C3)n1] | 21 | (6R)-7-[4-bromo-3-(trifluoromethyl) benzoyl]-2-(3,5-dimethylpyrazol-1-yl)-3-(7-fluoro-3-methyl-benzimidazol-5-yl)-6-methyl-6,8-dihydro-5H-pyrido[3,4-d] pyrimidin-4-one | 3 | 658/ 660 | (DMSO-$d_6$, 400 MHz, 80° C.): 1.27 (d, J = 6.8 Hz, 3H), 1.82 (s, 3H), 2.31 (s, 3H), 2.56 (d, J = 17.3 Hz, 1H), 2.73-2.81 (m, 1H), 3.78 (s, 3H), 4.29 (d, J = 19.0 Hz, 1H), 4.58 (br. s., 1H), 4.78 (br. s., 1H), 5.77 (s, 1H), 6.98 (d, J = 10.9 Hz, 1H), 7.34 (s, 1H), 7.70 (dd, J = 8.2 Hz, 1.9 Hz, 1H), 7.89 (d, J = 1.7 Hz, 1H), 8.00 (d, J = 8.2 Hz, 1H), 8.21 (s, 1H) ppm |
| 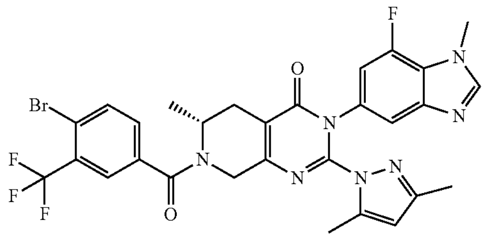 [SMILES: Cc1cc(C)n(-c2nc3c(c(=O)n2-c2cc(F)c4c(c2)ncn4C)C[C@@H](C)N(C(=O)c2ccc(Br)c(C(F)(F)F)c2)C3)n1] | 22 | (6R)-7-[4-bromo-3-(trifluoromethyl) benzoyl]-2-(3,5-dimethylpyrazol-1-yl)-3-(7-fluoro-1-methyl-benzimidazol-5-yl)-6-methyl-6,8-dihydro-5H-pyrido[3,4-d] pyrimidin-4-one | 3 | 658/ 660 | (DMSO-$d_6$, 400 MHz, 80° C.): 1.27 (d, J = 7.0 Hz, 3H), 1.83 (s, 3H), 2.31 (s, 3H), 2.55 (d, J = 17.3 Hz, 1H), 2.72-2.81 (m, 1H), 3.97 (s, 3H), 4.27 (d, J = 19.5 Hz, 1H), 4.57 (br. s., 1H), 4.77 (br. s., 1H), 5.77 (s, 1H), 7.05 (d, J = 11.8 Hz, 1H), 7.30 (s, 1H), 7.70 (dd, J = 8.1 Hz, 1.5 Hz, 1H), 7.89 (d, J = 1.4 Hz, 1H), 8.00 (d, J = 8.2 Hz, 1H), 8.15 (s, 1H) ppm |
| 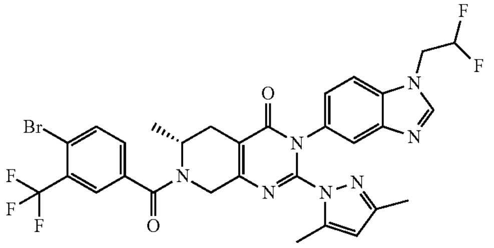 [SMILES: Cc1cc(C)n(-c2nc3c(c(=O)n2-c2ccc4c(c2)ncn4CC(F)F)C[C@@H](C)N(C(=O)c2ccc(Br)c(C(F)(F)F)c2)C3)n1] | 23 | (6R)-7-[4-bromo-3-(trifluoromethyl) benzoyl]-3-[1-(2,2-difluoro-ethyl)benzimi-dazol-5-yl]-2-(3,5-dimethyl-pyrazol-1-yl)-6-methyl-6,8-dihydro-5H-pyrido[3,4-d] pyrimidin-4-one | 3 | 690/ 692 | (DMSO-$d_6$, 400 MHz, 80° C.): 1.28 (d, J = 6.8 Hz, 3H); 1.79 (s, 3H); 2.30 (s, 3H); 2.53-2.63 (m, 1H); 2.73-2.82 (m, 1H); 4.21-4.70 (m, 2H); 4.78 (td, J = 16.0 Hz, 2.9 Hz, 2H); 4.70-4.87 (m, 1H); 5.74 (s, 1H); 6.41 (tt, J = 54.8 Hz, 3.0 Hz, 1H); 7.15 (d, J = 8.4 Hz, 1H); 7.50 (s, 1H); 7.58 (d, J = 8.5 Hz, 1H); 7.71 (dd, J = 8.4 Hz, 1.6 Hz, 1H); 7.9 (d, J = 1.4 Hz, 1H); 8.00 (d, J = 8.1 Hz, 1H); 8.21 (s, 1H) ppm |
| 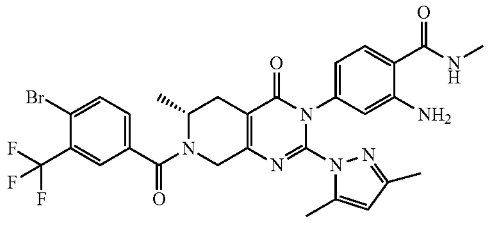 [SMILES: CNC(=O)c1ccc(-n2c(-n3nc(C)cc3C)nc3c(c2=O)C[C@@H](C)N(C(=O)c2ccc(Br)c(C(F)(F)F)c2)C3)cc1N] | 24 | 2-amino-4-[(6R)-7-[4-bromo-3-(trifluoromethyl) benzoyl]-2-(3,5-dimethylpyrazol-1-yl)-6-methyl-4-oxo-6,8-dihydro-5H-pyrido[3,4-d] pyrimidin-3-yl]-N-methyl-benzamide | 3 | 658/ 660 | (DMSO-$d_6$, 400 MHz, 80° C.): 1.25 (d, J = 6.9 Hz, 3H), 1.93 (s, 3H), 2.27 (s, 3H), 2.50-2.55 (m, 1H), 2.73-2.78 (m, 4H), 4.22-4.27 (m, 1H), 4.55-4.75 (m, 2H), 5.84 (s, 1H), 6.28-6.34 (m, 3H), 6.53 (d, J = 2.0 Hz, 1H), 7.37 (d, J = 8.4 Hz, 1H), 7.69 (dd, J = 8.2 Hz, 1.9 Hz, 1H), 7.88 (d, J = 2.0 Hz, 1H), 7.98-8.00 (m, 2H) ppm |
| 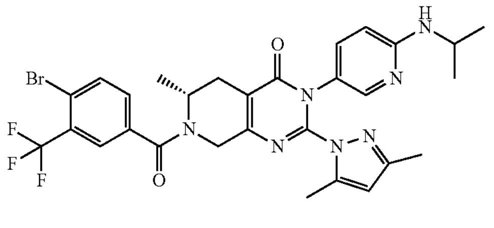 [SMILES: Cc1cc(C)n(-c2nc3c(c(=O)n2-c2ccc(NC(C)C)nc2)C[C@@H](C)N(C(=O)c2ccc(Br)c(C(F)(F)F)c2)C3)n1] | 25 | (6R)-7-[4-bromo-3-(trifluoromethyl) benzoyl]-2-(3,5-dimethylpyrazol-1-yl)-3-[6-(isopropylamino)-3-pyridyl]-6-methyl-6,8-dihydro-5H-pyrido[3,4-d] pyrimidin-4-one | 3 | 644/ 646 | (DMSO-$d_6$, 400 MHz, 80° C.): 1.13 (d, J = 6.5 Hz, 6H), 1.25 (d, J = 6.7 Hz, 3H), 1.94 (s, 3H), 2.27 (s, 3H), 2.52-2.56 (m, 1H), 2.71-2.79 (m, 1H) 3.88-3.99 (m, 1H), 4.24 (d, J = 19.8 Hz, 1H), 4.55 (bs, 1H), 4.75 (bs, 1H), 5.85 (s, 1H), 6.25 (d, J = 6.3 Hz, 1H), 6.35 (d, J = 7.5 Hz, 1H), 7.16 (dd, J = 8.6, 2.9 Hz, 1H), 7.67 (d, J = 2.0 Hz, 1H), 7.69 (dd, J = 7.9, 2.0 Hz, 1H), 7.88 (d, J = 1.7 Hz, 1H), 7.99 (d, J = 8.2 Hz, 1H) ppm |

TABLE 2-continued

| Structure | Cmpd. # | Name | Meth-od | LCMS [M + H]+ | $^1$H NMR |
|---|---|---|---|---|---|
| 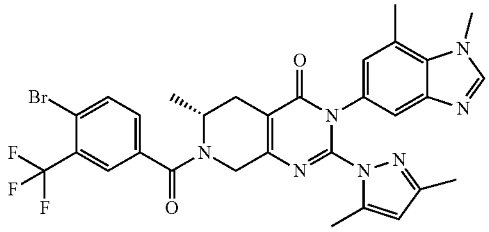 [SMILES: Cc1cc(C)n(-c2nc3c(c(=O)n2-c2cc(C)c4c(c2)ncn4C)C[C@@H](C)N(C(=O)c2ccc(Br)c(C(F)(F)F)c2)C3)n1] | 26 | (6R)-7-[4-bromo-3-(trifluoromethyl) benzoyl]-3-(1,7-dimethylbenz-imidazol-5-yl)-2-(3,5-dimethyl-pyrazol-1-yl)-6-methyl-6,8-dihydro-5H-pyrido[3,4-d] pyrimidin-4-one | 3 | 654/ 656 | (DMSO-$d_6$, 400 MHz, 80° C.): 1.25 (d, J = 7.1 Hz, 3H), 1.84 (s, 3H), 2.23 (s, 3H), 2.50-2.56 (m, 1H), 2.63 (s, 3H), 2.70-2.79 (m, 1H), 4.01 (s, 3H), 4.25 (d, J = 18.0 Hz, 1H), 4.55 (br. s., 1H), 4.75 (br. s., 1H), 5.71 (s, 1H), 6.81 (s, 1H), 7.25 (s, 1H), 7.69 (dd, J = 8.3 Hz, 1.6 Hz, 1H), 7.88 (d, J = 1.7 Hz, 1H), 7.98 (d, J = 8.0 Hz, 1H), 8.00 (s, 1H) ppm |
| 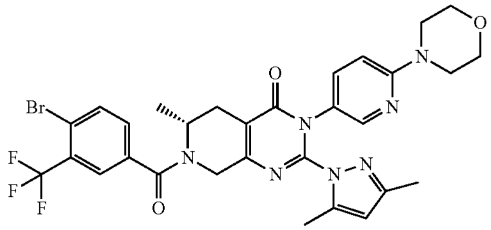 [SMILES: Cc1cc(C)n(-c2nc3c(c(=O)n2-c2ccc(N4CCOCC4)nc2)C[C@@H](C)N(C(=O)c2ccc(Br)c(C(F)(F)F)c2)C3)n1] | 27 | (6R)-7-[4-bromo-3-(trifluoromethyl) benzoyl]-2-(3,5-dimethylpyrazol-1-yl)-6-methyl-3-(6-morpholino-3-pyridyl)-6,8-dihydro-5H-pyrido[3,4-d] pyrimidin-4-one | 3 | 672/ 674 | (DMSO-$d_6$, 400 MHz, 80° C.): 1.24 (d, J = 6.8 Hz, 3H), 1.91 (s, 3H), 2.28 (s, 3H), 2.50-2.55 (m, 1H), 2.70-2.78 (m, 1H), 3.40-3.47 (m, 4H), 3.62-3.70 (m, 4H), 4.23 (d, J = 18.5 Hz, 1H), 4.54 (br. s., 1H), 4.75 (br. s., 1H), 5.85 (s, 1H), 6.72 (d, J = 9.1 Hz, 1H), 7.37 (dd, J = 9.0 Hz, 2.6 Hz, 1H), 7.68 (dd, J = 8.1 Hz, 1.6 Hz, 1H), 7.85 (d, J = 2.7 Hz, 1H), 7.86 (d, J = 1.6 Hz, 1H), 7.98 (d, J = 8.2 Hz, 1H) ppm |
| 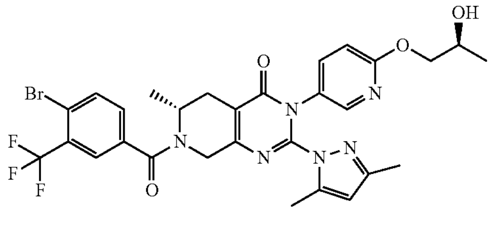 [SMILES: Cc1cc(C)n(-c2nc3c(c(=O)n2-c2ccc(OC[C@H](C)O)nc2)C[C@@H](C)N(C(=O)c2ccc(Br)c(C(F)(F)F)c2)C3)n1] | 28 | (6R)-7-[4-bromo-3-(trifluoromethyl) benzoyl]-2-(3,5-dimethylpyrazol-1-yl)-3-[6-[(2S)-2-hydroxypro-poxy]-3-pyridyl]-6-methyl-6,8-dihydro-5H-pyrido[3,4-d] pyrimidin-4-one | 2 | 661/ 663 | (DMSO-$d_6$, 400 MHz, 80° C.): 1.11 (d, J = 6.5 Hz, 3H), 1.25 (d, J = 6.8 Hz, 3H), 1.88 (s, 3H), 2.31 (s, 3H), 2.50-2.55 (m, 1H), 2.69-2.80 (m, 1H), 3.88-3.97 (m, 1H), 4.01-4.16 (m, 2H), 4.25 (d, J = 19.0 Hz, 1H), 4.39-4.90 (m, 3H), 5.85 (s, 1H), 6.75 (d, J = 8.8 Hz, 1H), 7.55 (dd, J = 8.8 Hz, 2.6 Hz, 1H), 7.68 (dd, J = 8.1 Hz, 1.7 Hz, 1H), 7.86 (d, J = 1.7 Hz, 1H), 7.90 (d, J = 2.3 Hz, 1H), 7.98 (d, J = 8.0 Hz, 1H) ppm |
| 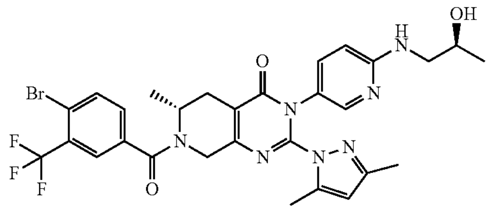 [SMILES: Cc1cc(C)n(-c2nc3c(c(=O)n2-c2ccc(NC[C@H](C)O)nc2)C[C@@H](C)N(C(=O)c2ccc(Br)c(C(F)(F)F)c2)C3)n1] | 29 | (6R)-7-[4-bromo-3-(trifluoromethyl) benzoyl]-2-(3,5-dimethylpyrazol-1-yl)-3-[6-[[(2S)-2-hydroxy-propyl]amino]-3-pyridyl]-6-methyl-6,8-dihydro-5H-pyrido[3,4-d] pyrimidin-4-one | 3 | 660/ 662 | (DMSO-$d_6$, 400 MHz, 80° C.): 1.07 (d, J = 6.2 Hz, 3H), 1.25 (d, J = 7.1 Hz, 3H), 1.94 (s, 3H), 2.27 (s, 3H), 2.52-2.57 (m, 1H), 2.70-2.80 (m, 1H), 3.12-3.25 (m, 2H), 3.71-3.83 (m, 1H), 4.24 (d, J = 18.7 Hz, 1H), 4.39-4.97 (m, 3H), 5.85 (s, 1H), 6.39 (t, J = 5.5 Hz, 1H), 6.44 (d, J = 9.3 Hz, 1H), 7.18 (dd, J = 8.8 Hz, 2.2 Hz, 1H), 7.64-7.71 (m, 2H), 7.88 (d, J = 1.7 Hz, 1H), 7.99 (d, J = 8.2 Hz, 1H) ppm |
| 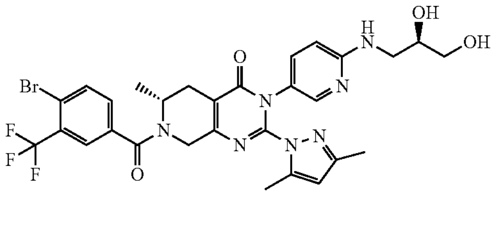 [SMILES: Cc1cc(C)n(-c2nc3c(c(=O)n2-c2ccc(NC[C@@H](O)CO)nc2)C[C@@H](C)N(C(=O)c2ccc(Br)c(C(F)(F)F)c2)C3)n1] | 30 | (6R)-7-[4-bromo-3-(trifluoromethyl) benzoyl]-3-[6-[[(2R)-2,3-dihydroxy-propyl]amino]-3-pyridyl]-2-(3,5-dimethylpyrazol-1-yl)-6-methyl-6,8-dihydro-5H-pyrido[3,4-d] pyrimidin-4-one | 3 | 676/ 678 | (DMSO-$d_6$, 400 MHz, 80° C.): 1.23 (d, J = 7.0 Hz, 3H), 1.93 (s, 3H0, 2.26 (s, 3H), 2.50-2.55 (m, 1H), 2.68-2.79 (m, 1H), 3.10-3.21 (m, 1H), 3.30-3.43 (m, 3H), 3.56-3.65 (m, 1H), 4.16-4.34 (m, 2H), 4.38-4.94 (br. s., 3H), 5.84 (s, 1H), 6.37 (t, J = 5.3 Hz, 1H), 6.44 (d, J = 8.9 Hz, 1H), 7.18 (dd, J = 8.9 Hz, 2.3 Hz, 1H), 7.63-7.70 (m, 2H), 7.86 (d, J = 0.8 Hz, 1H), 7.97 (d, J = 8.5 Hz, 1H) ppm |
| 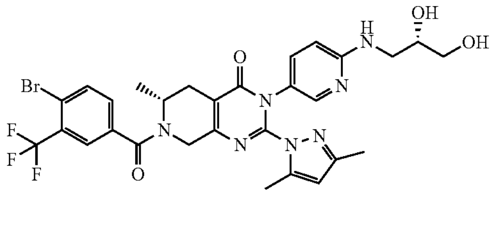 [SMILES: Cc1cc(C)n(-c2nc3c(c(=O)n2-c2ccc(NC[C@H](O)CO)nc2)C[C@@H](C)N(C(=O)c2ccc(Br)c(C(F)(F)F)c2)C3)n1] | 31 | (6R)-7-[4-bromo-3-(trifluoromethyl) benzoyl]-3-[6-[[(2S)-2,3-dihydroxy-propyl]amino]-3-pyridyl]-2-(3,5-dimethylpyrazol- | 3 | 676/ 678 | (DMSO-$d_6$, 400 MHz, 80° C.): 1.25 (d, J = 6.9 Hz, 3H), 1.95 (s, 3H), 2.27 (s, 3H), 2.50-2.55 (m, 1H), 2.71-2.78 (m, 1H), 3.12-3.20 (m, 1H), 3.34-3.40 (m, 3H), 3.58-3.65 (m, 1H), 4.21-4.29 (m, 2H), 4.51-4.79 (m, 3H), 5.85 (s, 1H), 6.38 (t, J = 5.8 Hz, 1H), 6.45 (d, J = 8.9 Hz, 1H), 7.19 (dd, J = 8.9 Hz, 2.7 Hz, 1H), |

TABLE 2-continued

| Structure | Cmpd. # | Name | Meth-od | LCMS [M + H]+ | $^{1}$H NMR |
|---|---|---|---|---|---|
| | | 1-yl)-6-methyl-6,8-dihydro-5H-pyrido[3,4-d]pyrimidin-4-one | | | 7.67-7.70 (m, 2H), 7.88 (d, J = 1.9 Hz, 1H), 7.99 (d, J = 8.2 Hz, 1H) ppm |
| 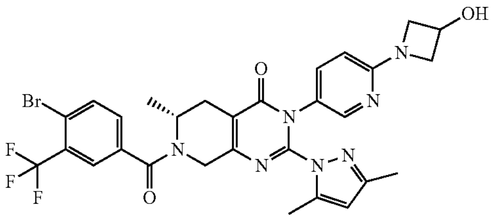 [SMILES: Cc1cc(C)n(-c2nc3c(c(=O)n2-c2ccc(N4CC(O)C4)nc2)C[C@@H](C)N(C(=O)c2ccc(Br)c(C(F)(F)F)c2)C3)n1] | 32 | (6R)-7-[4-bromo-3-(trifluoromethyl)benzoyl]-2-(3,5-dimethylpyrazol-1-yl)-3-[6-(3-hydroxyazetidin-1-yl)-3-pyridyl]-6-methyl-6,8-dihydro-5H-pyrido[3,4-d]pyrimidin-4-one | 4 | 658/660 | (DMSO-$d_6$, 400 MHz, 80° C.): 1.25 (d, J = 6.8 Hz, 3H), 1.93 (s, 3H), 2.28 (s, 3H), 2.51-2.56 (m, 1H), 2.70-2.79 (m, 1H), 3.64-3.70 (m, 2H), 4.10-4.17 (m, 2H), 4.24 (d, J = 18.9 Hz, 1H), 4.42-4.88 (m, 3H), 5.42 (d, J = 6.2 Hz, 1H), 5.85 (s, 1H), 6.28 (d, J = 8.7 Hz, 1H), 7.32 (dd, J = 8.9 Hz, 2.5 Hz, 1H), 7.69 (dd, J = 8.2 Hz, 1.7 Hz, 1H), 7.77 (d, j = 2.3 Hz, 1H), 7.88 (d, J = 1.8 Hz, 1H), 7.99 (d, J = 8.2 Hz, 1H) ppm |
| 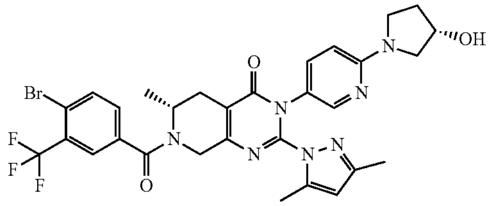 [SMILES: Cc1cc(C)n(-c2nc3c(c(=O)n2-c2ccc(N4CC[C@H](O)C4)nc2)C[C@@H](C)N(C(=O)c2ccc(Br)c(C(F)(F)F)c2)C3)n1] | 33 | (6R)-7-[4-bromo-3-(trifluoromethyl)benzoyl]-2-(3,5-dimethylpyrazol-1-yl)-3-[6-[(3S)-3-hydroxy-pyrrolidin-1-yl]-3-pyridyl]-6-methyl-6,8-dihydro-5H-pyrido[3,4-d]pyrimidin-4-one | 5 | 672/674 | (DMSO-$d_6$, 400 MHz, 80° C.): 1.24 (d, J = 6.4 Hz, 3H), 1.83-1.92 (m, 1H), 1.95 (s, 3H), 1.98-2.09 (m, 1H), 2.27 (s, 3H), 2.52-2.59 (m, 1H), 2.70-2.81 (m, 1H), 3.27 (d, J = 10.5 Hz, 1H), 3.37-3.52 (m, 3H), 4.25 (d, J = 20.3 Hz, 1H), 4.39 (br. s., 1H), 4.45-4.92 (m, 3H), 5.85 (s, 1H), 6.34 (d, J = 8.9 Hz, 1H), 7.31 (dd, J = 8.6 Hz, 1.9 Hz, 1H), 7.69 (d, J = 8.3 Hz, 1H), 7.77 (d, J = 2.2 Hz, 1H), 7.88 (s, 1H), 7.99 (d, J = 7.6 Hz, 1H) ppm |
| 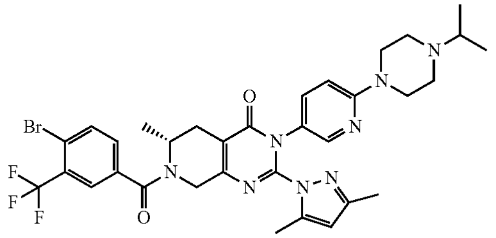 [SMILES: Cc1cc(C)n(-c2nc3c(c(=O)n2-c2ccc(N4CCN(C(C)C)CC4)nc2)C[C@@H](C)N(C(=O)c2ccc(Br)c(C(F)(F)F)c2)C3)n1] | 34 | (6R)-7-[4-bromo-3-(trifluoromethyl)benzoyl]-2-(3,5-dimethylpyrazol-1-yl)-3-[6-(4-isopropyl-piperazin-1-yl)-3-pyridyl]-6-methyl-6,8-dihydro-5H-pyrido[3,4-d]pyrimidin-4-one | 5 | 713/715 | (DMSO-$d_6$, 400 MHz, 80° C.): 1.00 (d, J = 6.6 Hz, 6H), 1.25 (d, J = 6.9 Hz, 3H), 1.92 (s, 3H), 2.30 (s, 3H), 2.52-2.58 (m, 1H), 2.64-2.70 (m, 1H), 2.70-2.80 (m, 1H), 3.43-3.52 (m, 4H), 4.14-4.33 (m, 1H), 4.55 (br. s, 1H), 4.76 (br. s, 1H), 5.86 (s, 1H), 6.70 (d, J = 9.1 Hz, 1H), 7.33 (dd, J = 9.0 Hz, 2.5 Hz, 1H), 7.69 (dd, J = 8.3 Hz, 1.6 Hz, 1H), 7.82 (d, J = 2.5 Hz, 1H), 7.88 (d, J = 1.8 Hz, 1H), 7.99 (d, J = 8.0 Hz, 1H) ppm |
| 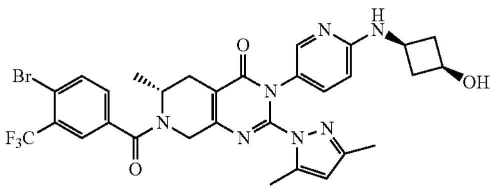 [SMILES: Cc1cc(C)n(-c2nc3c(c(=O)n2-c2ccc(N[C@H]4C[C@@H](O)C4)nc2)C[C@@H](C)N(C(=O)c2ccc(Br)c(C(F)(F)F)c2)C3)n1] | 35 | (R)-7-(4-bromo-3-(trifluoromethyl)benzoyl)-2-(3,5-dimethyl-1H-pyrazol-1-yl)-3-(6-(((1s,3S)-3-hydroxycyclo-butyl)amino)pyridin-3-yl)-6-methyl-5,6,7,8-tetrahydropyrido[3,4-d]pyrimidin-4(3H)-one | 5 | 672/674 | $^{1}$H NMR (DMSO-d6, 400 MHz, 80° C.): 1.25 (d, J = 6.8 Hz, 3H), 1.73-1.84 (m, 2H), 1.94 (s, 3H), 2.31 (s, 3H), 2.51-2.57 (m, 1H), 2.65-2.79 (m, 3H), 3.69-3.80 (m, 1H), 3.82-3.93 (m, 1H), 4.16-4.31 (m, 1H), 4.40-4.95 (m, 2H), 5.89 (s, 1H), 6.63 (d, J = 9.1 Hz, 1H), 7.45 (dd, J = 9.0 Hz, 1.4 Hz, 1H), 7.69 (dd, J = 8.1 Hz, 1.8 Hz, 1H), 7.78 (d, J = 1.9 Hz, 1H), 7.87 (d, J = 1.8 Hz, 1H), 7.99 (d, J = 8.1 Hz, 1H) ppm. |
| 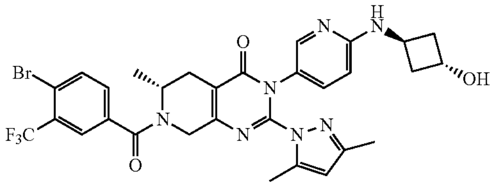 [SMILES: Cc1cc(C)n(-c2nc3c(c(=O)n2-c2ccc(N[C@H]4C[C@H](O)C4)nc2)C[C@@H](C)N(C(=O)c2ccc(Br)c(C(F)(F)F)c2)C3)n1] | 36 | (R)-7-(4-bromo-3-(trifluoromethyl)benzoyl)-2-(3,5-dimethyl-1H-pyrazol-1-yl)-3-(6-(((1r,3R)-3-hydroxycyclo-butyl)amino)pyridin-3-yl)-6-methyl-5,6,7,8-tetrahydropyrido[3,4-d]pyrimidin-4(3H)-one | 5 | 672/674 | $^{1}$H NMR (DMSO-d6, 400 MHz, 80° C.): 1.23 (d, J = 6.7 Hz, 3H), 1.92 (s, 3H), 2.07-2.19 (m, 4H), 2.26 (s, 3H), 2.50-2.54 (m, 1H), 2.71-2.76 (m, 1H), 4.14-4.32 (m, 3H), 4.54-4.72 (m, 3H), 5.83 (s, 1H), 6.29 (d, J = 8.9 Hz, 1H), 6.68 (d, J = 6.1 Hz, 1H), 7.18 (dd, J = 8.9 Hz, J = 2.6 Hz, 1H), 7.67-7.69 (m, 2H), 7.87 (s, 1H), 7.97 (d, J = 8.3 Hz, 1H) ppm. |

TABLE 2-continued

| Structure | Cmpd. # | Name | Meth-od | LCMS [M + H]+ | $^1$H NMR |
|---|---|---|---|---|---|
| 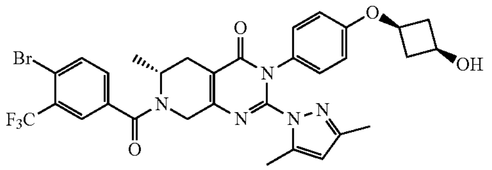 [SMILES: Cc1cc(C)n(-c2nc3c(c(=O)n2-c2ccc(O[C@H]4C[C@@H](O)C4)cc2)C[C@@H](C)N(C(=O)c2ccc(Br)c(C(F)(F)F)c2)C3)n1] | 37 | (R)-7-(4-bromo-3-(trifluoromethyl)benzoyl)-2-(3,5-dimethyl-1H-pyrazol-1-yl)-3-(4-((1s,3S)-3-hydroxycyclo-butoxy)phenyl)-6-methyl-5,6,7,8-tetrahydropyrido[3,4-d]pyrimidin-4(3H)-one | 5 | 672/674 | $^1$H NMR (DMSO-$d_6$, 400 MHz, 80° C.): 1.25 (d, J = 6.8 Hz, 3H), 1.84-1.93 (m, 5H), 2.26 (s, 3H), 2.51-2.58 (m, 1H), 2.69-2.86 (m, 3H), 3.85 (quint, J = 7.1 Hz, 1H), 4.16-4.33 (m, 2H), 4.37-5.25 (m, 3H), 5.80 (s, 1H), 6.75 (d, J = 8.8 Hz, 2H), 7.05 (d, J = 8.8 Hz, 2H), 7.69 (dd, J = 8.1 Hz, 1.8 Hz, 1H), 7.88 (d, J = 1.8 Hz, 1H), 7.99 (d, J = 8.1 Hz, 1H) ppm. |
| 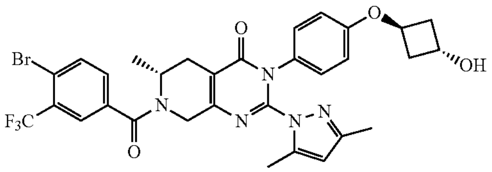 [SMILES: Cc1cc(C)n(-c2nc3c(c(=O)n2-c2ccc(O[C@H]4C[C@H](O)C4)cc2)C[C@@H](C)N(C(=O)c2ccc(Br)c(C(F)(F)F)c2)C3)n1] | 38 | (R)-7-(4-bromo-3-(trifluoromethyl)benzoyl)-2-(3,5-dimethyl-1H-pyrazol-1-yl)-3-(4-((1r,3R)-3-hydroxycyclo-butoxy)phenyl)-6-methyl-5,6,7,8-tetrahydropyrido[3,4-d]pyrimidin-4(3H)-one | 5 | 672/674 | $^1$H NMR (DMSO-d6, 400 MHz, 80° C.): 1.26 (d, J = 6.9 Hz, 3H), 1.89 (s, 3H), 2.24-2.31 (m, 7H), 2.51-2.57 (m, 1H), 2.71-2.79 (m, 1H); 4.25 (d, J = 19.4 Hz, 1H); 4.37 (d, J = 5.6 Hz, 1H); 4.43-4.86 (m, 3H), 4.90 (d, J = 4.6 Hz, 1H), 5.81 (s, 1H), 6.72 (d, J = 9.0 Hz, 2H), 7.05 (d, J = 8.6 Hz, 2H), 7.69 (dd, J = 8.1 HZ, 1.6 Hz, 1H), 7.88 (d, J = 1.6 Hz, 1H), 7.99 (d, J = 8.1 Hz, 1H) ppm. |
| 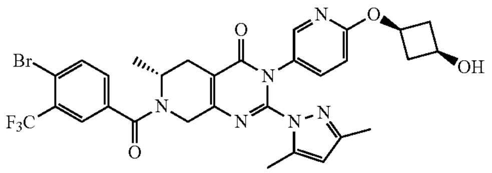 [SMILES: Cc1cc(C)n(-c2nc3c(c(=O)n2-c2ccc(O[C@H]4C[C@@H](O)C4)nc2)C[C@@H](C)N(C(=O)c2ccc(Br)c(C(F)(F)F)c2)C3)n1] | 39 | (R)-7-(4-bromo-3-(trifluoromethyl)benzoyl)-2-(3,5-dimethyl-1H-pyrazol-1-yl)-3-(6-((1s,3S)-3-hydroxycyclo-butoxy)pyridin-3-yl)-6-methyl-5,6,7,8-tetrahydro-pyrido[3,4-d]pyrimidin-4(3H)-one | 5 | 673/675 | $^1$H NMR (DMSO-$d_6$, 400 MHz, 80° C.): 1.26 (d, J = 6.9 Hz, 3H), 1.84-1.95 (m, 5H), 2.33 (s, 3H), 2.51-2.58 (m, 1H), 2.69-2.83 (m, 3H), 3.78-3.92 (m, 1H), 4.26 (d, J = 19.8 Hz, 1H), 4.36-5.00 (m, 4H), 5.86 (s, 1H), 6.73 (d, J = 6.72 Hz, 1H), 7.54 (dd, J = 8.8 Hz, 2.6 Hz, 1H), 7.69 (dd, J = 8.1 Hz, 1.6 Hz, 1H), 7.86-7.91 (m, 2H), 7.99 (d, J = 8.3 Hz, 1H) ppm. |
| 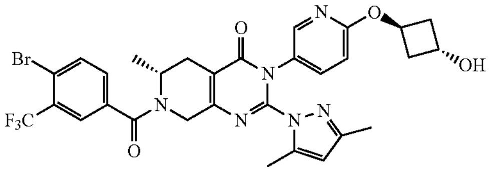 [SMILES: Cc1cc(C)n(-c2nc3c(c(=O)n2-c2ccc(O[C@H]4C[C@H](O)C4)nc2)C[C@@H](C)N(C(=O)c2ccc(Br)c(C(F)(F)F)c2)C3)n1] | 40 | (R)-7-(4-bromo-3-(trifluoromethyl)benzoyl)-2-(3,5-dimethyl-1H-pyrazol-1-yl)-3-(6-((1r,3R)-3-hydroxycyclo-butoxy)pyridin-3-yl)-6-methyl-5,6,7,8-tetrahydropyrido[3,4-d]pyrimidin-4(3H)-one | 5 | 673/675 | $^1$H NMR (DMSO-$d_6$, 400 MHz, 80° C.): 1.24 (d, J = 6.8 Hz, 3H), 1.87 (s, 3H), 2.26 (t, J = 5.6 Hz, 4H), 2.31 (s, 3H), 2.50-2.58 (m, 1H), 2.69-2.80 (m, 1H), 4.24 (d, J = 19.4 Hz, 1H), 4.32-4.41 (m, 1H), 4.43-5.05 (m, 3H), 5.20-5.28 (m, 1H), 5.85 (s, 1H), 6.71 (d, J = 8.6 Hz, 1H), 7.53 (dd, J = 8.6 Hz, 2.7 Hz, 1H), 7.68 (dd, J = 8.1 Hz, 2.0 Hz, 1H), 7.86 (d, J = 1.3 Hz, 1H), 7.88 (d, J = 2.4 Hz, 1H), 7.98 (d, J = 8.0 Hz, 1H) ppm |
| 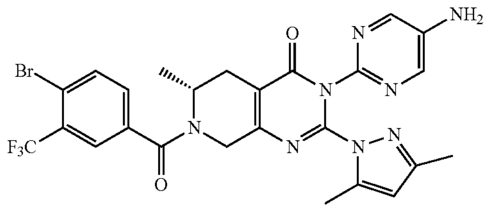 [SMILES: Cc1cc(C)n(-c2nc3c(c(=O)n2-c2ncc(N)cn2)C[C@@H](C)N(C(=O)c2ccc(Br)c(C(F)(F)F)c2)C3)n1] | 41 | (R)-3-(5-amino-pyrimidin-2-yl)-7-(4-bromo-3-(trifluoromethyl)benzoyl)-2-(3,5-dimethyl-1H-pyrazol-1-yl)-6-methyl-5,6,7,8-tetrahydropyrido[3,4-d]pyrimidin-4(3H)-one | 5 | 603/605 | $^1$H NMR (DMSO-$d_6$, 400 MHz, 80° C.): 1.22 (d, J = 6.9 Hz, 3H), 1.84 (s, 3H), 2.34 (s, 3H), 2.50-2.52 (m, 1H), 2.71-2.77 (m, 1H), 4.24-4.26 (m, 1H), 4.45-4.84 (m, 2H), 5.56 (br. s, 2H), 5.89 (s, 1H), 7.69 (dd, J = 8.2 Hz, 2.3 Hz, 1H), 7.88 (d, J = 2.1 Hz, 1H), 7.97 (d, J = 8.1 Hz, 1H), 8.0 (s, 2H) ppm |

TABLE 2-continued

| Structure | Cmpd. # | Name | Meth-od | LCMS [M + H]+ | $^1$H NMR |
|---|---|---|---|---|---|
| 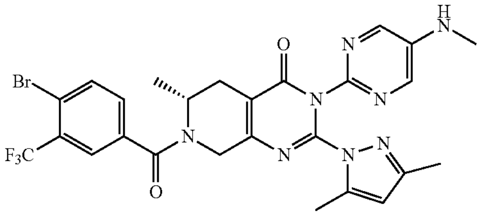 [SMILES: CNc1cnc(-n2c(-n3nc(C)cc3C)nc3c(c2=O)C[C@@H](C)N(C(=O)c2ccc(Br)c(C(F)(F)F)c2)C3)nc1] | 42 | (R)-7-(4-bromo-3-(trifluoromethyl) benzoyl)-2-(3,5-dimethyl-1H-pyrazol-1-yl)-6-methyl-3-(5-(methylamino) pyrimidin-2-yl)-5,6,7,8-tetra-hydropyrido[3,4-d]pyrimidin-4(3H)-one | 5 | 617/ 618 | $^1$H NMR (DMSO-$d_6$, 400 MHz, 80° C.): 1.24 (d, J = 7.0 Hz, 3H), 1.84 (s, 3H), 2.37 (s, 3H), 2.50-5.54 (m, 1H), 2.73-2.79 (m, 4H), 4.22-4.28 (m, 1H), 4.41-4.84 (m, 2H), 5.90 (s, 1H), 6.12 (q, J = 5.1 Hz, 1H), 7.71 (dd, J = 8.1 Hz, 2.1 Hz, 1H), 7.9 (d, J = 2.2 Hz, 1H), 7.98-8.01 (m, 3H) ppm. |
| 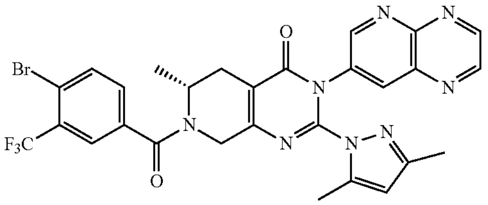 [SMILES: Cc1cc(C)n(-c2nc3c(c(=O)n2-c2cnc4nccnc4c2)C[C@@H](C)N(C(=O)c2ccc(Br)c(C(F)(F)F)c2)C3)n1] | 43 | (R)-7-(4-bromo-3-(trifluoromethyl) benzoyl)-2-(3,5-dimethyl-1H-pyrazol-1-yl)-6-methyl-3-(pyrido[2,3-b] pyrazin-7-yl)-5,6,7,8-tetra-hydropyrido[3,4-d] pyrimidin-4(3H)-one | 5 | 639/ 641 | $^1$H NMR (DMSO-$d_6$, 400 MHz, 80° C.): 1.30 (d, J = 6.9 Hz, 3H), 1.64 (s, 3H), 2.46 (s, 3H), 2.50-2.61 (m, 1H), 2.77-2.83 (m, 1H), 4.29-4.34 (m, 1H), 4.58-4.84 (m, 2H), 5.85 (s, 1H), 7.71 (dd, J = 8.1, 2.3 Hz, 1H), 7.89 (d, J = 2.3 Hz, 1H), 8.01 (d, J = 8.0 Hz, 1H), 8.42 (d, J = 2.6 Hz, 1H), 9.04 (d, J = 1.8 Hz, 1H), 9.08 (d, J = 2.4 Hz, 1H), 9.15 (d, J = 1.8 Hz, 1 H) ppm |
| 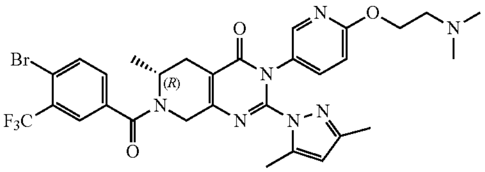 | 44 | (R)-7-(4-bromo-3-(trifluoromethyl) benzoyl)-2-(3,5-dimethyl-1H-pyrazol-1-yl)-3-(6-(2-(dimethyl-amino)ethoxy) pyridin-3-yl)-6-methyl-5,6,7,8-tetrahydropyrido [3,4-d]pyrimidin-4(3H)-one | 5 | 674/ 676 | $^1$H NMR (DMSO-d6, 400 MHz, 80° C.): 1.25 (d, J = 6.9 Hz, 3H), 1.88 (s, 3H), 2.30-2.37 (m, 9H), 2.50-2.56 (m, 1H), 2.69-2.83 (m, 3H), 4.25 (d, J = 19.7 Hz, 1H), 4.38 (t, 5.7 Hz, 2H), 4.55 (br. s., 1H), 4.75 (br. s., 1H), 5.86 (s, 1H), 6.76 (d, J = 8.7 Hz, 1H), 7.56 (dd, J = 8.7 Hz, 2.2 Hz, 1H), 7.68 (dd, J = 8.1 Hz, 1.4 Hz, 1H), 7.86 (d, J = 1.7 Hz, 1H), 7.92 (d, J = 2.5 Hz, 1H), 7.98 (d, J = 8.1 Hz, 1H) ppm |

Additional Compounds

Additional compounds can be prepared using similar materials and methods described herein, such as those described herein.

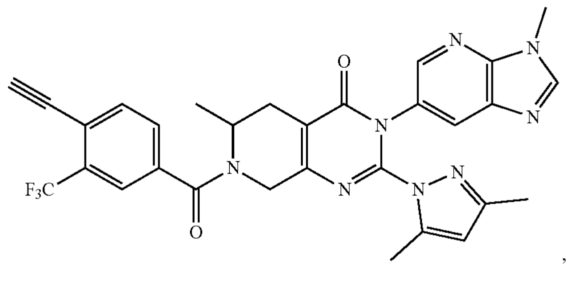

,

-continued

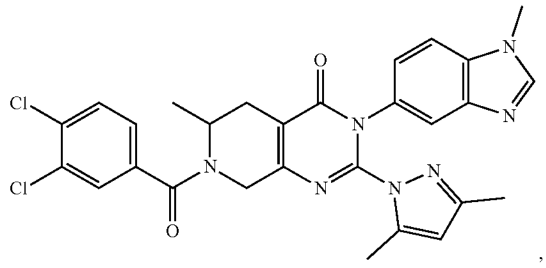

,

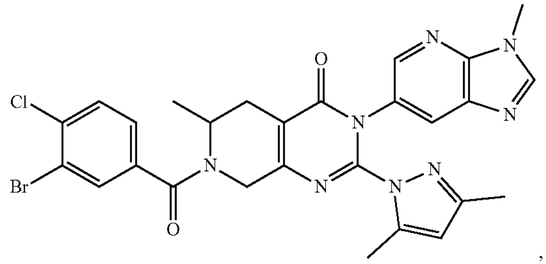

,

-continued
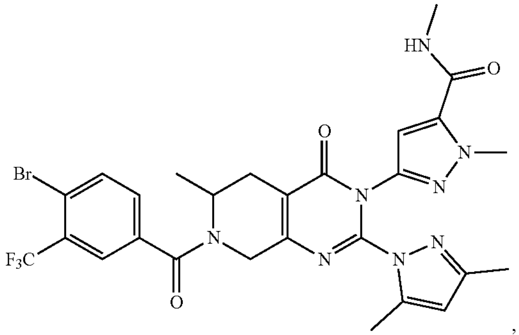
,
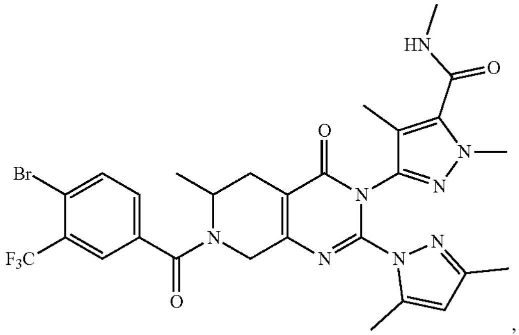
,
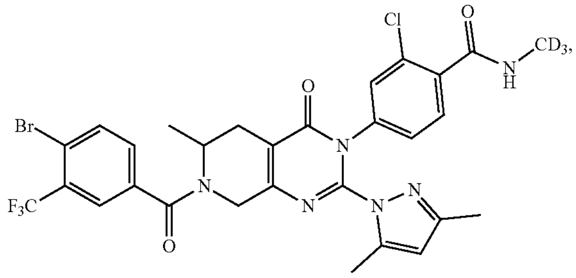
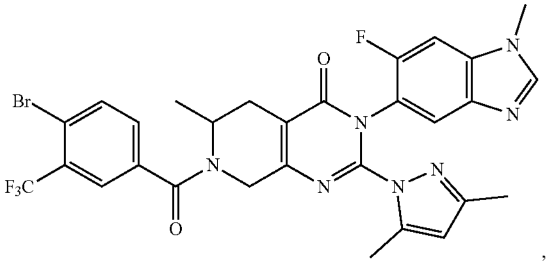
,
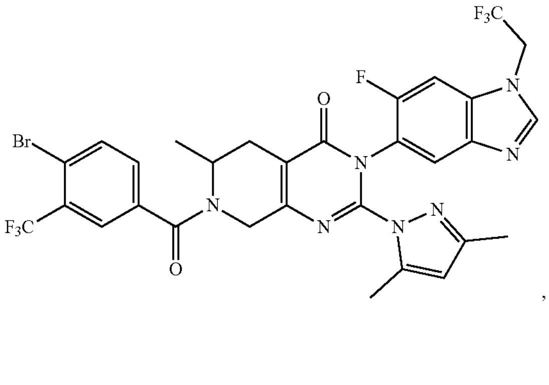
,
-continued
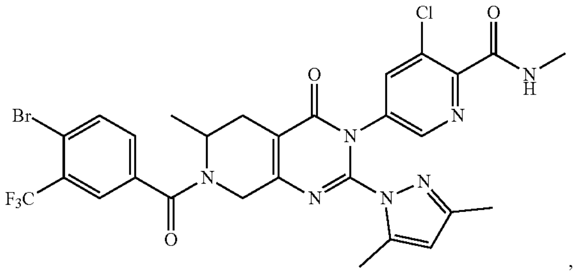
,
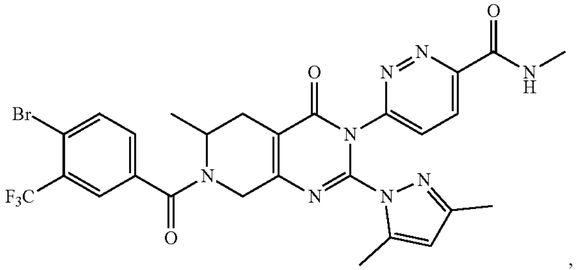
,
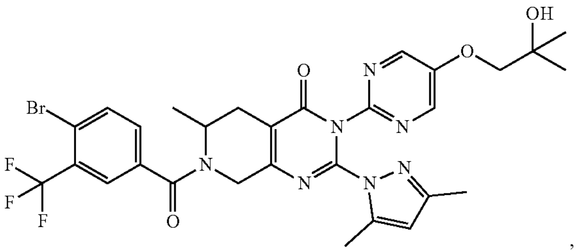
,
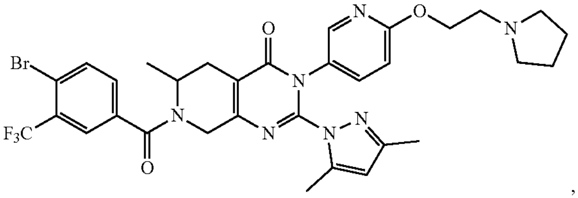
,
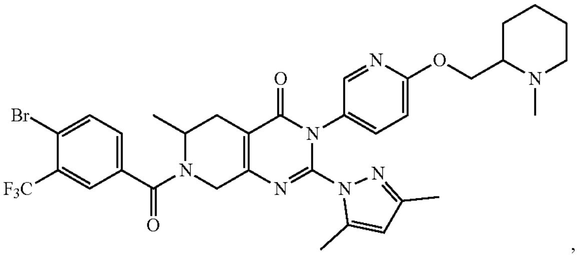
,
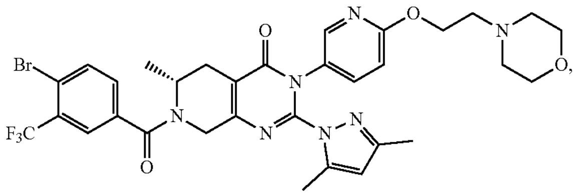
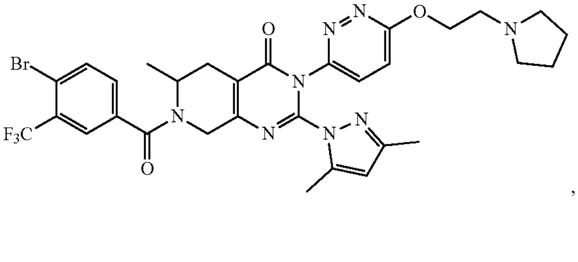
, -continued
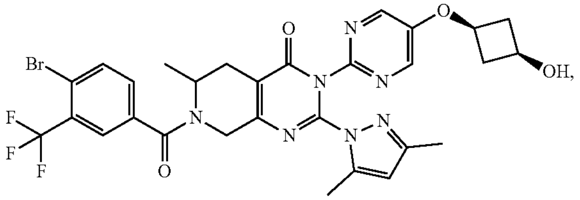
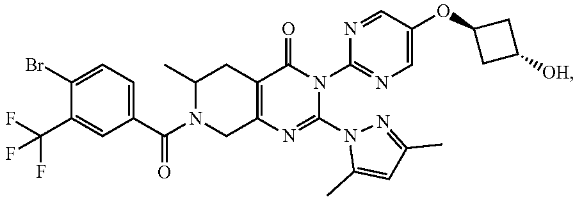
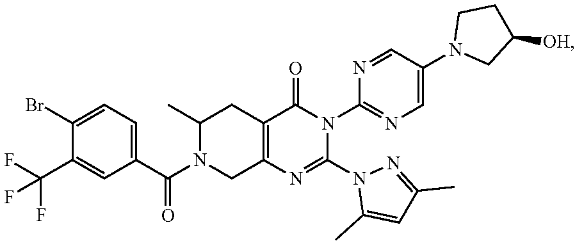
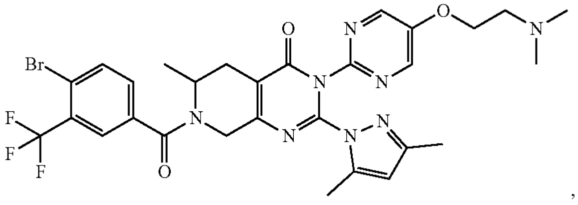
,
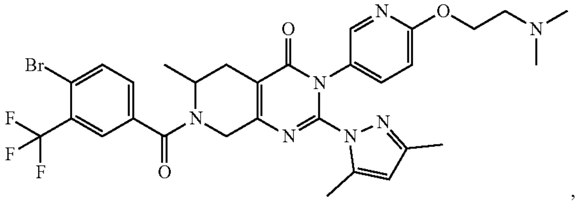
,
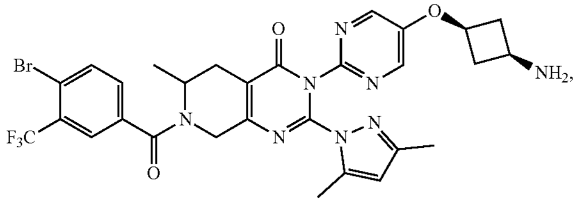
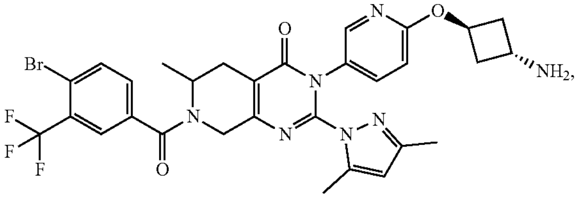
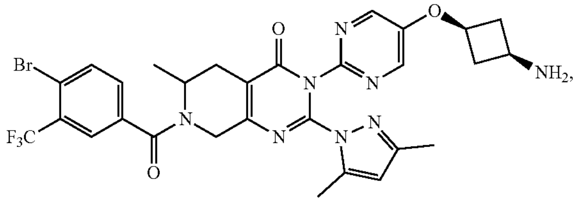
-continued
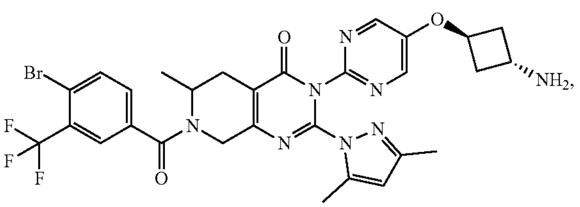
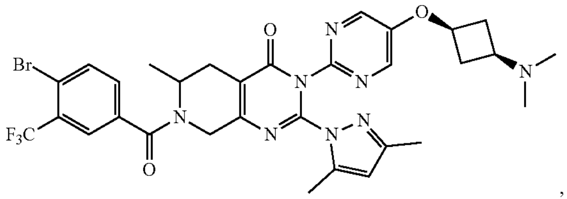
,
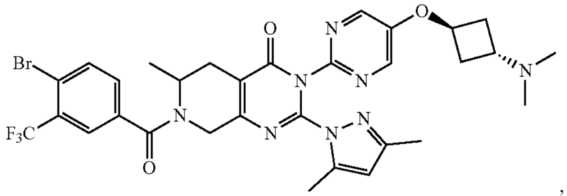
,
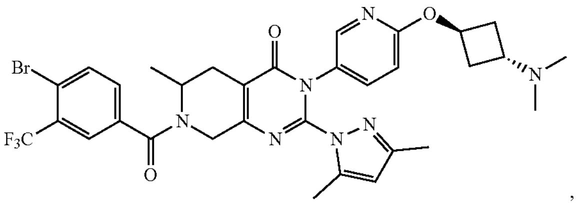
,
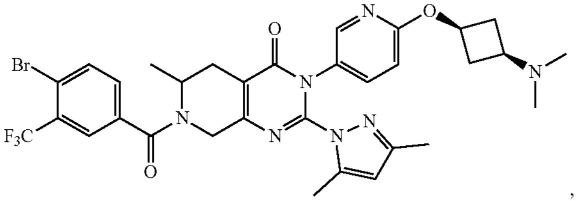
,
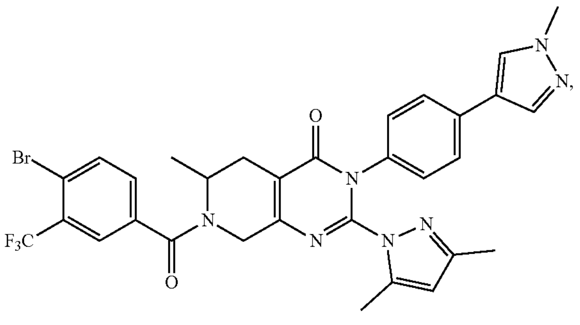
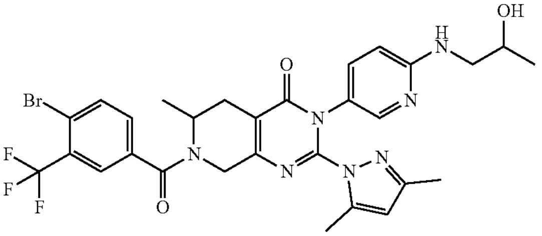
and -continued

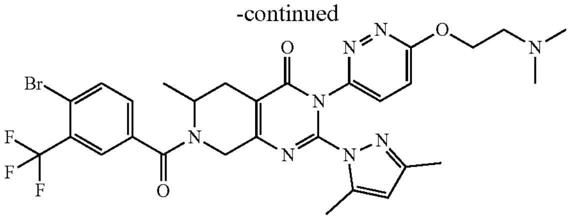

(including pharmaceutically acceptable salts of any of the foregoing).

Example 14

Intermediates I1 to I24

Intermediate I1

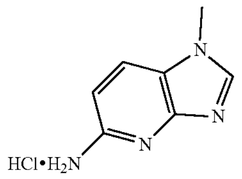

NaHMDS 2M in THF (1.5 eq., 24.42 mL, 48.84 mmol) was added dropwise to a solution of 5-chloro-1H-imidazo[4,5-b]pyridine (1 eq., 5 g, 32.56 mmol) in anhydrous THF (162 mL) at 0° C. MeI (3 eq., 6.081 mL, 97.68 mmol) was added, and the mixture was stirred at rt for 1 h. Sat. aq. $NH_4Cl$ was added to the mixture and the THF was evaporated under vacuum. The aqueous phase was extracted with DCM (3×). The combined organic layers were washed with brine and dried over $MgSO_4$. The solids were removed by filtration and the filtrate was evaporated to dryness to give the crude mixture as a brown solid. The solid was purified by flash chromatography on silica gel (from 0 to 10% of MeOH in DCM) to afford 5-chloro-1-methyl-1H-imidazo[4,5-b]pyridine (3.65 g, 67%) as a colorless oil. $^1$H-NMR (DMSO-$d_6$, 400 MHz) δ 3.88 (s, 3H), 7.37 (d, J=8.2 Hz, 1H), 8.13 (d, J=8.4 Hz, 1H), 8.50 (s, 1H) ppm.

$Pd_2(dba)_3$ (0.1 eq., 0.55 g. 0.6 mmol), (+/−)-BINAP (0.2 eq., 0.74 g. 1.19 mmol), benzophenone imine (1.5 eq., 1.502 mL. 8.95 mmol) and $Cs_2CO_3$ (2.5 eq., 4.86 g. 14.92 mmol) were added to a solution of 5-chloro-1-methyl-1H-imidazo[4,5-b]pyridine (1 eq., 1 g, 5.97 mmol) in DME (50 mL). The mixture was purged with $N_2$ and stirred at 120° C. for 18 h. The mixture was evaporated to dryness to give the crude product which was purified by flash chromatography on silica gel (from 0 to 100% of EA in CyH, then from 0 to 10% of MeOH in DCM) to give N-(1-methyl-1H-imidazo[4.5-b]pyridin-5-yl)-1,1-diphenylmethanimine (1.49 g, 80%) as a beige solid. $^1$H-NMR (DMSO-$d_6$, 400 MHz) δ 3.77 (s, 3H), 6.60 (d. J=8.2 Hz, 1H). 7.13-7.18 (m, 2H), 7.23-7.29 (m, 3H), 7.46-7.52 (m, 2H), 7.54-7.60 (m, 1H), 7.67-7.73 (m, 2H), 7.80 (d, J=8.2 Hz. 1H), 8.23 (s, 1H) ppm.

HCl 1M (1.5 eq., 8.64 mL, 8.64 mmol) was added to a solution of N-(1-methyl-1H-imidazo[4,5-b]pyridin-5-yl)-1,1-diphenylmethanimine (1 eq., 1.8 g, 5.76 mmol) in THF (55 mL). The mixture was stirred at rt for 18 h. The THF was evaporated under vacuum and the resulting aqueous phase was extracted with $Et_2O$ (3×20 mL). The aqueous phase was evaporated to dryness to give 1-methyl-1H-imidazo[4,5-b]pyridin-5-amine hydrochloride (1.05 g. 99%) as a beige solid. LCMS: $C_7H_8N_4$. $[M+H]^+$: 149.

Intermediate I2

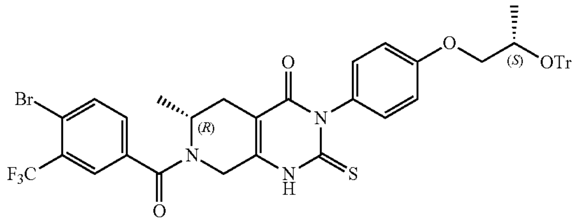

Ethyl L(−)-lactate (5 g, 42.33 mmol) in anhydrous $CH_2Cl_2$ (30 mL) was added to a solution of DBU (8.85 mL, 59.26 mmol) and triphenylmethyl chloride (11.8 g, 42.33 mmol) in anhydrous $CH_2Cl_2$ (30 mL) under $N_2$. The mixture was stirred at rt for 3 days. The mixture was diluted with cold water (20 mL), extracted with $Et_2O$ (3×50 mL), washed with brine and dried over $Na_2SO_4$. The solids were removed by filtration, and the filtrate was evaporated to dryness to give the crude product which was purified by chromatography on silica gel (0 to 10% EA in CyH) to afford ethyl (S)-2-(trityloxy)propanoate (15.9 g, 99%) as a colorless oil. $^1$H-NMR (DMSO-$d_6$, 400 MHz) δ 0.98 (t, J=7.0 Hz, 3H), 1.22 (d, J=6.7 Hz, 3H), 3.62 (q, J=7.0 Hz, 2H), 4.01 (q, J=6.7 Hz, 1H), 7.24-7.29 (m, 3H), 7.30-7.35 (m, 6H), 7.37-7.41 (m, 6H) ppm.

$LiAlH_4$ (1M) in THF (42.33 mL, 42.33 mmol) was added, dropwise at −78° C. to a solution of ethyl (S)-2-(trityloxy)propanoate (15.26 g, 42.33 mmol) in anhydrous THF (200 mL) under $N_2$. The mixture was stirred at −78° C. for 4 h. The mixture was diluted with $Et_2O$ (100 mL) and cooled to 0° C. Water (42 mL) was added slowly followed by NaOH (42 mL, aq., 15%) and water (170 mL), respectively. The mixture was stirred at rt for 15 mins, and $MgSO_4$ was added. The mixture was stirred for 15 mins. The salts were removed by filtration and washed with $Et_2O$, and the filtrate was evaporated to dryness to afford (S)-2-(trityloxy)propan-1-ol (9.3 g, 69%) as a white solid. $^1$H-NMR (DMSO-$d_6$, 400 MHz) δ 0.69 (d, J=6.1 Hz, 3H), 2.94-3.13 (m, 2H), 3.43-3.54 (m, 1H), 4.46-4.49 (m, 1H), 7.23-7.28 (m, 3H), 7.30-7.36 (m, 6H), 7.43-7.47 (m, 6H) ppm.

$Cs_2CO_3$ (697 mg, 2.14 mmol) was added to a solution of 4-fluoronitrobenzene (201 mg, 1.43 mmol) and (S)-2-(trityloxy)propan-1-ol (500 mg, 1.57 mmol) in anhydrous DMSO (6 mL) under $N_2$. The mixture was stirred at 50° C. for 4 h. The mixture was diluted with $NaHCO_3$ (20 mL) and extracted with EA (3×25 mL). The combined organic phases were washed with water and brine, and dried over $Na_2SO_4$. The solids were removed by filtration, and the filtrate was evaporated to dryness to give the crude product which was purified by chromatography on silica gel (0 to 20% EA in CyH) to afford (S)-(((1-(4-nitrophenoxy)propan-2-yl)oxy)methanetriyl)tribenzene (567 mg, 90%) as a white solid. $^1$H-NMR (DMSO-$d_6$, 400 MHz) δ 0.89 (d, J=6.2 Hz, 3H), 3.65-3.76 (m, 2H), 3.82-3.90 (m, 1H), 6.94-7.00 (m, 2H), 7.24-7.28 (m, 3H), 7.30-7.36 (m, 6H), 7.42-7.50 (m, 6H), 8.12-8.18 (m, 2H) ppm.

10% Pd/C (1.04 g, 0.98 mmol) was added to a solution of (S)-(((1-(4-nitrophenoxy)propan-2-yl)oxy)methanetriyl)tribenzene (4.3 g, 9.78 mmol) in EtOH (170 mL). The mixture was purged with $N_2$, then purged with $H_2$ and stirred at rt for 3 days. The mixture was filtered over a pad of celite and evaporated to dryness to give (S)-4-(2-(trityloxy) propoxy)aniline (3.8 g, 95%) as a colorless oil. LC-MS: $C_{28}H_{27}NO_2$ $[M+H]^+$: 410.

(S)-4-(2-(trityloxy)propoxy)aniline (1.03 g, 2.51 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 g, 2.095 mmol) and $Et_3N$ (2.0 mL, 4.19 mmol) in anhydrous $CH_3CN$ (8 mL) under $N_2$. The mixture was stirred at 110° C. for 4 h. The mixture was evaporated to dryness and purified by flash chromatography on silica gel (0 to 100% EA in CyH) to afford (R)-7-(4-bromo-3-(trifluoromethyl)benzoyl)-6-methyl-2-thioxo-3-(4-((S)-2-(trityloxy)propoxy)phenyl)-2,3,5,6,7,8-hexahydropyrido[3,4-d]pyrimidin-4(1H)-one (1.20 g, 68%) as a yellow solid. LC-MS: $C_{44}H_{37}BrF_3N_3O_4S$ $[M+H]^+$: 840/842.

Intermediate I3

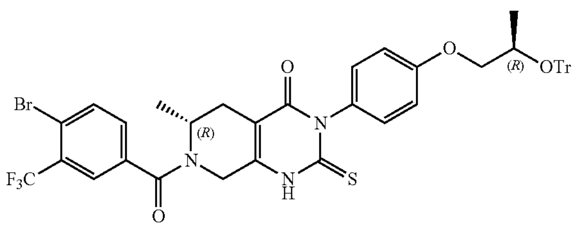

Intermediate I3 was synthesized following the procedure reported for the synthesis of intermediate 12, using ethyl D(+)-lactate in place of ethyl L(−)-lactate in the first step. LC-MS: $C_{44}H_{37}BrF_3N_3O_4S$ $[M+H]^+$: 840/842.

Intermediate I4

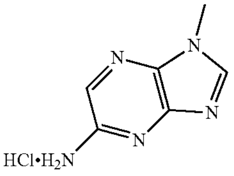

MeI (1 eq., 1.49 mL, 23.99 mmol) and LiHMDS (1 M in THF, 1 eq., 23.99 mL, 23.99 mmol) were added to a solution of 5-bromo-3-chloropyrazin-2-amine (1 eq., 5 g, 23.99 mmol) in anhydrous DMF (150 mL) at 0° C. The mixture was stirred at rt for 2 h. Water and EA were then added. The aqueous phase was extracted with EA (3×). The combined organic layers were washed with water (2×) and brine (2×), and dried over $Na_2SO_4$. The solids were removed by filtration. The filtrate was evaporated to dryness to give the crude product which was purified by flash chromatography on silica gel (from 0 to 50% of EA in cyclohexane) to afford 5-bromo-3-chloro-N-methylpyrazin-2-amine (2.72 g, 51%) as a colorless oil. $^1H$-NMR (DMSO-$d_6$, 400 MHz) δ 2.85 (d, J=4.5 Hz, 31), 7.25-7.31 (m, 11), 8.18 (s, 1H) ppm.

A solution of 5-bromo-3-chloro-N-methylpyrazin-2-amine (1 eq., 2.5 g. 11.24 mmol) in $NH_4OH$ (33% in water, 50 eq., 72.93 mL. 561.87 mmol) was stirred at 120° C. for 2 days. The mixture was evaporated to dryness to give the crude product which was washed with $CH_2Cl_2$ (3×) to give 5-bromo-$N^2$-methylpyrazine-2,3-diamine (2.36 g, 99%) as a beige powder. LCMS: $C_5H_7BrN_4$, $[M+H]^+$: 203/205.

A solution of 5-bromo-$N^2$-methylpyrazine-2,3-diamine (1 eq. 5.11 g, 25.17 mmol) and p-TsOH (0.12 eq., 0.51 g, 2.97 mmol) in triethyl orthoformate (24.39 eq., 102.2 mL, 613.74 mmol) was stirred and heated at 130° C. for 2 h. The mixture was cooled to 0° C. The resulting solid was filtered to give 5-bromo-1-methyl-1H-imidazo[4,5-b]pyrazine (4.73 g, 88%) as a brown solid. $^1H$-NMR (DMSO-$d_6$, 400 MHz) δ 3.87 (s, 3H), 8.59 (s, 1H), 8.80 (s, 1H) ppm. LCMS: $C_6H_5BrN_4$, [MII]+: 213/215.

$Pd_2(dba)_3$ (0.1 eq., 0.64 g, 0.704 mmol), (+/−)-BINAP (0.2 eq., 0.88 g, 1.408 mmol), benzophenone imine (1.5 eq., 1.77 mL, 10.56 mmol) and $Cs_2CO_3$ (2.5 eq., 5.74 g, 17.602 mmol) were added to a solution of 5-bromo-1-methyl-1H-imidazo[4,5-b]pyrazine (1 eq., 1.5 g, 7.041 mmol) in DME (59 mL). The mixture was purged with $N_2$ (3×) and then stirred at 120° C. for 18 h. The mixture was evaporated to dryness to give the crude product which was purified by flash chromatography on silica gel (from 0 to 100% EA in CyH. then from 0 to 10% of MeOH in DCM) to afford N-(1-methyl-1H-imidazo[4,5-b]pyrazin-5-yl)-1,1-diphenylmethanimine (2.11 g, 96%). $^1H$-NMR (DMSO-$d_6$, 400 MHz) δ 3.78 (s, 3H), 7.16-7.21 (m, 2H), 7.28-7.32 (m, 3H), 7.49-7.64 (m, 3H), 7.71-7.76 (m, 2H), 7.84 (s, 1H), 8.54 (s, 1H) ppm.

HCl 1 N (1.5 eq., 10.1 mL, 10.1 mmol) was added to a solution of N-(1-methyl-1H-imidazo[4,5-b]pyrazin-5-yl)-1,1-diphenylmethanimine (1 eq., 2.11 g, 6.73 mmol) in THF (60 mL). The mixture was stirred at rt for 18 h and then the THF was evaporated under vacuum. The resulting aqueous phase was extracted with $Et_2O$. The aqueous phase was evaporated to dryness to give 1-methyl-1H-imidazo[4,5-b] pyrazin-5-amine hydrochloride (1.15 g, 92%) as an orange solid. $^1H$-NMR (DMSO-$d_6$, 400 MHz) δ 3.90 (s, 3H), 7.96 (s, 1H), 9.23 (s, 1H) ppm.

Intermediate I5

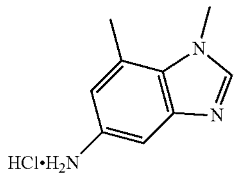

Tetrabutylammonium hydrogen sulfate (0.1 eq., 1.47 g, 4.33 mmol) and dimethyl sulfate (1.1 eq., 4.51 mL, 47.609 mmol) were added to a solution of 4-bromo-2-methyl-6-nitroaniline (1 eq., 10 g, 43.28 mmol) in toluene (80 mL) and a solution of NaOH 50% (24 eq., 80 mL, 1040 mmol). The mixture was stirred at rt for 2 h and then water was added. The organic layers were separated, washed with water and brine, and dried over $Na_2SO_4$. The solids were removed by filtration. The filtrate was evaporated to dryness to give a red solid which was triturated with n-pentane to afford 4-bromo-N,2-dimethyl-6-nitroaniline (10.2 g, 96%) as a red solid. $^1H$-NMR (DMSO-$d_6$, 400 MHz) δ 2.26 (s, 3H), 2.70 (d, J=5.2 Hz, 3H), 6.45-6.54 (m, 1H), 7.48 (d, J=2.0 Hz, 1H), 7.77 (d, J=2.4 Hz, 1-H) ppm. LCMS: $C_8H_9BrN_2O_2$, $[M+H]^+$: 245/247.

Fe (5 eq., 5.7 g 102.009 mmol) was added to a solution of 4-bromo-N,2-dimethyl-6-nitroaniline (1 eq., 5 g, 20.402 mmol) and AcOH (10 eq., 11.69 mL, 204.018 mmol) in EtOH (130 mL) and water (70 mL). The mixture was stirred at 80° C. for 2 h. The mixture was filtered through a pad of celite and washed with EtOAc. The filtrate was concentrated to removed EtOH and then sat. aq. $NaHCO_3$ was added. The aqueous phase was extracted with EtOAc (3×). The combined organics layers were washed with brine and dried over $Na_2SO_4$. The solids were removed by filtration. The filtrate was evaporated to dryness to give 4-bromo-$N^1$,6-dimethylbenzene-1,2-diamine (5.54 g, crude) as a brown oil. A solution of 4-bromo-$N_{1,6}$-dimethylbenzene-1,2-diamine (1 eq., 4.5 g, 20.92 mmol) and p-TsOH (0.1 eq., 0.36 g, 2.092 mmol) in trimethyl orthoformate (25 eq., 57.22 mL, 523.027 mmol) was heated at 80° C. for 1 h. The mixture was evaporated to dryness and purified by flash chromatography on silica gel (from 0 to 100% of EA in CyH, then, from 0 to 10% of MeOH in DCM) to afford 5-bromo-1,7-dimethyl-1H-benzo[d]imidazole (3.59 g, 72%) as a beige solid. $^1$H-NMR (DMSO-$d_6$, 400 MHz) δ 2.69 (s, 3H), 4.03 (s, 3H), 7.10-7.15 (m, 1H), 7.60-7.65 (m, 1H), 8.11 (s, 1-H) ppm. LCMS: $C_6H_9BrN_2$, $[M+H]^+$: 225/227.

$Pd_2(dba)_3$ (0.1 eq., 1.38 g, 1.51 mmol), (+/−)-BINAP (0.2 eq., 1.88 g, 3.021 mmol), benzophenone imine (1.5 eq., 3.802 mL, 22.66 mmol) and $Cs_2CO_3$ (2.5 eq., 12.304 g, 37.76 mmol) were added to a solution of 5-bromo-1,7-dimethyl-1H-benzo[d]imidazole (1 eq. 3.4 g, 15.105 mmol) in DME (126 mL). The mixture was purged with $N_2$ and stirred at 100° C. for 24 h. The mixture was filtered through a pad of celite. The filtrate was evaporated to dryness and purified by flash chromatography on silica gel (from 0 to 100% of EA in CyH, then from 0 to 10% of MeOH in DCM) to afford N-(1,7-dimethyl-1H-benzo[d]imidazol-5-yl)-1,1-diphenylmethanimine (4.08 g, 83%) as an orange oil. $^1$H-NMR (DMSO-$d_6$, 400 MHz) δ 2.56 (s, 3H), 3.94 (s, 3H), 6.48 (br. s., 11H), 6.65 (d, i=1.9 Hz, 1H), 7.13-7.20 (m, 2H), 7.25-7.34 (m, 3H). 7.42-7.54 (m, 3H), 7.62-7.69 (m, 2H), 7.90 (s. 1H) ppm. LCMS: $C_{22}H_{19}N_3$, $[M+H]^+$: 326.

[HCl 1N (1.5 eq., 19.96 mL, 19.96 mmol) was added to a solution of N-(1,7-dimethyl-1H-benzo[d]imidazol-5-yl)-1,1-diphenylmethanimine (1 eq., 4.33 g, 13.306 mmol) in THF (125 mL). The mixture was stirred at rt for 2 days. The THF was evaporated under vacuum. The resulting aqueous phase was extracted with $Et_2O$ (2×) and AcOEt (2×). The aqueous phase was evaporated to dryness to give 1,7-dimethyl-1H-benzo[d]imidazol-5-amine hydrochloride (2.96 g, 99%) as a beige solid. LCMS: $C_9H_{11}N_3$, $[M+H]^+$: 162.

Intermediate I6

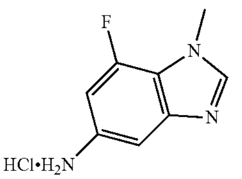

MeI (1.5 eq., 1.74 mL. 27.904 mmol) and isopropylmagnesium chloride 2M in THF (1.5 eq., 13.95 mL, 27.904 mmol) were added to a solution of 5-bromo-7-fluoro-1H-1, 3-benzodiazole (1 eq., 4 g, 18.602 mmol) in anhydrous THF (160 mL) at 0° C. The mixture was stirred for 5 min and then heated at 50° C. for 18 h. Sat. aq. $NaHCO_3$ was added to the mixture. The aqueous layer was extracted with EA (3×). The combined organic layers were washed with brine and dried over $Na_2SO_4$. The solids were removed by filtration. The filtrate was evaporated to dryness and purified by flash chromatography on silica gel (from 0 to 10% of MeOH in DCM) to afford a mixture of 5-bromo-7-fluoro-1-methyl-1H-benzo[d]imidazole/6-bromo-4-fluoro-1-methyl-1H-benzo[d]imidazole (1.85 g, 43%, 2/2'3:1) as a brown solid. $^1$H-NMR (DMSO-$d_6$, 400 MHz) δ 2.26 (s, 3H), 2.70 (d, J=5.2 Hz. 3H). 6.45-6.54 (m, 1H), 7.48 (d. J=2.0 Hz, 1H), 7.77 (d, J=2.4 Hz, 1H) ppm. LCMS: $C_8H_6BrN_2$, $[M+H]^+$: 229/231.

$Pd_2(dba)_3$ (0.1 eq., 0.68 g, 0.74 mmol), (+/−)-BINAP (0.2 eq., 0.92 g, 1.48 mmol), benzophenone imine (1.5 eq., 1.87 mL, 11.13 mmol) and $Cs_2CO_3$ (2.5 eq., 6.045 g, 18.55 mmol) were added to a solution of 5-bromo-7-fluoro-1-methyl-1H-benzo[d]imidazole/6-bromo-4-fluoro-1-methyl-1H-benzo[d]imidazole (1 eq., 1.7 g, 7.42 mmol) in DME (62 mL). The mixture was purged with $N_2$ (3×) and stirred at 100° C. for 35 h. The mixture was filtered through a pad of celite. The filtrate was evaporated to dryness and purified by flash chromatography on silica gel (from 0 to 100% of EA in CyH, then from 0 to 10% of MeOH in DCM) to afford N-(7-fluoro-1-methyl-1H-benzo[d]imidazol-5-yl)-1,1-diphenylmethanimine/N-(4-fluoro-1-methyl-1H-benzo[d]imidazol-6-yl)-1,1-diphenylmethanimine (4.08 g, 83%, in a ratio 3:1) as a yellow solid. LCMS: $C_{21}H_{16}FN_3$, $[M+H]^+$: 330.

HCl 1N (1.5 eq., 12.3 mL, 12.3 mmol) was added to a solution of N-(7-fluoro-1-methyl-1H-benzo[d]imidazol-5-yl)-1.1-diphenylmethanimine/N-(4-fluoro-1-methyl-1H-benzo[d]imidazol-6-yl)-1.1-diphenylmethanimine (1 eq., 2.7 g, 8.02 mmol) in THF (80 mL). The mixture was stirred at rt for 2 days and the THF was evaporated under vacuum. The aqueous phase was extracted with $Et_2O$ (2×) and then evaporated to dryness to give 7-fluoro-1-methyl-1H-benzo[d]imidazol-5-amine hydrochloride/4-fluoro-1-methyl-1H-benzo[d]imidazol-6-amine hydrochloride (1.60 g, 99% in a ratio of 3:1) as a beige solid. LCMS: $C_8H_8FN_3$, $[M+H]^+$: 166.

Intermediate I7

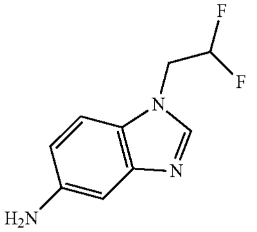 [SMILES: Nc1ccc2c(c1)ncn2CC(F)F]

$Et_3N$ (2 eq., 6.32 mL, 45.46 mmol) was added to a solution of 4-bromo-1-fluoro-2-nitrobenzene (1 eq., 2.8 mL, 22.73 mmol) and 2,2-difluoroethan-1-amine (1.5 eq., 2.76 g, 34.091 mmol) in anhydrous THF (50 mL). The mixture was heated to 70° C. for 2 h. The mixture was evaporated to dryness, dissolved in AcOEt and washed with HCl 1 N. The organic layer was dried over $Na_2SO_4$ and evaporated to dryness to afford 4-bromo-N-(2,2-difluoroethyl)-2-nitroaniline (6.3 g, 99%) as an orange solid. $^1$H-NMR ($CDCl_3$, 400 MHz) δ 3.67-3.77 (m, 2H), 5.96 (tt, J=55.2 Hz, 3.7 Hz, 1H), 6.82 (d, J=9.2 Hz, 1H), 7.54 (dd, J=9.0 Hz, 2.3 Hz, 1H), 8.08-8.17 (m, 1H), 8.32 (d, J=2.5 Hz, 1H) ppm. LCMS: $C_8H_7BrF_2N_{202}$ $[M+H]^+$: 281/283.

Iron (5 eq., 6.04 g, 108.16 mmol) was added to a solution of 4-bromo-N-(2,2-difluoroethyl)-2-nitroaniline (1 eq., 6.08 g, 21.63 mmol) and $NH_4Cl$ (10 eq., 11.57 g, 216.33 mmol) in EtOH (20 mL) and water (20 mL). The mixture was stirred at 70° C. for 22 h. The mixture was filtered through a celite pad and concentrated to remove the EtOH. EA (150 mL) and sat. $NaHCO_3$ (120 mL) were added to the resulting suspension. The layers were separated and the aqueous layer was extracted using EA (3×150 mL). The combined organic layers were washed with water (100 mL) and brine (2×100 mL), and dried over $Na_2SO_4$. The solids were removed by filtration and the filtrate was evaporated to dryness to give 4-bromo-$N_1$-(2,2-difluoroethyl)benzene-1,2-diamine (5.7 g, quant.) as a black wax which was used as such for the next step without purification. LCMS: $C_8H_9BrF_2N_2[M+H]^+$: 251/253.

pTsOH•$H_2O$ (0.1 eq., 0.43 g, 2.27 mmol) was added to a solution of 4-bromo-$N_1$-(2,2-difluoroethyl)benzene-1,2-diamine (1 eq., 5.7 g, 22.70 mmol) in trimethyl orthoformate (60 mL). The mixture was heated to 100° C. for 1 h. The mixture was evaporated to dryness to give the crude product which was purified by flash chromatography on silica gel (from 0 to 100% of AcOEt in CyH, then, from 0 to 5% of MeOH in DCM) to afford 5-bromo-1-(2,2-difluoroethyl)-1H-benzo[d]imidazole (4.72 g, 83% over 2 steps) as a yellow solid. $^1$H-NMR (DMSO-$d_6$, 400 MHz) δ 4.83 (td, J=16.4 Hz, 3.0 Hz, 2H), 5.46 (tt, J=54.4 Hz, 3.0 Hz, 1H), 7.45 (dd, J=8.7 Hz, 2.0 Hz, 1H), 7.66 (d, J=8.7 Hz, 1H), 7.89 (d, J=1.7 Hz, 1H), 8.28 (s, 1H) ppm. LCMS: $C_9H_7BrF_2N_2$ $[M+H]^+$: 261/263.

$Pd_2(dba)_3$ (0.1 eq., 0.702 g, 0.77 mmol), (+/−)-BINAP (0.2 eq., 0.95 g, 1.53 mmol) and $Cs_2CO_3$ (4 eq., 9.98 g, 30.64 mmol) were added to a solution of 5-bromo-1-(2,2-difluoroethyl)-1H-benzo[d]imidazole (1 eq., 2.0 g, 7.66 mmol) and benzophenone imine (1.5 eq., 1.93 mL, 11.49 mmol) in DME (30 mL). The mixture was heated and stirred at 100° C. for 16 h. The mixture was filtered through a pad of celite and the filtrate was concentrated to dryness and purified by flash chromatography on silica gel (from 0 to 100% of EA in CyH over 5CV, then, from 0 to 10% of MeOH in DCM) to afford N-(1-(2,2-difluoroethyl)-1H-benzo[d]imidazol-5-yl)-1,1-diphenylmethanimine (2.48 g, 90%) as an orange solid. $^1$H-NMR ($CDCl_3$, 400 MHz) δ 4.70 (td, J=15.9 Hz, 3.0 Hz, 2H), 6.22-6.60 (m, 1H), 6.73 (dd, J=8.6 Hz, 1.5 Hz, 1H), 6.92 (d, J=1.5 Hz, 1H), 7.16-7.20 (m, 2H), 7.24-7.33 (m, 3H), 7.38-7.56 (m, 4H), 7.63-7.70 (m, 2H), 8.09 (s, 1H) ppm. LCMS: $C_{22}H_{17}F_2N_3$ $[M+H]^+$: 362.

HCl 1 M (1.5 eq., 10.29 mL, 10.29 mmol) was added to a solution of N-(1-(2,2-difluoroethyl)-1H-benzo[d]imidazol-5-yl)-1,1-diphenylmethanimine (1 eq., 2.48 g, 6.86 mmol) in THF (65 mL). The mixture was stirred at rt and then the THF was evaporated under reduced pressure. The resulting solution was filtered and washed with $Et_2O$ (3×20 mL). The aqueous solution was evaporated to dryness to give 1-(2,2-difluoroethyl)-1H-benzo[d]imidazol-5-amine hydrochloride (1.35 g, 84%) as a red solid. $^1$H-NMR ($CDCl_3$, 400 MHz) δ 5.07 (td, J=15.9 Hz, 3.1 Hz, 2H), 6.58 (tt, J=54.2 Hz, 2.9 Hz, 1H), 7.46 (dd, J=6.6 Hz, 1.6 Hz, 1H), 7.78 (d, J=1.5 Hz, 1H), 7.97 (d, J=8.8 Hz, 1H), 8.06-8.94 (m, 3H), 9.36 (s, 1H) ppm. LCMS: $C_9H_{10}ClF_2N_3[M+H]^+$: 198.

Intermediate I8

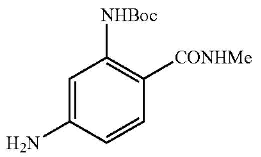

A solution of sulfuric acid (1.87 eq., 5.6 mL, 102.52 mmol) in MeOH (56 mL) was added to a solution of 4-nitroanthranilic acid (1 eq., 10 g, 54.9 mmol) in MeOH (110 mL) under $N_2$. The mixture was stirred at 70° C. for 2 d. The mixture was diluted with a saturated solution of $NaHCO_3$. The precipitate was filtered and washed with water (3×) to give methyl 2-amino-4-nitrobenzoate (10 g, 93%) as a yellow solid which was used as such in the next step. $^1$H-NMR (DMSO-$d_6$, 400 MHz) δ 3.84 (s, 3H), 7.13 (br.s, 2H), 7.26 (dd, J=8.9 Hz, 2.4 Hz, 1H), 7.67 (d, J=2.4 Hz, 1H), 7.92 (d, J=8.8 Hz, 1H) ppm. LCMS: $C_8H_8N_2O_4$ [M+H]+: 197.

$Boc_2O$ (1.5 eq., 8.34 g, 38.23 mmol) and $Et_3N$ (1.5 eq., 5.31 mL, 38.23 mmol) were added to a solution of methyl 2-amino-4-nitrobenzoate (1 eq., 5 g, 25.49 mmol) and DMAP (0.1 eq., 0.31 g, 2.55 mmol) in anhydrous THF (120 mL) under $N_2$. The mixture was stirred at rt for 4 h and then water was added. The resulting solution was extracted with EA (3×). The combined organic layers were washed with brine (2×) and dried over $Na_2SO_4$. The solids were removed by filtration, and the filtrate was evaporated to dryness. The crude mixture was purified by flash chromatography on silica gel (0 to 100% EA in PE) to give methyl 2-(bis(tert-butoxycarbonyl)amino)-4-nitrobenzoate (4.54 g, 45%) as a beige solid. $^1$H-NMR (DMSO-$d_6$, 400 MHz) δ 1.33 (s, 18H), 3.85 (s, 3H), 8.13 (d, J=8.6 Hz, 1H), 8.28 (d, J=2.3 Hz, 1H), 8.32 (dd, J=8.5 Hz, 2.4 Hz, 1H) ppm.

A solution of methyl 2-(bis(tert-butoxycarbonyl)amino)-4-nitrobenzoate (1 eq., 4.2 g, 10.6 mmol) in methylamine 2M in THF (15 eq., 79.5 mL, 158.93 mmol) was stirred at 60° C. for 3 d. The mixture was evaporated under reduced pressure to give tert-butyl (2-(methylcarbamoyl)-5-nitrophenyl)carbamate (3.13 g, 99%) as a brown solid which was used as such in the next step. $^1$H-NMR (DMSO-$d_6$, 400 MHz) δ 1.36 (s, 6H), 1.48 (s, 9H), 2.81 (d, J=4.5 Hz, 3H), 6.64 (br.s, 1H), 7.88-7.93 (m, 2H), 9.02-9.05 (m, 2H) ppm. LCMS: $C_{13}H_{17}N_3O_5$ $[M+H]^+$: 296.

A solution of (2-(methylcarbamoyl)-5-nitrophenyl)carbamate (1 eq., 2.9 g, 9.82 mmol) in EtOH (145 mL) was purged with $N_2$ (3×). Pd/C (0.1 eq., 1.04 g, 0.98 mmol) was added. The mixture was purged with $N_2$ and then purged with $H_2$ (3×). The mixture was stirred at rt for 20 h. The mixture was filtered through a pad of celite using EA and evaporated to dryness to give tert-butyl (5-amino-2-(methylcarbamoyl)phenyl)carbamate (2.6 g, 99%) as an orange solid which was used as such in the next step. $^1$H-NMR (DMSO-$d_6$, 400 MHz) δ 1.45 (s, 9H), 2.69 (d, J=4.5 Hz, 3H), 5.73 (br., s, 2H), 6.15 (dd, J=8.6 Hz, 2.3 Hz, 1H), 7.4 (d, J=8.7 Hz, 1H), 7.49 (d, J=2.3 Hz, 1H), 8.16 (q, J=4.6 Hz, 1H), 11.38 (s, 1H) ppm. LCMS: $C_{13}H_{19}N_3O_3$ $[M+H]^+$: 266.

Intermediate I9

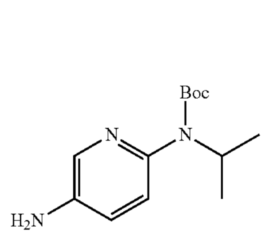 [SMILES: CC(C)N(C(=O)OC(C)(C)C)c1ccc(N)cn1]

Isopropylamine (1.2 eq., 1.809 mL, 21.11 mmol) was added to a solution of 2-fluoro-5-nitropyridine (1 eq., 2.5 g, 17.59 mmol) and $Cs_2CO_3$ (1.5 eq., 8.6 g, 26.39 mmol) in anhydrous DMSO (50 mL). The mixture was stirred at 50° C. for 3 h and then water was added. The aqueous layer was extracted with EA (3×50 mL). The organic layers were combined and washed with a 10% of citric acid solution (in water) (2×50 mL) and brine (4×50 mL), dried over $Na_2SO_4$, filtered and evaporated to dryness to give N-isopropyl-5-nitropyridin-2-amine (3.015 g, 95%) as a yellow solid. $^1$H-NMR ($CDCl_3$, 400 MHz) δ 1.27 (d, J=6.5 Hz, 6H), 3.96-4.13 (m, 1H), 5.08-5.27 (m, 1H), 6.30 (d, J=8.8 Hz, 1H), 8.15 (dd, J=9.3, 2.6 Hz, 1H), 8.98 (d, J=2.8 Hz, 1H) ppm. LCMS: $C_8H_{11}N_3O_2$ $[M+H]^+$: 182.

$Boc_2O$ (1.2 eq., 2.3 g, 10.53 mmol) and DMAP (1.2 eq., 1.29 g, 10.53 mmol) were added to a solution of N-isopropyl-5-nitropyridin-2-amine (1 eq., 1.59 g, 8.78 mmol) in anhydrous MeCN (46 mL). The mixture was stirred for 3 h. The mixture was diluted in EA (100 mL), washed with 20% citric acid solution (3×50 mL), sat. $NaHCO_3$ solution (50 mL), and brine (50 mL), and dried over $Na_2SO_4$. The solids were removed by filtration and the filtrate was evaporated to dryness to give the crude product which was purified by flash chromatography on silica gel (from 0 to 30% of EA in CyH) to afford tert-butyl isopropyl(5-nitropyridin-2-yl)carbamate (1.76 g, 71%) as a colorless oil. $^1$H-NMR ($CDCl_3$, 400 MHz) δ 1.37 (d, J=7.0 Hz, 6H), 1.50 (s, 9H), 4.82 (heptet, J=6.8 Hz, 1H), 7.59 (d, J=9.1 Hz, 1H), 8.33 (dd, J=9.1, 2.8 Hz, 1H), 9.2 (d, J=2.8 Hz, 1H) ppm. LCMS: $C_{13}H_{19}N_3O_4$ $[M+H]^+$: 282.

Pd/C 10% (0.05 eq., 320 mg, 0.30 mmol) was added to a solution of tert-butyl isopropyl(5-nitropyridin-2-yl)carbamate (1 eq., 1.76 g, 6.26 mmol) in MeOH (40 mL). The mixture was purged with $N_2$ and then purged with $H_2$ (3×). The mixture was stirred at rt for 3 h. The mixture was filtered through a pad of celite using EA and evaporated to dryness to give tert-butyl (5-aminopyridin-2-yl)(isopropyl)carbamate (1.57 g, 95%) as a white solid. $^1$H-NMR ($CDCl_3$, 400 MHz) δ 1.14 (d, J=6.6 Hz, 6H), 1.36 (s, 9H), 3.67 (bs, 2H), 4.42 (heptet, J=6.7 Hz, 1H), 6.86 (d, J=7.8 Hz, 1H), 6.96 (dd, J=7.8 Hz, 2.8 Hz, 1H), 7.92 (d, J=2.8 Hz, 1H) ppm. LCMS: $C_{13}H_{21}N_3O_2$ $[M+H]^+$: 252.

Intermediate I10

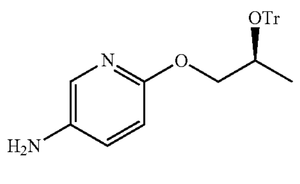

Ethyl L(−)-lactate (1 eq., 5 g, 42.33 mmol) in anhydrous $CH_2Cl_2$ (30 mL) was added to a solution of DBU (1.4 eq., 8.85 mL, 59.26 mmol) and triphenylmethyl chloride (1 eq., 11.8 g, 42.33 mmol) in anhydrous $CH_2Cl_2$ (30 mL) under $N_2$. The mixture was stirred at rt for 3 d. The mixture was diluted with cold water (20 mL), extracted with $Et_2O$ (3×50 mL), washed with brine and dried over $Na_2SO_4$. The solids were removed by filtration and the filtrate was evaporated to dryness to give the crude product which was purified by flash chromatography on silica gel (from 0 to 10% of EA in CyH) to afford ethyl (S)-2-(trityloxy)propanoate (15.9 g, 99%) as a colorless oil. $^1$H-NMR (DMSO-$d_6$, 400 MHz) δ 0.98 (t, J=7.0 Hz, 3H), 1.22 (d, J=6.7 Hz, 3H), 3.62 (q, J=7.0 Hz, 2H), 4.01 (q, J=6.7 Hz, 1H), 7.24-7.29 (m, 3H), 7.30-7.35 (m, 6H), 7.37-7.41 (m, 6H) ppm.

$LiAlH_4$ 1 M in THF (1 eq., 42.33 mL, 42.33 mmol) was added, dropwise at −78° C. to a solution of ethyl (S)-2-(trityloxy)propanoate (1 eq., 15.26 g, 42.33 mmol) in anhydrous THF (200 mL) under $N_2$. The mixture was stirred at −78° C. for 4 h. The mixture was diluted with $Et_2O$ (100 mL) and cooled at 0° C. Water (42 mL) was slowly added, followed by aq. NaOH (15%) (42 mL) and a second portion of water (170 mL). The mixture was stirred at rt for 15 mins and then $MgSO_4$ was added. The mixture was stirred for 15 mins. The salts were removed by filtration and washed with $Et_2O$. The filtrate was evaporated to dryness to give (S)-2-(trityloxy)propan-1-ol (9.3 g, 69%) as a white solid. $^1$H-NMR (DMSO-$d_6$, 400 MHz) δ 0.69 (d, J=6.1 Hz, 3H), 2.94-3.13 (m, 2H), 3.43-3.54 (m, 1H), 4.46-4.49 (m, 1H), 7.23-7.28 (m, 3H), 7.30-7.36 (m, 6H), 7.43-7.47 (m, 6H) ppm.

(S)-2-(trityloxy)propan-1-ol (1.2 eq., 12.33 g, 38.7 mmol) was added to a solution of 2-fluoro-5-nitropyridine (1 eq., 5.5 g, 38.7 mmol) and $Cs_2CO_3$ (1.5 eq., 18.9 g, 58.06 mmol) in anhydrous DMSO (100 mL). The mixture was stirred at 50° C. for 3 h and then water was added. The aqueous layer was extracted with EA:iPrOH (85:15) (3×). The organic layers were combined and washed with water (2×) and brine (4×), dried over $Na_2SO_4$, filtered and evaporated to dryness to afford the crude product which was purified by flash chromatography on silica gel (from 0 to 30% of EtOAc in CyH) to give (S)-5-nitro-2-(2-(trityloxy)propoxy)pyridine (6.95 g, 41%). $^1$H-NMR (DMSO-$d_6$, 400 MHz) δ 0.85 (d, J=6.2 Hz, 3H), 3.84-3.95 (m, 1H), 4.07-4.11 (m, 2H), 6.98 (d, J=9.2 Hz, 1H), 7.17-7.35 (m, 11H), 7.41-7.47 (m, 4H), 8.45 (dd, J=9.2 Hz, 3.0 Hz, 1H), 8.99 (d, J=3.0 Hz, 1H) ppm.

Pd/C 10% (0.1 eq., 1.65 g, 1.57 mmol) was added to a solution of (S)-5-nitro-2-(2-(trityloxy)propoxy)pyridine (1 eq., 6.9 g, 15.66 mmol) in AcOEt (100 mL). The mixture was purged with $N_2$, and then $H_2$ (3×). The mixture was stirred at rt for 18 h. The mixture was filtered through a pad of celite using EA and evaporated to dryness to give (S)-6-(2-(trityloxy)propoxy)pyridin-3-amine (6.33 g, 98%) as a beige solid. $^1$H-NMR (DMSO-$d_6$, 400 MHz) δ 0.70 (d, J=5.5 Hz, 3H), 3.77-3.88 (m, 3H), 4.70 (s, 2H), 6.48 (d, J=8.7 Hz, 1H), 6.97 (dd, J=8.8 Hz, 2.8 Hz, 1H), 7.17-7.35 (m, 12H), 7.38-7.50 (m, 4H) ppm.

Intermediate I11

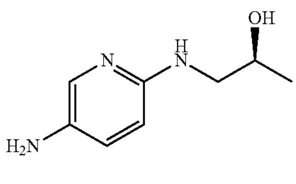

(S)-(−)-1-amino-2-propanol (1.2 eq., 1 mL, 12.67 mmol) was added to a solution of 2-fluoro-5-nitropyridine (1 eq., 1.5 g, 10.56 mmol) and $Cs_2CO_3$ (1.5 eq., 5.16 g, 15.84 mmol) in anhydrous DMSO (30 mL). The mixture was stirred at 50° C. for 2 h and then water was added. The aqueous layer was extracted with EA (3×50 mL). The organic layers were combined and washed with a 10% of citric acid solution (in water) (2×50 mL) and brine (4×50 mL) dried over $Na_2SO_4$, filtered and evaporated to dryness to give (S)-1-((5-nitropyridin-2-yl)amino)propan-2-ol (1.76 g, 85%) as a yellow solid. $^1$H-NMR (DMSO-$d_6$, 400 MHz) δ 1.08 (d, J=6.0 Hz, 3H), 3.76-3.84 (m, 1H), 3.22-3.30 (m, 1H), 4.82 (d, J=4.3 Hz, 1H), 6.63 (d, J=9.5 Hz, 1H), 8.00-8.23 (m, 2H), 8.89 (d, J=2.7 Hz, 1H) ppm. LCMS: $C_8H_{11}N_3O_3$[M+H]$^+$: 198.

Pd/C 10% (0.1 eq., 0.95 g, 0.89 mmol) was added to a solution of (S)-1-((5-nitropyridin-2-yl)amino)propan-2-ol (1 eq., 1.76 g, 8.93 mmol) in EtOH (60 mL). The mixture was purged with $N_2$ and then $H_2$ (3×). The mixture was stirred at rt for 18 h. The mixture was filtered through a pad of celite using EA and evaporated to dryness to give (S)-1-((5-aminopyridin-2-yl)amino)propan-2-ol (1.42 g, 95%) as a beige solid. $^1$H-NMR (DMSO-$d_6$, 400 MHz) δ 1.04 (d, J=6.4 Hz, 3H), 2.94-3.13 (m, 2H), 3.71-3.78 (m, 1H), 5.45-5.54 (m, 1H), 6.33 (d, J=8.5 Hz, 1H), 6.82 (dd, J=8.5 Hz, 2.8 Hz, 1H), 7.42 (d, J=2.8 Hz, 1H) ppm. LCMS: $C_8H_{13}N_3O$ [M+H]$^+$: 168.

Intermediate I12

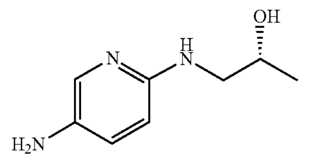

(R)-1-((5-aminopyridin-2-yl)amino)propan-2-ol was synthesized following the protocol described for the synthesis of (S)-1-((5-aminopyridin-2-yl)amino)propan-2-ol, using (L)-(+)-1-amino-2-propanol in place of (S)-(−)-1-amino-2-propanol in the first step. LCMS: $C_8H_{13}N_3O$ [M+H]$^+$: 168.

Intermediate I13

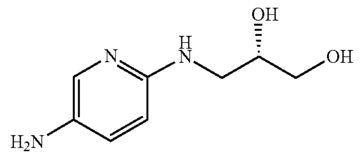 [SMILES: Nc1ccc(NC[C@H](O)CO)nc1]

(2S)-3-amino-1,2-propanediol (1 eq., 1.22 g, 13.37 mmol) was added to a solution of 2-fluoro-5-nitropyridine 1 (1 eq., 1.9 g, 13.37 mmol) and $Et_3N$ (2 eq., 3.72 mL, 26.74 mmol) in anhydrous THF (40 mL). The mixture was stirred at 70° C. for 3 h and then concentrated to dryness to give a yellow oil. DCM was added and the resulting precipitate was filtrated to give (S)-3-((5-nitropyridine-2-yl)amino)propane-1,2-diol (1.75 g, 61%) as a yellow solid. LCMS: $C_8H_{11}N_3O_4$ [M+H]$^+$: 214.

A solution of (S)-3-((5-nitropyridin-2-yl)amino)propane-1,2-diol (1 eq., 1.75 g, 8.20 mmol) in MeOH (60 mL) was purged with $N_2$ (3×). Pd/C (0.1 eq., 870 mg, 0.82 mmol) was added. The mixture was purged with $N_2$ (3×), and then $H_2$ (3×). The mixture was stirred at rt for 18 h. The mixture was filtered through a pad of celite using MeOH and evaporated to dryness to give (S)-3-((5-aminopyridin-2-yl)amino)propane-1,2-diol (1.50 g, quant.) as a red oil which was used as such in the next step. $^1$H-NMR (DMSO-$d_6$, 400 MHz) δ 3.01-3.07 (m, 1H), 3.22-3.25 (m, 5H), 3.51-3.55 (m, 1H), 4.25 (br.s., 2H), 5.57 (m, 1H), 6.35 (d, J=8.7 Hz, 1H), 6.83 (m, 1H), 7.4 (d, J=2.6 Hz, 1H) ppm. LCMS: $C_8H_{13}N_3O_2$ [M+H]+: 183.

Intermediate I14

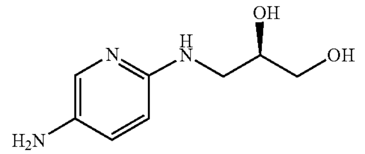 [SMILES: Nc1ccc(NC[C@@H](O)CO)nc1]

(R)-3-((5-aminopyridin-2-yl)amino)propane-1,2-diol was synthesized following the pathway reported for the synthesis of (S)-3-((5-aminopyridin-2-yl)amino)propane-1,2-diol, using (2R)-3-amino-1,2-propanediol instead of (2S)-3-amino-1,2-propanediol. LCMS: $C_8H_{13}N_3O_2$ [M+H]$^+$: 183.

Intermediate I15

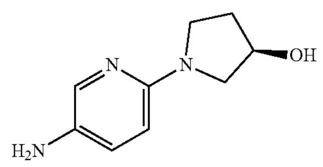 [SMILES: Nc1ccc(N2CC[C@@H](O)C2)nc1]

(3R)-3-pyrrolidinol (1.1 eq., 0.97 mL, 11.6 mmol) was added to a solution of 2-fluoro-5-nitropyridine (1 eq., 1.5 g, 10.56 mmol) and $Cs_2CO_3$ (1.5 eq., 5.1 g, 15.84 mmol) in anhydrous DMSO (30 mL). The mixture was stirred at 50° C. for 3 h. Water was added and the aqueous layer was extracted with EA (3×50 mL). The organic layers were combined and washed with a 10% of citric acid solution (in water) (2×50 mL) and brine (4×50 mL), dried over $Na_2SO_4$, filtered and evaporated to dryness to give (R)-1-(5-nitropyridin-2-yl)pyrrolidin-3-ol (1.9 g, 86%) as a yellow solid. $^1$H-NMR (DMSO-$d_6$, 400 MHz) δ 1.83-2.12 (m, 2H), 3.45-3.82 (m, 4H), 4.42 (d, J=19.5 Hz, 1H), 5.09 (d, J=29.7 Hz, 1H), 6.52-6.62 (m, 1H), 8.20 (dd, J=9.3 Hz, 1.8 Hz, 1H), 8.97 (d, J=2.7 Hz, 1H) ppm. LCMS: $C_9H_{11}N_3O_3$[M+H]$^+$: 210.

Pd/C 10% (0.1 eq., 1.1 g, 1.06 mmol) was added to a solution of (R)-1-(5-nitropyridin-2-yl)pyrrolidin-3-ol (1 eq., 2.2 g, 10.56 mmol) in EtOH (110 mL). The mixture was purged with $N_2$ and then $H_2$ (3×). The mixture was stirred at rt for 18 h. The mixture was filtered through a pad of celite using EA and evaporated to dryness to give (R)-1-(5-aminopyridin-2-yl)pyrrolidin-3-ol (1.45 g, 77%) as a beige solid. $^1$H-NMR (DMSO-$d_6$, 400 MHz) δ 1.74-1.91 (m, 1H), 1.92-2.03 (m, 1H), 3.10-3.19 (m, 1H), 3.26-3.33 (m, 2H), 3.39-3.51 (m, 1H), 4.21-4.44 (m, 3H), 4.86 (s, 1H), 6.23 (d, J=8.7 Hz, 1H), 6.90 (dd, J=8.5 Hz, 2.5 Hz, 1H), 7.55 (d, J=2.1 Hz, 1H) ppm. LCMS: $C_9H_{13}N_3O_1$ $[M+H]^+$: 180.

Intermediate I16

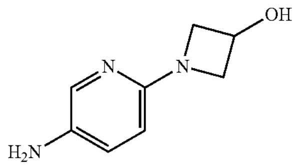 [SMILES: Nc1ccc(N2CC(O)C2)nc1]

$Cs_2CO_3$ (1.5 eq., 5.57 g, 17.1 mmol) was added to a solution of 2-fluoro-5-nitropyridine (1 eq., 1.62 g, 11.4 mmol) and azetidin-3-ol (1.2 eq., 1.0 g, 13.7 mmol) in anhydrous DMSO (30 mL). The mixture was stirred at 50° C. for 20 h. Water was added and the aqueous layer was extracted with EA (3×50 mL). The organic layers were combined and washed with a 10% of citric acid solution (in water) (2×50 mL) and brine (4×50 mL) dried over $Na_2SO_4$, filtered and evaporated to dryness to give 1-(5-nitropyridin-2-yl)azetidin-3-ol (1.4 g, 63%) as a yellow solid. $^1$H-NMR ($CDCl_3$, 400 MHz) δ 3.86-3.90 (m, 2H), 4.32-4.38 (m, 2H), 4.59-4.67 (m, 1H), 5.86 (d, J=6.4 Hz, 1H), 6.42 (d, J=9.3 Hz, 1H), 8.19 (dd, J=9.3, 2.8 Hz, 1H), 8.93 (d, J=2.7 Hz, 1H) ppm. LCMS: $C_8H_9N_3O_3$$[M+H]^+$: 196.

Pd/C 10% (0.1 eq., 760 mg, 0.720 mmol) was added to a solution of 1-(5-nitropyridin-2-yl)azetidin-3-ol (1 eq., 1.4 g, 7.17 mmol) in MeOH (30 mL). The mixture was purged with $N_2$ and then $H_2$ (3×). The mixture was stirred at rt for 18 h. The mixture was filtered through a pad of celite and evaporated to dryness to give 1-(5-aminopyridin-2-yl)azetidin-3-ol (1.16 g, 98%) as a black wax. $^1$H-NMR ($CDCl_3$, 400 MHz) δ 3.50-3.55 (m, 2H), 3.99-4.05 (m, 2H), 4.46-4.53 (m, 1H), 5.56 (br.s., 2H), 6.29 (d, J=8.5 Hz, 1H), 6.99 (dd, J=8.8, 2.8 Hz, 1H), 7.52 (d, J=2.6 Hz, 1H) ppm. LCMS: $C_8H_{11}N_3O$ $[M+H]^+$: 166.

Intermediate I17

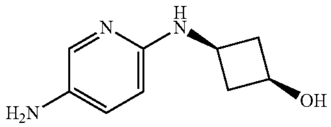 [SMILES: Nc1ccc(N[C@H]2C[C@@H](O)C2)nc1]

$Cs_2CO_3$ (4.0 eq., 18.34 g, 56.30 mmol) was added to a solution of 2-fluoro-5-nitropyridine (1 eq., 2.0 g, 14.08 mmol) and cis-3-aminocyclobutanolhydrochloride (1.1 eq., 1.91 g, 15.48 mmol) in anhydrous DMSO (60 mL). The mixture was stirred at rt for 1 h. $NaHCO_3$ (sat., aq., 50 mL) was added and the aqueous layer was extracted with EA (3×50 mL). The organic layers were combined and washed with water (4×50 mL) and brine (50 mL), and dried over $Na_2SO_4$. The solids were removed by filtration and the solvent of the filtrate was evaporated to dryness to give (1s,3s)-3-((5-nitropyridin-2-yl)amino)cyclobutan-1-ol (2.46 g, 84%) as a yellow solid. $^1$H-NMR ($CDCl_3$, 400 MHz) δ 1.73-1.84 (m, 2H), 2.59-2.68 (m, 2H), 3.82-3.92 (m, 1H), 3.94-4.03 (m, 1H), 5.14 (d, J=5.8 Hz, 1H), 6.50 (d, J=8.3 Hz, 1H), 8.04-8.13 (m, 1H), 8.33 (d, J=6.7 Hz, 1H), 8.88 (d, J=2.6 Hz, 1H) ppm. LCMS: $C_9H_{11}N_3O_3$ $[M+H]^+$: 210.

Pd/C 10% (0.1 eq., 1.25 g, 1.18 mmol) was added to a solution of (1s,3s)-3-((5-nitropyridin-2-yl)amino)cyclobutan-1-ol (1 eq., 2.46 g, 11.76 mmol) in EA (125 mL). The mixture was purged with $N_2$, then with $H_2$ (3×). The mixture stirred at rt for 3 h, then filtered through a pad of celite and evaporated to dryness to give (1s,3s)-3-((5-aminopyridin-2-yl)amino)cyclobutan-1-ol (1.87 g, 89%). $^1$H-NMR ($CDCl_3$, 400 MHz) δ 1.56-1.65 (m, 2H), 2.52-2.59 (m, 2H), 3.48-3.58 (m, 1H), 3.74-3.84 (m, 1H), 4.24 (bs, 2H), 4.94 (d, J=5.6 Hz, 1H), 5.64 (d, J=7.4 Hz, 1H), 6.21 (d, J=8.2 Hz, 1H), 6.79 (m, 1H), 7.43 (d, J=2.8 Hz, 1H) ppm. LCMS: $C_9H_{13}N_3O$ $[M+H]^+$: 180.

Intermediate I18

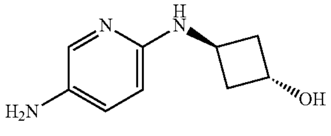 [SMILES: Nc1ccc(N[C@H]2C[C@H](O)C2)nc1]

$Cs_2CO_3$ (2.5 eq., 11.47 g, 35.19 mmol) was added to a solution of 2-fluoro-5-nitropyridine (1 eq., 2.0 g, 14.08 mmol) and trans-3-aminocyclobutanol HCl (1.2 eq., 2.09 g, 16.89 mmol) in anhydrous DMSO (40 mL). The mixture was stirred at 50° C. for 3 h. Water (50 mL) was added, and the aqueous layer was extracted with EA (3×50 mL). The organic layers were combined and washed with 10% citric acid (aq.) (2×50 mL) and brine (4×50 mL), and dried over $Na_2SO_4$. The solids were removed by filtration and the solvent of the filtrate was evaporated to dryness to afford (1r,3r)-3-((5-nitropyridin-2-yl)amino)cyclobutan-1-ol (2.42 g, 82%) as a yellow solid. $^1$H-NMR ($CDCl_3$, 400 MHz) δ 2.14-2.25 (m, 4H), 4.27-4.35 (m, 1H), 4.45 (bs, 1H), 5.09 (d, J=4.4 Hz, 1H), 6.51 (bs, 1H), 8.09 (bs, 1H), 8.39 (d, J=5.1 Hz, 1H), 8.90 (d, J=2.7 Hz, 1H) ppm. LCMS: $C_9H_{11}N_3O_3$ $[M+H]^+$: 210.

Pd/C 10% (0.1 eq., 1.23 g, 1.15 mmol) was added to a solution of (1r,3r)-3-((5-nitropyridin-2-yl)amino)cyclobutan-1-ol (1 eq., 2.42 g, 11.54 mmol) in MeOH (50 mL). The mixture was purged with $N_2$, then with $H_2$ (3×). The mixture was stirred at rt for 18 h. The mixture was filtered through a pad of Celite, and the filtrate was evaporated to dryness to give (1r,3r)-3-((5-aminopyridin-2-yl)amino)cyclobutan-1-ol (2.02 g, 98%). $^1$H-NMR ($CDCl_3$, 400 MHz) δ 2.02-2.16 (m, 4H), 3.98-4.06 (m, 1H), 4.27 (m, 1H), 4.73-5.36 (m, 2H), 4.94 (d, J=5.5 Hz, 1H), 6.12 (bs, 1H), 6.28 (m, 1H), 6.91 (m, 1H), 7.40 (d, J=2.7 Hz, 1H) ppm. LCMS: $C_9H_{13}N_3O$ $[M+H]^+$: 180.

Intermediate I19

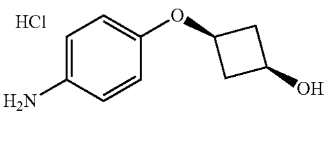 [SMILES: Cl ; Nc1ccc(O[C@H]2C[C@@H](O)C2)cc1]

cis-3-(Benzyloxy)cyclobutanol (1.1 eq., 1.0 g, 5.61 mmol) was added to a solution of 4-fluoronitrobenzene (1 eq., 0.72 g, 5.10 mmol) and $Cs_2CO_3$ (1.5 eq., 2.49 g, 7.65 mmol) in anhydrous DMSO (15 mL). The mixture was stirred at 80° C. for 18 h. Water was added and the aqueous layer was extracted with EA (3×50 mL). The organic layers were combined and washed with 10% citric acid (aq.) (2×50 mL) and brine (4×50 mL), and dried over $Na_2SO_4$. The solids were removed by filtration and the solvent of the filtrate was evaporated to dryness to afford 1-((1s,3s)-3-(benzyloxy)cyclobutoxy)-4-nitrobenzene (1.53 g, 99%) as a yellow solid. $^1$H-NMR (DMSO-$d_6$, 400 MHz) δ 1.95-2.04 (m, 2H), 2.85-2.96 (m, 2H), 3.82 (m, 1H), 4.41 (s, 2H), 4.55 (m, 1H), 7.04-7.08 (m, 2H), 7.26-7.37 (m, 5H), 8.16-8.22 (m, 2H) ppm.

Pd/C 10% (0.2 eq., 1.1 g, 1.04 mmol) was added to a solution of 1-((1s,3s)-3-(benzyloxy)cyclobutoxy)-4-nitrobenzene (1 eq., 1.4 g, 5.2 mmol) in MeOH (25 mL) and 1 N HCl in water (4.8 eq., 25 mmol, 25 mL). The mixture was purged with $N_2$, then with $H_2$ (3×) and stirred at rt for 18 h. The mixture was filtered through a pad of Celite, and the filtrate was evaporated to dryness to give (1s,3s)-3-(4-aminophenoxy)cyclobutan-1-ol hydrochloride (1.2 g, quant.) as a beige solid. $^1$H-NMR (DMSO-$d_6$, 400 MHz) δ 1.83-1.95 (m, 2H), 2.77-2.86 (m, 2H), 3.83 (m, 1H), 4.25 (m, 1H), 6.89 (m, 2H), 7.28-7.33 (m, 2H), 10.25 (s, 3H) ppm. LCMS: $C_{10}H_{13}NO_2$ $[M+H]^+$: 180.

Intermediate I20

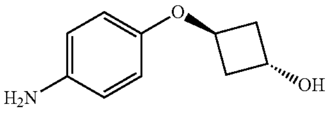

trans-3-(Benzyloxy)cyclobutanol (1.1 eq., 1.0 g, 5.61 mmol) was added to a solution of 4-fluoronitrobenzene (1 eq., 0.72 g, 5.10 mmol) and $Cs_2CO_3$ (1.5 eq., 2.49 g, 7.65 mmol) in anhydrous DMSO (15 mL). The mixture was stirred at 80° C. for 18 h. Water was added and the aqueous layer was extracted with EA (3×50 mL). The organic layers were combined, washed with 10% citric acid (aq.) (2×50 mL) and brine (4×50 mL), and dried over $Na_2SO_4$. The solids were removed by filtration and the solvent of the filtrate was evaporated to dryness to afford 1-((1r,3r)-3-(benzyloxy)cyclobutoxy)-4-nitrobenzene (1.53 g, 99%) as a yellow solid. $^1$H-NMR (DMSO-$d_6$, 400 MHz) δ 2.32-2.41 (m, 2H), 2.53-2.60 (m, 2H), 4.25-4.33 (m, 1H), 4.42 (s, 2H), 4.98-5.05 (m, 1H), 7.01-7.08 (m, 2H), 7.26-7.37 (m, 5H), 8.16-8.22 (m, 2H) ppm.

$BBr_3$ (1 M in DCM, 3.0 eq., 16.4 mL, 16.14 mmol) was added to a solution of 1-((1r,3r)-3-(benzyloxy)cyclobutoxy)-4-nitrobenzene (1.0 eq., 1.6 g, 5.38 mmol) in anhydrous DCM (50 mL at −78° C. The mixture was stirred for 1 h, then allowed to warm to 0° C. The mixture was stirred for 1 h. $NH_4Cl$ (sat., aq.) was added. The organic layer was collected, and the aqueous layer was extracted with DCM (3×). The combined organic layers were dried over $Na_2SO_4$. The solids were removed by filtration and the solvent of the filtrate was evaporated to dryness and purified by normal phase chromatography (0 to 70% EA in CyH) to afford (1r,3r)-3-(4-nitrophenoxy)cyclobutan-1-ol (0.96 g, 85%) as a white solid. $^1$H-NMR (DMSO-$d_6$, 400 MHz) δ 2.35 (m, 4H), 4.38 (m, 1H), 4.98 (m, 1H), 5.24 (m, 1H), 6.99-7.04 (m, 2H), 8.16-8.22 (m, 2H) ppm. LCMS: $C_{10}H_{11}NO_4$ $[M+H]^+$: 210.

Pd/C 10% (0.2 eq., 0.98 g, 0.92 mmol) was added to a solution of (1r,3r)-3-(4-nitrophenoxy)cyclobutan-1-ol (1 eq., 0.96 g, 4.59 mmol) in MeOH (25 mL). The mixture was purged with $N_2$, then with $H_2$ (3×). The mixture was stirred at rt for 18 h, then filtered through a pad of celite. The filtrate was evaporated to dryness to give (1r,3r)-3-(4-aminophenoxy)cyclobutan-1-ol (0.80 g, 97%) as a beige solid. $^1$H-NMR (DMSO-$d_6$, 400 MHz) δ 2.13-2.22 (m, 4H), 4.27-4.37 (m, 1H), 4.57 (s, 2H), 4.59-4.67 (m, 1H), 5.07 (m, 1H), 6.44-6.55 (m, 4H) ppm. LCMS: $C_{10}H_{13}NO_2$ $[M+H]^+$: 180.

Intermediate I21

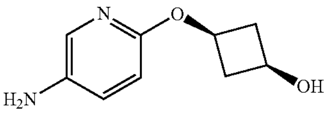

cis-3-(Benzyloxy)cyclobutanol (1.1 eq., 2.2 g, 12.34 mmol) was added to a solution of 2-fluoro-5-nitropyridine (1 eq., 1.59 g, 11.22 mmol) and $Cs_2CO_3$ (1.5 eq., 5.48 g, 16.83 mmol) in anhydrous DMSO (22 mL). The mixture was stirred at 80° C. for 2 h. Water was added and the aqueous layer was extracted with EA (3×). The organic layers were combined and washed with water (2×) and brine (2×), and dried over $Na_2SO_4$. The solids were removed by filtration and the solvent of the filtrate was evaporated to dryness. The product was purified by normal phase chromatography (0 to 20% EA in CyH) to afford 2-((1s,3s)-3-(benzyloxy)cyclobutoxy)-5-nitropyridine (2.2 g, 65%) as a colourless oil. $^1$H-NMR (DMSO-$d_6$, 400 MHz) δ 1.99-2.09 (m, 2H), 2.81-2.91 (m, 2H), 3.85 (m, 1H), 4.40 (s, 2H), 4.93 (m, 1H), 7.03 (d, J=9.1 Hz, 1H), 7.24-7.39 (m, 5H), 8.48 (m, 1H), 9.05 (m, 1H) ppm. LCMS: $C_{16}H_{16}N_2O_4$ $[M+H]^+$: 301.

$BBr_3$ (1 M in DCM, 3.0 eq., 18.98 mL, 18.98 mmol) was added to a solution of 2-((1s,3s)-3-(benzyloxy)cyclobutoxy)-5-nitropyridine (1.0 eq., 1.9 g, 6.33 mmol) in anhydrous DCM (50 mL) at −78° C. The mixture was stirred for 1 h, then allowed to warm to 0° C. The mixture was stirred for 1 h. $NH_4Cl$ (sat., aq.) was added. The organic layer was collected. The aqueous layer was extracted with DCM (3×) and the combined organic layers were dried over $Na_2SO_4$. The solids were removed by filtration and the solvent of the filtrate was evaporated to dryness. The product was purified by normal phase chromatography (0 to 70% EA in CyH) to afford (1s,3s)-3-((5-nitropyridin-2-yl)oxy)cyclobutan-1-ol (1.25 g, 94%) as a white solid. $^1$H-NMR (DMSO-$d_6$, 400 MHz) δ 1.90-2.00 (m, 2H), 2.76-2.86 (m, 2H), 3.87 (m, 1H), 4.82 (m, 1H), 5.23 (d, J=6.5 Hz, 1H), 7.01 (d, J=9.1 Hz, 1H), 8.47 (m, 1H), 9.04 (m, 1H) ppm. LCMS: $C_9H_{10}N_2O_4$$[M+H]^+$: 211.

Pd/C 10% (0.2 eq., 1.27 g, 1.19 mmol) was added to a solution of (1s,3s)-3-((5-nitropyridin-2-yl)oxy)cyclobutan-1-ol (1 eq., 1.25 g, 6.66 mmol) in MeOH (25 mL). The mixture was purged with $N_2$, then with $H_2$ (3×). The mixture was stirred at rt for 18 h. The mixture was filtered through a pad of Celite, and the filtrate was evaporated to dryness to give (1s,3s)-3-((5-aminopyridin-2-yl)oxy)cyclobutan-1-ol (1.0 g, 93%) as a beige solid. $^1$H-NMR (DMSO-$d_6$, 400 MHz) δ 1.76-1.87 (m, 2H), 2.65-2.75 (m, 2H), 3.72-3.84 (m, 1H), 4.53 (m, 1H), 4.72 (s, 2H), 5.07 (s, 1H), 6.49 (m, 1H), 6.97 (m, 1H), 7.45 (d, J=2.8 Hz, 1H) ppm. LCMS: $C_9H_{12}N_2O_2$ $[M+H]^+$: 181.

Intermediate I22

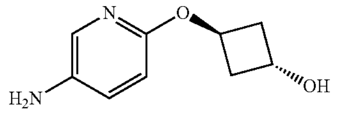 [SMILES: Nc1ccc(O[C@H]2C[C@H](O)C2)nc1]

trans-3-(Benzyloxy)cyclobutanol (1.1 eq., 2.4 g, 13.47 mmol) was added to a mixture of 2-fluoro-5-nitropyridine (1 eq., 1.74 g, 12.24 mmol) and $Cs_2CO_3$ (1.5 eq., 5.98 g, 18.36 mmol) in anhydrous DMSO (22 mL). The mixture was stirred at 80° C. for 2 h. Water was added and the aqueous layer was extracted with EA (3×). The organic layers were combined and washed with water (2×) and brine (2×), and dried over $Na_2SO_4$. The solids were removed by filtration and the solvent of the filtrate was evaporated to dryness. The product was purified by normal phase chromatography (0 to 20% EA in CyH) to afford 2-((1r,3r)-3-(benzyloxy)cyclobutoxy)-5-nitropyridine (2.86 g, 78%) as a colourless oil. $^1$H-NMR (DMSO-$d_6$, 400 MHz) δ 2.30-2.40 (m, 2H), 2.47-2.55 (m, 2H), 4.25-4.33 (m, 1H), 4.41 (s, 2H), 5.37-5.42 (m, 1H), 7.03 (d, J=8.9 Hz, 1H), 8.47 (m, 1H), 9.06 (d, J=2.9 Hz, 1H) ppm. LCMS: $C_{16}H_{16}N_2O_4$ $[M+H]^+$: 301.

$BBr_3$ (1 M in DCM, 3.0 eq., 28.60 mL, 28.60 mmol) was added to a solution of 2-((1r,3r)-3-(benzyloxy)cyclobutoxy)-5-nitropyridine (1.0 eq., 2.86 g, 9.52 mmol) in anhydrous DCM (110 mL) at −78° C. The mixture was stirred for 1 h, then allowed to warm to 0° C. The mixture was stirred for 1 h. $NH_4Cl$ (sat., aq.) was added and the organic layer was collected. The aqueous layer was extracted with DCM (3×). The combined organic layers were dried over $Na_2SO_4$, and the solids were removed by filtration. The solvent of the filtrate was evaporated to dryness and purified by normal phase chromatography (0 to 70% EA in CyH) to afford (1r,3r)-3-((5-nitropyridin-2-yl)oxy)cyclobutan-1-ol (2.0 g, 99%) as a white solid. $^1$H-NMR (DMSO-$d_6$, 400 MHz) δ 2.31-2.40 (m, 4H), 4.34-4.44 (m, 1H), 5.20 (d, J=5.3 Hz, 1H), 5.36-5.42 (m, 1H), 7.01 (m, 1H), 8.47 (m, 1H), 9.06 (m, 1H). LCMS: $C_9H_{10}N_2O_4$ $[M+H]^+$: 211.

Pd/C 10% (0.2 eq., 1.01 g, 0.95 mmol) was added to a solution of (1r,3r)-3-((5-nitropyridin-2-yl)oxy)cyclobutan-1-ol (1 eq., 2.0 g, 9.52 mmol) in MeOH (60 mL). The mixture was purged with $N_2$, then with $H_2$ (3×). The mixture was stirred at rt for 18 h. The mixture was filtered through a pad of Celite, and the filtrate was evaporated to dryness to give (1r,3r)-3-((5-aminopyridin-2-yl)oxy)cyclobutan-1-ol (1.56 g, 91%) as a beige solid. $^1$H-NMR (DMSO-$d_6$, 400 MHz) δ 2.17-2.25 (m, 4H), 4.28-4.37 (m, 1H), 4.70 (s, 2H), 5.02-5.12 (m, 2H), 6.49 (d, J=8.5 Hz, 1H), 6.97 (m, 1H), 7.46 (m, 1H) ppm. LCMS: $C_9H_{12}N_2O_2$ [M+H]+: 181.

Intermediate I23

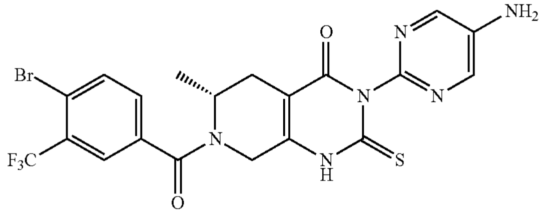 [SMILES: C[C@@H]1Cc2c([nH]c(=S)n(-c3ncc(N)cn3)c2=O)CN1C(=O)c1ccc(Br)c(C(F)(F)F)c1]

NaH 60% (2.2 eq., 3.38 g, 84.58 mmol) was added to a solution of methyl 2-aminopyrimidine-5-carboxylate (1.1 eq., 6.48 g, 42.29 mmol) in anhydrous DMF (140 mL) at 0° C., under $N_2$. The mixture was stirred for 30 min from 0° C. to rt, then a solution of ethyl (R)-1-(4-bromo-3-(trifluoromethyl)benzoyl)-5-isothiocyanato-2-methyl-1,2,3,6-tetrahydropyridine-4-carboxylate (1 eq., 18.35 g, 38.45 mmol) in anhydrous DMF (140 mL) was added. The mixture was stirred at rt for 1.5 h and then cooled to 0° C. Brine was added, and then 1 N HCl was added. The precipitate was collected by filtration and further dried under reduced pressure to afford (R)-2-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)pyrimidine-5-carboxylic acid (14.53 g, 66%) as brown solid, which used without further purification in the next step. LCMS: $C_{21}H_{15}BrF_3N_5O_4S$ $[M+H]^+$: 570/572.

$Et_3N$ (1.5 eq., 6.59 mL, 47.45 mmol) and diphenyl phosphoryl azide (1.5 eq., 10.22 mL, 47.45 mmol) were added to a solution of (R)-2-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)pyrimidine-5-carboxylic acid (1 eq., 18.04 g, 31.63 mmol) in anhydrous DMF (180 mL) under $N_2$. The mixture was stirred at rt for 1.5 h. Water (35 mL) was added. The round bottom flask was equipped with a condenser and the mixture was stirred at 100° C. for 30 min. The mixture was cooled to rt. Water was added. The precipitate was isolated by filtration and washed with water (3×). The crude mixture was purified by flash chromatography on silica gel (0 to 10% MeOH in DCM) to give (R)-3-(5-aminopyrimidin-2-yl)-7-(4-bromo-3-(trifluoromethyl)benzoyl)-6-methyl-2-thioxo-2,3,5,6,7,8-hexahydropyrido[3,4-d]pyrimidin-4(1H)-one (8.15 g, 48%) as a beige solid that was used in the next step without further purification. $^1$H-NMR (DMSO-$d_6$, 400 MHz, 80° C.) δ 1.17-1.20 (m, 6H), 2.22-2.30 (m, 1H), 3.95-4.30 (m, 3H), 5.07-5.15 (m, 1H), 5.82 (br.s, 2H), 7.68-7.70 (m, 1H), 7.91-7.93 (m, 1H), 8.01-8.02 (m, 2H), 8.12-8.15 (m, 2H) ppm. LCMS: $C_{20}H_{16}BrF_3N_6O_2S$ $[M+H]^+$: 541/543.

Intermediate I23

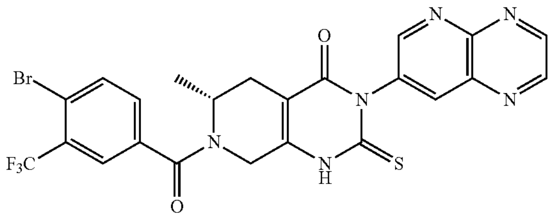 [SMILES: C[C@@H]1Cc2c([nH]c(=S)n(-c3cnc4nccnc4c3)c2=O)CN1C(=O)c1ccc(Br)c(C(F)(F)F)c1]

4-methoxybenzylamine (1.5 eq., 3.1 mL, 23.44 mmol) was added to a solution of 2-amino-5-bromo-3-nitropyridine (1 eq., 3.41 g, 15.63 mmol), cesium acetate (3 eq., 9 g, 46.89 mmol), Cu (0.1 eq., 99 mg, 1.56 mmol) in anhydrous DMSO (23 mL) under $N_2$. The mixture was stirred at 90° C. for 16 h. The mixture was filtered through a pad of Celite, and rinsed with EA. Water was added and the layers were separated. The aqueous layer was extracted with EA (2×). The organic phase was washed with water (3×) and brine, and dried over $Na_2SO_4$. The solids were removed by filtration and the filtrate was evaporated to dryness. The crude mixture was purified by flash chromatography on silica gel (0 to 100% EA in CyH) to afford $N_5$-(4-methoxybenzyl)-3-nitropyridine-2,5-diamine (1.29 g, 30%) as a red solid which was used as such in the next step. $^1$H-NMR (DMSO-$d_6$, 400 MHz) δ 3.72 (s, 3H), 4.18 (m, 2H), 6.19 (m, 1H), 6.88-6.91 (m, 2H), 7.28-7.33 (m, 4H), 7.38 (m, 1H), 8.12 (m, 1H) ppm. LCMS: $C_{13}H_{14}N_4O_3$ $[M+H]^+$: 275.

TFA (50 eq., 17.5 mL, 235.16 mmol) was added to a solution of $N_5$-(4-methoxybenzyl)-3-nitropyridine-2,5-diamine (1 eq., 1.29 g, 4.70 mmol) in anhydrous DCM (45 mL) under $N_2$. The mixture was stirred at rt for 3 h. DCM was evaporated. Water was added, and the aqueous layer was extracted with EA (3×). The combined organic layers were washed with brine and dried over $Na_2SO_4$. The solids were removed by filtration and the filtrate was evaporated to dryness. The crude mixture was purified by flash chromatography on silica gel (0 to 10% MeOH in DCM) to afford 3-nitropyridine-2,5-diamine (420 mg, 58%) as a red solid that was used without further purification in the next step. $^1$H-NMR (DMSO-$d_6$, 400 MHz) δ 5.04 (br.s, 2H), 7.24 (br.s, 2H), 7.58 (m, 1H), 8.02 (m, 1H) ppm. LCMS: $C_5H_6N_4O_2$ $[M+H]^+$: 155.

$NEt_3$ (4 eq., 1.38 mL, 9.91 mmol) was added to a solution of ethyl (R)-1-(4-bromo-3-(trifluoromethyl)benzoyl)-5-isothiocyanato-2-methyl-1,2,3,6-tetrahydropyridine-4-carboxylate (1 eq., 1182.4 mg, 2.48 mmol) and 3-nitropyridine-2,5-diamine (1.1 eq., 420 mg, 2.72 mmol) in anhydrous $CH_3CN$ (24 mL) under $N_2$. The mixture was stirred at 100° C. for 3 h. The mixture was evaporated to dryness and purified by flash chromatography on silica gel (0 to 5% MeOH in DCM) to give (R)-3-(6-amino-5-nitropyridin-3-yl)-7-(4-bromo-3-(trifluoromethyl)benzoyl)-6-methyl-2-thioxo-2,3,5,6,7,8-hexahydropyrido[3,4-d]pyrimidin-4(1H)-one (1.26 g, 87%) as a brown solid which was used as such in the next step. LCMS: $C_{21}H_{16}BrF_3N_6O_4S$ $[M+H]^+$: 586.

Fe (5 eq., 1.07 g, 19.22 mmol) was added to a solution of (R)-3-(6-amino-5-nitropyridin-3-yl)-7-(4-bromo-3-(trifluoromethyl)benzoyl)-6-methyl-2-thioxo-2,3,5,6,7,8-hexahydropyrido[3,4-d]pyrimidin-4(1H)-one (1 eq., 2.25 g, 3.84 mmol) and $NH_4Cl$ (5 eq., 1.03 g, 19.22 mmol) in EtOH (15 mL) and water (15 mL) under $N_2$. The mixture was stirred at 80° C. for 3 h. The mixture was diluted in EA and filtered over packed Celite. The organic layer was washed with brine (2×) and dried over $Na_2SO_4$. The solids were removed by filtration and the filtrate was evaporated to dryness to give (R)-7-(4-bromo-3-(trifluoromethyl)benzoyl)-3-(5,6-diaminopyridin-3-yl)-6-methyl-2-thioxo-2,3,5,6,7,8-hexahydropyrido[3,4-d]pyrimidin-4(1H)-one (1.6 g, 75%) as a brown solid that was used in the next step without further purification. LCMS: $C_{21}H_{18}BrF_3N_6O_4S$ $[M+H]^+$: 555/557.

Glyoxal, 40% w/w aq. (1.1 eq., 0.46 g, 3.17 mmol) was added to a solution of (R)-7-(4-bromo-3-(trifluoromethyl)benzoyl)-3-(5,6-diaminopyridin-3-yl)-6-methyl-2-thioxo-2,3,5,6,7,8-hexahydropyrido[3,4-d]pyrimidin-4(1H)-one (1 eq., 1.6 g, 2.88 mmol) in EtOH (10 mL) under $N_2$. The mixture was stirred at rt for 18 h, then poured in water. The precipitate was isolated by filtration and washed with water. The crude mixture was purified by reverse phase chromatography (5 to 100% $CH_3CN$ in $H_2O$ (+0.1% FA)) to afford (R)-7-(4-bromo-3-(trifluoromethyl)benzoyl)-6-methyl-3-(pyrido[2,3-b]pyrazin-7-yl)-2-thioxo-2,3,5,6,7,8-hexahydropyrido[3,4-d]pyrimidin-4(1H)-one (638 mg, 38%) as a beige solid which was used without further purification in the next step. $^1$H-NMR (DMSO-$d_6$, 400 MHz, 80° C.) δ 1.26 (m, 3H), 2.35-2.48 (m, 1H), 2.58-2.64 (m, 1H), 4.11-4.16 (m, 1H), 4.5-4.85 (m, 2H), 7.67 (m, 1H), 7.87 (m, 1H), 8.0 (m, 1H), 8.48 (br.s, 1H), 9.01 (br.s, 1H), 9.07 (m, 1H), 9.17 (m, 1H), 12.68 (br.s, 1H) ppm. LCMS: $C_{23}H_{16}BrF_3N_6O_2S$ $[M+H]^+$: 577/579.

Intermediate I24

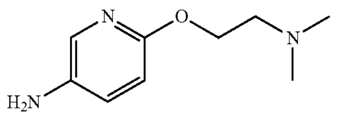

N,N-dimethylethanolamine (1 eq., 0.70 mL, 7.03 mmol) was added to a mixture of 2-fluoro-5-nitropyridine (1 eq., 1.0 g, 7.03 mmol) and $Cs_2CO_3$ (1.5 eq., 3.44 g, 10.56 mmol) in anhydrous DMSO (20 mL). The mixture was stirred at 50° C. for 1 h. Water was added and the aqueous layer was extracted with EA (3×). The organic layers were combined and washed water (2×) and brine (2×), and dried over $Na_2SO_4$. The solids were removed by filtration and the solvent of the filtrate was evaporated to dryness to afford N,N-dimethyl-2-((5-nitropyridin-2-yl)oxy)ethan-1-amine (1.05 g, 67%) as a yellow solid. $^1$H-NMR (DMSO-$d_6$, 400 MHz) δ 2.21 (s, 6H), 2.66 (m, 2H), 4.49 (t, J=5.8 Hz, 2H), 7.03 (m, 1H), 8.47 (m, 1H), 9.08 (m, 1H) ppm. LCMS: $C_9H_{13}N_3O_3$ $[M+H]^+$: 212.

Pd/C 10% (0.1 eq., 0.50 g, 0.47 mmol) was added to a solution of N,N-dimethyl-2-((5-nitropyridin-2-yl)oxy)ethan-1-amine (1 eq., 1.05 g, 4.73 mmol) in EtOH (35 mL). The mixture was purged with $N_2$, then with $H_2$ (3×). The mixture was stirred at rt for 2 d, then filtered through a pad of celite. The filtrate was evaporated to dryness to afford 6-(2-(dimethylamino)ethoxy)pyridin-3-amine (800 mg, 93%) as an orange oil. $^1$H-NMR (DMSO-$d_6$, 400 MHz) δ 2.17 (s, 6H), 2.54 (m, 2H), 4.16 (m, 2H), 4.72 (s, 2H), 6.52 (d, J=8.7 Hz, 1H), 6.99 (m, 1H), 7.48 (m, 1H) ppm. LCMS: $C_9H_{15}N_3O$ $[M+H]^+$: 182.

Final Step in the Synthesis of Compound 43

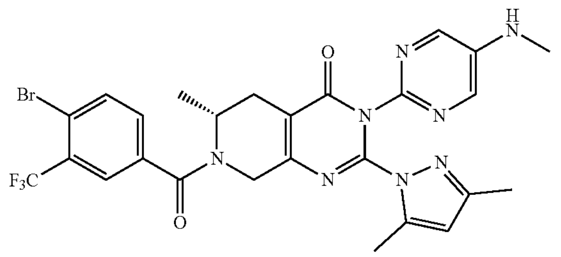 [SMILES: CNc1cnc(-n2c(-n3nc(C)cc3C)nc3c(c2=O)C[C@@H](C)N(C(=O)c2ccc(Br)c(C(F)(F)F)c2)C3)nc1]

Formaldehyde 37% (2 eq., 62 μL, 0.83 mmol) was added to a solution of (R)-3-(5-aminopyrimidin-2-yl)-7-(4-bromo-3-(trifluoromethyl)benzoyl)-2-(3,5-dimethyl-1H-pyrazol-1-yl)-6-methyl-5,6,7,8-tetrahydropyrido[3,4-d]pyrimidin-4(3H)-one, compound 42 (1 eq., 250 mg, 0.41 mmol) in EtOH (2.5 mL), THF (2.5 mL) and AcOH (0.5 mL) under $N_2$. The mixture was stirred at 85° C. for 6 h. $NaCNBH_3$ (2 eq., 52 mg, 0.83 mmol) was then added and the mixture was stirred at rt for 16 h. This procedure was repeated 3 times. The mixture was poured into brine at 0° C., then extracted with EA (3×). The combined organic layers were washed with $NaHCO_3$ (sat., aq., 2×), brine (lx) and dried over $Na_2SO_4$. The solids were removed by filtration and the filtrate was evaporated to dryness. The crude mixture was purified by flash chromatography on silica gel (0 to 100% EA in CyH, then from 0 to 10% MeOH in DCM), followed by reverse phase chromatography (5 to 100% of $CH_3CN$ in $H_2O$ (+0.1% FA)) and further purified by prep-HPLC (Agilent 5 prep C18, 5 μm, from 2% to 100% $CH_3CN$ in $H_2O$ (+0.4% $NH_4HCO_3$) over 30 min at 30 mL/min) to give (R)-7-(4-bromo-3-(trifluoromethyl)benzoyl)-2-(3,5-dimethyl-1H-pyrazol-1-yl)-6-methyl-3-(5-(methylamino)pyrimidin-2-yl)-5,6,7,8-tetrahydropyrido[3,4-d]pyrimidin-4(3H)-one compound 43 (44 mg, 17%) as a white solid. $^1$H-NMR (DMSO-$d_6$, 400 MHz, 80° C.) δ 1.24 (m, 3H), 1.84 (s, 3H), 2.37 (s, 3H), 2.50-5.54 (m, 1H), 2.73-2.79 (m, 4H), 4.22-4.28 (m, 1H), 4.41-4.84 (m, 2H), 5.90 (s, 1H), 6.12 (m, 1H), 7.71 (m, 1H), 7.9 (d, J=2.2 Hz, 1H), 7.98-8.01 (m, 3H) ppm. LCMS: $C_{26}H_{24}BrF_3N_8O_2$ $[M+H]^+$: 617/618.

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using CellTiter-Glo 2.0 (Promega).

On day 0, HepG2.117 cells (which are maintained in routine cell culture with doxycycline present in the medium at a final concentration of 1 μg/mL) are seeded in 96-well plates (white with clear bottom) at a density of $2.0\times10^4$ cells/well (0.1 mL/well) in medium without doxycycline to induce pgRNA transcription and subsequent formation of HBV particles. The cells are incubated at 37° C. and 5% $CO_2$.

On day 1, medium is removed from each well, the test articles are diluted in culture medium without doxcycyline and 100 μL was added to cell culture wells (9 concentrations, 4-fold dilution). For each plate, 6 untreated (merely DMSO) wells are included. The final concentration of DMSO in the culture medium is 2%. Each plate is prepared in duplicate (one for HBV DNA extraction, one for CellTiter-Glo 2.0 measurement). The cells are incubated at 37° C. and 5% $CO_2$ for 3 days.

On day 4, cell viability is assessed using CellTiter-Glo 2.0 and cell lysates are prepared for HBV DNA extraction and subsequent quantification by qPCR.

HBV DNA Quantification by qPCR

Medium is removed from each well and 100 μL of 0.33% NP-40 in $H_2O$ was added to each well. Plates are sealed, incubated at 4° C. for 5 mins, vortexed extensively and centrifuged briefly. Next, 35 μL of lysate is added to 65 μL QuickExtract DNA Extraction Solution (Epicentre) in a PCR plate for each well. PCR plate is incubated at 65° C. for 6 mins, 98° C. for 2 mins and finally cooled to 4° C. HBV DNA is then quantified by qPCR with HBV-specific primers and probes as specified in Table 3 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 3

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM/CCTCTKCAT/ZEN/CCTGCTGCTATGCCTCATC/3IABkFQ/ (SEQ ID NO: 3) |

A DNA standard is prepared by dilution of an IDT gBlock corresponding to the amplicon with concentrations ranging from 10^2 to 10^8 copies/input (i.e., per 4 μL) and used to generate a standard curve by plotting Cq values vs. HBV DNA standard concentration. The quantity of HBV DNA in each sample is determined by interpolating from the standard curve.

Cell Viability

Using the other plates, the cell viability is quantified by CellTiter-Glo 2.0 according to the manufacturer's manual. In brief, 100 μL of reagent solution is added to the culture plates and shaken for 2'. The plates are incubated at rt for 10 min and luminescence signal is subsequently measured on a VarioSkan Lux (ThermoFisher) plate reader.

Data Analysis

Cell viability is calculated as follows: % Cell viability=(luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir is required due to the excellent dynamic window of this assay. The $CC_{50}$, $EC_{50}$ and $EC_{90}$ values were determined by dose-response curves fitted using non-linear regression.

As shown in Table 4, compounds of Formula (I) are active against HBV, where 'A' indicates an $EC_{50}\leq50$ nM, 'B' indicates an $EC_{50}<50$ nM and ≤500 nM, 'C' indicates an $EC_{50}<500$ nM and ≤5000 nM, and 'D' indicates an $EC_{50}<5000$ nM. Cell viability assessments indicated a large window between effective antiviral concentrations and cytotoxic compound concentrations.

TABLE 4

| Compound | $EC_{50}$ (nM) | $CC_{50}$ (nM) |
|---|---|---|
| 1 | A | >500 |
| 2 | A | >500 |
| 3 | A | >500 |
| 4 | A | >500 |
| 5 | A | >500 |
| 6 | B | >500 |
| 7 | A | >500 |
| 8 | A | >500 |
| 9 | A | >500 |

TABLE 4-continued

| Compound | $EC_{50}$ (nM) | $CC_{50}$ (nM) |
|---|---|---|
| 10 | A | >500 |
| 11 | A | >500 |
| 12 | B | >500 |
| 13 | A | >500 |
| 14 | A | >500 |
| 15 | A | >500 |
| 16 | A | >500 |
| 17 | A | >500 |
| 18 | A | >500 |
| 19 | A | >500 |
| 20 | A | >500 |
| 21 | A | >500 |
| 22 | A | >500 |
| 23 | A | >500 |
| 24 | A | >500 |
| 25 | A | >500 |
| 26 | A | >500 |
| 27 | A | >500 |
| 28 | A | >500 |
| 29 | A | >500 |
| 30 | B | >500 |
| 31 | B | >500 |
| 32 | A | >500 |

TABLE 4-continued

| Compound | $EC_{50}$ (nM) | $CC_{50}$ (nM) |
|---|---|---|
| 33 | A | >500 |
| 34 | A | >500 |
| 35 | A | >500 |
| 36 | A | >500 |
| 37 | A | >500 |
| 38 | A | >500 |
| 39 | A | >500 |
| 40 | A | >500 |
| 41 | A | >500 |
| 42 | A | >500 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

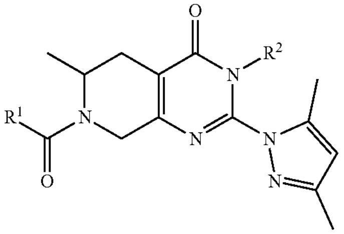

(I)

wherein:

$R^1$ is selected from the group consisting of

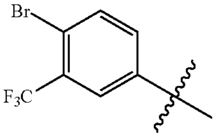 , 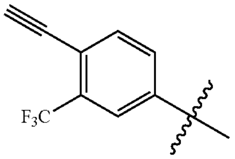 ,

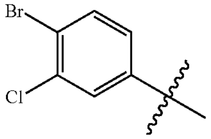 , 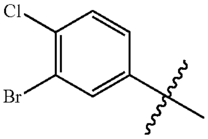 ,

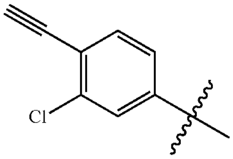 , 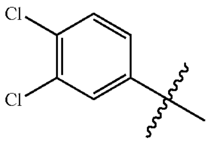 and

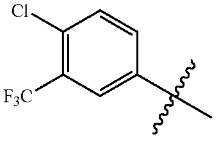 ;

$R^2$ is selected from the group consisting of

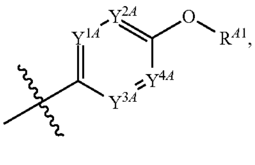 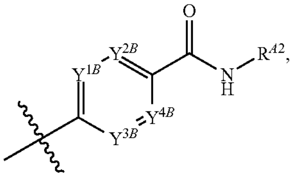

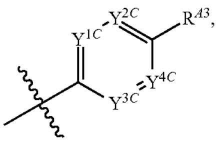 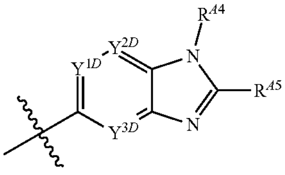 ,

-continued

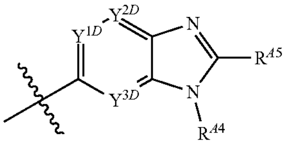 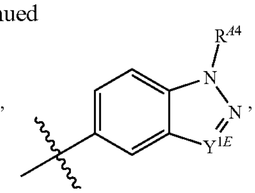

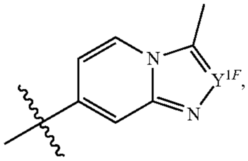 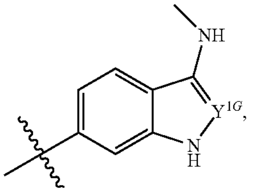

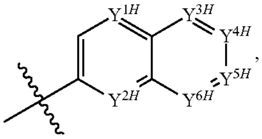 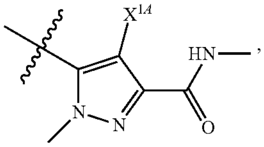

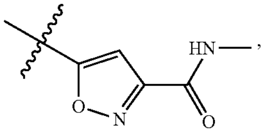 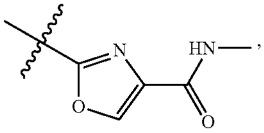

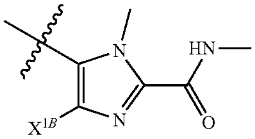 , 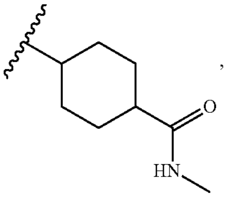 ,

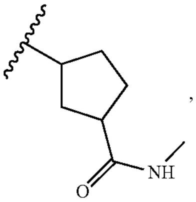 , 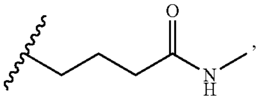 ,

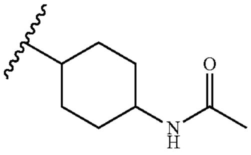 and 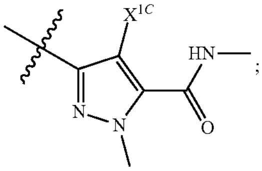 ;

$X^{1A}$, $X^{1B}$ and $X^{1C}$ are independently selected from the group consisting of hydrogen, halogen, an unsubstituted $C_{1-5}$ alkyl and an unsubstituted $C_{1-5}$ haloalkyl;

$Y^{1A}$ is CH, C—$CHF_2$, C—F, C—Cl, C—($NH_2$), C(NH (unsubstituted $C_{1-5}$ alkyl)), C(N(unsubstituted $C_{1-5}$ alkyl)$_2$) or N;

$Y^{2A}$ is CH, C-halogen, C—$OCH_3$, C—($NH_2$), C(NH (unsubstituted $C_{1-5}$ alkyl)), C(N(unsubstituted $C_{1-5}$ alkyl)$_2$) or N;

$Y^{3A}$ is CH or N;

$Y^{4A}$ is CH or N;

$Y^{1B}$ is CH, C—$CHF_2$, C—F, C—Cl, C—($NH_2$), C(NH (unsubstituted $C_{1-5}$ alkyl)), C(N(unsubstituted $C_{1-5}$ alkyl)$_2$) or N;

$Y^{2B}$ is CH, C-halogen, C—$OCH_3$, C—($NH_2$), C(NH (unsubstituted $C_{1-5}$ alkyl)), C(N(unsubstituted $C_{1-5}$ alkyl)$_2$) or N;

$Y^{3B}$ is CH or N;

$Y^{4B}$ is CH or N;

$Y^{1C}$, $Y^{2C}$, $Y^{3C}$ and $Y^{4C}$ are each independently CH, C-(halogen) or N;

$Y^{1D}$ is CH, C—$CH_3$, C—$OCH_3$, C-(halogen), C—$CHF_2$, C—$CF_3$ or N;

$Y^{2D}$ is CH, C—$CH_3$, C—$OCH_3$, C-(halogen), C—$CHF_2$, C—$CF_3$ or N;

$Y^{3D}$ is CH, C-(halogen) or N;

$Y^{1E}$, $Y^{1F}$ and $Y^{1G}$ are each independently CH, C-(halogen) or N;

$Y^{1H}$, $Y^{2H}$, $Y^{3H}$, $Y^{4H}$, $Y^{5H}$ and $Y^{6H}$ are each independently CH, C-(halogen) or N;

$R^{A1}$ is hydrogen, an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl are substituted with one or more groups selected from the group consisting of hydroxy, —$NH_2$, an unsubstituted $C_{1-5}$ alkoxy, an unsubstituted-NH (an unsubstituted $C_{1-5}$ alkyl), —N(an unsubstituted $C_{1-5}$ alkyl)$_2$, —C(═O) $NH_2$, —O—P(═O)(OH)$_2$, an unsubstituted 5- or 6-membered monocyclic heterocyclyl and 5- or 6-membered monocyclic heterocyclyl substituted by one or more unsubstituted $C_{1-4}$ alkyl groups;

$R^{A2}$ is —$CH_3$ or —$CD_3$;

$R^{A3}$ is —$NH_2$, —NH (an unsubstituted or a substituted $C_{1-5}$ alkyl), —N(an unsubstituted or a substituted $C_{1-5}$ alkyl)$_2$, —NH (an unsubstituted or a substituted $C_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl;

$R^{A4}$ is an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl are substituted with one or more groups selected from the group consisting of hydroxy, —C(═O) OH and —C(═O) $NH_2$; and $R^{A5}$ is selected from the group consisting of hydrogen, halogen, —CN, —OH, —$NH_2$, —C(═O) OH, —CH═$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl is substituted with one or more hydroxy groups; and wherein the compound of Formula (I), or a pharmaceutically acceptable salt thereof, is not:

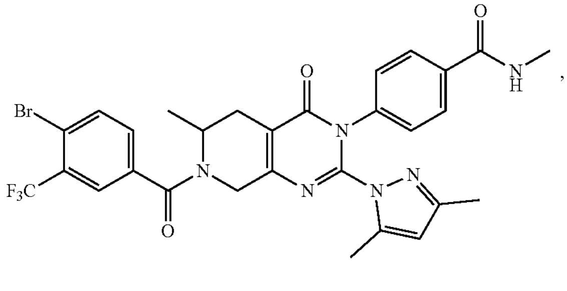 [SMILES: CNC(=O)c1ccc(-n2c(-n3nc(C)cc3C)nc3c(c2=O)CC(C)N(C(=O)c2ccc(Br)c(C(F)(F)F)c2)C3)cc1]

or a pharmaceutically acceptable salt thereof.

2. The compound of claim 1, wherein $R^1$ is

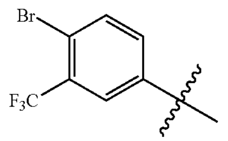

3. The compound of claim 2, wherein $R^2$ is

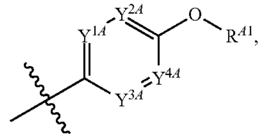

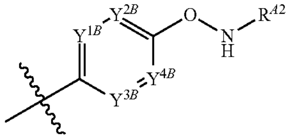

or

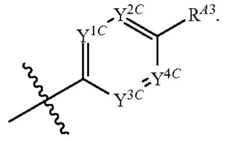

4. The compound of claim 3, wherein $R^2$ is

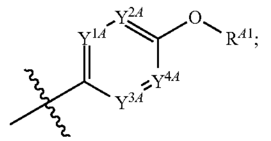

$Y^{1A}$, $Y^{2A}$, $Y^{3A}$ and $Y^{4A}$ are each CH, or one of $Y^{1A}$, $Y^{2A}$, $Y^{3A}$ and $Y^{4A}$ is N.

5. The compound of claim 4, wherein $R^{A1}$ is a $C_{1-5}$ alkyl substituted with one or more groups selected from the group consisting of hydroxy, —$NH_2$, an unsubstituted $C_{1-5}$ alkoxy, an unsubstituted-NH (an unsubstituted $C_{1-5}$ alkyl), —N(an unsubstituted $C_{1-5}$ alkyl)$_2$, —C(═O) $NH_2$, —O—P(═O)(OH)$_2$, an unsubstituted 5- or 6-membered monocyclic heterocyclyl and 5- or 6-membered monocyclic heterocyclyl substituted by one or more unsubstituted $C_{1-4}$ alkyl groups; or RAL is a monocyclic $C_{3-6}$ cycloalkyl substituted with one or more groups selected from the group consisting of hydroxy, —$NH_2$, an unsubstituted $C_{1-5}$ alkoxy, an unsubstituted-NH (an unsubstituted $C_{1-5}$ alkyl), —N(an unsubstituted $C_{1-5}$ alkyl)$_2$, C(═O) $NH_2$, —O—P(═O)(OH)$_2$, an unsubstituted 5- or 6-membered monocyclic heterocyclyl and 5- or 6-membered monocyclic heterocyclyl substituted by one or more unsubstituted $C_{1-4}$ alkyl groups.

6. The compound of claim 3, wherein $R^2$ is

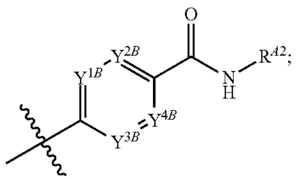

$Y^{1B}$, $Y^{2B}$, $Y^{3B}$ and $Y^{4B}$ are each CH, or one of $Y^{1B}$, $Y^{2B}$, $Y^{3B}$ and $Y^{4B}$ is N.

7. The compound of claim 3, wherein $R^2$ is

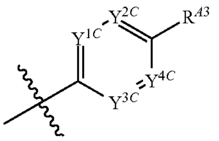

$Y^{1C}$, $Y^{2C}$, $Y^{3C}$ and $Y^{4C}$ are each CH, or one of $Y^{1C}$, $Y^{2C}$, $Y^{3C}$ and $Y^{4C}$ is N; $R^{A3}$ is —$NH_2$, —NH (an unsubstituted or a substituted $C_{1-5}$ alkyl), —NH (an unsubstituted or a substituted $C_{3-6}$ monocyclic cycloalkyl), an unsubstituted or a substituted 5-membered-monocyclic heteroaryl, an unsubstituted or a substituted 4-membered-monocyclic heterocyclyl, an unsubstituted or a substituted 5-membered-monocyclic heterocyclyl or an unsubstituted or a substituted 6-membered-monocyclic heterocyclyl.

8. The compound of claim 2, wherein $R^2$ is

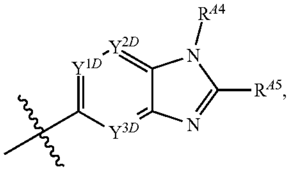

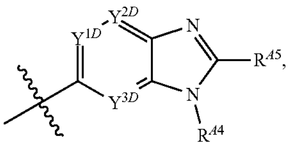 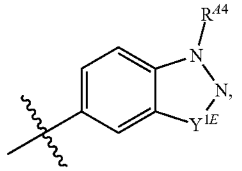

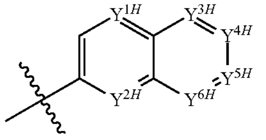 or 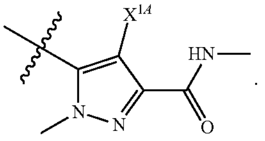

9. The compound of claim 8, wherein $R^2$ is

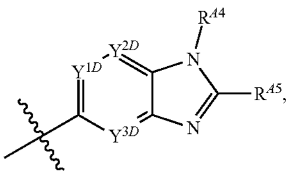

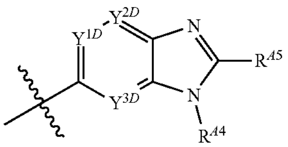 or 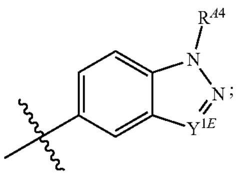

and $R^{A4}$ is an unsubstituted $C_{1-5}$ alkyl.

10. The compound of claim 1, wherein $R^2$ is selected from the group consisting of:

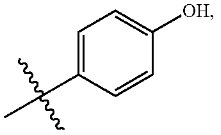 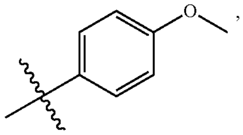

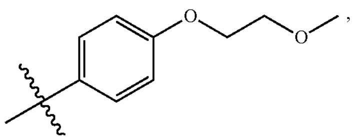

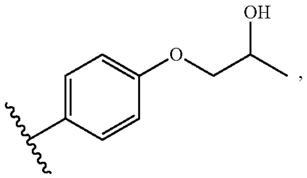

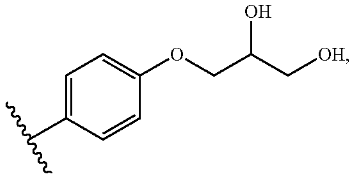

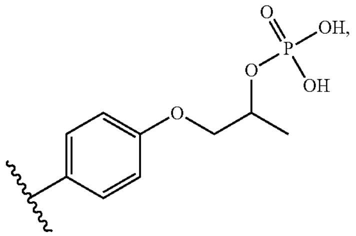

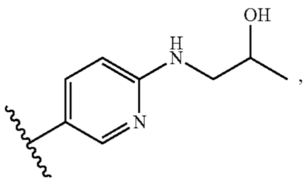

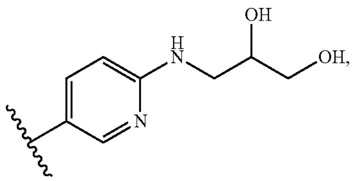

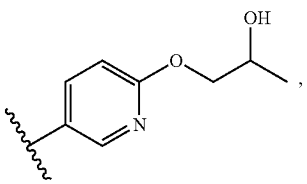

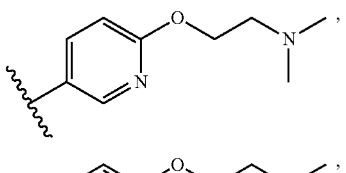

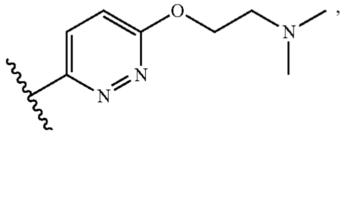

-continued
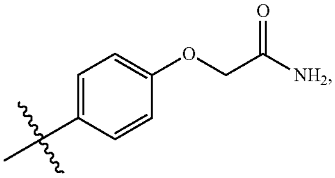
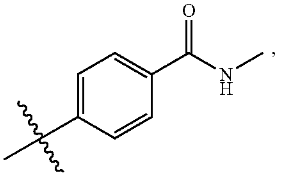
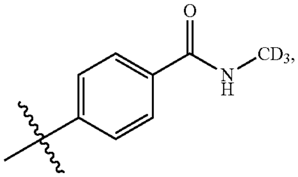
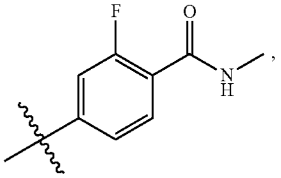
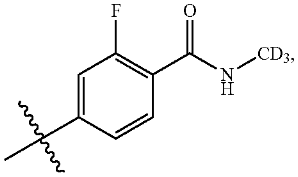
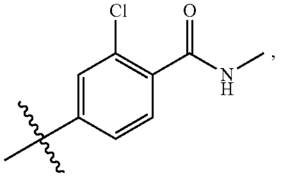
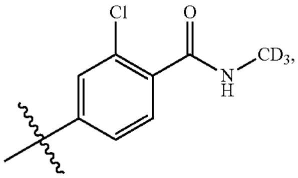
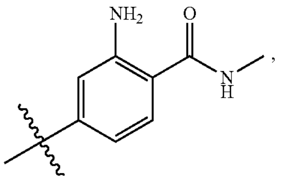
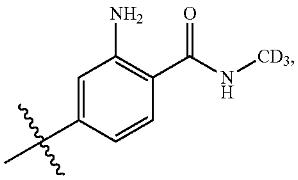
-continued
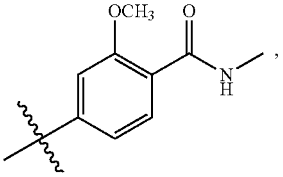
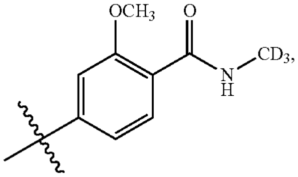
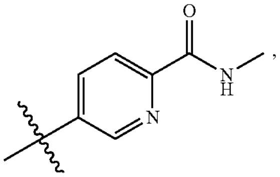
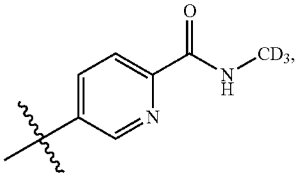
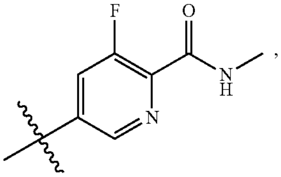
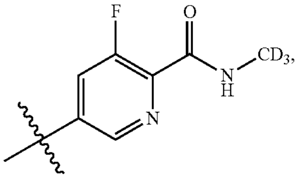
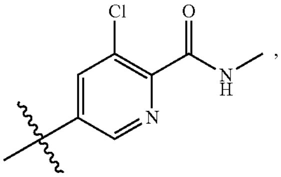
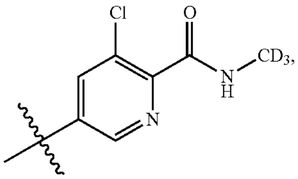
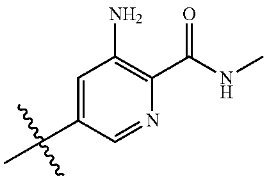

-continued
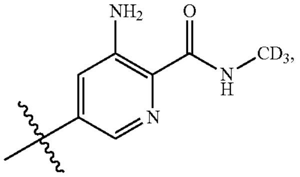
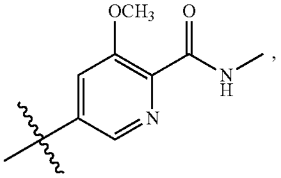
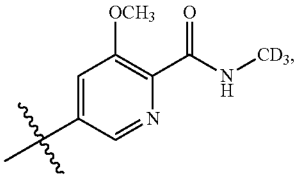
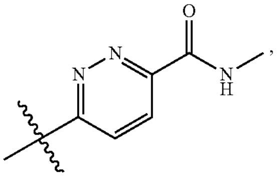
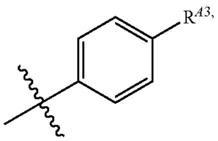
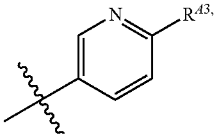
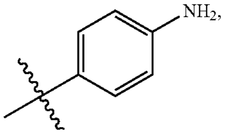
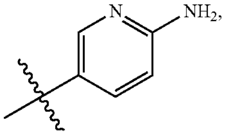
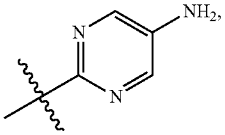
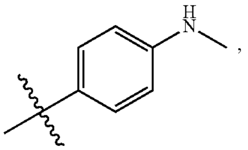
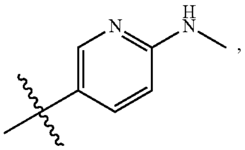
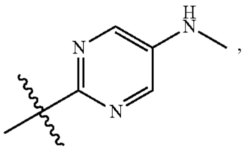
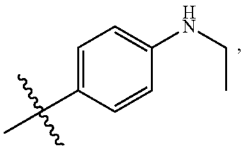
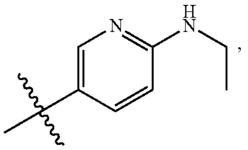
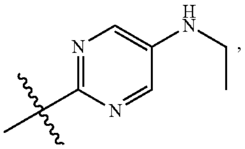
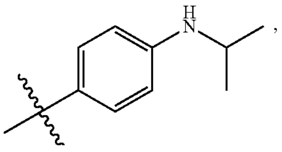
-continued
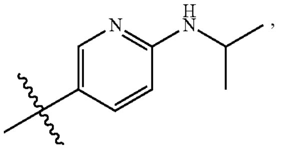
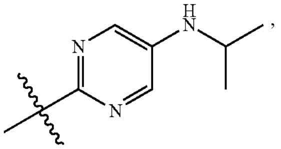
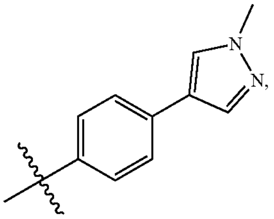
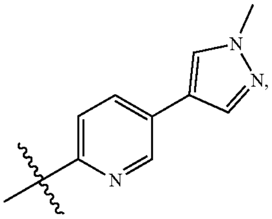
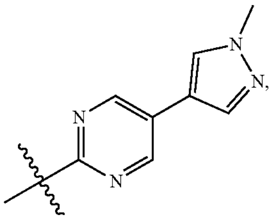
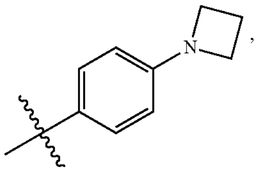
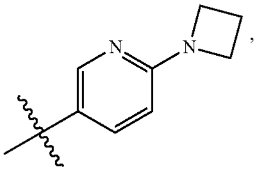
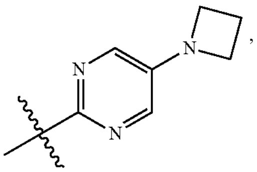
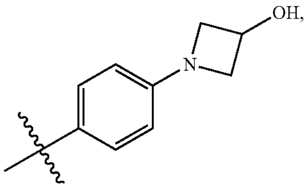
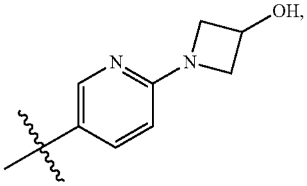
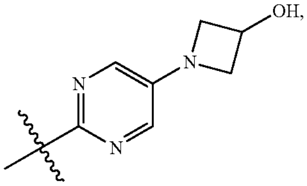
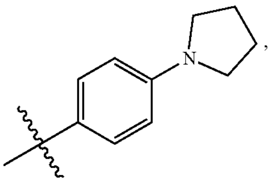
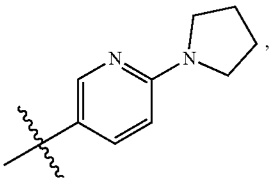

-continued
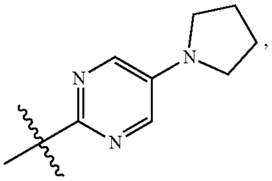,
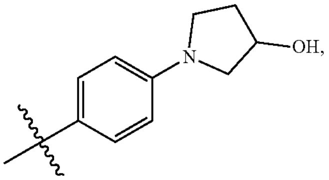,
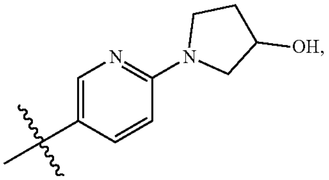,
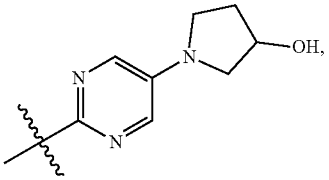,
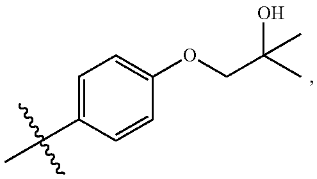,
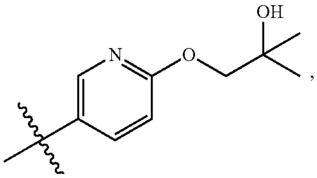,
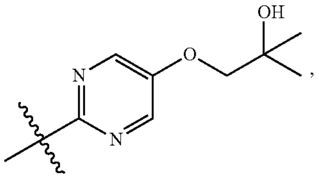,
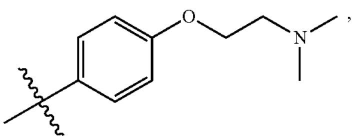,
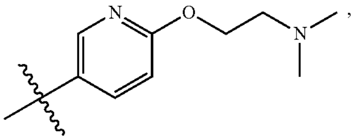,
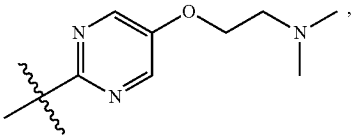,
-continued
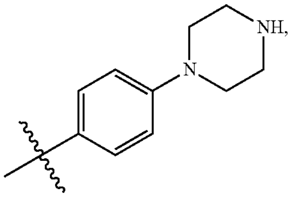,
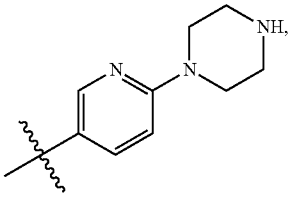,
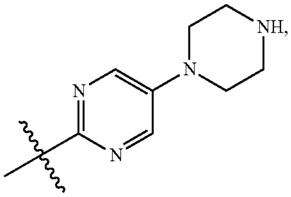,
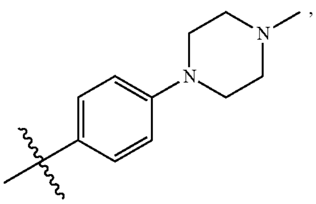,
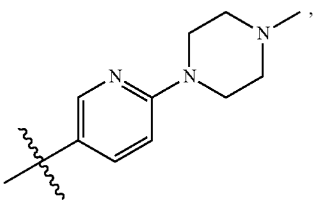,
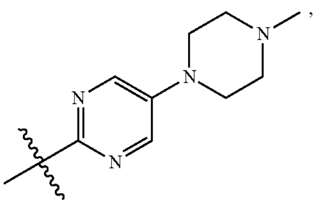,
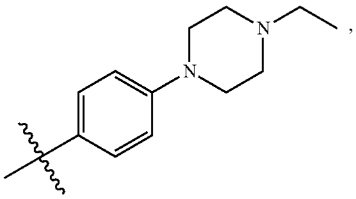,
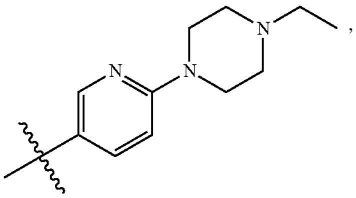, -continued
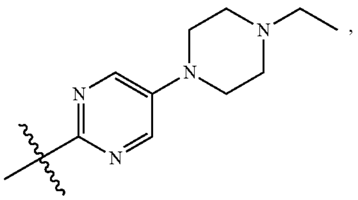,
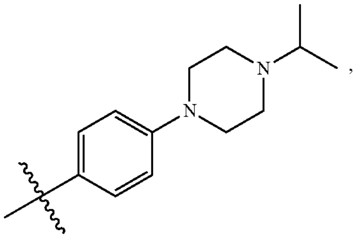,
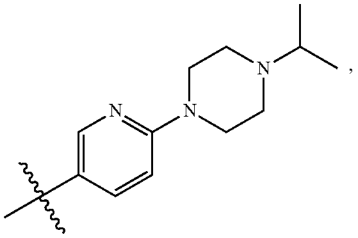,
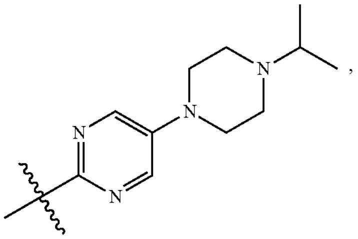,
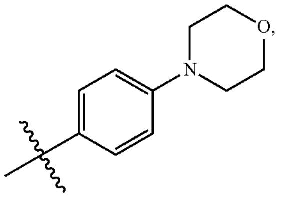,
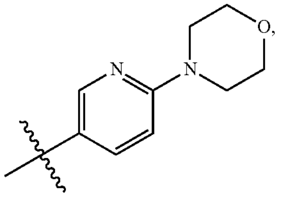,
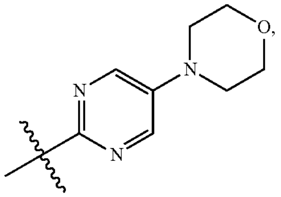,
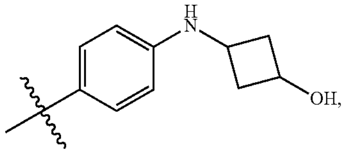,
-continued
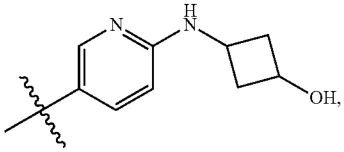,
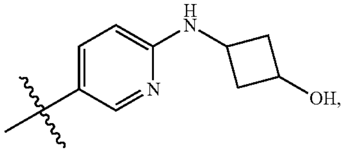,
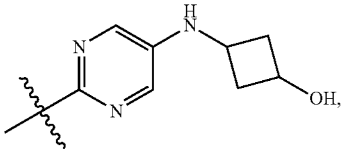,
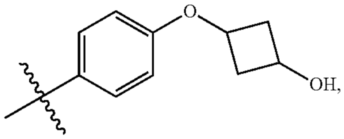,
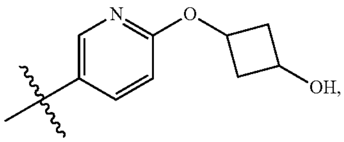,
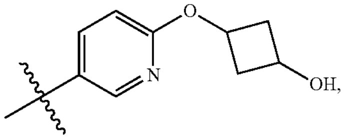,
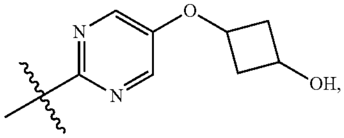,
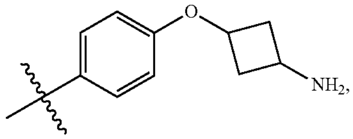,
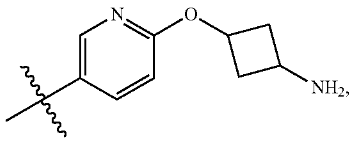,
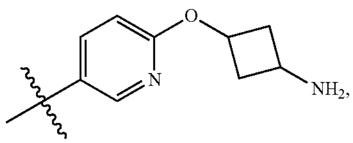,
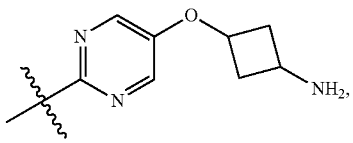,
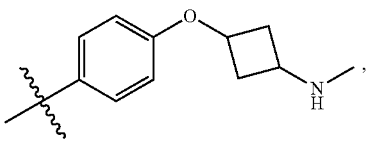, -continued
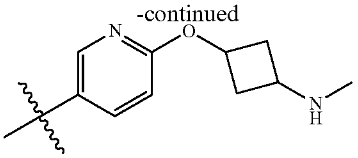,
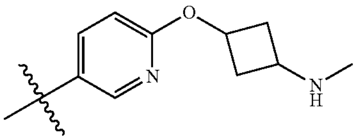,
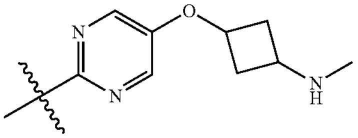,
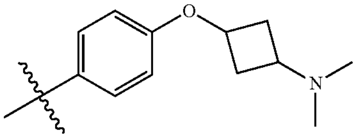,
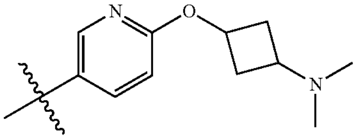,
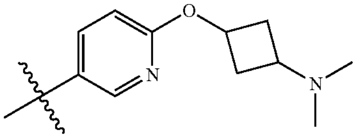,
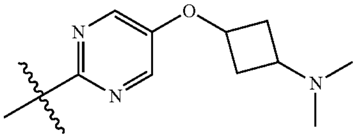,
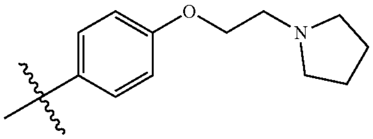,
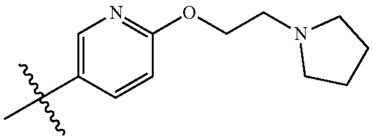,
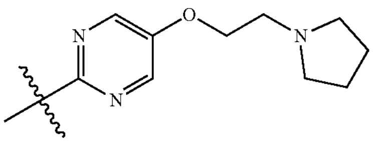,
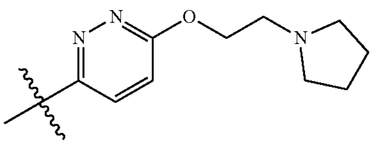,
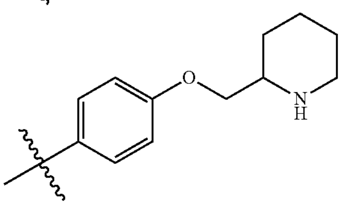,
-continued
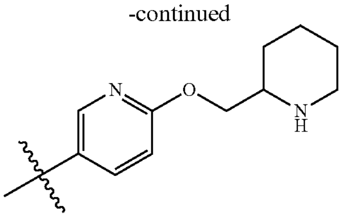,
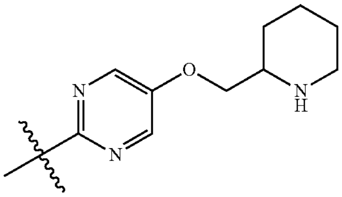,
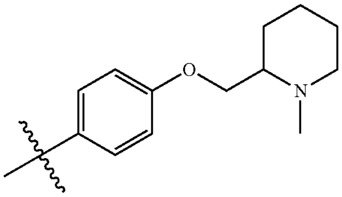,
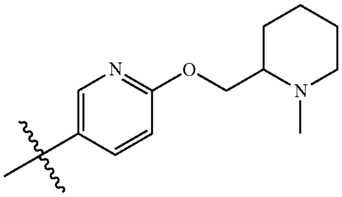,
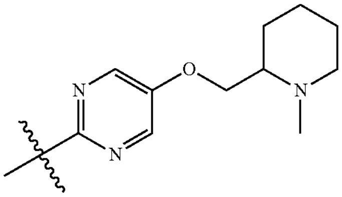,
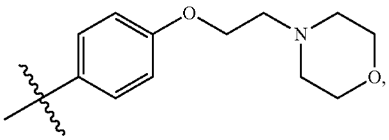,
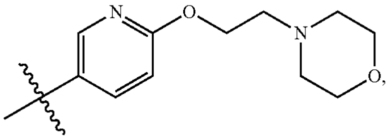,
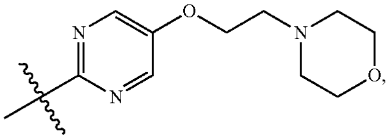,
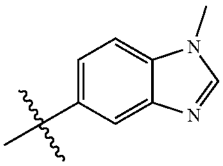, 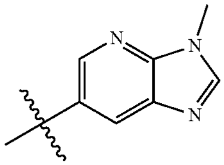,
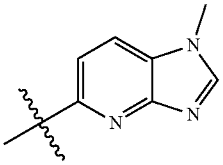, 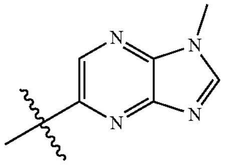, -continued
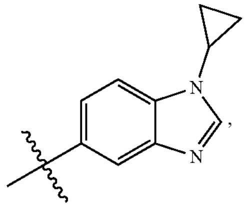,
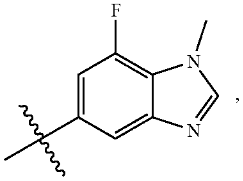,
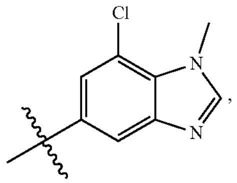,
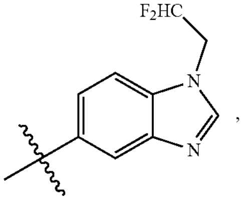,
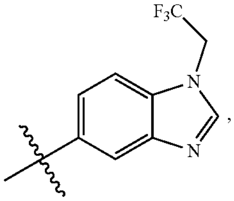,
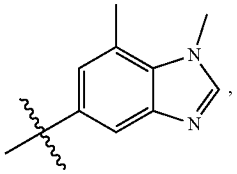,
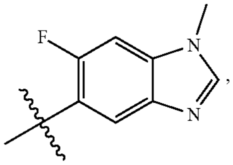,
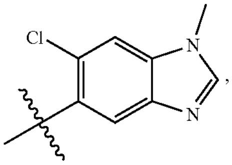,
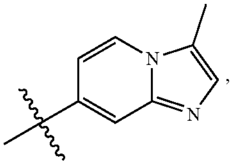,
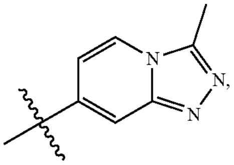,
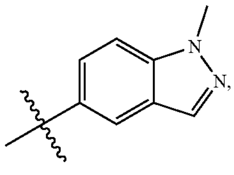,
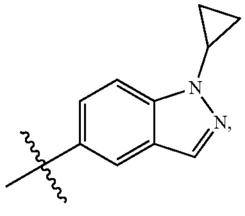,
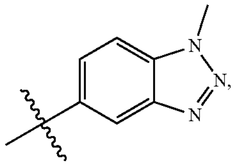,
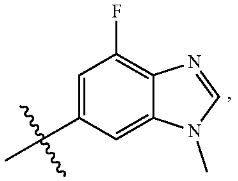,
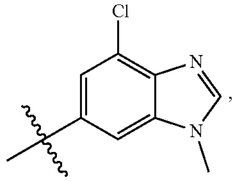,
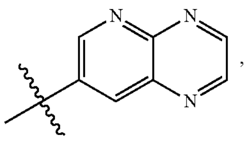,
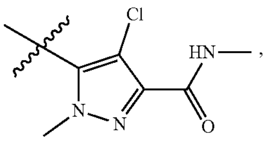,
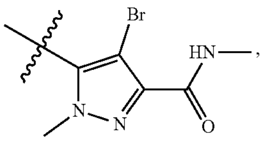,
-continued
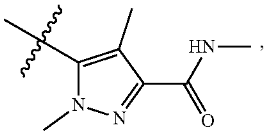,
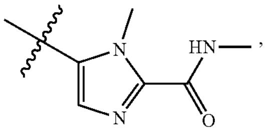,
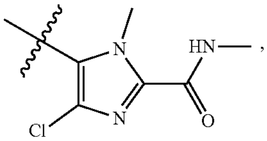,
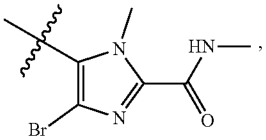,
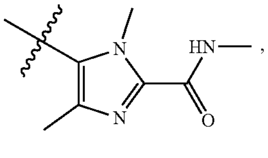,
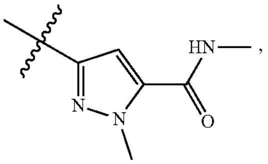,
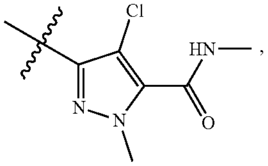,
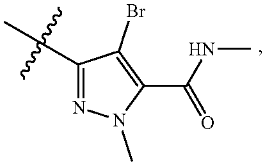,
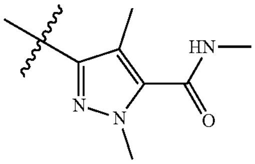 and
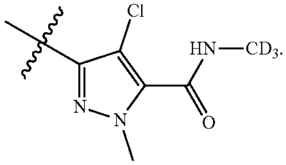.
11. A compound selected from the group consisting of:
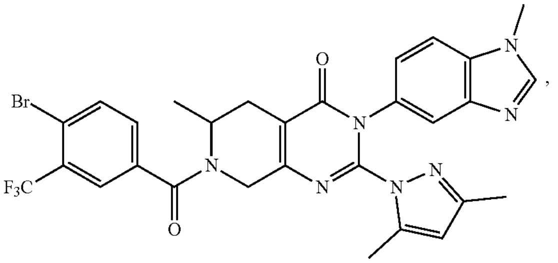,
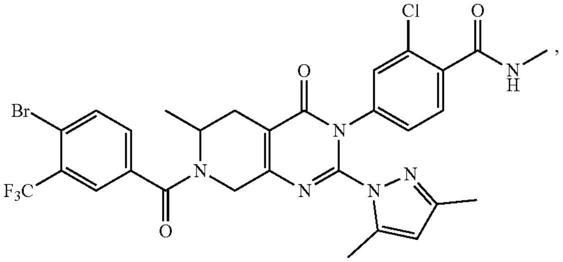, -continued
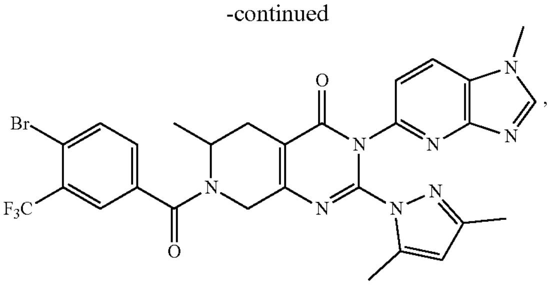
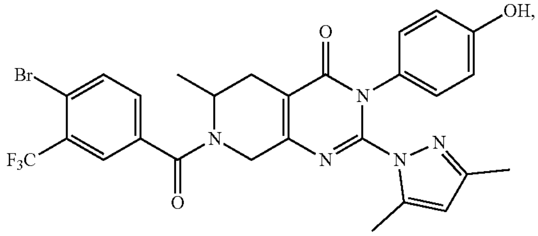
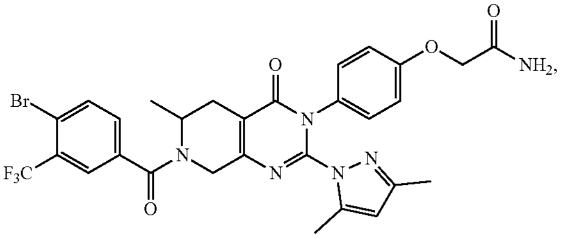
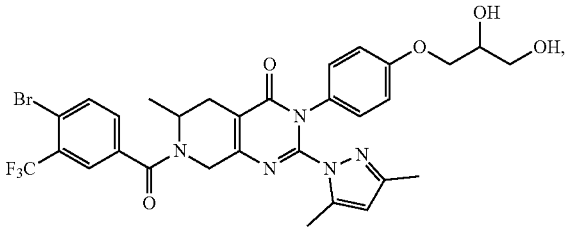
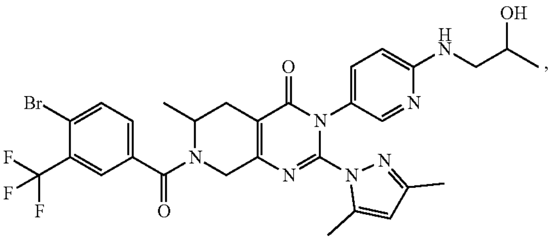
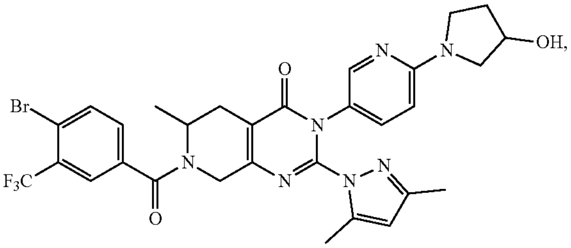
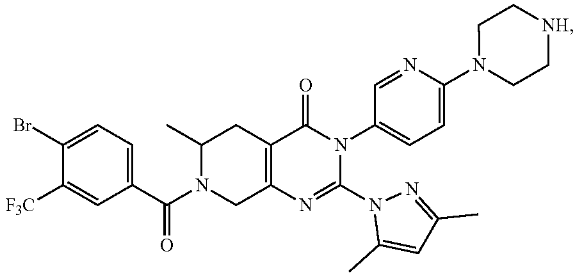
-continued
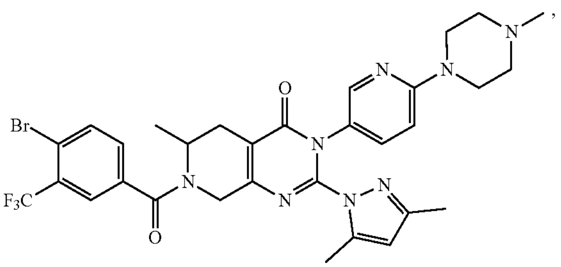
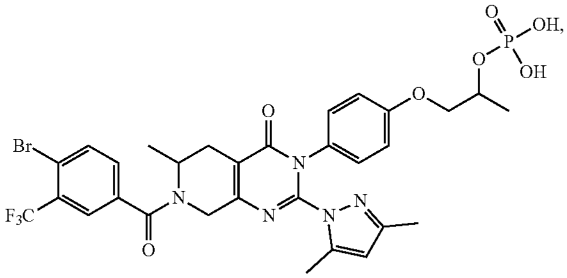
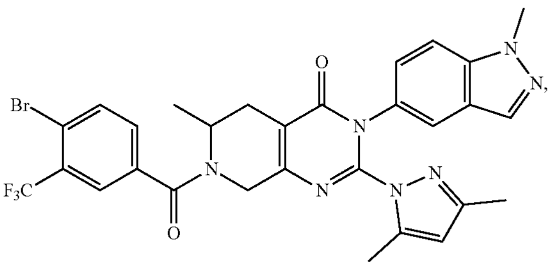
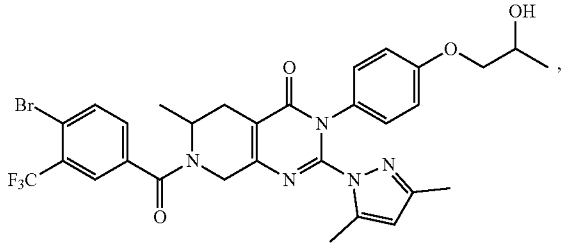
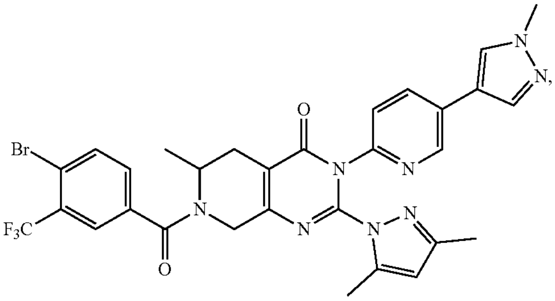
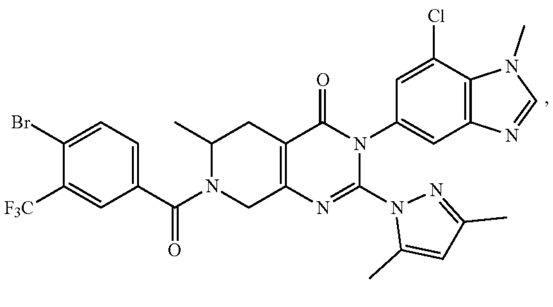

-continued
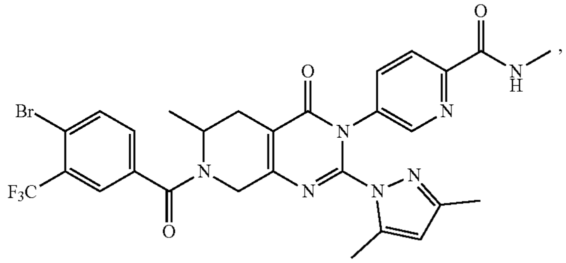,
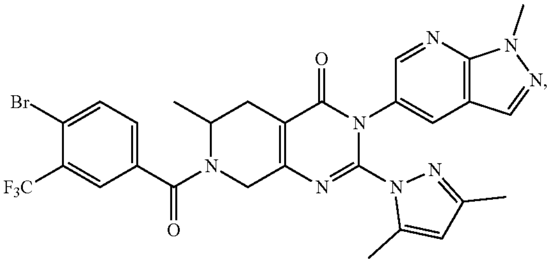,
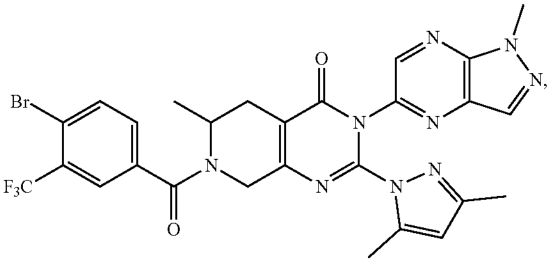,
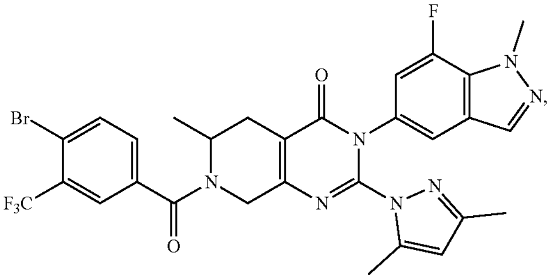,
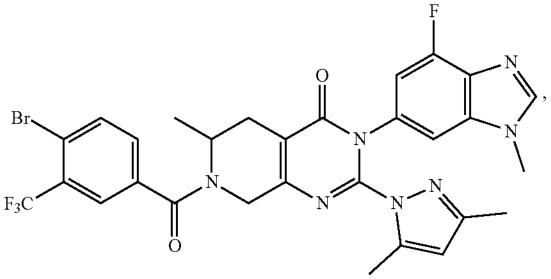,
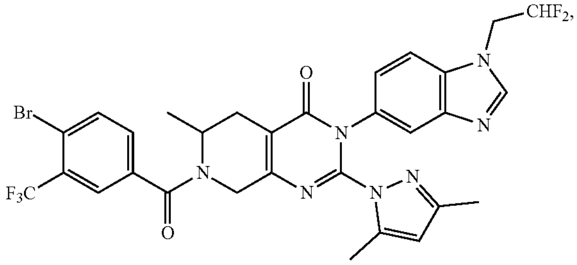,
-continued
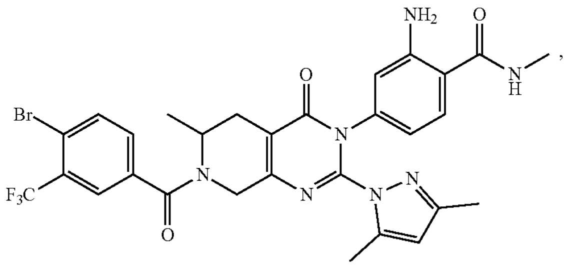,
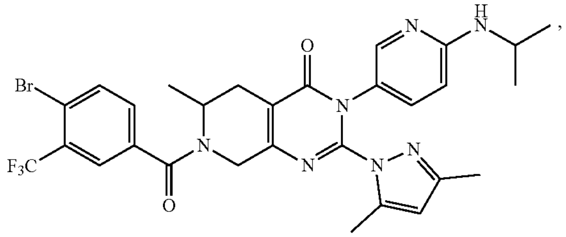,
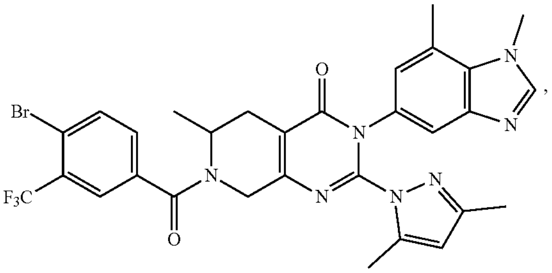,
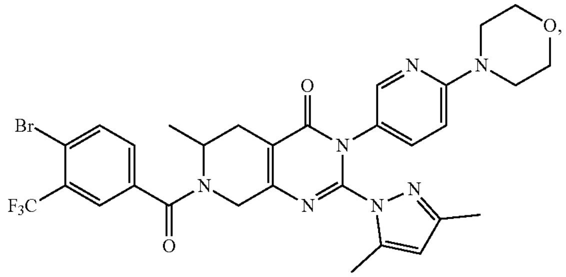,
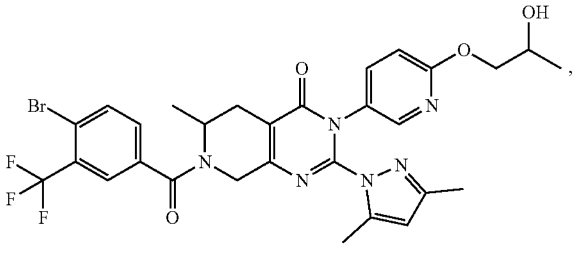,
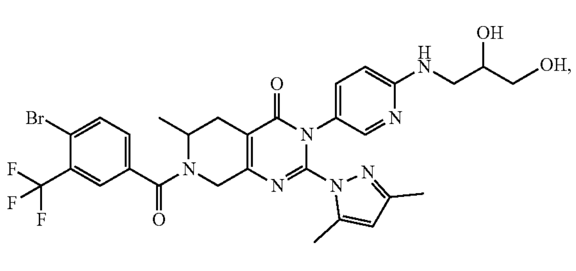, -continued
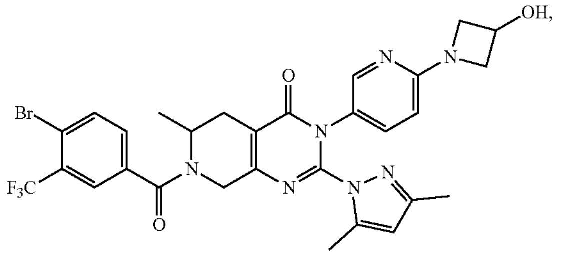
,
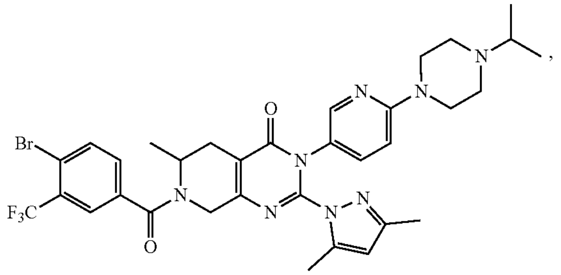
,
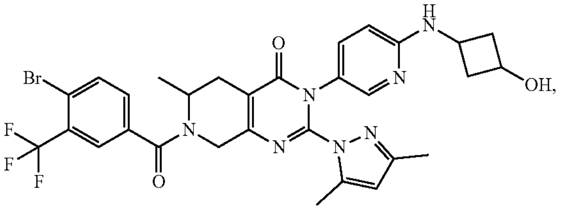
,
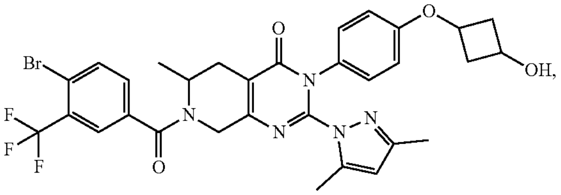
,
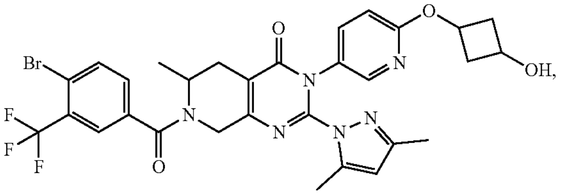
,
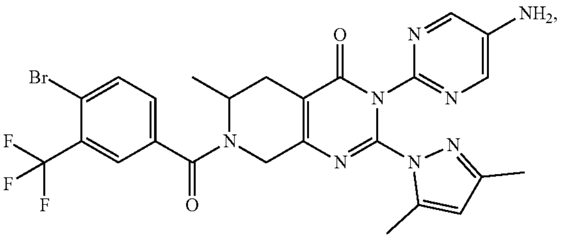
,
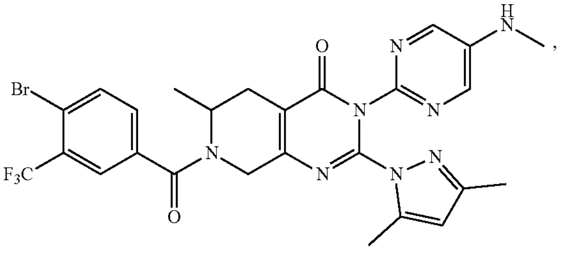
,
-continued
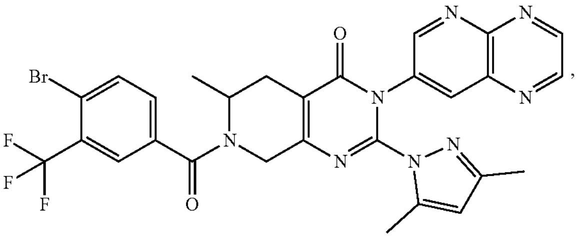
,
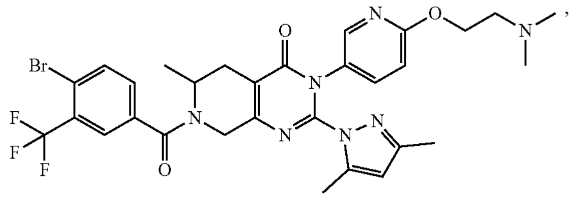
,
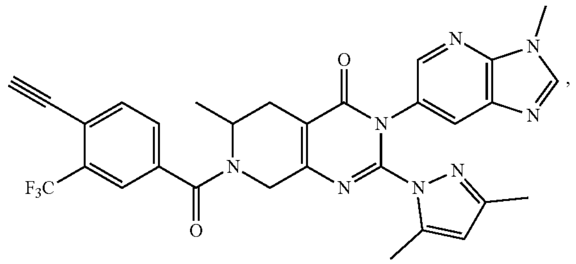
,
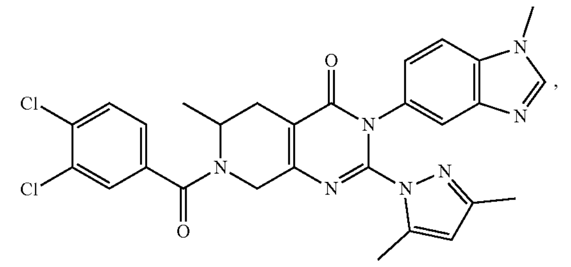
,
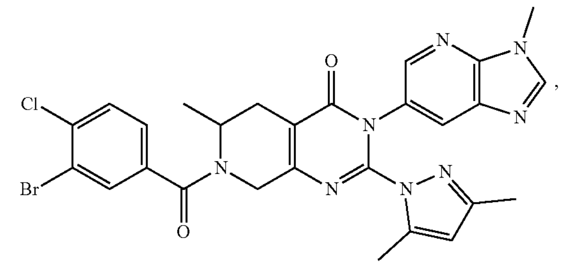
,
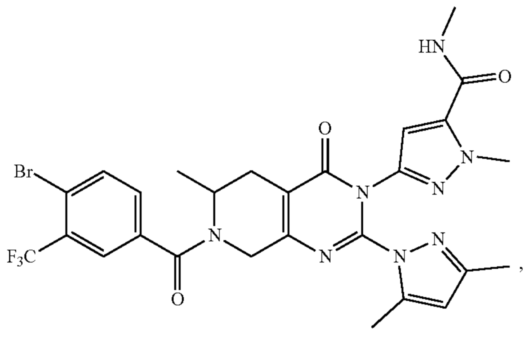
, -continued
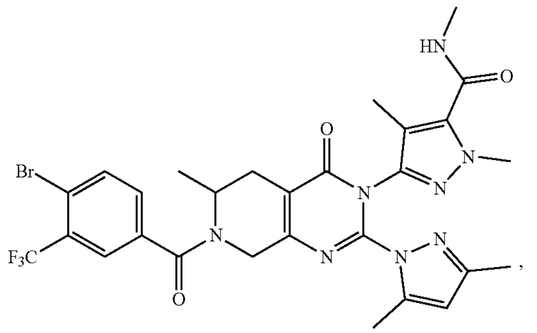
,
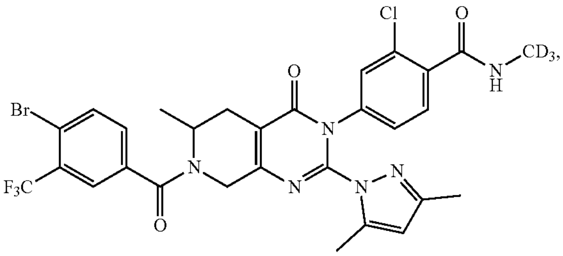
,
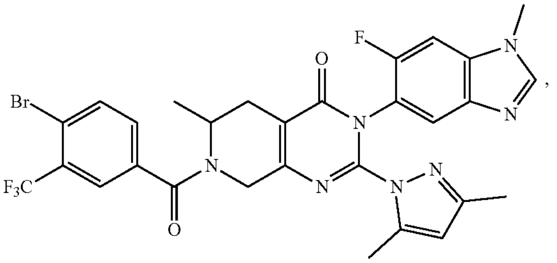
,
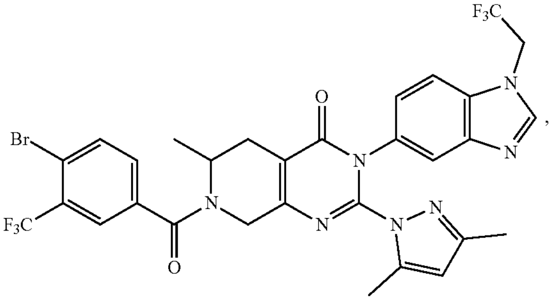
,
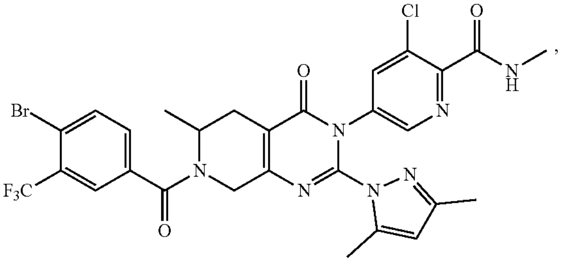
,
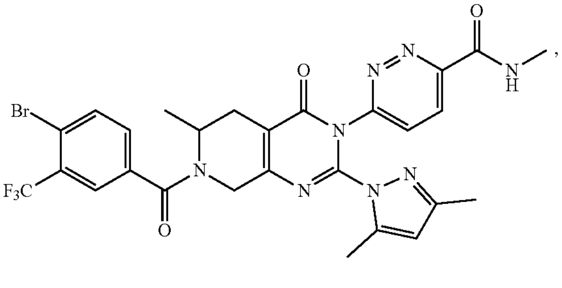
,
-continued
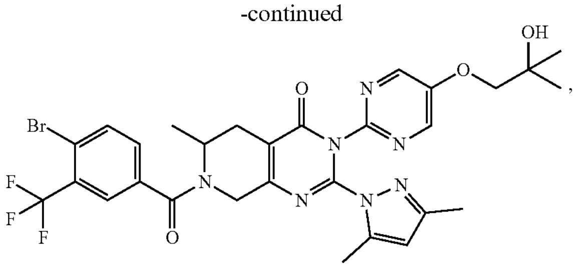
,
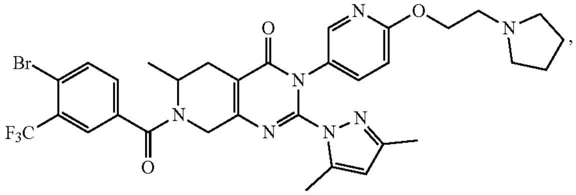
,
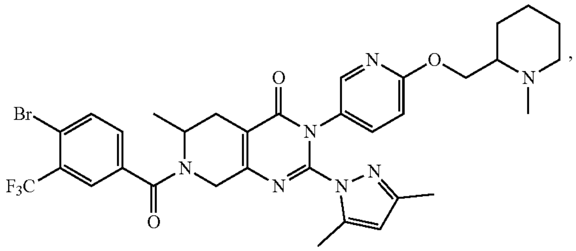
,
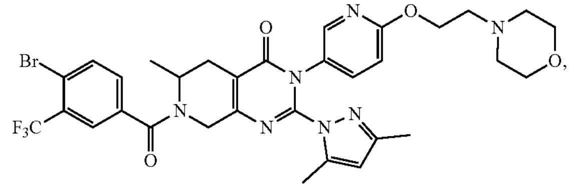
,
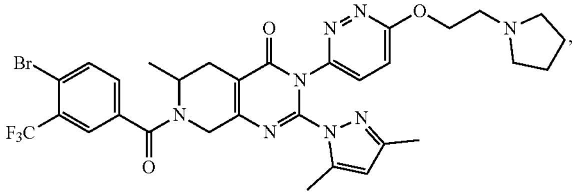
,
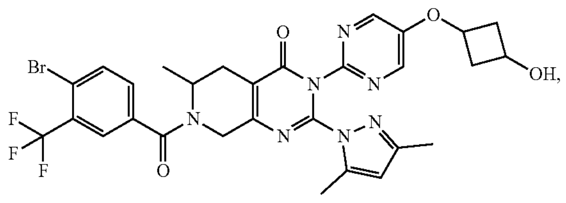
,
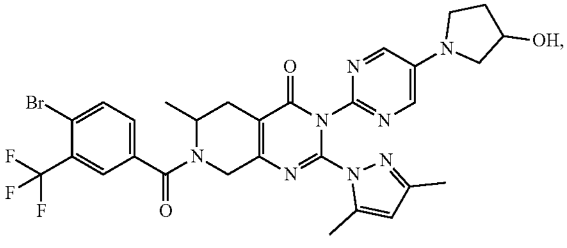
,
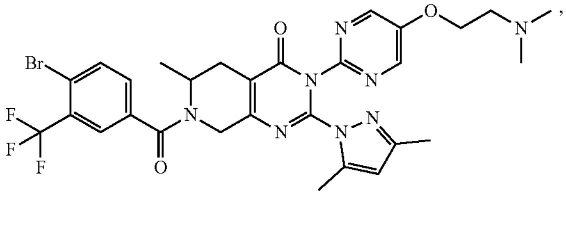
, -continued
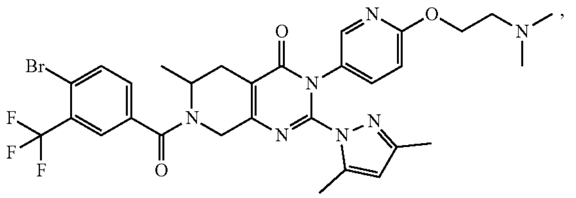
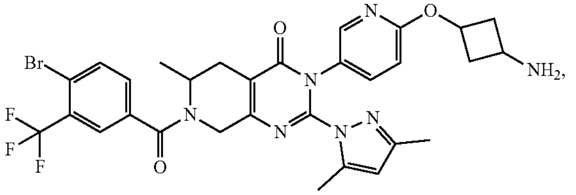
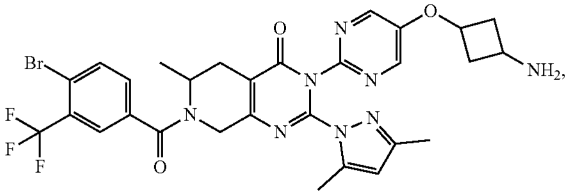
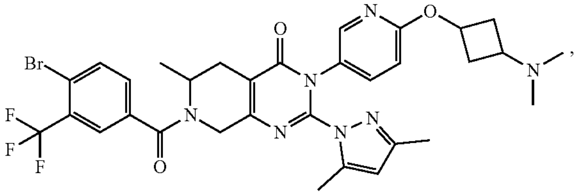
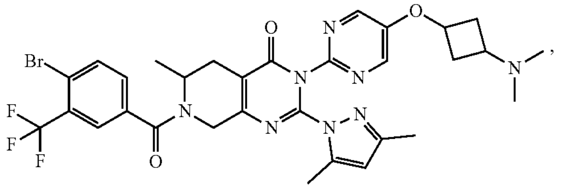
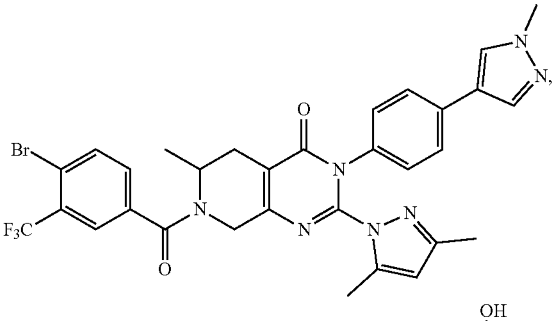
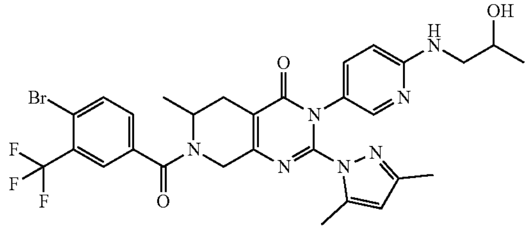
and
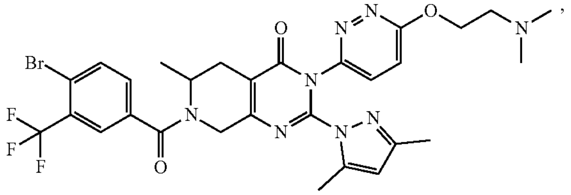
or a pharmaceutically acceptable salt of any of the foregoing.
12. The compound of claim 1 selected from the group consisting of:
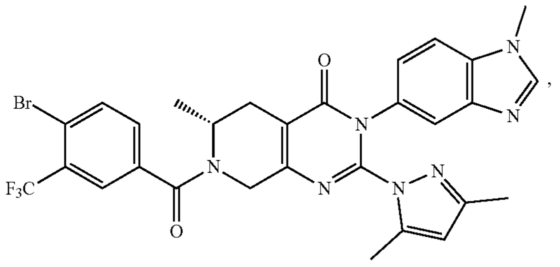
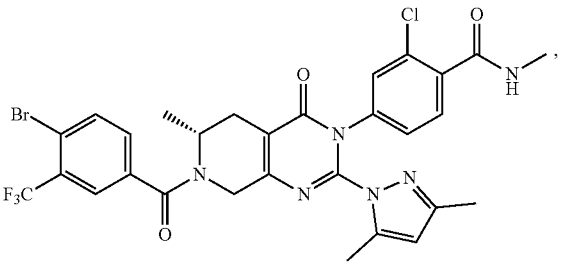
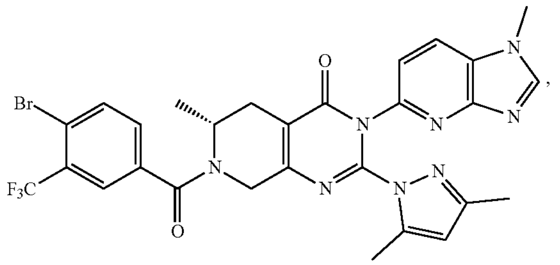
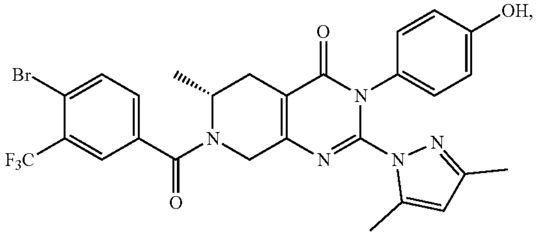
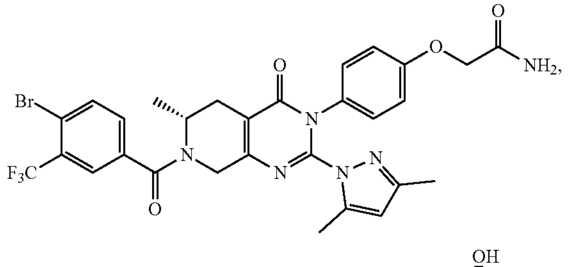
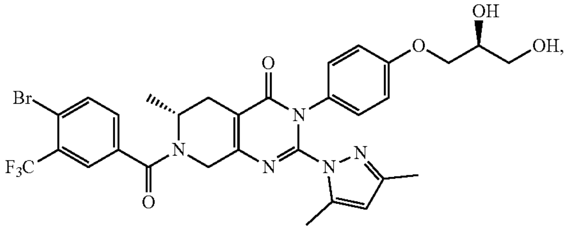

-continued
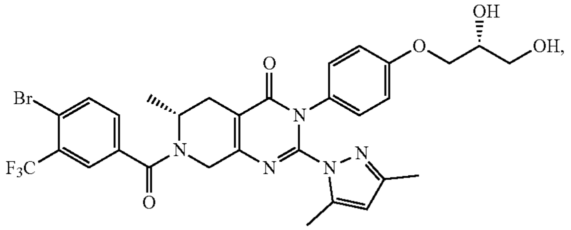
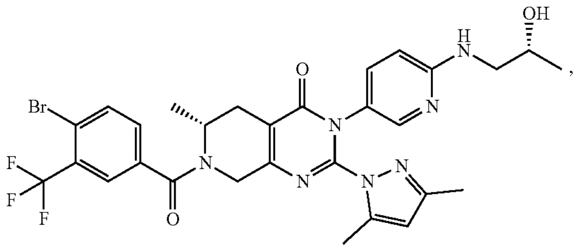
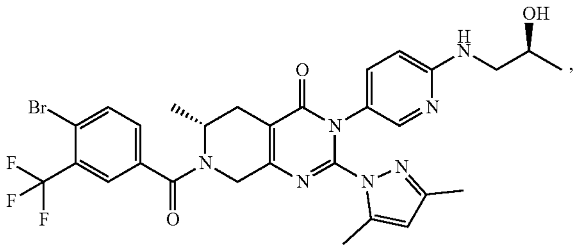
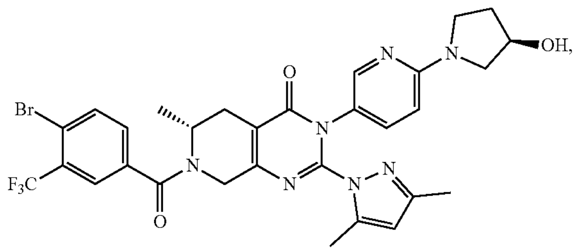
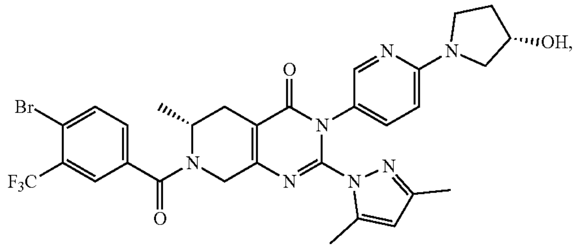
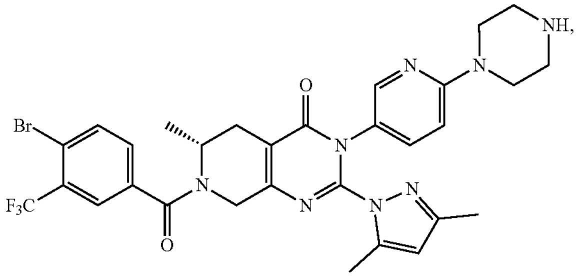
-continued
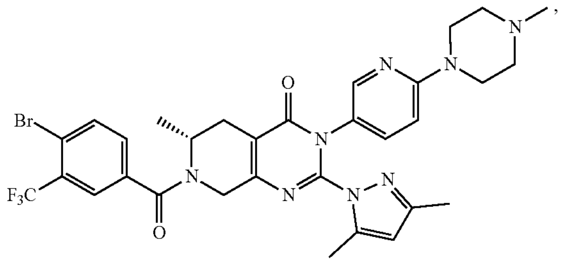
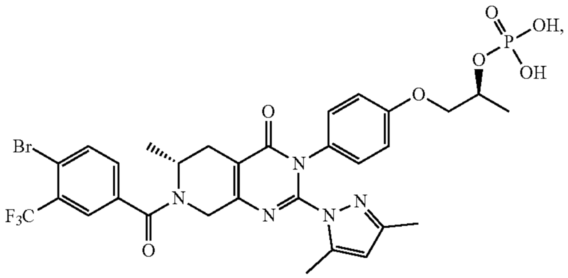
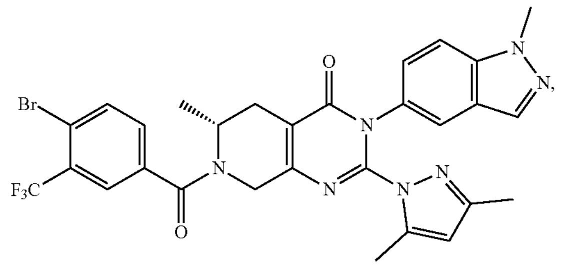
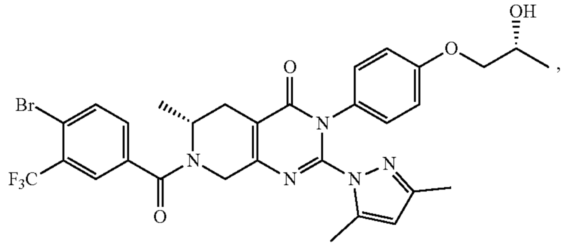
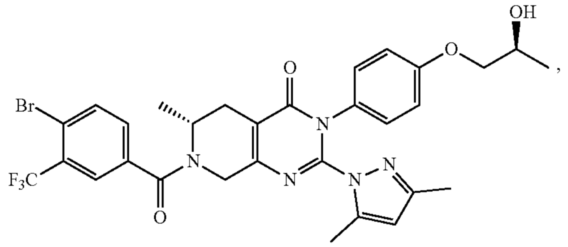
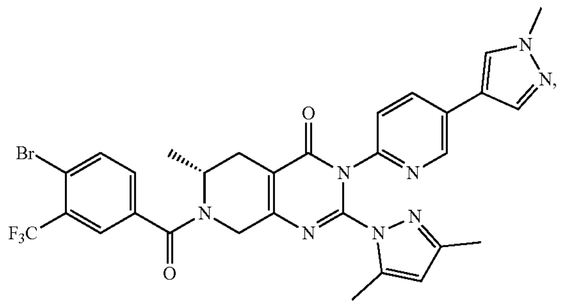

-continued
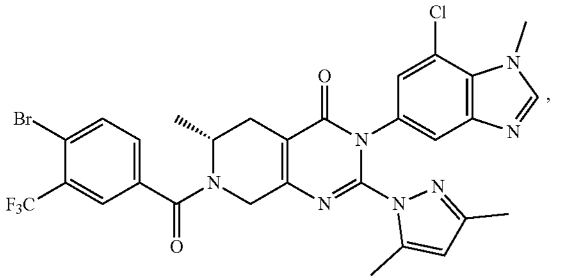
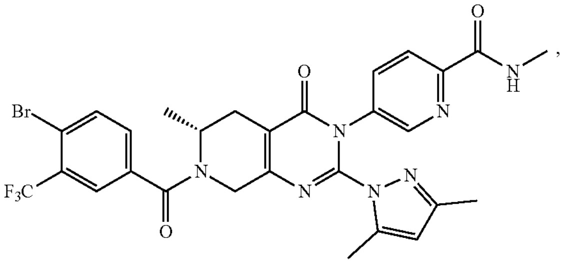
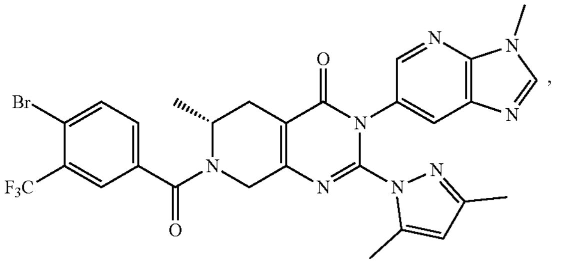
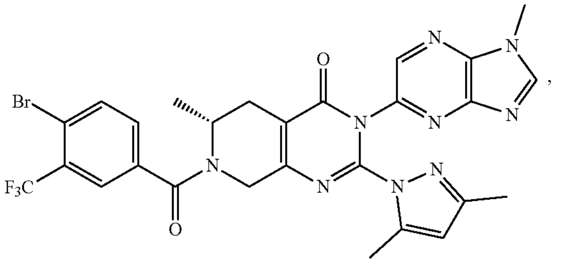
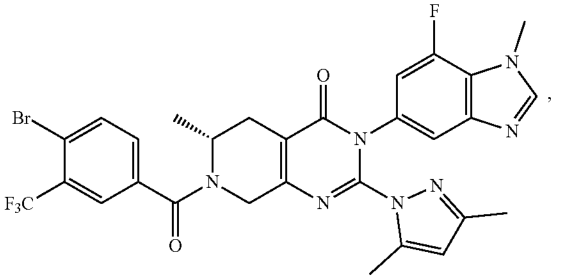
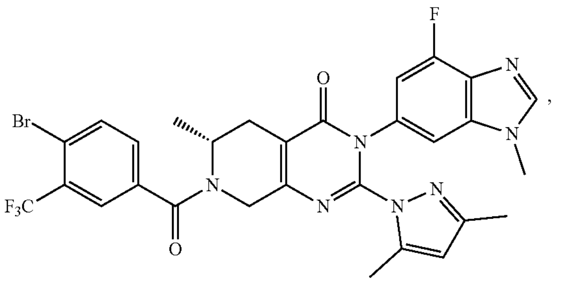
-continued
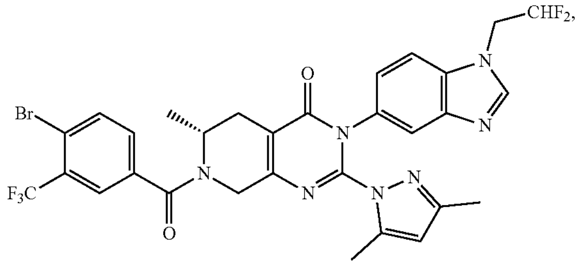
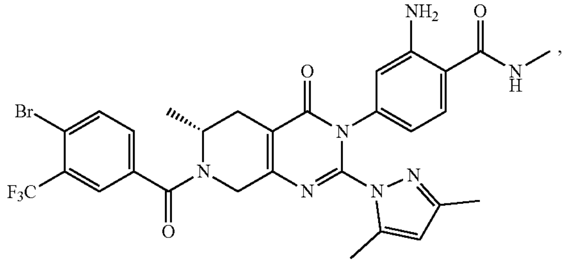
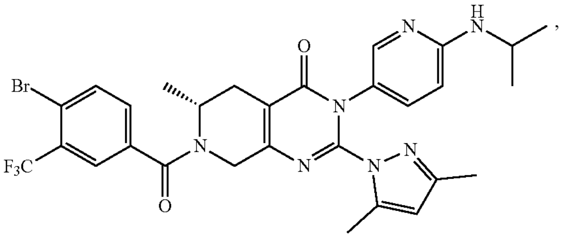
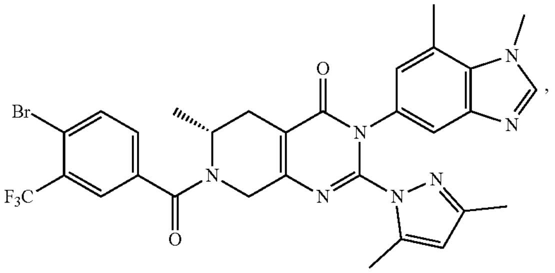
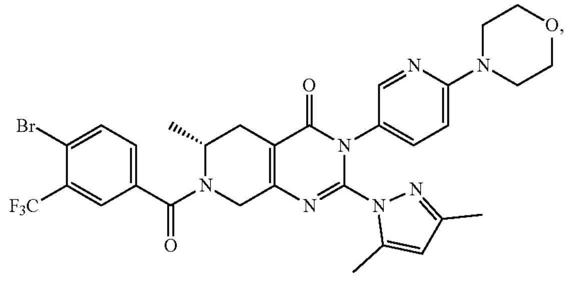
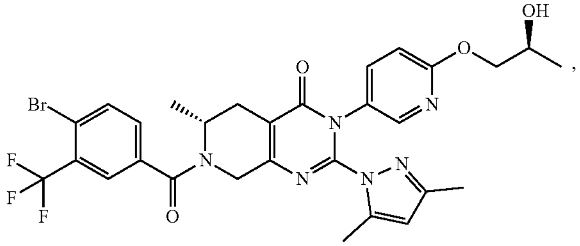

-continued
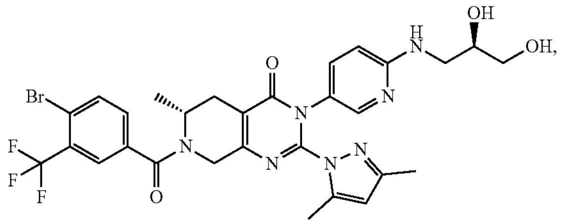
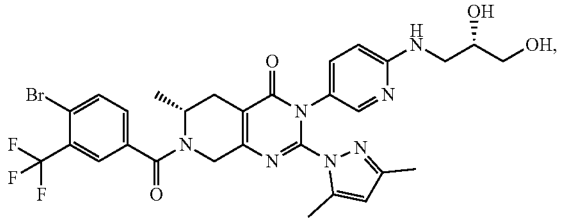
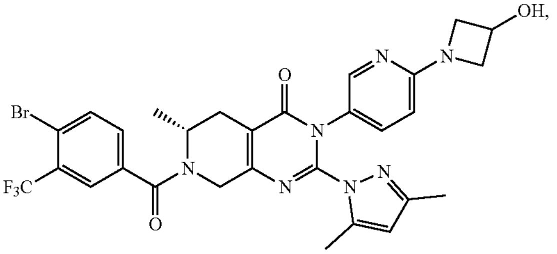
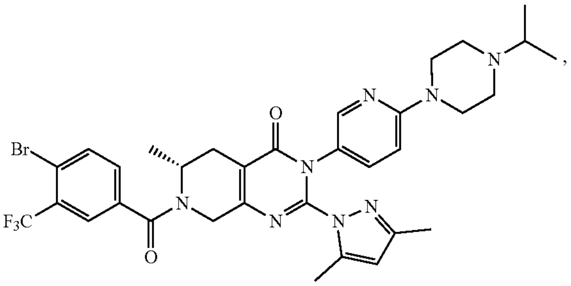
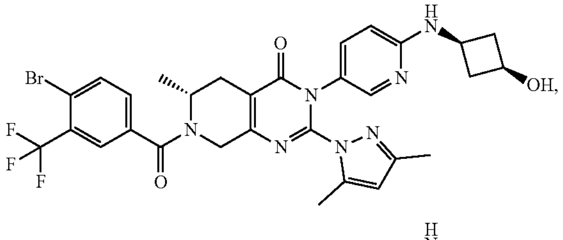
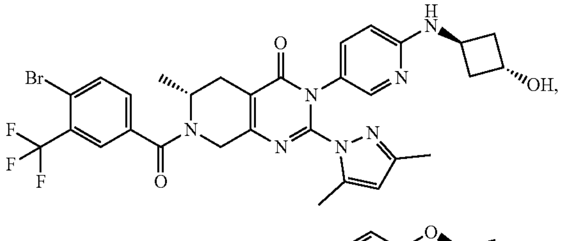
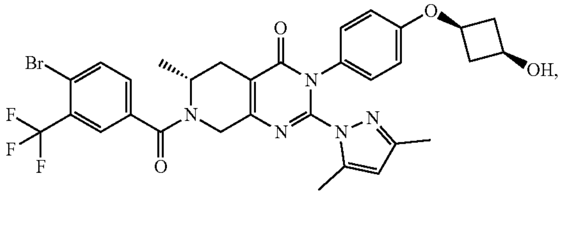
-continued
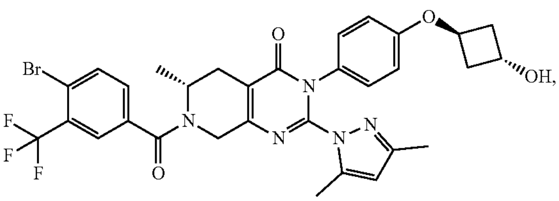
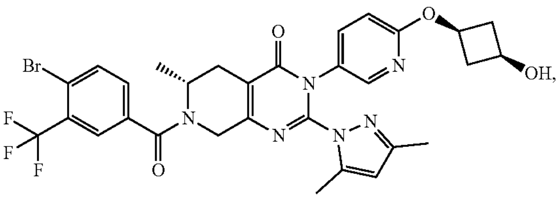
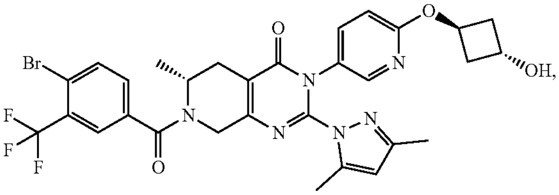
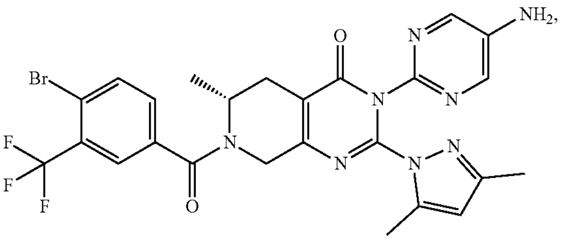
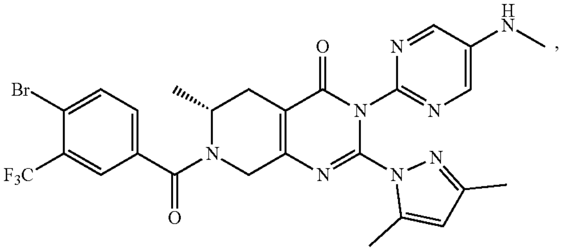
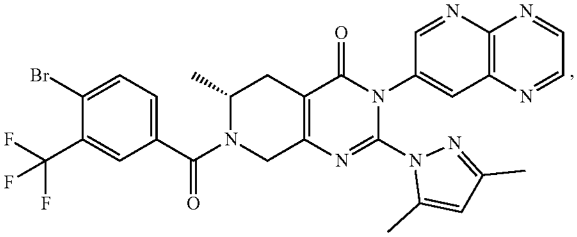
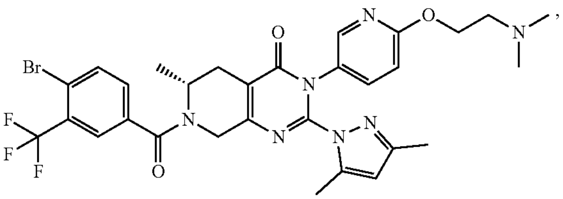

-continued
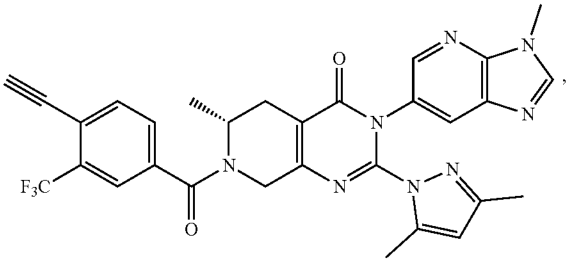
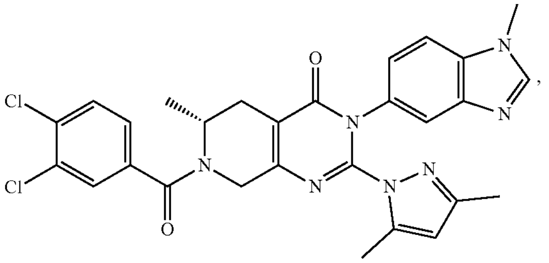
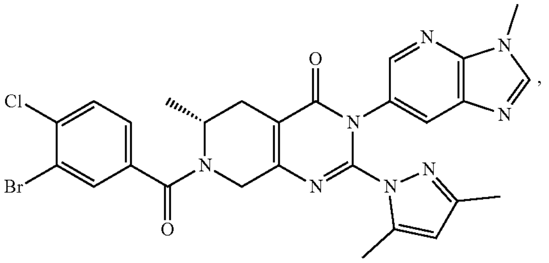
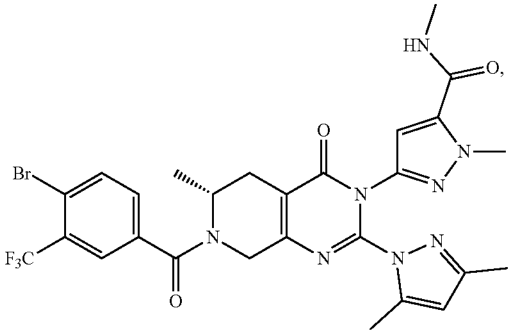
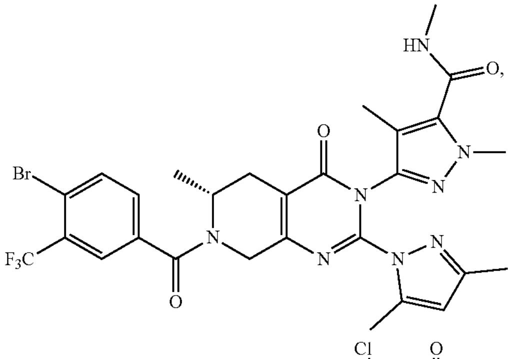
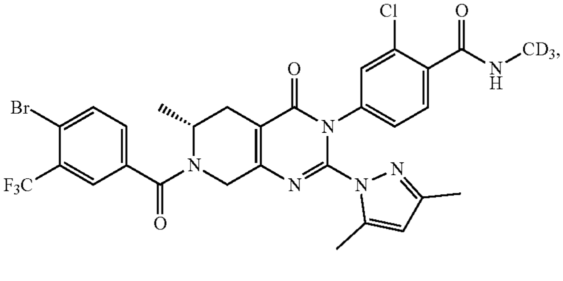
-continued
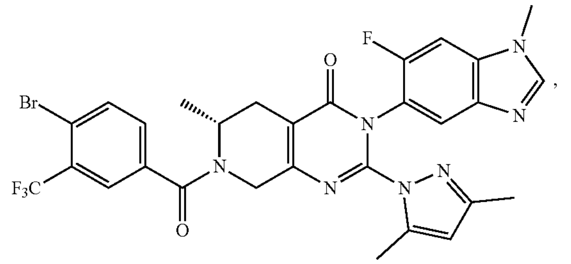
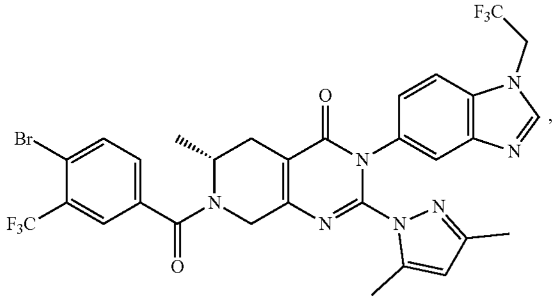
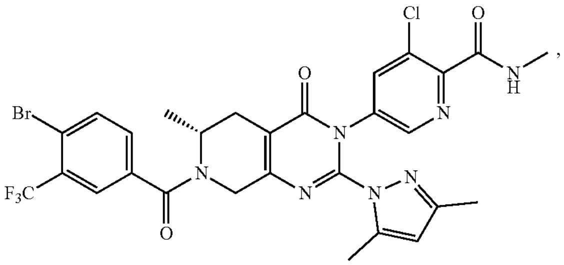
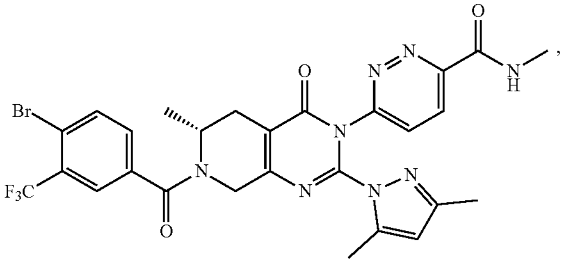
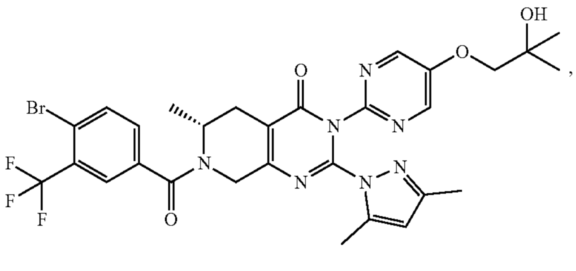
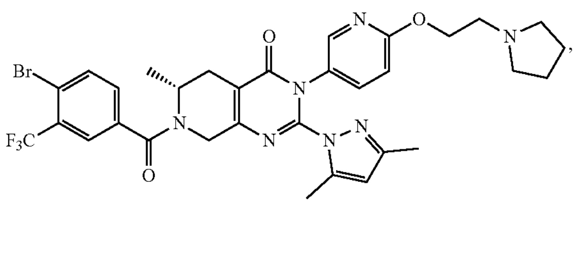

-continued
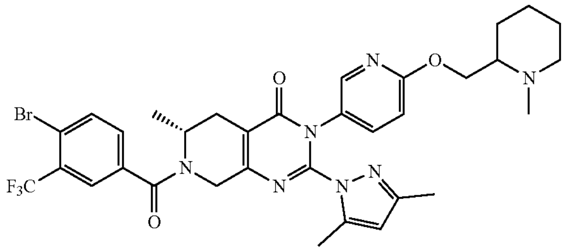
,
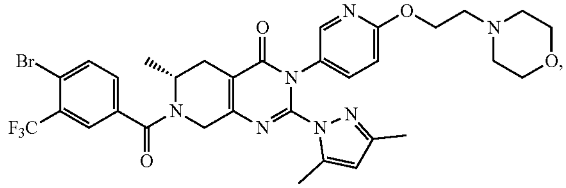
,
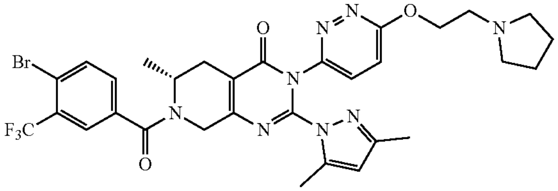
,
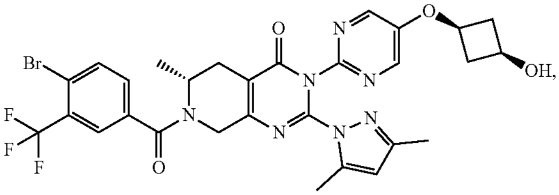
,
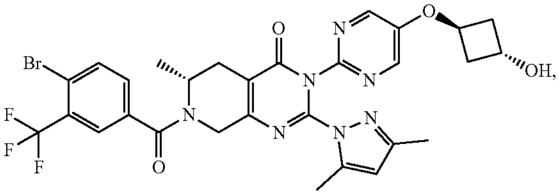
,
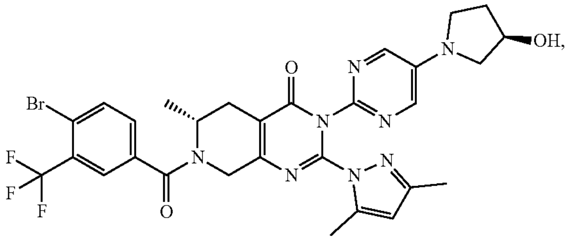
,
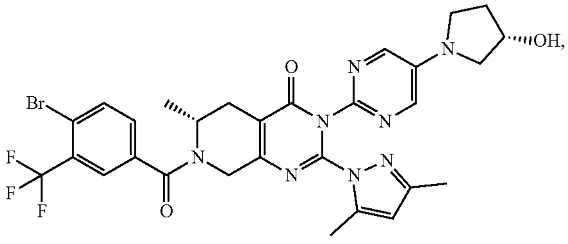
,
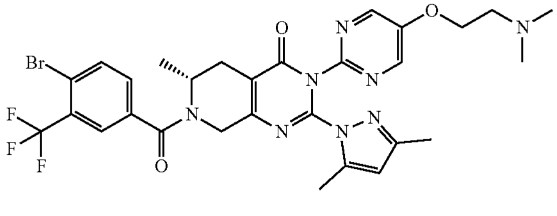
,
-continued
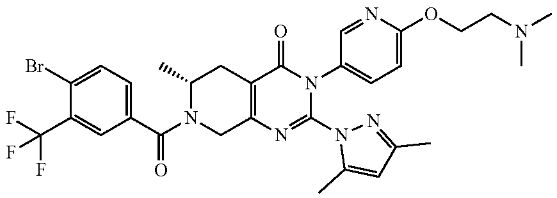
,
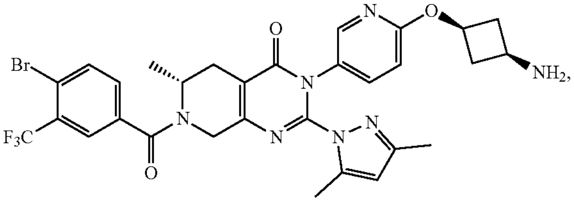
,
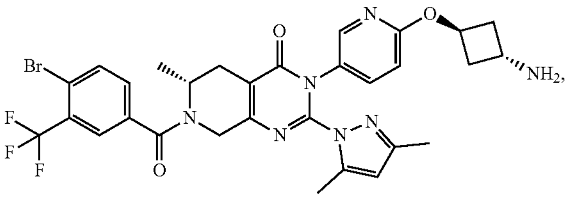
,
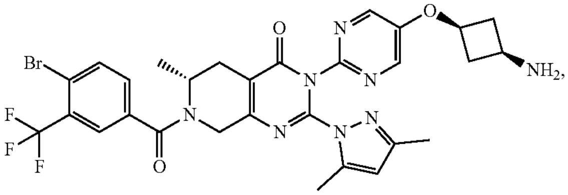
,
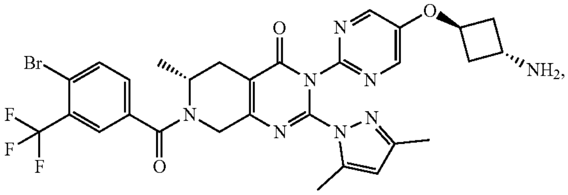
,
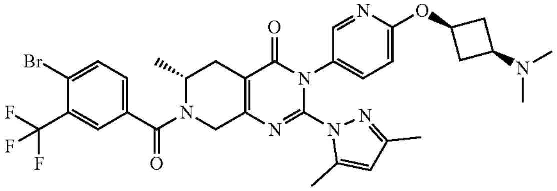
,
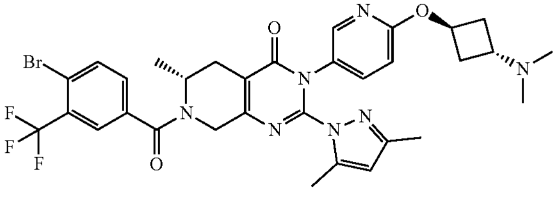
,
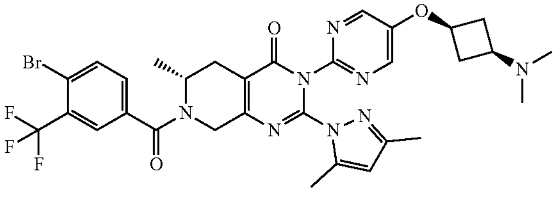
, -continued

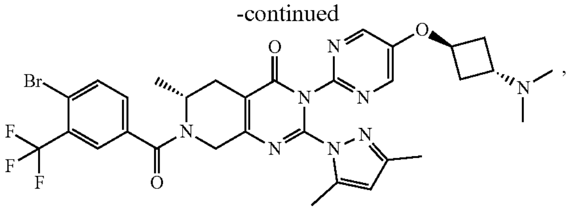

,

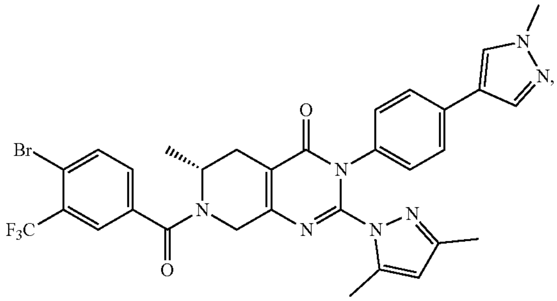

,

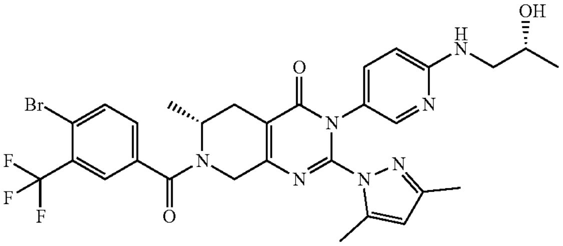

,

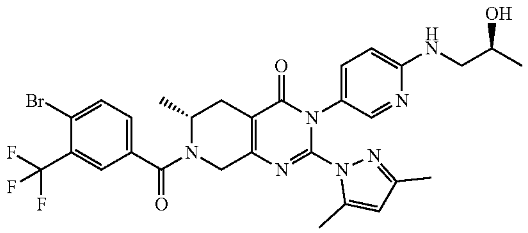

and

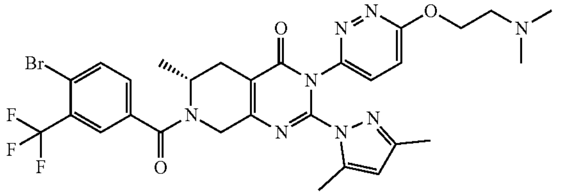

, or a pharmaceutically acceptable salt of any of the foregoing.

13. A pharmaceutical composition comprising an effective amount of a compound of claim 1, or a pharmaceutically acceptable salt thereof, and excipient.

14. A method for treating hepatitis B in a subject comprising administering to the subject in need thereof an effective amount of a compound of claim 11, or a pharmaceutically acceptable salt thereof, suffering from hepatitis B.

15. The compound of claim 11 selected from the group consisting of:

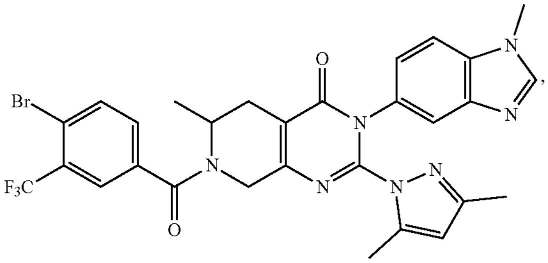

,

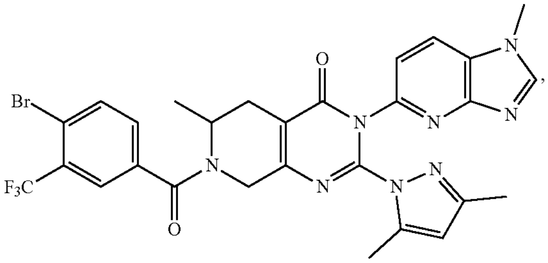

,

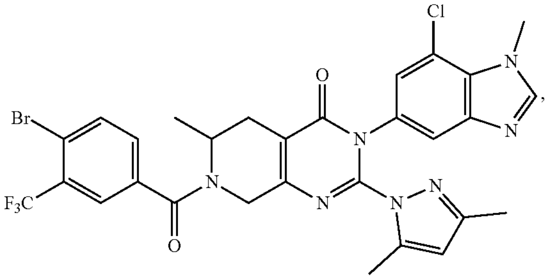

,

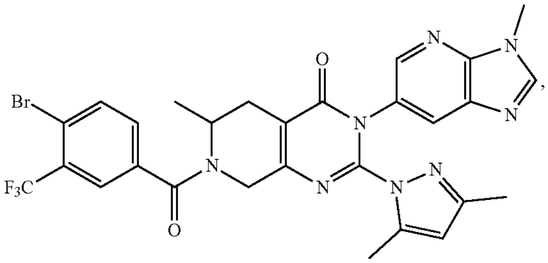

,

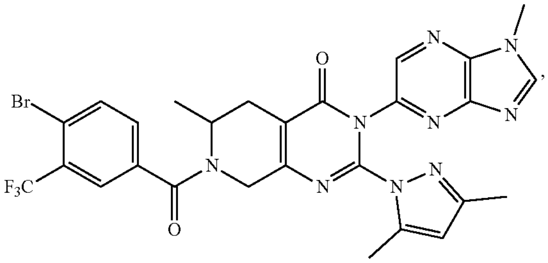

,

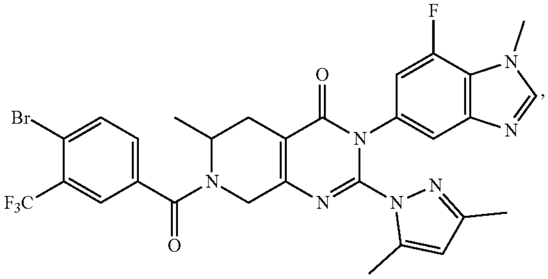

,

-continued
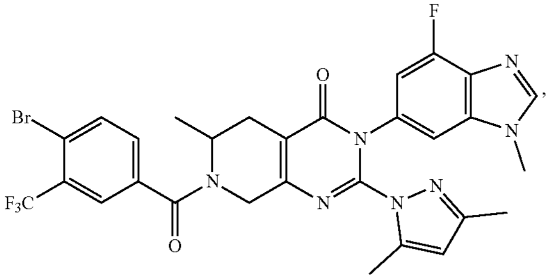
,
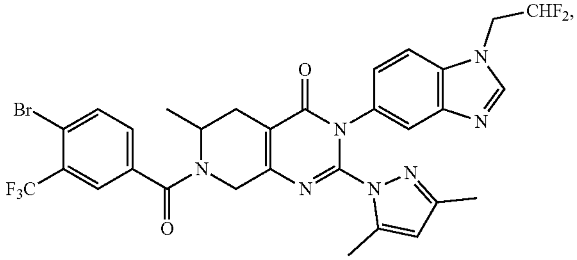
,
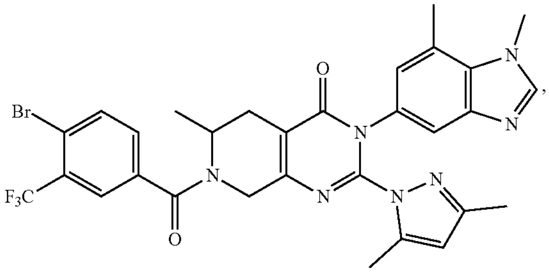
,
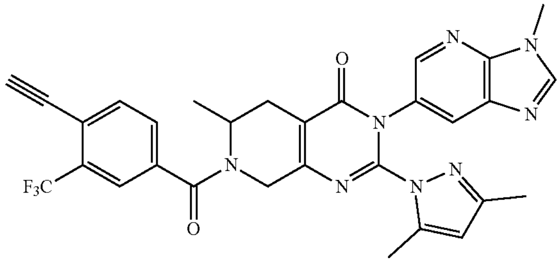
,
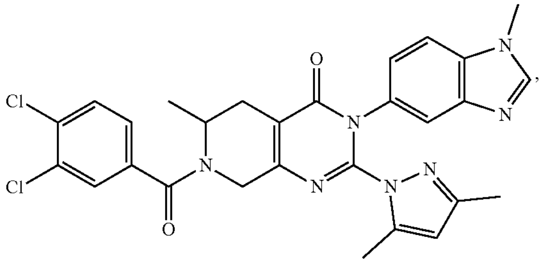
,
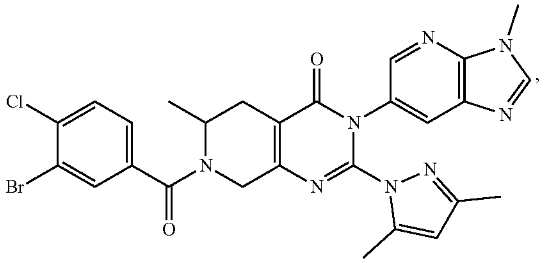
,
-continued
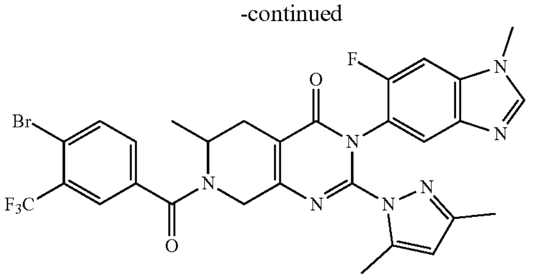
and
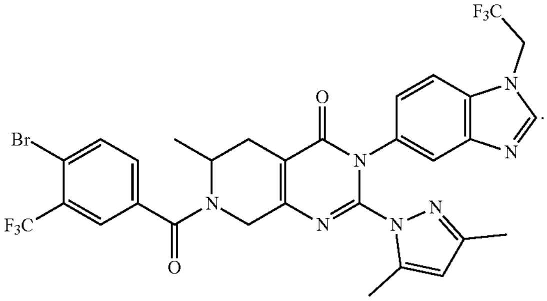
.
or a pharmaceutically acceptable salt of any of the foregoing.
16. The compound of claim 11, wherein the compound is
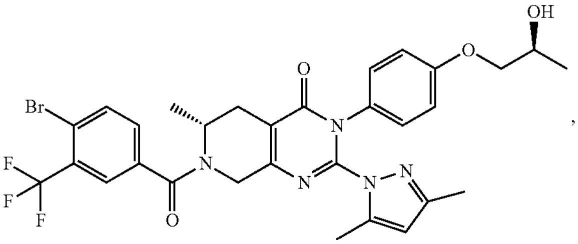 [SMILES: Cc1cc(C)n(-c2nc3c(c(=O)n2-c2ccc(OC[C@H](C)O)cc2)C[C@@H](C)N(C(=O)c2ccc(Br)c(C(F)(F)F)c2)C3)n1]
,
or a pharmaceutically acceptable salt thereof.
17. The compound of claim 11, wherein the compound is
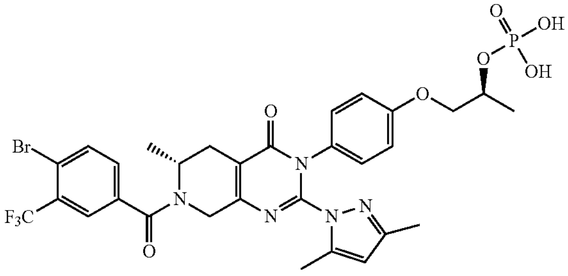
,
or a pharmaceutically acceptable salt thereof.

18. The compound of claim 11, wherein the compound is

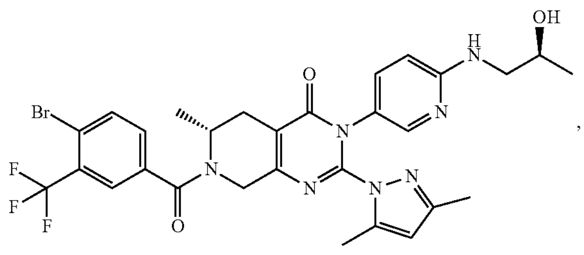 [SMILES: Cc1cc(C)n(-c2nc3c(c(=O)n2-c2ccc(NC[C@H](C)O)nc2)C[C@@H](C)N(C(=O)c2ccc(Br)c(C(F)(F)F)c2)C3)n1]

, or a pharmaceutically acceptable salt thereof.

19. The compound of claim 11, wherein the compound is

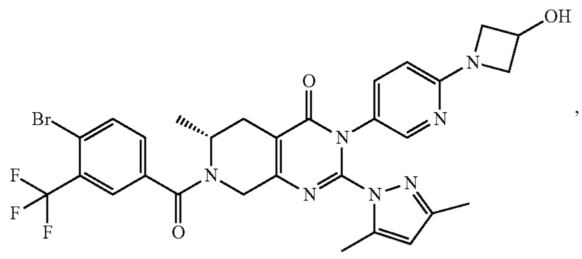 [SMILES: Cc1cc(C)n(-c2nc3c(c(=O)n2-c2ccc(N4CC(O)C4)nc2)C[C@@H](C)N(C(=O)c2ccc(Br)c(C(F)(F)F)c2)C3)n1]

, or a pharmaceutically acceptable salt thereof.

20. The compound of claim 11, wherein the compound is

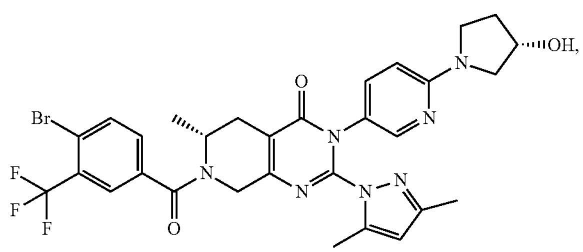 [SMILES: Cc1cc(C)n(-c2nc3c(c(=O)n2-c2ccc(N4CC[C@H](O)C4)nc2)C[C@@H](C)N(C(=O)c2ccc(Br)c(C(F)(F)F)c2)C3)n1]

or a pharmaceutically acceptable salt thereof.

21. The compound of claim 11, wherein the compound is

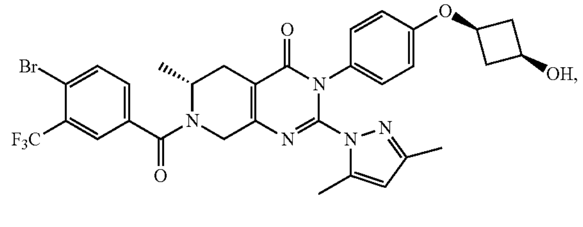 [SMILES: Cc1cc(C)n(-c2nc3c(c(=O)n2-c2ccc(O[C@H]4C[C@@H](O)C4)cc2)C[C@@H](C)N(C(=O)c2ccc(Br)c(C(F)(F)F)c2)C3)n1]

or a pharmaceutically acceptable salt thereof.

22. The compound of claim 15, wherein the compound is

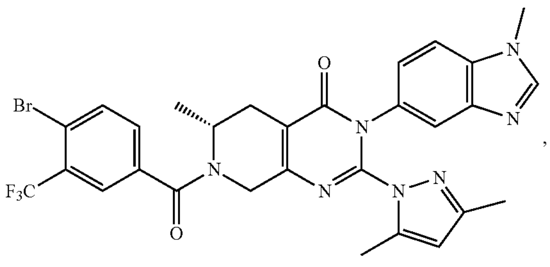 [SMILES: Cc1cc(C)n(-c2nc3c(c(=O)n2-c2ccc4c(c2)ncn4C)C[C@@H](C)N(C(=O)c2ccc(Br)c(C(F)(F)F)c2)C3)n1]

, or a pharmaceutically acceptable salt thereof.

23. The compound of claim 15, wherein the compound is

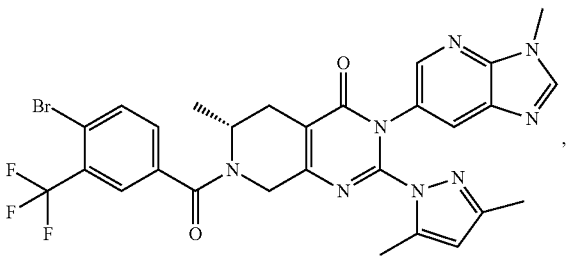 [SMILES: Cc1cc(C)n(-c2nc3c(c(=O)n2-c2cnc4c(c2)ncn4C)C[C@@H](C)N(C(=O)c2ccc(Br)c(C(F)(F)F)c2)C3)n1]

, or a pharmaceutically acceptable salt thereof.

24. The compound of claim 15, wherein the compound is

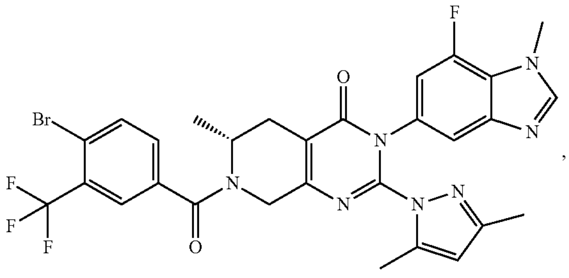 [SMILES: Cc1cc(C)n(-c2nc3c(c(=O)n2-c2cc(F)c4c(c2)ncn4C)C[C@@H](C)N(C(=O)c2ccc(Br)c(C(F)(F)F)c2)C3)n1]

, or a pharmaceutically acceptable salt thereof.

25. The compound of claim 9, wherein $R^2$ is

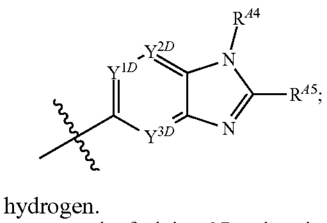

and $R^{45}$ is hydrogen.

26. The compound of claim 25, wherein $Y^{1D}$ is CH or C-(halogen); $Y^{2D}$ is N; and $Y^{3D}$ is CH, C—$CH_3$, C—$OCH_3$, C-(halogen), C—$CHF_2$ or C—$CF_3$.

27. The compound of claim 25, wherein $Y^{1D}$ is CH or C-(halogen); $Y^{2D}$ is CH, C—$CH_3$, C—$OCH_3$, C-(halogen), C—$CHF_2$ or C—$CF_3$; and $Y^{3D}$ is CH, C—$CH_3$, C—$OCH_3$, C-(halogen), C—$CHF_2$ or C—$CF_3$.

* * * * *

SEQUENCE LISTING

```
Sequence total quantity: 3
SEQ ID NO: 1            moltype = DNA  length = 20
FEATURE                 Location/Qualifiers
misc_feature            1..20
                        note = Synthetic HBV-forward primer
source                  1..20
                        mol_type = other DNA
                        organism = synthetic construct
SEQUENCE: 1
gtgtctgcgg cgttttatca                                              20

SEQ ID NO: 2            moltype = DNA  length = 21
FEATURE                 Location/Qualifiers
misc_feature            1..21
                        note = Synthetic HBV-reverse primer
source                  1..21
                        mol_type = other DNA
                        organism = synthetic construct
SEQUENCE: 2
gacaaacggg caacatacct t                                            21

SEQ ID NO: 3            moltype = DNA  length = 28
FEATURE                 Location/Qualifiers
misc_feature            1..28
                        note = Synthetic HBV-probe
modified_base           1
                        mod_base = OTHER
                        note = N=FAM-C
modified_base           9
                        mod_base = OTHER
                        note = N=T-ZEN
modified_base           28
                        mod_base = OTHER
                        note = N=C-3IABkFQ
source                  1..28
                        mol_type = other DNA
                        organism = synthetic construct
SEQUENCE: 3
nctctkcanc ctgctgctat gcctcatn                                     28
```